US008580788B2

(12) United States Patent
Dolle et al.

(10) Patent No.: US 8,580,788 B2
(45) Date of Patent: *Nov. 12, 2013

(54) OPIOID ANTAGONISTS

(75) Inventors: Roland E. Dolle, Hopkinton, MA (US); Bertrand Le Bourdonnec, Spring City, PA (US); Allan James Goodman, Media, PA (US)

(73) Assignee: Adolor Corporation, Exton, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/479,622

(22) Filed: May 24, 2012

(65) Prior Publication Data

US 2012/0231543 A1 Sep. 13, 2012

Related U.S. Application Data

(62) Division of application No. 12/463,814, filed on May 11, 2009, now Pat. No. 8,278,323, which is a division of application No. 11/552,827, filed on Oct. 25, 2006, now Pat. No. 7,538,110.

(60) Provisional application No. 60/730,609, filed on Oct. 27, 2005.

(51) Int. Cl.
*A61K 31/50* (2006.01)
*A61K 31/495* (2006.01)
*C07D 241/36* (2006.01)
*C07D 471/00* (2006.01)
*C07D 487/00* (2006.01)

(52) U.S. Cl.
USPC .......................................... 514/249; 544/349

(58) Field of Classification Search
USPC .......................................... 544/349; 514/249
See application file for complete search history.

(56) References Cited

U.S. PATENT DOCUMENTS

| 4,176,186 | A | 11/1979 | Goldberg et al. |
| 4,236,010 | A | 11/1980 | Imhof et al. |
| 4,987,126 | A | 1/1991 | Bargiotti et al. |
| 5,159,081 | A | 10/1992 | Cantrell et al. |
| 5,250,542 | A | 10/1993 | Cantrell et al. |
| 5,270,328 | A | 12/1993 | Cantrell et al. |
| 5,422,356 | A | 6/1995 | Zimmerman et al. |
| 5,434,171 | A | 7/1995 | Frank et al. |
| 5,972,954 | A | 10/1999 | Foss et al. |
| 6,251,893 | B1 | 6/2001 | Maddaford et al. |
| 6,451,806 | B2 | 9/2002 | Farrar |
| 6,531,481 | B2 | 3/2003 | Carroll et al. |
| 6,552,032 | B2 | 4/2003 | Carroll et al. |
| 6,593,348 | B2 | 7/2003 | Carroll et al. |
| 6,900,228 | B1 | 5/2005 | Carroll et al. |
| 7,087,749 | B2 | 8/2006 | Dolle et al. |
| 7,265,226 | B2 | 9/2007 | Wentland |
| 7,381,721 | B2 | 6/2008 | Dolle et al. |
| 7,767,814 | B2 | 8/2010 | Dolle et al. |
| 7,884,102 | B2 | 2/2011 | Dolle et al. |
| 2002/0099216 | A1 | 7/2002 | Gibson et al. |
| 2003/0100562 | A1 | 5/2003 | Cheng et al. |
| 2005/0203123 | A1 | 9/2005 | Dolle et al. |
| 2005/0222204 | A1 | 10/2005 | Mitch et al. |

FOREIGN PATENT DOCUMENTS

| EP | 1072592 | 1/2001 |
| EP | 1359146 | 5/2003 |
| WO | 99/45925 | 9/1999 |
| WO | 02/30896 | 4/2002 |
| WO | 02/053533 A2 | 7/2002 |

OTHER PUBLICATIONS

Alt, A. et al., "Mu and Delta opioid receptors activate the same G proteins in human neuroblastoma SH-SY5Y cells," *British Journal of Pharmacology*, 2002, 135, 217-225.
Bagnol, D., et al., "Cellular localization and distribution of the cloned mu and kappa opioid receptors in rat gastrointestinal tract," *Neuroscience*, 1997, 81(2), 579-591.
Bagnol, D., et al., "Changes in enkephalin immunoreactivity of sympathetic ganglia and digestive tract for the cat after splanchnic nerve ligation," *Regul. Pept.*, 1993, 47, 259-273.
Bates, J.J. et al, "Are Peripheral Opioid Antagonists the Solution to Opioid Side Effects," *Anesth. Analg.*, 2004,98,116-122.
Barratt S. McG. et al., "Approaches to Reducing Postoperative Opioid Requirements," CNS Drugs, Disease Management, Oct. 1998, 10 (4), 257-270.
Barratt S., McG., "Advances in Acute Pain Management," Int. Anesthesiol. Clin. 1997 Spring; 35(2):27-47.
Becker et al., New Drug Class, 2009, vol. 373, pp. 1198-1206.
Bilsky, E.J. et al., "Effects of naloxone and D-Phe-Cys-Tyr-D-Trp-Arg-Thr-Pen-Thr-NH$_2$ and the protein kinase inhibitions H7 and H8 on acute morphine dependence and antinociceptive tolerance in mice," *J. Pharmacol. Exp. Ther.*, 1996, 277(1), 484-490.
Bhargava, H.N., et al., "Effect of nitric oxide synthase inhibition on tolerance to the analgesic action of D-Pen$^2$, D-Pen$^5$ enkephalin and morphine in the mouse," *Neuropeptides*, 1996, 30(3), 219-223.
*Doland's Illustrated Medical Dictionary*, 27$^{th}$ Ed. W.B. Saunders Co., Phila., PA, 1988, p. 816.
*Doland's Illustrated Medical Dictionary*, 27$^{th}$ Ed., W.B. Saunders Co., Phila., PA 1988, p. 375.
Dourish, C.T., et al., "Enhancement of morphine analgesia and prevention of morphine tolerance in the rat by the cholecystokinin antagonist L-364,718," *Eur. J. Pharmacol.*, 1988, 147, 469-472.
DeHaven, R.N. et al., "Characterization of opioid receptors," *Current Protocols in Pharmacology*, 2000, 1.4.1-1.4.12.
Gastroenterology, A730 AGA Abstracts, 114(4), 1998.
Jain, K.K., "A guide to drug evalutaion for chronic pain," *Emerging Drugs*, 2000, 5(2), 241-257.
Koch, T.R., et al., "Inhibitory neuropeptides and intrinsic inhibitory innervation of descending human colon," *Digestive Diseases and Sciences*, 1991,36(6), 712-718.

(Continued)

*Primary Examiner* — Niloofar Rahmani
(74) *Attorney, Agent, or Firm* — Feldman Gale, P.A.; Walter C. Frank

(57) ABSTRACT

Certain quinolizidine and octahydropyridopyrazine compounds, pharmaceutical compositions, and methods of their use, inter alia, as opioid receptor antagonists are disclosed.

18 Claims, No Drawings

(56) References Cited

OTHER PUBLICATIONS

Kreek, M.J., et al., "Naloxone, a specific opioid antagonist, reverses chronic idiopathic constipation," *The Lancet*, 1983, 1(8319), 261-262.

Livingston, E.H. et al., "Postoperative Ileus," *Digestive Diseases and Sciences*, 1990, 35(1), 121-132.

LY246736 Dihydrate, Opioid Receptor Antagonist, Drugs of the Future, 1994, 19(12), pp. 1078-1083.

Mack, D.J., et al., "Paralytic lieus: response to naloxone," *Br. J. Surg.*, 1989, 76(10), p. 1101.

Mao, M.J., et al., "Oral administration of dextromethorphan prevents the development of morphine tolerance and dependence in rats," *Pain*, 1996, 67, pp. 361-368.

Nichols, M.L., et al., "Enhancement of the antiallodynic and antinociceptive efficacy of spinal morphine by antisera to dynorphin A (1-3) or MK-801 in a nerve-ligation model of peripheral neuropathy," *Pain*, 1997, vol. 69, pp. 317,322.

Parrish et al., Practical gastroenterology, 2008, pp. 37-50.

Raynor, K. et al., "Pharmacological characterization of the cloned k-, δ-, and μ- opioid receptors," *Molecular Pharmacology*, 1994, vol. 45, pp. 330-334.

Reisine, T. et al., "Opioid analgesics and antagonists," Gilman's the Pharmacological Basis of Therapeutics, 9th Goldman & Ed., McGraw-Hill, 1996, pp. 521-555.

Resnick, J., "Delayed gastric emptying and postoperative Ileus after nongastric abdominal surgery: Part I," *Am. J. of Gastroenterology*, 1997, vol. 92, No. 5, pp. 751-762.

Resnick, J., "Delayed gastric emptying and postoperative Ileus after nongstric abdominal surgery: Part II," *Am J. of Gastroenterology*, 1997, 92(6), 934-940.

Schang, J.C. et al., "Beneficial effects of naloxone in a patient with intestinal pseudoobstruction," *Am. J. Gastroenerol*, 1985, 80(6), 407-411.

Schuller, A.G.P., et al., "M6G, But not morphine, inhibits GI transit in MU opioid receptor deficient mice," Society of Neuroscience Abstracts, 1998, 24.

Shaw, W.N., et al., "Effect phenylpiperidine opioid antagonists on food consumption and weight gain of the obese Zucker rat," *J. Pharm. and Exp. Ther.*, 1990, 253(1), 85-89.

William et al., Expert opin. Pharmacother, 2009, 10(11), pp. 1841-1845.

Wittert, G., "Tissue distribution of opioid receptor gene expression in the rat," *Biochemical and Biophysical Res. Communications*, 1996, 218, 877-881.

Zimmerman, D.M., et al., "Discovery of a potent, peripherally selective trans-3, 4-dimethyl-4-(3-hydroxyphenyl)piperidine opioid antagonist for the treatment of gastrointestinal motility disorders," *J. Med. Chem.*, 1994, 37, 2262-2265.

OPIOID ANTAGONISTS

CROSS REFERENCE TO RELATED APPLICATIONS

This application is a divisional application of U.S. application Ser. No. 12/463,814, filed May 11, 2009, which is a divisional application of U.S. Pat. No. 7,538,110, issued May 26, 2009, which claims the benefit of U.S. Provisional Application Ser. No. 60/730,609, filed Oct. 27, 2005, the disclosure of each of which is hereby incorporated herein by reference in its entirety.

FIELD OF THE INVENTION

The invention relates to compounds that affect the opioid receptor system and, more particularly, to quinolizidine and octahydropyridopyrazine compounds, pharmaceutical compositions containing such compounds that are, inter alia, antagonists of opioid receptors, and methods of their use.

BACKGROUND OF THE INVENTION

It is well known that opioid drugs target three types of endogenous opioid receptors (i.e., μ, δ, and κ receptors) in biological systems. Many opiates, such as morphine, are μ opioid agonists that are often used as analgesics for the treatment of severe pain due to their activation of μ opioid receptors in the brain and central nervous system (CNS). Opioid receptors are, however, not limited to the CNS, and may be found in other tissues throughout the body, i.e., peripheral to the CNS. A number of side effects of opioid drugs may be caused by activation of these peripheral receptors. For example, administration of μ opioid agonists often results in intestinal dysfunction due to the large number of receptors in the wall of the gut (Wittert, G., Hope, P. and Pyle, D., *Biochemical and Biophysical Research Communications,* 1996, 218, 877-881; Bagnol, D., Mansour, A., Akil, A. and Watson, S. J., *Neuroscience,* 1997, 81, 579-591). Specifically, opioids are generally known to cause nausea and vomiting, as well as inhibition of normal propulsive gastrointestinal function in animals and man (Reisine, T., and Pasternak, G., *Goodman & Gilman's The Pharmacological Basis of Therapeutics, Ninth Edition,* 1996, 521-555), resulting in side effects such as, for example, constipation.

Recent evidence has indicated that naturally-occurring endogenous opioid compounds may also affect propulsive activity in the gastrointestinal (GI) tract. Met-enkephalin, which activates μ and δ receptors in both the brain and gut, is one of several neuropeptides found in the GI tract (Koch, T. R., Carney, J. A., Go, V. L., and Szurszewski, J. H., *Digestive Diseases and Sciences,* 1991, 36, 712-728). Additionally, receptor knockout techniques have shown that mice lacking μ opioid receptors may have faster GI transit times than wild-type mice, suggesting that endogenous opioid peptides may tonically inhibit GI transit in normal mice (Schuller, A. G. P., King, M., Sherwood, A. C., Pintar, J. E., and Pasternak, G. W., *Society of Neuroscience Abstracts* 1998, 24, 524). Studies have shown that opioid peptides and receptors located throughout the GI tract may be involved in normal regulation of intestinal motility and mucosal transport of fluids in both animals and man (Reisine, T., and Pasternak, G., Goodman & Gilman's *The Pharmacological Basis of Therapeutics, Ninth Edition,* 1996, 521-555). Other studies show that the sympathetic nervous system may be associated with endogenous opioids and control of intestinal motility (Bagnol, D., Herbrecht, F., Jule, Y., Jarry, T., and Cupo, A., *Regul. Pept.,* 1993, 47, 259-273). The presence of endogenous opioid compounds associated with the GI tract suggests that an abnormal physiological level of these compounds may lead to bowel dysfunction.

It is a common problem for patients having undergone surgical procedures, especially surgery of the abdomen, to suffer from a particular bowel dysfunction called post-surgical (or post-operative) ileus. "Ileus," as used herein, refers to the obstruction of the bowel or gut, especially the colon. See, e.g., *Dorland's Illustrated Medical Dictionary,* 27th ed., page 816, (W.B. Saunders Company, Philadelphia, Pa., 1988). Ileus should be distinguished from constipation, which refers to infrequency of or difficulty in feces evacuation. See, e.g., *Dorland's Illustrated Medical Dictionary,* 27th ed., page 375, (W.B. Saunders Company, Philadelphia, 1988). Ileus may be diagnosed by the disruption of normal coordinated movements of the gut, resulting in failure of intestinal contents propulsion. See, e.g., Resnick, J., *Am. J. of Gastroenterology,* 1997, 92, 751 and Resnick, J. *Am. J. of Gastroenterology,* 1997, 92, 934. In some instances, particularly following surgery, including surgery of the abdomen, the bowel dysfunction may become quite severe, lasting for more than a week and affecting more than one portion of the GI tract. This condition is often referred to as post-surgical (or post-operative) paralytic ileus and most frequently occurs after laparotomy (see Livingston, E. H. and Passaro, Jr., E. D., *Digestive Diseases and Sciences,* 1990, 35, 121). Similarly, post-partum ileus is a common problem for women in the period following childbirth, and is thought to be caused by similar fluctuations in natural opioid levels as a result of birthing stress.

Gastrointestinal dysmotility associated with post-surgical ileus is generally most severe in the colon and typically lasts for 3 to 5 days. The administration of opioid analgesics to a patient after surgery may often contribute to bowel dysfunction, thereby delaying recovery of normal bowel function. Since virtually all patients receive opioid analgesics, such as morphine or other narcotics, for pain relief after surgery, particularly major surgery, current post-surgical pain treatment may actually slow recovery of normal bowel function, resulting in a delay in hospital discharge and increasing the cost of medical care.

Post-surgical and post-partum ileus may also occur in the absence of exogenous opioid agonists. It would be of benefit to inhibit the natural activity of endogenous opioids during and/or after periods of biological stress, such as surgery and childbirth, so that ileus and related forms of bowel dysfunction can be prevented and/or treated. Currently, therapies for ileus include functional stimulation of the intestinal tract, stool softeners, laxatives, lubricants, intravenous hydration, and nasogastric decompression. These prior art methods suffer from drawbacks, for example, as lacking specificity for post-surgical or post-partum ileus. And these prior art methods offer no means for prevention. If ileus could be prevented, hospital stays, recovery times, and medical costs would be significantly decreased, in addition to the benefit of minimizing patient discomfort. Thus, drugs that selectively act on opioid receptors in the gut would be ideal candidates for preventing and/or treating post-surgical and post-partum ileus. Of those, drugs that do not interfere with the effects of opioid analgesics in the CNS would be of special benefit in that they could be administered simultaneously for pain management with limited side effects.

Peripheral opioid antagonists that do not cross the blood-brain barrier into the CNS are known in the literature and have been tested in relation to their activity on the GI tract. In U.S. Pat. No. 5,250,542, U.S. Pat. No. 5,434,171, U.S. Pat. No.

5,159,081, and U.S. Pat. No. 5,270,328, peripherally selective piperidine-N-alkylcarboxylate opioid antagonists are described as being useful in the treatment of idiopathic constipation, irritable bowel syndrome, and opioid-induced constipation. In addition, U.S. Pat. No. 4,176,186 describes quaternary derivatives of noroxymorphone (i.e., methylnaltrexone) that are said to prevent or relieve the intestinal immobility side effect of narcotic analgesics without reducing analgesic effectiveness. U.S. Pat. No. 5,972,954 describes the use of methylnaltrexone, enteric-coated methylnaltrexone, or other quaternary derivatives of noroxymorphone for preventing and/or treating opioid- and/or non-opioid-induced side effects associated with opioid administration.

General opioid antagonists, such as naloxone and naltrexone, have also been implicated as being useful in the treatment of GI tract dysmotility. For example, U.S. Pat. No. 4,987,126 and Kreek, M. J., Schaefer, R. A., Hahn, E. F., Fishman, *J. Lancet,* 1983, 1, 8319, 261 disclose naloxone and other morphinan-based opioid antagonists (i.e., naltrexone) for the treatment of idiopathic gastrointestinal dysmotility. In addition, naloxone has been shown to effectively treat non-opioid induced bowel obstruction, implying that the drug may act directly on the GI tract or in the brain (Schang, J. C., Devroede, G., *Am. J. Gastroenterol.,* 1985, 80, 6, 407). Furthermore, it has been implicated that naloxone may provide therapy for paralytic ileus (Mack, D. J. Fulton, J. D., *Br. J. Surg.,* 1989, 76, 10, 1101). However, it is well known that activity of naloxone and related drugs is not limited to peripheral systems and may interfere with the analgesic effects of opioid narcotics.

Alvimopan is an orally active, gastrointestinal (GI) restricted μ opioid antagonist being developed to alleviate the GI side effects associated with narcotic therapy. Alvimopan inhibits [$^3$H]diprenorphine binding to cloned human opioid receptors with $K_i$ values of 0.44 nM, 10 nM and 92 nM for μ, δ, and κ receptors respectively. This compound differs from previously characterized peripherally selective opioid antagonists by its potency and degree of peripheral receptor selectivity [Zimmerman, et al., *J. Med. Chem.,* 1994, 37, 2262-2265].

The μ opioid antagonist family of trans-3,4-dimethyl-4-phenylpiperidines has been indicated as food consumption reducing agents [W. N. Shaw, et al., *J. Pharm. and Exp. Ther.,* 1990, 253(1), 85-89]. Long-term chronic administration significantly reduced food consumption in obese test animals for as long as a phenylpiperidine μ opioid antagonist was administered, resulting in a significant decrease in weight gain compared to control. Accordingly, compounds with μ opioid antagonist properties are likely to have benefit in the treatment or management of obesity in patients, especially those non-zwitterionic compounds that would be able to cross the blood-brain barrier.

Inasmuch as post-surgical and post-partum ileus, for example, are common illnesses that add to the cost of health care and as yet have no specific treatment, there is a need for a specific and effective remedy. The majority of currently known opioid antagonist therapies are not peripherally selective and have the potential for undesirable side effects resulting from penetration into the CNS. Given the estimated 21 million inpatient surgeries and 26 million outpatient surgeries each year, and an estimate of 4.7 million patients experiencing post-surgical ileus, methods involving opioid antagonists that are not only specific for peripheral systems, but also specific for the gut, are desirable for treating post-surgical and post-partum ileus.

There is still an unfulfilled need for compounds that may be used in methods to antagonize opioid receptors, particularly where undesirable symptoms or conditions are side effects of administering exogenous opioids. The present invention is directed to these, as well as other important ends.

SUMMARY OF THE INVENTION

The present invention is generally directed to quinolizidine and octahydropyridopyrazine derivatives, pharmaceutical compositions containing these compounds, and methods of their pharmaceutical use.

In one embodiment, the invention is directed to compounds of formula I:

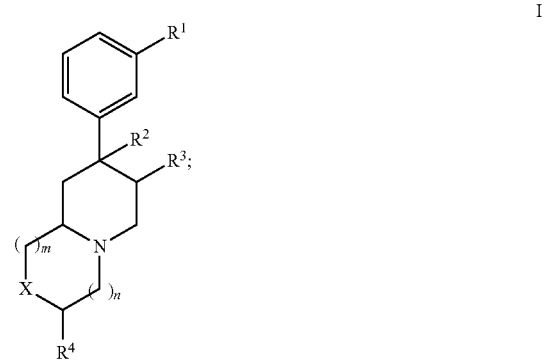

wherein:

$R^1$ is —OH, —OR$^a$, —CH$_2$OH, —C(=O)OR$^6$, —C(=O)NR$^6$R$^7$, or —NR$^6$R$^7$;

$R^2$ and $R^3$ are each independently alkyl or alkenyl;

$R^4$ is H, alkyl, cycloalkyl, cycloalkylalkyl, aryl, heteroaryl, aralkyl, alkylaralkyl, or heteroarylalkyl;

X is CH$_2$ or NR$^5$;

$R^5$ is H, alkyl, cycloalkyl, cycloalkylalkyl, aryl, heteroaryl, aralkyl, alkylaralkyl, heteroarylalkyl, —C(=O)OR$^{8a}$, —S(=O)$_2$R$^{8a}$, —C(=O)R$^{8b}$, or —C(=O)NR$^{8b}$R$^{8c}$;

$R^6$ is H, alkyl, cycloalkyl, alkylcycloalkyl, or aralkyl;

$R^7$ is H, alkyl, aralkyl, or aryl;

$R^{8a}$ is alkyl, cycloalkyl, cycloalkylalkyl, heteroaryl, heteroarylalkyl, aralkyl, or aryl;

$R^{8b}$ and $R^{8c}$ are each independently H, alkyl, cycloalkyl, cycloalkylalkyl, heteroaryl, heteroarylalkyl, aralkyl, or aryl; or $R^{8b}$ and $R^{8c}$ taken together with the nitrogen atom to which they are connected form a 4- to 8-membered heterocycloalkyl ring;

$R^a$ is a hydroxyl protecting group;

m is 1 or 2; and n is 0, 1, or 2;

with the provisos that:

at least one of m and n is other than 2; and when X is NR$^5$, then n is 1 or 2;

or a pharmaceutically acceptable salt thereof.

In another embodiment, the invention is directed to compounds of formula III:

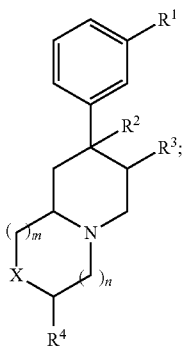

wherein:
R$^1$ is —OH, —OR$^a$, —CH$_2$OH, —C(=O)OR$^6$, —C(=O)NR$^6$R$^7$, or —NR$^6$R$^7$;
R$^2$ and R$^3$ are each independently alkyl or alkenyl;
R$^4$ is H, alkyl, cycloalkyl, cycloalkylalkyl, aryl, heteroaryl, aralkyl, alkylaralkyl, or heteroarylalkyl;
X is CH$_2$ or NR$^5$;
R$^5$ is H, alkyl, cycloalkyl, cycloalkylalkyl, aryl, heteroaryl, aralkyl, alkylaralkyl, heteroarylalkyl, heterocycloalkylalkyl, —C(=O)OR$^{8a}$, —S(=O)$_2$R$^{8a}$, —C(=O)R$^{8b}$, or —C(=O)NR$^{8b}$R$^{8c}$;
R$^6$ is H, alkyl, cycloalkyl, alkylcycloalkyl, or aralkyl;
R$^7$ is H, alkyl, aralkyl, or aryl;
R$^{8a}$ is alkyl, cycloalkyl, cycloalkylalkyl, heteroaryl, heteroarylalkyl, aralkyl, or aryl;
R$^{8b}$ and R$^{8c}$ are each independently H, alkyl, cycloalkyl, cycloalkylalkyl, heteroaryl, heterocycloalkyl, heterocycloalkylalkyl, heteroarylalkyl, aralkyl, or aryl; or R$^{8b}$ and R$^{8c}$ taken together with the nitrogen atom to which they are connected form a 4- to 8-membered heterocycloalkyl ring;
R$^a$ is a hydroxyl protecting group;
m is 1 or 2; and
n is 0, 1, or 2;
with the provisos that:
at least one of m and n is other than 2; and
when X is NR$^5$, then n is 1 or 2;
or a pharmaceutically acceptable salt thereof.

In still another embodiment, the invention is directed to pharmaceutical compositions comprising:
a pharmaceutically acceptable carrier; and
an effective amount of a compound of the invention, preferably a compound of formula Ia:

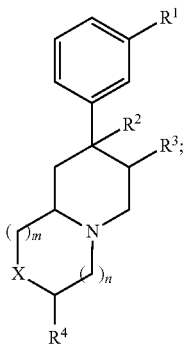

wherein:
R$^1$ is —OH, —CH$_2$OH, —C(=O)OR$^6$, —C(=O)NR$^6$R$^7$, or —NR$^6$R$^7$;
R$^2$ and R$^3$ are each independently alkyl or alkenyl;
R$^4$ is H, alkyl, cycloalkyl, cycloalkylalkyl, aryl, heteroaryl, aralkyl, alkylaralkyl, or heteroarylalkyl;
X is CH$_2$ or NR$^5$;
R$^5$ is H, alkyl, cycloalkyl, cycloalkylalkyl, aryl, heteroaryl, aralkyl, alkylaralkyl, heteroarylalkyl, —C(=O)OR$^{8a}$, —S(=O)$_2$R$^{8a}$, —C(=O)R$^{8b}$, or —C(=O)NR$^{8b}$R$^{8c}$;
R$^6$ is H, alkyl, cycloalkyl, alkylcycloalkyl, or aralkyl;
R$^7$ is H, alkyl, aralkyl, or aryl;
R$^{8a}$ is alkyl, cycloalkyl, cycloalkylalkyl, heteroaryl, heteroarylalkyl, aralkyl, or aryl;
R$^{8b}$ and R$^{8c}$ are each independently H, alkyl, cycloalkyl, cycloalkylalkyl, heteroaryl, heteroarylalkyl, aralkyl, or aryl; or R$^{8b}$ and R$^{8c}$ taken together with the nitrogen atom to which they are connected form a 4- to 8-membered heterocycloalkyl ring;
m is 1 or 2; and
n is 0, 1, or 2;
with the provisos that:
at least one of m and n is other than 2; and
when X is NR$^5$, then n is 1 or 2;
or a pharmaceutically acceptable salt thereof.

In another embodiment, the invention is directed to pharmaceutical compositions comprising:
a pharmaceutically acceptable carrier; and
an effective amount of a compound of the invention, preferably a compound of formula IIIa:

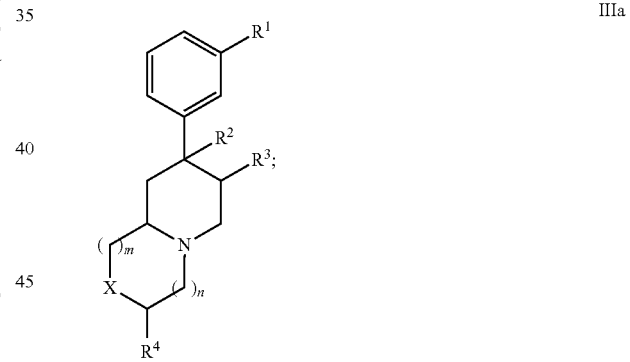

wherein:
R$^1$ is —OH, —CH$_2$OH, —C(=O)OR$^6$, —C(=O)NR$^6$R$^7$, or —NR$^6$R$^7$;
R$^2$ and R$^3$ are each independently alkyl or alkenyl;
R$^4$ is H, alkyl, cycloalkyl, cycloalkylalkyl, aryl, heteroaryl, aralkyl, alkylaralkyl, or heteroarylalkyl;
X is CH$_2$ or NR$^5$;
R$^5$ is H, alkyl, cycloalkyl, cycloalkylalkyl, aryl, heteroaryl, aralkyl, alkylaralkyl, heteroarylalkyl, —C(=O)OR$^{8a}$, —S(=O)$_2$R$^{8a}$, —C(=O)R$^{8b}$, or —C(=O)NR$^{8b}$R$^{8c}$;
R$^6$ is H, alkyl, cycloalkyl, alkylcycloalkyl, or aralkyl;
R$^7$ is H, alkyl, aralkyl, or aryl;
R$^{8a}$ is alkyl, cycloalkyl, cycloalkylalkyl, heteroaryl, heteroarylalkyl, aralkyl, or aryl;
R$^{8b}$ and R$^{8c}$ are each independently H, alkyl, cycloalkyl, cycloalkylalkyl, heteroaryl, heteroarylalkyl, aralkyl, or aryl; or R$^{8b}$ and R$^{8c}$ taken together with the nitrogen atom to which they are connected form a 4- to 8-membered heterocycloalkyl ring;

m is 1 or 2; and n is 0, 1, or 2;

with the provisos that:
    at least one of m and n is other than 2; and
    when X is NR$^5$, then n is 1 or 2;

or a pharmaceutically acceptable salt thereof.

In yet another embodiment, the invention is directed to methods for binding opioid receptors, in a patient in need thereof, comprising the step of:

administering to the patient a composition comprising an effective amount of a compound of the invention, preferably a compound of formula Ia:

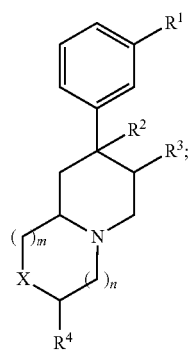

wherein:
R$^1$ is —OH, —CH$_2$OH, —C(=O)OR$^6$, —C(=O)NR$^6$R$^7$, or —NR$^6$R$^7$;

R$^2$ and R$^3$ are each independently alkyl or alkenyl;

R$^4$ is H, alkyl, cycloalkyl, cycloalkylalkyl, aryl, heteroaryl, aralkyl, alkylaralkyl, or heteroarylalkyl;

X is CH$_2$ or NR$^5$;

R$^5$ is H, alkyl, cycloalkyl, cycloalkylalkyl, aryl, heteroaryl, aralkyl, alkylaralkyl, heteroarylalkyl, —C(=O)OR$^{8a}$, —S(=O)$_2$R$^{8a}$, —C(=O)R$^{8b}$, or —C(=O)NR$^{8b}$R$^{8c}$;

R$^6$ is H, alkyl, cycloalkyl, alkylcycloalkyl, or aralkyl;

R$^7$ is H, alkyl, aralkyl, or aryl;

R$^{8a}$ is alkyl, cycloalkyl, cycloalkylalkyl, heteroaryl, heteroarylalkyl, aralkyl, or aryl;

R$^{8b}$ and R$^{8c}$ are each independently H, alkyl, cycloalkyl, cycloalkylalkyl, heteroaryl, heteroarylalkyl, aralkyl, or aryl; or R$^{8b}$ and R$^{8c}$ taken together with the nitrogen atom to which they are connected form a 4- to 8-membered heterocycloalkyl ring;

m is 1 or 2; and n is 0, 1, or 2;

with the provisos that:
    at least one of m and n is other than 2; and
    when X is NR$^5$, then n is 1 or 2;

or a pharmaceutically acceptable salt thereof.

In other embodiments, the invention is directed to methods of treating gastrointestinal dysfunction, comprising the step of:

administering to a patient in need thereof, a composition comprising an effective amount of a compound of the invention, preferably a compound of formula Ia:

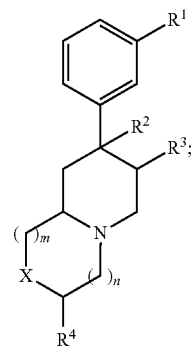

wherein:
R$^1$ is —OH, —CH$_2$OH, —C(=O)OR$^6$, —C(=O)NR$^6$R$^7$, or —NR$^6$R$^7$;

R$^2$ and R$^3$ are each independently alkyl or alkenyl;

R$^4$ is H, alkyl, cycloalkyl, cycloalkylalkyl, aryl, heteroaryl, aralkyl, alkylaralkyl, or heteroarylalkyl;

X is CH$_2$ or NR$^5$;

R$^5$ is H, alkyl, cycloalkyl, cycloalkylalkyl, aryl, heteroaryl, aralkyl, alkylaralkyl, heteroarylalkyl, —C(=O)OR$^{8a}$, —S(=O)$_2$R$^{8a}$, —C(=O)R$^{8b}$, or —C(=O)NR$^{8b}$R$^{8c}$;

R$^6$ is H, alkyl, cycloalkyl, alkylcycloalkyl, or aralkyl;

R$^7$ is H, alkyl, aralkyl, or aryl;

R$^{8a}$ is alkyl, cycloalkyl, cycloalkylalkyl, heteroaryl, heteroarylalkyl, aralkyl, or aryl;

R$^{8b}$ and R$^{8c}$ are each independently H, alkyl, cycloalkyl, cycloalkylalkyl, heteroaryl, heteroarylalkyl, aralkyl, or aryl; or R$^{8b}$ and R$^{8c}$ taken together with the nitrogen atom to which they are connected form a 4- to 8-membered heterocycloalkyl ring;

m is 1 or 2; and n is 0, 1, or 2;

with the provisos that:
    at least one of m and n is other than 2; and
    when X is NR$^5$, then n is 1 or 2;

or a pharmaceutically acceptable salt thereof.

In yet other embodiments, the invention is directed to methods of treating ileus, comprising the step of:

administering to a patient in need thereof, a composition comprising an effective amount of a compound of the invention, preferably a compound of formula Ia:

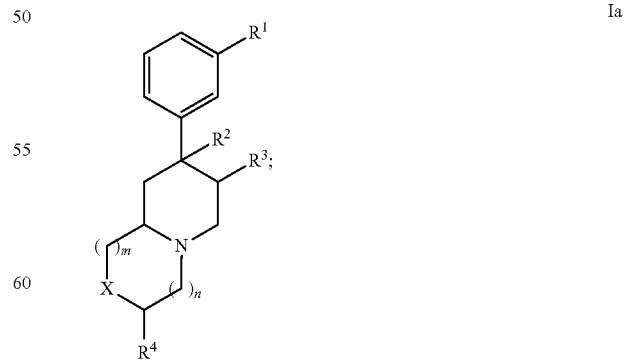

wherein:
R$^1$ is —OH, —CH$_2$OH, —C(=O)OR$^6$, —C(=O)NR$^6$R$^7$, or —NR$^6$R$^7$;

$R^2$ and $R^3$ are each independently alkyl or alkenyl;

$R^4$ is H, alkyl, cycloalkyl, cycloalkylalkyl, aryl, heteroaryl, aralkyl, alkylaralkyl, or heteroarylalkyl;

X is $CH_2$ or $NR^5$;

$R^5$ is H, alkyl, cycloalkyl, cycloalkylalkyl, aryl, heteroaryl, aralkyl, alkylaralkyl, heteroarylalkyl, —C(=O)$OR^{8a}$, —S(=O)$_2R^{8a}$, —C(=O)$R^{8b}$, or —C(=O)$NR^{8b}R^{8c}$;

$R^6$ is H, alkyl, cycloalkyl, alkylcycloalkyl, or aralkyl;

$R^7$ is H, alkyl, aralkyl, or aryl;

$R^{8a}$ is alkyl, cycloalkyl, cycloalkylalkyl, heteroaryl, heteroarylalkyl, aralkyl, or aryl;

$R^{8b}$ and $R^{8c}$ are each independently H, alkyl, cycloalkyl, cycloalkylalkyl, heteroaryl, heteroarylalkyl, aralkyl, or aryl; or $R^{8b}$ and $R^{8c}$ taken together with the nitrogen atom to which they are connected form a 4- to 8-membered heterocycloalkyl ring;

m is 1 or 2; and n is 0, 1, or 2;

with the provisos that:
  at least one of m and n is other than 2; and
  when X is $NR^5$, then n is 1 or 2;

or a pharmaceutically acceptable salt thereof.

In still other embodiments, the invention is directed to methods of treating obesity, comprising the step of:

administering to a patient in need thereof, a composition comprising an effective amount of a compound of the invention, preferably a compound of formula Ia:

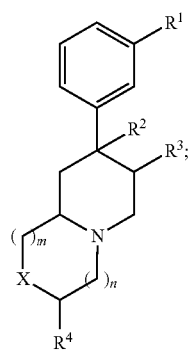

Ia wherein:

$R^1$ is —OH, —$CH_2OH$, —C(=O)$OR^6$, —C(=O)$NR^6R^7$, or —$NR^6R^7$;

$R^2$ and $R^3$ are each independently alkyl or alkenyl;

$R^4$ is H, alkyl, cycloalkyl, cycloalkylalkyl, aryl, heteroaryl, aralkyl, alkylaralkyl, or heteroarylalkyl;

X is $CH_2$ or $NR^5$;

$R^5$ is H, alkyl, cycloalkyl, cycloalkylalkyl, aryl, heteroaryl, aralkyl, alkylaralkyl, heteroarylalkyl, —C(=O)$OR^{8a}$, —S(=O)$_2R^{8a}$, —C(=O)$R^{8b}$, or —C(=O)$NR^{8b}R^{8c}$;

$R^6$ is H, alkyl, cycloalkyl, alkylcycloalkyl, or aralkyl;

$R^7$ is H, alkyl, aralkyl, or aryl;

$R^{8a}$ is alkyl, cycloalkyl, cycloalkylalkyl, heteroaryl, heteroarylalkyl, aralkyl, or aryl;

$R^{8b}$ and $R^{8c}$ are each independently H, alkyl, cycloalkyl, cycloalkylalkyl, heteroaryl, heteroarylalkyl, aralkyl, or aryl; or $R^{8b}$ and $R^{8c}$ taken together with the nitrogen atom to which they are connected form a 4- to 8-membered heterocycloalkyl ring;

m is 1 or 2; and n is 0, 1, or 2;

with the provisos that:
  at least one of m and n is other than 2; and
  when X is $NR^5$, then n is 1 or 2;

or a pharmaceutically acceptable salt thereof.

In another embodiment, the invention is directed to methods of treating a side effect associated with an opioid, comprising the step of:

administering to a patient in need thereof, a composition comprising an effective amount of a compound of the invention, preferably a compound of formula Ia:

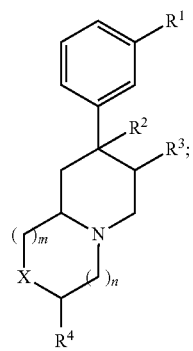

Ia wherein:

$R^1$ is —OH, —$CH_2OH$, —C(=O)$OR^6$, —C(=O)$NR^6R^7$, or —$NR^6R^7$;

$R^2$ and $R^3$ are each independently alkyl or alkenyl;

$R^4$ is H, alkyl, cycloalkyl, cycloalkylalkyl, aryl, heteroaryl, aralkyl, alkylaralkyl, or heteroarylalkyl;

X is $CH_2$ or $NR^5$;

$R^5$ is H, alkyl, cycloalkyl, cycloalkylalkyl, aryl, heteroaryl, aralkyl, alkylaralkyl, heteroarylalkyl, —C(=O)$OR^{8a}$, —S(=O)$_2R^{8a}$, —C(=O)$R^{8b}$, or —C(=O)$NR^{8b}R^{8c}$;

$R^6$ is H, alkyl, cycloalkyl, alkylcycloalkyl, or aralkyl;

$R^7$ is H, alkyl, aralkyl, or aryl;

$R^{8a}$ is alkyl, cycloalkyl, cycloalkylalkyl, heteroaryl, heteroarylalkyl, aralkyl, or aryl;

$R^{8b}$ and $R^{8c}$ are each independently H, alkyl, cycloalkyl, cycloalkylalkyl, heteroaryl, heteroarylalkyl, aralkyl, or aryl; or $R^{8b}$ and $R^{8c}$ taken together with the nitrogen atom to which they are connected form a 4- to 8-membered heterocycloalkyl ring;

m is 1 or 2; and n is 0, 1, or 2;

with the provisos that:
  at least one of m and n is other than 2; and
  when X is $NR^5$, then n is 1 or 2;

or a pharmaceutically acceptable salt thereof.

In yet another embodiment, the invention is directed to methods of treating pain, comprising the step of administering to a patient in need thereof, a composition, comprising an effective amount of an opioid, and an effective amount of a compound of the invention, preferably a compound of formula Ia:

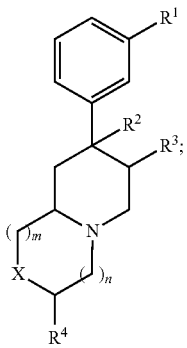

Ia wherein:
R¹ is —OH, —CH₂OH, —C(=O)OR⁶, —C(=O)NR⁶R⁷, or —NR⁶R⁷;
R² and R³ are each independently alkyl or alkenyl;
R⁴ is H, alkyl, cycloalkyl, cycloalkylalkyl, aryl, heteroaryl, aralkyl, alkylaralkyl, or heteroarylalkyl;
X is CH₂ or NR⁵;
R⁵ is H, alkyl, cycloalkyl, cycloalkylalkyl, aryl, heteroaryl, aralkyl, alkylaralkyl, heteroarylalkyl, —C(=O)OR$^{8a}$, —S(=O)₂R$^{8a}$, —C(=O)R$^{8b}$, or —C(=O)NR$^{8b}$R$^{8c}$;
R⁶ is H, alkyl, cycloalkyl, alkylcycloalkyl, or aralkyl;
R⁷ is H, alkyl, aralkyl, or aryl;
R$^{8a}$ is alkyl, cycloalkyl, cycloalkylalkyl, heteroaryl, heteroarylalkyl, aralkyl, or aryl;
R$^{8b}$ and R$^{8c}$ are each independently H, alkyl, cycloalkyl, cycloalkylalkyl, heteroaryl, heteroarylalkyl, aralkyl, or aryl; or R$^{8b}$ and R$^{8c}$ taken together with the nitrogen atom to which they are connected form a 4- to 8-membered heterocycloalkyl ring;
m is 1 or 2; and
n is 0, 1, or 2;
with the provisos that:
at least one of m and n is other than 2; and
when X is NR⁵, then n is 1 or 2;
or a pharmaceutically acceptable salt thereof.

In yet another embodiment, the invention is directed to methods for binding opioid receptors, in a patient in need thereof, comprising the step of administering to the patient a composition comprising an effective amount of a compound of the invention, preferably a compound of formula IIIa:

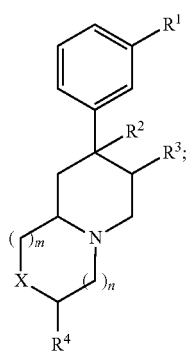

IIIa wherein:
R¹ is —OH, —CH₂OH, —C(=O)OR⁶, —C(=O)NR⁶R⁷, or —NR⁶R⁷;
R² and R³ are each independently alkyl or alkenyl;
R⁴ is H, alkyl, cycloalkyl, cycloalkylalkyl, aryl, heteroaryl, aralkyl, alkylaralkyl, or heteroarylalkyl;
X is CH₂ or NR⁵;
R⁵ is H, alkyl, cycloalkyl, cycloalkylalkyl, aryl, heteroaryl, aralkyl, alkylaralkyl, heteroarylalkyl, heterocycloalkylalkyl, —C(=O)OR$^{8a}$, —S(=O)₂R$^{8a}$, —C(=O)R$^{8b}$, or —C(=O)NR$^{8b}$R$^{8c}$;
R⁶ is H, alkyl, cycloalkyl, alkylcycloalkyl, or aralkyl;
R⁷ is H, alkyl, aralkyl, or aryl;
R$^{8a}$ is alkyl, cycloalkyl, cycloalkylalkyl, heteroaryl, heteroarylalkyl, aralkyl, or aryl;
R$^{8b}$ and R$^{8c}$ are each independently H, alkyl, cycloalkyl, cycloalkylalkyl, heteroaryl, heterocycloalkyl, heterocycloalkylalkyl, heteroarylalkyl, aralkyl, or aryl; or R$^{8b}$ and R$^{8c}$ taken together with the nitrogen atom to which they are connected form a 4- to 8-membered heterocycloalkyl ring;
m is 1 or 2; and
n is 0, 1, or 2;
with the provisos that:
at least one of m and n is other than 2; and
when X is NR⁵, then n is 1 or 2;
or a pharmaceutically acceptable salt thereof.

In other embodiments, the invention is directed to methods of treating gastrointestinal dysfunction, comprising the step of administering to a patient in need thereof, a composition comprising an effective amount of a compound of the invention, preferably a compound of formula IIIa.

In yet other embodiments, the invention is directed to methods of treating ileus, comprising the step of administering to a patient in need thereof, a composition comprising an effective amount of a compound of the invention, preferably a compound of formula IIIa.

In still other embodiments, the invention is directed to methods of treating obesity, comprising the step of administering to a patient in need thereof, a composition comprising an effective amount of a compound of the invention, preferably a compound of formula IIIa.

In another embodiment, the invention is directed to methods of treating a side effect associated with an opioid, comprising the step of administering to a patient in need thereof, a composition comprising an effective amount of a compound of the invention, preferably a compound of formula IIIa.

In yet another embodiment, the invention is directed to methods of treating pain, comprising the step of administering to a patient in need thereof, a composition, comprising an effective amount of an opioid; and an effective amount of a compound of the invention, preferably a compound of formula IIIa.

DETAILED DESCRIPTION OF ILLUSTRATIVE EMBODIMENTS

The present invention is generally directed to quinolizidine and octahydro-pyridopyrazine compounds, pharmaceutical compositions containing these compounds, and methods of their pharmaceutical use.

As employed above and throughout the disclosure, the following terms, unless otherwise indicated, shall be understood to have the following meanings.

As used herein, the term "alkyl" refers to an optionally substituted, saturated, straight or branched hydrocarbon having from about 1 to about 20 carbon atoms (and all combinations and subcombinations of ranges and specific numbers of carbon atoms therein), with from about 1 to about 8 carbon atoms, herein referred to as "lower alkyl," being preferred.

Alkyl groups include, but are not limited to, methyl, ethyl, n-propyl, isopropyl, n-butyl, isobutyl, sec-butyl, t-butyl, n-pentyl, isopentyl, neopentyl, n-hexyl, isohexyl, 3-methylpentyl, 2,2-dimethylbutyl, and 2,3-dimethylbutyl.

As used herein, the term "cycloalkyl" refers to an optionally substituted alkyl group having one or more rings in their structures and having from about 3 to about 20 carbon atoms (and all combinations and subcombinations of ranges and specific numbers of carbon atoms therein), with from about 3 to about 10 carbon atoms being preferred. Multi-ring structures may be bridged or fused ring structures. Groups include, but are not limited to, cyclopropyl, cyclobutyl, cyclopentyl, cyclohexyl, cyclooctyl, 2-[4-isopropyl-1-methyl-7-oxa-bicyclo[2.2.1]heptanyl], 2-[1,2,3,4-tetrahydro-naphthalenyl], and adamantyl.

As used herein, the term "cycloalkylalkyl" refers to an optionally substituted ring system comprising an alkyl radical bearing a cycloalkyl substituent, and having from about 6 to about 50 carbon atoms (and all combinations and subcombinations of ranges and specific numbers of carbon atoms therein), with from about 6 to about 10 carbon atoms being preferred, wherein alkyl and cycloalkyl are as previously defined. Non-limiting examples include, for example, cyclopropylmethyl, cyclobutylethyl, cyclopentylpropyl, cyclohexylmethyl, 2-cyclooctyl-1-methylethyl, 2-[4-isopropyl-1-methyl-7-oxa-bicyclo[2.2.1]heptanyl]methyl, 2-[1,2,3,4-tetrahydro-naphthalenyl]ethyl, and adamantylpropyl.

As used herein, the term "alkylcycloalkyl" refers to an optionally substituted ring system comprising a cycloalkyl group having one or more alkyl substituents, wherein cycloalkyl and alkyl are each as previously defined. Exemplary alkylcycloalkyl groups include 2-methylcyclohexyl, 3,3-dimethylcyclopentyl, trans-2,3-dimethylcyclooctyl, and 4-methyldecahydronaphthalenyl.

As used herein, the term "heterocycloalkyl" refers to an optionally substituted, mono-, di-, tri-, or other multicyclic aliphatic ring system that includes at least one, and preferably from 1 to about 4 sulfur, oxygen, or nitrogen heteroatom ring members. Heterocycloalkyl groups can have from about 3 to about 20 carbon atoms (and all combinations and subcombinations of ranges and specific numbers of carbon atoms therein), with from about 4 to about 10 carbons being preferred. In more preferred embodiments, the heterocycloalkyl groups have from about 4 to about 8 ring members, wherein 1 or 2 members are sulfur, oxygen, or nitrogen and the remaining members are carbon atoms. The heterocycloalkyl group may be unsaturated, and may also be fused to aromatic rings. Examples of heterocycloalkyl groups include, for example, tetrahydrofuranyl, tetrahydrothienyl, piperidinyl, pyrrolidinyl, isoxazolidinyl, isothiazolidinyl, pyrazolidinyl, oxazolidinyl, thiazolidinyl, piperazinyl, morpholinyl, piperadinyl, decahydroquinolyl, octahydrochromenyl, octahydro-cyclopenta[c]pyranyl, 1,2,3,4,-tetrahydroquinolyl, octahydro-[2]pyridinyl, decahydro-cycloocta[c]furanyl, and imidazolidinyl.

As used herein, the term "alkenyl" refers to an optionally substituted alkyl group having from about 2 to about 10 carbon atoms and one or more double bonds (and all combinations and subcombinations of ranges and specific numbers of carbon atoms therein), wherein alkyl is as previously defined.

As used herein, the term "alkynyl" refers to an optionally substituted alkyl group having from about 2 to about 10 carbon atoms and one or more triple bonds (and all combinations and subcombinations of ranges and specific numbers of carbon atoms therein), wherein alkyl is as previously defined.

As used herein, the term "aryl" refers to an optionally substituted, mono-, di-, tri-, or other multicyclic aromatic ring system having from about 5 to about 50 carbon atoms (and all combinations and subcombinations of ranges and specific numbers of carbon atoms therein), with from about 6 to about 10 carbons being preferred. Non-limiting examples include, for example, phenyl, naphthyl, anthracenyl, and phenanthrenyl.

As used herein, the term "aralkyl" refers to an optionally substituted ring system comprising an alkyl radical bearing an aryl substituent and having from about 6 to about 50 carbon atoms (and all combinations and subcombinations of ranges and specific numbers of carbon atoms therein), with from about 6 to about 10 carbon atoms being preferred. Non-limiting examples include, for example, benzyl, diphenylmethyl, triphenylmethyl, phenylethyl, and diphenylethyl.

As used herein, the term "alkylaralkyl" refers to an optionally substituted ring system comprising an alkyl radical bearing an aralkyl substituent and having from about 6 to about 50 carbon atoms (and all combinations and subcombinations of ranges and specific numbers of carbon atoms therein), with from about 6 to about 10 carbon atoms being preferred, wherein alkyl and aralkyl are as previously defined. Non-limiting examples include, for example, tolylmethyl, bis(isopropylphenyl)methyl, 1-tolyl-1-ethylphenylmethyl, tert-butylphenylethyl, and ortho-methyl-para-butylphenylethyl.

As used herein, the term "alkoxyl" refers to an optionally substituted alkyl-O— group wherein alkyl is as previously defined. In some preferred embodiments, the alkyl moieties of the alkoxy groups have from about 1 to about 4 carbon atoms. Exemplary alkoxy groups include, but are not limited to, methoxy, ethoxy, n-propoxy, i-propoxy, n-butoxy, and heptoxy.

As used herein, the term "aryloxyl" refers to an optionally substituted aryl-O— group wherein aryl is as previously defined. Exemplary aryloxy groups include, but are not limited to, phenoxyl and naphthoxyl.

As used herein, the term "aralkoxyl" refers to an optionally substituted aralkyl-O— group wherein aralkyl is as previously defined. Exemplary aralkoxy groups include, but are not limited to, benzyloxy, 1-phenylethoxy, 2-phenylethoxy, and 3-naphthylheptoxy.

As used herein, the term "halo" refers to a fluoro, chloro, bromo, or iodo moiety attached to a compound of the invention.

As used herein, the term "heteroaryl" refers to an optionally substituted, mono-, di-, tri- or other multicyclic aromatic ring system that includes at least one, and preferably from 1 to about 4 sulfur, oxygen, or nitrogen heteroatom ring members. Heteroaryl groups can have, for example, from about 3 to about 50 carbon atoms (and all combinations and subcombinations of ranges and specific numbers of carbon atoms therein), with from about 4 to about 10 carbons being preferred. Non-limiting examples of heteroaryl groups include, for example, pyrryl, furyl, pyridyl, 1,2,4-thiadiazolyl, pyrimidyl, thienyl, isothiazolyl, imidazolyl, tetrazolyl, pyrazinyl, pyrimidyl, quinolyl, isoquinolyl, thiophenyl, benzothienyl, isobenzofuryl, pyrazolyl, indolyl, purinyl, carbazolyl, benzimidazolyl, and isoxazolyl. Heteroaryl may be optionally attached via a carbon or a heteroatom to the rest of the molecule.

As used herein, the term "heteroarylalkyl" refers to an optionally substituted ring system comprising an alkyl radical bearing a heteroaryl substituent, having from about 2 to about 50 carbon atoms (and all combinations and subcombinations of ranges and specific numbers of carbon atoms therein), with from about 6 to about 25 carbon atoms being preferred. Non-limiting examples include 2-(1H-pyrrol-3-yl)ethyl, 3-pyridylmethyl, 5-(2H-tetrazolyl)methyl, and 3-(pyrimidin-2-yl)-2-methylcyclopentanyl.

As used herein, the term "spiroalkyl" refers to an optionally substituted alkylene diradical, both ends of which are bonded to the same carbon atom of the parent group to form a spirocyclic group. The spirocyclic group, as herein defined, has 3 to 20 ring atoms, preferably with 3 to 10 ring atoms. Exemplary spiroalkyl groups taken together with its parent group include, but are not limited to, 1-(1-methyl-cyclopropyl)-propan-2-one, 2-(1-phenoxy-cyclopropyl)-ethylamine, and 1-methyl-spiro[4.7]dodecane.

Typically, substituted chemical moieties include one or more substituents that replace hydrogen. Exemplary substituents include, for example, halo (e.g., F, Cl, Br, I), alkyl, cycloalkyl, alkylcycloalkyl, alkenyl, alkynyl, aralkyl, aryl, heteroaryl, heteroarylalkyl, spiroalkyl, heterocycloalkyl, hydroxyl (—OH), alkoxyl, aryloxyl, aralkoxyl, nitro (—NO$_2$), cyano (—CN), amino (—NH$_2$), N-substituted amino (—NHR"), N,N-disubstituted amino (—N(R")R"), carboxyl (—COOH), —C(=O)R", —OR", —C(=O)OR", —C(=O)NHSO$_2$R", —NHC(=O)R", aminocarbonyl (—C(=O)NH$_2$), N-substituted aminocarbonyl (—C(=O)NHR"), N,N-disubstituted aminocarbonyl (—C(=O)N(R")R"), thiolato (SR"), sulfonic acid and its esters (—SO$_3$R"), phosphonic acid and its mono-ester (—P(=O)(OR")(OH) and di-esters (—P(=O)(OR")(OR"), —S(=O)$_2$R", —S(=O)$_2$NH$_2$, —S(=O)$_2$NHR", —S(=O)$_2$NR"R", —SO$_2$NHC(=O)R", —NHS(=O)$_2$R", —NR"S(=O)$_2$R", —CF$_3$, —CF$_2$CF$_3$, —NHC(=O)NHR", —NHC(=O)NR"R", —NR"C(=O)NHR", —NR"C(=O)NR"R", —NR"C(=O)R" and the like. Aryl substituents may also include (CH$_2$)$_u$SO$_2$NR"(CH$_2$)$_v$ and (CH$_2$)$_u$CO$_2$NR"(CH$_2$)$_v$, where u and v are, independently, 0 to 3, where the methylene units are attached in a 1,2 arrangement yielding substituted aryls of the type:

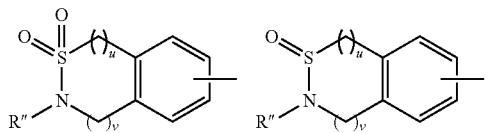

In relation to the aforementioned substituents, each moiety R" can be, independently, any of H, alkyl, cycloalkyl, alkenyl, aryl, aralkyl, heteroaryl, or heterocycloalkyl, or when (R" (R")) is attached to a nitrogen atom, R" and R" can be taken together with the nitrogen atom to which they are attached to form a 4- to 8-membered nitrogen heterocycle, wherein the heterocycloalkyl ring is optionally interrupted by one or more additional —O—, —S—, —SO, —SO$_2$—, —NH—, —N(alkyl)-, or —N(aryl)-groups, for example.

As used herein, the term "antagonist" refers to a compound that binds to a receptor to form a complex that preferably does not elicit any response, in the same manner as an unoccupied receptor, and does not alter the equilibrium between inactive and active receptor.

As used herein, the term "prodrug" refers to compounds that may serve to maximize the amount of active species that reaches the desired site of reaction that are themselves typically inactive or minimally active for the activity desired, but through biotransformation are converted into biologically active metabolites.

As used herein, the term "stereoisomers" refers to compounds that have identical chemical constitution, but differ as regards the arrangement of the atoms or groups in space.

As used herein, the term "partial stereoisomers" refers to stereoisomers having two or more chiral centers wherein at least one of the chiral centers has defined stereochemistry (i.e., R or S) and at least one has undefined stereochemistry (i.e., R or S). When the term "partial stereoisomers thereof" is used herein, it refers to any compound within the described genus whose configuration at chiral centers with defined stereochemistry centers is maintained and the configuration of each undefined chiral center is independently selected from R or S. For example, if a stereoisomer has three chiral centers and the stereochemical configuration of the first center is defined as having "S" stereochemistry, the term "or partial stereoisomer thereof" refers to stereoisomers having SRR, SRS, SSR, or SSS configurations at the three chiral centers, and mixtures thereof.

As used herein, the term "optically enriched" denotes the presence of one or more non-racemic stereoisomeric centers in a molecule, wherein the configuration of at least one stereoisomeric center has a predominance of one stereoisomeric configuration (R or S). For example, one stereoisomeric center in a molecule, typically a carbon atom, may have greater than 50% of its attached atoms spatially arranged in the (R) configuration. Alternatively, more than 50% may be spatially arranged in the (S) configuration. A predominance of one stereoisomeric configuration (R or S) occurring at one or more centers in a given molecule is considered non-racemic within the definition herein provided. For example, if a compound has three stereoisomeric centers and at least one of the stereoisomeric centers has greater than 50% of its attached atoms spatially arranged in the (R) configuration (or the (S) configuration), the molecule is non-racemic. In compounds having more than one stereoisomeric center, all stereoisomers possible from any combination of (R) or (S) stereoisomeric center configurations, including those combinations that are optically pure at each stereoisomeric center are within the ambit of the term "non-racemic stereoisomer", so long as at least one stereoisomeric center has greater than 50% of its attached atoms spatially arranged in either the (R) configuration or the (S) configuration. More preferably the molecule, or its stereoisomeric center, is substantially optically enriched, and even more preferably is substantially enantiomerically pure.

As used herein, the term "substantially optically enriched", when referring to a stereoisomer or stereoisomeric center, denotes that at least about 60%, preferably about 70%, more preferably about 80%, still more preferably about 90% of one stereoisomer or one stereoisomeric center configuration predominates in the mixture, with at least about 95% of one stereoisomer or one stereoisomeric center configuration being even more preferred. In some preferred embodiments, the compound is "substantially enantiomerically pure", that is, at least about 97.5%, more preferably about 99%, even more preferably about 99.5% of one stereoisomeric configuration predominates.

In some compounds, several stereoisomeric centers may be present. The presence of multiple stereoisomeric centers in a single structure indicates that multiple (R)/(S) racemic pairs of stereoisomers may be present, but that each pair of stereoisomers is diastereomeric relative to the other pair. As such, the first pair of enantiomers having, for example, two chiral centers may have the configurations, for example, (R, R) and (S, S). The second pair then have configurations, for example, (R, S) and (S, R).

As used herein, the term "N-oxide" refers to compounds wherein the basic nitrogen atom of either a heteroaromatic ring or tertiary amine is oxidized to give a quaternary nitrogen bearing a positive formal charge and an attached oxygen atom bearing a negative formal charge.

As used herein, the term "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. These physiologically acceptable salts are prepared by methods known in the art, e.g., by dissolving the free amine bases with an excess of the acid in aqueous alcohol, or neutralizing a free carboxylic acid with an alkali metal base such as a hydroxide, or with an amine.

Compounds described herein throughout may exist in alternate forms and such alternate forms are intended to be included within the scope of the compounds described and claimed in the present application. Accordingly, reference herein to compounds of formula I is intended to include reference to these alternate forms. For example, many amino-containing compounds can be used or prepared as an acid addition salt. Often such salts improve isolation and handling properties of the compound. For example, depending on the reagents, reaction conditions, and the like, compounds as described herein can be used or prepared, for example, as their hydrochloride or tosylate salts. Alternate forms of the compounds described herein also include, for example, isomorphic crystalline forms, all chiral and racemic forms, including stereoisomeric and partial stereoisomeric forms, N-oxides, hydrates, solvates, and acid salt hydrates.

Certain acidic or basic compounds of the present invention may exist as zwitterions. All forms of the compounds, including free acid, free base, and zwitterions, are contemplated to be within the scope of the present invention. It is well known in the art that compounds containing both basic nitrogen atom and acidic groups often exist in equilibrium with their zwitterionic forms. Thus, any of the compounds described herein throughout that contain, for example, both basic nitrogen and acidic groups, also include reference to their corresponding zwitterions.

As used herein, the term "effective amount" refers to an amount of a compound as described herein that may be therapeutically effective to inhibit, prevent, or treat the symptoms of particular disease, disorder, or side effect. Such diseases, disorders, and side effects include, but are not limited to, those pathological conditions associated with the administration of opioids (for example, in connection with the treatment and/or prevention of pain), wherein the treatment or prevention comprises, for example, inhibiting the activity thereof by contacting cells, tissues, or receptors with compounds of the present invention. Thus, for example, the term "effective amount," when used in connection with opioids, for example, for the treatment of pain, refers to the treatment and/or prevention of the painful condition. The term "effective amount," when used in connection with opioid antagonist compounds, refers to the treatment and/or prevention of side effects typically associated with opioids including, for example, such side effects as constipation, nausea, and/or vomiting, as well as other side effects, discussed in further detail below. The term "effective amount," when used in connection with compounds active against gastrointestinal dysfunction, refers to the treatment and/or prevention of symptoms, diseases, disorders, and conditions typically associated with gastrointestinal dysfunction. The term "effective amount," when used in connection with anti-ileus compounds, refers to the treatment and/or prevention of symptoms, diseases, disorders, and conditions typically associated with ileus. The term "effective amount," when used in connection with compounds effective against obesity, refers to the treatment and/or prevention of the obese condition.

As used herein, the term "pharmaceutically acceptable" refers to those compounds, materials, compositions, and/or dosage forms that are, within the scope of sound medical judgment, suitable for contact with the tissues of human beings and animals without excessive toxicity, irritation, allergic response, or other problems or complications commensurate with a reasonable benefit/risk ratio. The term specifically encompasses veterinary uses.

As used herein, the expressions "in combination with," "combination therapy," and "combination products" refer, in certain embodiments, to the concurrent administration to a patient of opioids, an anesthetic agent (inhaled anesthetic, hypnotic, anxiolytic, neuromuscular blocker and opioid) and/or optional ingredients (antibiotics, antivirals, antifungals, anti-inflammatories, anesthetics, and mixtures thereof) and the compounds of the invention, preferably compounds of formula Ia. When administered in combination, each component may be administered at the same time or sequentially in any order at different points in time. Thus, each component may be administered separately but sufficiently closely in time so as to provide the desired therapeutic effect.

As used herein, the term "dosage unit" refers to physically discrete units suited as unitary dosages for the particular individual to be treated. Each unit may contain a predetermined quantity of active compound(s) calculated to produce the desired therapeutic effect(s) in association with the required pharmaceutical carrier. The specification for the dosage unit forms of the invention may be dictated by (a) the unique characteristics of the active compound(s) and the particular therapeutic effect(s) to be achieved, and (b) the limitations inherent in the art of compounding such active compound(s).

The term "treatment" as used herein includes preventative (e.g., prophylactic), curative or palliative treatment and "treating" as used herein also includes preventative, curative and palliative treatment.

As used herein, the term "pain" refers to the perception or condition of unpleasant sensory or emotional experience, associated with actual or potential tissue damage or described in terms of such damage. "Pain" includes, but is not limited to, two broad categories of pain: acute and chronic pain (Buschmann, H.; Christoph, T; Friderichs, E.; Maul, C.; Sundermann, B; eds.; *Analgesics*, Wiley-VCH, Verlag GMbH & Co. KgaA, Weinheim; 2002; Jain, K. K. "A Guide to Drug Evaluation for Chronic Pain"; *Emerging Drugs*, 5(2), 241-257 (2000)). Non-limiting examples of pain include nociceptive pain, inflammatory pain, visceral pain, somatic pain, neuropathic pain, AIDS pain, cancer pain, phantom pain, and psychogenic pain, and pain resulting from hyperalgesia, pain caused by rheumatoid arthritis, migraine, allodynia, and the like.

As used herein, the term "gastrointestinal dysfunction" refers collectively to maladies of the stomach, and small and large intestines. Non-limiting examples of gastrointestinal dysfunction include, for example, diarrhea, nausea, emesis, post-operative emesis, opioid-induced emesis, irritable bowel syndrome, opioid-bowel dysfunction, opioid induced constipation, post-operative ileus, opioid-induced ileus, colitis, decreased gastric motility, decreased gastric emptying, inhibition of small intestinal propulsion, inhibition of large intestinal propulsion, increased amplitude of non-propulsive segmental contractions, constriction of sphincter of Oddi, increased anal sphincter tone, impaired reflex relaxation with rectal distention, diminished gastric, biliary, pancreatic or intestinal secretions, increased absorption of water from bowel contents, gastro-esophageal reflux, gastroparesis, cramping, bloating, distension, abdominal or epigastric pain and discomfort, non-ulcerogenic dyspepsia, gastritis, constipation, or delayed absorption of orally administered medications or nutritive substances.

As used herein, the term "ileus" refers to the obstruction of the bowel or gut, especially the colon. See, e.g., *Dorland's Illustrated Medical Dictionary*, p. 816, 27th ed. (W.B. Saunders Company, Philadelphia 1988). Ileus should be distinguished from constipation, which refers to infrequent or difficulty in evacuating the feces. See, e.g., *Dorland's Illustrated Medical Dictionary*, p. 375, 27th ed. (W.B. Saunders Company, Philadelphia 1988). Ileus may be diagnosed by the disruption of normal coordinated movements of the gut, resulting in failure of the propulsion of intestinal contents. See, e.g., Resnick, J. *Am. J. of Gastroenterology* 1997, 92, 751 and Resnick, J., *Am. J. of Gastroenterology,* 1997, 92, 934. In some instances, particularly following surgery, including surgery of the abdomen, the bowel dysfunction may become quite severe, lasting for more than a week and affecting more than one portion of the GI tract. This condition is often referred to as post-surgical (or post-operative) paralytic ileus and most frequently occurs after laparotomy (see Livingston, E. H. and Passaro, E. D. Jr. *Digestive Diseases and Sciences* 1990, 35, 121). Similarly, post-partum ileus is a common problem for women in the period following childbirth, and is thought to be caused by similar fluctuations in natural opioid levels as a result of birthing stress.

As used herein, the term "patient" refers to animals, including mammals, preferably humans.

As used herein, the term "side effect" refers to a consequence other than the one(s) for which an agent or measure is used, as the adverse effects produced by a drug, especially on a tissue or organ system other than the one sought to be benefited by its administration. In the case, for example, of opioids, the term "side effect" may refer to such conditions as, for example, constipation, nausea, and/or vomiting.

When any variable occurs more than one time in any constituent or in any formula, its definition in each occurrence is independent of its definition at every other occurrence. Combinations of substituents and/or variables are permissible only if such combinations result in stable compounds.

It is believed the chemical formulas and names used herein correctly and accurately reflect the underlying chemical compounds. However, the nature and value of the present invention does not depend upon the theoretical correctness of these formulae, in whole or in part. Thus it is understood that the formulas used herein, as well as the chemical names attributed to the correspondingly indicated compounds, are not intended to limit the invention in any way, including restricting it to any specific tautomeric form or to any specific optical or geometric isomer, except where such stereochemistry is clearly defined.

In certain preferred embodiments, the compounds, pharmaceutical compositions and methods of the present invention may involve an opioid antagonist compound. The term "peripheral" designates that the compound acts primarily on physiological systems and components external to the central nervous system. In preferred form, the opioid antagonist compounds employed in the methods of the present invention exhibit high levels of activity with respect to peripheral tissue, such as, gastrointestinal tissue, while exhibiting reduced, and preferably substantially no, CNS activity. The phrase "substantially no CNS activity," as used herein, means that less than about 50% of the pharmacological activity of the compounds employed in the present methods is exhibited in the CNS, preferably less than about 25%, more preferably less than about 10%, even more preferably less than about 5% and most preferably 0% of the pharmacological activity of the compounds employed in the present methods is exhibited in the CNS.

Furthermore, it is preferred in certain embodiments of the invention that the opioid antagonist compound does not substantially cross the blood-brain barrier. The phrase "does not substantially cross," as used herein, means that less than about 20% by weight of the compound employed in the present methods crosses the blood-brain barrier, preferably less than about 15% by weight, more preferably less than about 10% by weight, even more preferably less than about 5% by weight and most preferably 0% by weight of the compound crosses the blood-brain barrier. Selected compounds can be evaluated for CNS penetration by determining plasma and brain levels following i.v. administration.

Accordingly, in one embodiment, the present invention provides compounds of formula I:

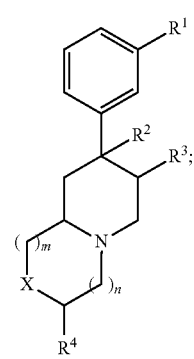

wherein:
R$^1$ is —OH, —OR$^a$, —CH$_2$OH, —C(=O)OR$^6$, —C(=O)NR$^6$R$^7$, or —NR$^6$R$^7$;
R$^2$ and R$^3$ are each independently alkyl or alkenyl;
R$^4$ is H, alkyl, cycloalkyl, cycloalkylalkyl, aryl, heteroaryl, aralkyl, alkylaralkyl, or heteroarylalkyl;
X is CH$_2$ or NR$^5$;
R$^5$ is H, alkyl, cycloalkyl, cycloalkylalkyl, aryl, heteroaryl, aralkyl, alkylaralkyl, heteroarylalkyl, —C(=O)OR$^{8a}$, —S(=O)$_2$R$^{8a}$, —C(=O)R$^{8b}$, or —C(=O)NR$^{8b}$R$^{8c}$;
R$^6$ is H, alkyl, cycloalkyl, alkylcycloalkyl, or aralkyl;
R$^7$ is H, alkyl, aralkyl, or aryl;

$R^{8a}$ is alkyl, cycloalkyl, cycloalkylalkyl, heteroaryl, heteroarylalkyl, aralkyl, or aryl;

$R^{8b}$ and $R^{8c}$ are each independently H, alkyl, cycloalkyl, cycloalkylalkyl, heteroaryl, heteroarylalkyl, aralkyl, or aryl; or $R^{8b}$ and $R^{8c}$ taken together with the nitrogen atom to which they are connected form a 4- to 8-membered heterocycloalkyl ring;

$R^a$ is a hydroxyl protecting group;

m is 1 or 2; and n is 0, 1, or 2;

with the provisos that:
  at least one of m and n is other than 2; and
  when X is $NR^5$, then n is 1 or 2;

or a pharmaceutically acceptable salt thereof.

In certain preferred embodiments, the compounds of formula I have the structure Ia:

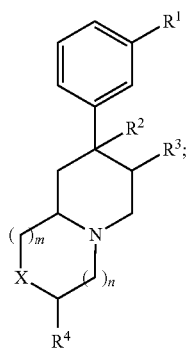

Ia wherein:

$R^1$ is —OH, —CH$_2$OH, —C(=O)OR$^6$, —C(=O)NR$^6$R$^7$, or —NR$^6$R$^7$;

$R^2$ and $R^3$ are each independently alkyl or alkenyl;

$R^4$ is H, alkyl, cycloalkyl, cycloalkylalkyl, aryl, heteroaryl, aralkyl, alkylaralkyl, or heteroarylalkyl;

X is CH$_2$ or NR$^5$;

$R^5$ is H, alkyl, cycloalkyl, cycloalkylalkyl, aryl, heteroaryl, aralkyl, alkylaralkyl, heteroarylalkyl, —C(=O)OR$^{8a}$, —S(=O)$_2$R$^{8a}$, —C(=O)R$^{8b}$, or —C(=O)NR$^{8b}$R$^{8c}$;

$R^6$ is H, alkyl, cycloalkyl, alkylcycloalkyl, or aralkyl;

$R^7$ is H, alkyl, aralkyl, or aryl;

$R^{8a}$ is alkyl, cycloalkyl, cycloalkylalkyl, heteroaryl, heteroarylalkyl, aralkyl, or aryl;

$R^{8b}$ and $R^{8c}$ are each independently H, alkyl, cycloalkyl, cycloalkylalkyl, heteroaryl, heteroarylalkyl, aralkyl, or aryl; or $R^{8b}$ and $R^{8c}$ taken together with the nitrogen atom to which they are connected form a 4- to 8-membered heterocycloalkyl ring;

m is 1 or 2; and n is 0, 1, or 2;

with the provisos that:
  at least one of m and n is other than 2; and
  when X is $NR^5$, then n is 1 or 2;

or a pharmaceutically acceptable salt thereof.

More preferably when compounds of formula I have the structure Ia, $R^1$ is —OH, —C(=O)OR$^6$, —C(=O)NR$^6$R$^7$, or —NR$^6$R$^7$, yet more preferably —OH, —C(=O)NR$^6$R$^7$, or —NR$^6$R$^7$, still more preferably —OH or —C(=O)NR$^6$R$^7$.

In certain preferred embodiments of compounds of formula I, $R^2$ and $R^3$ are each independently $C_1$-$C_6$alkyl or $C_2$-$C_6$alkenyl, more preferably $C_1$-$C_3$alkyl or $C_2$-$C_3$alkenyl, more preferably still $C_1$-$C_3$alkyl, yet more preferably $C_1$alkyl, still more preferably methyl.

In certain preferred embodiments of compounds of formula I, $R^4$ is H, alkyl, cycloalkyl, cycloalkylalkyl, aryl, heteroaryl, aralkyl, alkylaralkyl, or heteroarylalkyl, with H, alkyl, cycloalkyl, aryl, or aralkyl being more preferred. When $R^4$ is alkyl, it is preferably $C_1$-$C_6$alkyl, more preferably $C_1$-$C_3$alkyl, yet more preferably $C_1$alkyl, still more preferably methyl. When $R^4$ is cycloalkyl, it is preferably $C_3$-$C_{10}$cycloalkyl, more preferably $C_3$-$C_8$cycloalkyl, yet more preferably $C_3$-$C_6$cycloalkyl, still more preferably $C_5$-$C_6$cycloalkyl, still more preferably optionally substituted cyclopentyl or optionally substituted cyclohexyl. When $R^4$ is cycloalkylalkyl, it is preferably $C_3$-$C_{10}$cycloalkyl$C_1$-$C_6$alkyl, more preferably $C_3$-$C_8$cycloalkyl$C_1$-$C_3$alkyl, yet more preferably $C_3$-$C_6$cycloalkyl$C_1$-$C_3$alkyl, still more preferably $C_5$-$C_6$cycloalkyl$C_1$-$C_3$alkyl, still more preferably cyclopentyl$C_1$-$C_3$alkyl or cyclohexyl$C_1$-$C_3$alkyl, yet more preferably cyclopentyl$C_1$alkyl or cyclohexyl$C_1$alkyl, even more preferably optionally substituted cyclopentylmethyl or optionally substituted cyclohexylmethyl. When $R^4$ is aryl, it is preferably $C_6$-$C_{10}$aryl, more preferably $C_6$aryl, yet more preferably phenyl. When $R^4$ is heteroaryl, it is preferably $C_5$-$C_{10}$heteroaryl, more preferably $C_5$-$C_6$heteroaryl, still more preferably pyridinyl or thienyl. When $R^4$ is aralkyl, it is preferably $C_6$-$C_{10}$aryl$C_1$-$C_6$alkyl, more preferably $C_6$-$C_{10}$aryl$C_1$-$C_3$alkyl, yet more preferably $C_6$aryl$C_1$-$C_3$alkyl, still more preferably $C_6$aryl$C_1$alkyl, yet more preferably optionally substituted benzyl. When $R^4$ is alkylaralkyl, it is preferably $C_1$-$C_6$alkyl$C_6$-$C_{10}$aryl$C_1$-$C_6$alkyl, more preferably $C_1$-$C_4$alkyl$C_6$-$C_{10}$aryl$C_1$-$C_3$alkyl, yet more preferably $C_1$-$C_4$alkyl$C_6$aryl$C_1$-$C_3$alkyl, still more preferably $C_1$alkyl$C_6$aryl$C_1$alkyl, yet more preferably optionally substituted methylbenzyl. When $R^4$ is heteroarylalkyl, it is preferably $C_5$-$C_{10}$heteroaryl$C_1$-$C_6$alkyl, more preferably $C_5$-$C_{10}$heteroaryl$C_1$-$C_3$alkyl, yet more preferably $C_5$-$C_6$heteroaryl$C_1$-$C_3$alkyl, still more preferably $C_5$-$C_6$heteroaryl$C_1$alkyl. In certain preferred embodiments, $R^4$ is H.

In certain preferred embodiments of compounds of formula I, X is $NR^5$.

In certain preferred embodiments of compounds of formula I, $R^5$ is H, alkyl, aryl, cycloalkylalkyl, aralkyl, alkylaralkyl, heteroarylalkyl, —S(=O)$_2$R$^{8a}$, —C(=O)R$^{8b}$, or —C(=O)NR$^{8b}$R$^{8c}$, more preferably —C(=O)R$^{8b}$ or —S(=O)$_2$R$^{8a}$, still more preferably —C(=O)R$^{8b}$. In other preferred embodiments, $R^5$ is H, alkyl, aryl, cycloalkylalkyl, aralkyl, alkylaralkyl, heteroarylalkyl. When $R^5$ is alkyl, it is preferably $C_1$-$C_6$alkyl, more preferably $C_1$-$C_3$alkyl, yet more preferably $C_1$alkyl, still more preferably methyl optionally substituted with carboxy. When $R^5$ is cycloalkyl, it is preferably $C_3$-$C_{10}$cycloalkyl, more preferably $C_3$-$C_8$cycloalkyl, yet more preferably $C_3$-$C_6$cycloalkyl, still more preferably $C_5$-$C_6$cycloalkyl, still more preferably optionally substituted cyclopentyl or optionally substituted cyclohexyl. When $R^5$ is cycloalkylalkyl, it is preferably $C_3$-$C_{10}$cycloalkyl$C_1$-$C_6$alkyl, more preferably $C_3$-$C_8$cycloalkyl$C_1$-$C_3$alkyl, yet more preferably $C_3$-$C_6$cycloalkyl$C_1$-$C_3$alkyl, still more preferably $C_5$-$C_6$cycloalkyl$C_1$-$C_3$alkyl, still more preferably cyclopentyl$C_1$-$C_3$alkyl or cyclohexyl$C_1$-$C_3$alkyl, yet more preferably optionally substituted cyclopentylmethyl or optionally substituted cyclohexylmethyl. When $R^5$ is aryl, it is preferably $C_6$-$C_{10}$aryl, more preferably $C_6$aryl, yet more preferably phenyl. When $R^5$ is heteroaryl, it is preferably $C_5$-$C_{10}$heteroaryl, more preferably $C_5$-$C_6$heteroaryl, even more preferably pyridinyl or pyrimidinyl. When $R^5$ is aralkyl, it is preferably $C_6$-$C_{10}$aryl$C_1$-$C_6$alkyl, more preferably $C_6$-$C_{10}$aryl$C_1$-$C_3$alkyl, yet more preferably $C_6$aryl$C_1$-$C_3$alkyl, still more preferably $C_6$aryl$C_1$alkyl, yet more preferably benzyl optionally substituted with $C_1$-$C_6$alkyl, halo, hydroxy, or heteroaryl, yet more preferably 2-chlorobenzyl, 3-chlorobenzyl, 2-hydroxylbenzyl, 2-methylbenzyl, 3-methylbenzyl, 2,4,5-trimethylbenzyl, or 2-(pyrid-4-yl)benzyl. When $R^5$ is alkylaralkyl, it is preferably $C_1$-$C_6$alkyl$C_6$-$C_{10}$aryl$C_1$-$C_6$alkyl, more preferably $C_1$-$C_4$alkyl$C_6$-$C_{10}$aryl$C_1$-$C_3$alkyl, yet more preferably $C_1$-$C_4$alkyl$C_6$aryl$C_1$-$C_3$alkyl, still more preferably $C_1$alkyl$C_6$aryl$C_1$alkyl, yet more preferably optionally substituted methylbenzyl. When $R^5$ is heteroarylalkyl, it is preferably $C_5$-$C_{10}$heteroaryl$C_1$-$C_6$alkyl, more preferably $C_5$-$C_{10}$heteroaryl$C_1$-$C_3$alkyl, yet more preferably $C_5$-$C_6$heteroaryl$C_1$-$C_3$alkyl, still more preferably $C_5$-$C_6$heteroaryl$C_1$alkyl, yet more preferably optionally substituted thienylmethyl. In certain preferred embodiments, $R^5$ is H.

In certain preferred embodiments of compounds of formula I, $R^6$ is H, alkyl, cycloalkyl, alkylcycloalkyl, or aralkyl, with H, alkyl, alkylcycloalkyl, or aralkyl being more preferred. When $R^6$ is alkyl, it is preferably $C_1$-$C_6$alkyl, more preferably $C_1$-$C_3$alkyl, yet more preferably $C_1$alkyl, still more preferably methyl. When $R^6$ is cycloalkyl, it is preferably $C_3$-$C_{10}$cycloalkyl, more preferably $C_3$-$C_8$cycloalkyl, yet more preferably $C_3$-$C_6$cycloalkyl, still more preferably $C_5$-$C_6$cycloalkyl, still more preferably optionally substituted cyclopentyl or optionally substituted cyclohexyl. When $R^6$ is alkylcycloalkyl, it is preferably $C_1$-$C_6$alkyl$C_3$-$C_{10}$cycloalkyl$C_1$-$C_6$alkyl, more preferably $C_1$-$C_4$alkyl$C_3$-$C_8$cycloalkyl$C_1$-$C_3$alkyl, yet more preferably $C_1$-$C_4$alkyl$C_3$-$C_6$cycloalkyl$C_1$-$C_3$alkyl, still more preferably $C_1$alkyl$C_5$-$C_6$cycloalkyl$C_1$alkyl, yet more preferably optionally substituted methylcyclopentylmethyl or optionally substituted methylcyclohexylmethyl. When $R^6$ is aralkyl, it is preferably $C_6$-$C_{10}$aryl$C_1$-$C_6$alkyl, more preferably $C_6$-$C_{10}$aryl$C_1$-$C_3$alkyl, yet more preferably $C_6$aryl$C_1$-$C_3$alkyl, still more preferably $C_6$aryl$C_1$alkyl, yet more preferably benzyl. In certain preferred embodiments, $R^6$ is H.

In preferred embodiments of compounds of formula I, m is 1. Also in preferred embodiments of compounds of formula I, n is 0 or 1. In certain preferred embodiments, m and n are each 1.

In preferred embodiments of compounds of formula I, at least one of $R^4$ and $R^5$ is H.

In certain preferred embodiments of compounds of formula I, $R^7$ is H, alkyl, aralkyl, or aryl, with H being more preferred. When $R^7$ is alkyl, it is preferably $C_1$-$C_6$alkyl, more preferably $C_1$-$C_3$alkyl, yet more preferably $C_1$alkyl, still more preferably methyl. When $R^7$ is aralkyl, it is preferably $C_6$-$C_{10}$aryl$C_1$-$C_6$alkyl, more preferably $C_6$-$C_{10}$aryl$C_1$-$C_3$alkyl, yet more preferably $C_6$aryl$C_1$-$C_3$alkyl, still more preferably $C_6$aryl$C_1$alkyl, yet more preferably benzyl. When $R^7$ is aryl, it is preferably $C_6$-$C_{10}$aryl, more preferably $C_6$aryl, yet more preferably phenyl.

In certain preferred embodiments of compounds of formula I, $R^{8a}$ is alkyl, cycloalkyl, cycloalkylalkyl, heteroaryl, heteroarylalkyl, aralkyl, or aryl. When $R^{8a}$ is alkyl, it is preferably $C_1$-$C_6$alkyl, more preferably $C_1$-$C_3$alkyl, yet more preferably $C_1$alkyl, still more preferably methyl. When $R^{8a}$ is cycloalkyl, it is preferably $C_3$-$C_{10}$cycloalkyl, more preferably $C_3$-$C_8$cycloalkyl, yet more preferably $C_3$-$C_6$cycloalkyl, still more preferably $C_5$-$C_6$cycloalkyl, still more preferably optionally substituted cyclopentyl or optionally substituted cyclohexyl. When $R^{8a}$ is cycloalkylalkyl, it is preferably $C_3$-$C_{10}$cycloalkyl$C_1$-$C_6$alkyl, more preferably $C_3$-$C_8$cycloalkyl$C_1$-$C_3$alkyl, yet more preferably $C_3$-$C_6$cycloalkyl$C_1$-$C_3$alkyl, still more preferably $C_5$-$C_6$cycloalkyl$C_1$-$C_3$alkyl, still more preferably cyclopentyl$C_1$-$C_3$alkyl or cyclohexyl$C_1$-$C_3$alkyl, yet more preferably optionally substituted cyclopentylmethyl or optionally substituted cyclohexylmethyl. When $R^{8a}$ is aryl, it is preferably $C_6$-$C_{10}$aryl, more preferably $C_6$aryl, yet more preferably phenyl. When $R^{8a}$ is heteroaryl, it is preferably $C_5$-$C_{10}$heteroaryl, more preferably $C_5$-$C_6$heteroaryl, even more preferably pyridinyl or pyrimidinyl. When $R^{8a}$ is aralkyl, it is preferably $C_6$-$C_{10}$aryl$C_1$-$C_6$alkyl, more preferably $C_6$-$C_{10}$aryl$C_1$-$C_3$alkyl, yet more preferably $C_6$aryl$C_1$-$C_3$alkyl, still more preferably $C_6$aryl$C_1$alkyl, yet more preferably benzyl. When $R^{8a}$ is heteroarylalkyl, it is preferably $C_5$-$C_{10}$heteroaryl$C_1$-$C_6$alkyl, more preferably $C_5$-$C_{10}$heteroaryl$C_1$-$C_3$alkyl, yet more preferably $C_5$-$C_6$heteroaryl$C_1$-$C_3$alkyl, still more preferably $C_5$-$C_6$heteroaryl$C_1$alkyl.

In certain preferred embodiments of compounds of formula I, $R^{8b}$ and $R^{8c}$ are each independently H, alkyl, cycloalkyl, cycloalkylalkyl, heteroaryl, heteroarylalkyl, aralkyl, or aryl, with aryl or aralkyl being more preferred. When $R^{8b}$ or $R^{8c}$ is alkyl, it is preferably $C_1$-$C_6$alkyl, more preferably $C_1$-$C_3$alkyl, yet more preferably $C_1$alkyl, still more preferably methyl. When $R^{8b}$ or $R^{8c}$ is cycloalkyl, it is preferably $C_3$-$C_{10}$cycloalkyl, more preferably $C_3$-$C_8$cycloalkyl, yet more preferably $C_3$-$C_6$cycloalkyl, still more preferably $C_5$-$C_6$cycloalkyl, still more preferably optionally substituted cyclopentyl or optionally substituted cyclohexyl. When $R^{8b}$ or $R^{8c}$ is cycloalkylalkyl, it is preferably $C_3$-$C_{10}$cycloalkyl$C_1$-$C_6$alkyl, more preferably $C_3$-$C_8$cycloalkyl$C_1$-$C_3$alkyl, yet more preferably $C_3$-$C_6$cycloalkyl$C_1$-$C_3$alkyl, still more preferably $C_5$-$C_6$cycloalkyl$C_1$-$C_3$alkyl, still more preferably optionally substituted cyclopentylmethyl or optionally substituted cyclohexylmethyl. When $R^{8b}$ or $R^{8c}$ is aryl, it is preferably $C_6$-$C_{10}$aryl, more preferably $C_6$aryl, yet more preferably phenyl. When $R^{8b}$ or $R^{8c}$ is heteroaryl, it is preferably $C_5$-$C_{10}$heteroaryl, more preferably $C_5$-$C_6$heteroaryl, even more preferably pyridinyl. When $R^{8b}$ or $R^{8c}$ is aralkyl, it is preferably $C_6$-$C_{10}$aryl$C_1$-$C_6$alkyl, more preferably $C_6$-$C_{10}$aryl$C_1$-$C_3$alkyl, yet more preferably $C_6$aryl$C_1$-$C_3$alkyl, still more preferably $C_6$aryl$C_1$alkyl, yet more preferably benzyl. When $R^{8b}$ or $R^{8c}$ is heteroarylalkyl, it is preferably $C_5$-$C_{10}$heteroaryl$C_1$-$C_6$alkyl, more preferably $C_5$-$C_{10}$heteroaryl$C_1$-$C_3$alkyl, yet more preferably $C_5$-$C_6$heteroaryl$C_1$-$C_3$alkyl, still more preferably $C_5$-$C_6$heteroaryl$C_1$alkyl.

In certain other preferred embodiments of compounds of formula I, $R^{8b}$ and $R^{8c}$, taken together with the nitrogen atom to which they are connected, form a 4- to 8-membered heterocycloalkyl ring, more preferably a 5- to 7-membered heterocycloalkyl ring, more preferably still, a 5- to 6-membered heterocycloalkyl ring, yet more preferably an optionally substituted morpholine ring.

In some preferred embodiments, the compounds of formula I have the structure corresponding to formula IIa:

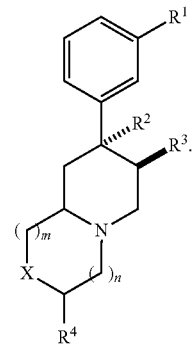

IIa

In some preferred embodiments, the compounds of formula I have the structure corresponding to formula IIb:

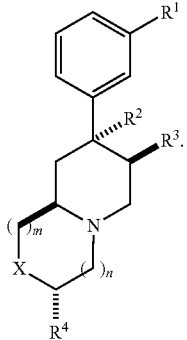

In particularly preferred embodiments, the compound of formula I is:
3-(2,3-dimethyl-7-phenyl-octahydro-1H-quinolizin-2-yl) phenol;
1-(8-(3-hydroxyphenyl)-7,8-dimethyl-hexahydro-1H-pyrido[1,2-α]pyrazin-2(6H)-yl)-2-phenylethanone;
3-(7,8-dimethyl-2-phenethyl-octahydro-1H-pyrido[1,2-α]pyrazin-8-yl)phenol;
(8-(3-hydroxyphenyl)-7,8-dimethyl-hexahydro-1H-pyrido[1,2-α]pyrazin-2(6H)-yl) (phenyl)methanone;
3-(2-benzyl-7,8-dimethyl-octahydro-1H-pyrido[1,2-α]pyrazin-8-yl)phenol;
3-(7,8-dimethyl-2-(phenylsulfonyl)-octahydro-1H-pyrido[1,2-α]pyrazin-8-yl)phenol;
3-(7,8-dimethyl-2-phenyl-octahydro-1H-pyrido[1,2-α]pyrazin-8-yl)phenol;
3-(7,8-dimethyl-3-phenyl-octahydro-1H-pyrido[1,2-α]pyrazin-8-yl)phenol;
3-(2,7,8-trimethyl-3-phenyl-octahydro-1H-pyrido[1,2-α]pyrazin-8-yl)phenol;
2-(8-(3-hydroxyphenyl)-7,8-dimethyl-3-phenyl-hexahydro-1H-pyrido[1,2-α]pyrazin-2(6H)-yl)acetic acid;
3-(8-(3-hydroxyphenyl)-7,8-dimethyl-3-phenyl-hexahydro-1H-pyrido[1,2-α]pyrazin-2(6H)-yl)propanoic acid;
3-(2-benzyl-7,8-dimethyl-3-phenyl-octahydro-1H-pyrido[1,2-α]pyrazin-8-yl)phenol;
3-(2-benzyl-7,8-dimethyl-3-phenyl-octahydro-1H-pyrido[1,2-α]pyrazin-8-yl)benzamide;
3-(7,8-dimethyl-3-phenyl-octahydro-1H-pyrido[1,2-α]pyrazin-8-yl)benzamide;
3-(3-benzyl-7,8-dimethyl-octahydro-1H-pyrido[1,2-α]pyrazin-8-yl)phenol;
3-(3-benzyl-7,8-dimethyl-octahydro-1H-pyrido[1,2-α]pyrazin-8-yl)phenol;
3-(3-cyclohexyl-7,8-dimethyl-octahydro-1H-pyrido[1,2-α]pyrazin-8-yl)phenol;
3-(2-benzyl-8,9-dimethyl-decahydropyrido[1,2-α][1,4]diazepin-9-yl)phenol;
3-(2-(3-methoxybenzyl)-7,8-dimethyl-octahydro-1H-pyrido[1,2-α]pyrazin-8-yl)phenol;
3-(7,8-dimethyl-2-(pyridin-2-ylmethyl)-octahydro-1H-pyrido[1,2-α]pyrazin-8-yl)phenol;
3-(2-(cyclohexylmethyl)-7,8-dimethyl-octahydro-1H-pyrido[1,2-α]pyrazin-8-yl)phenol;
3-(7,8-dimethyl-2-(4-methylbenzyl)-octahydro-1H-pyrido[1,2-α]pyrazin-8-yl)phenol;
3-(2-(2,5-dimethylbenzyl)-7,8-dimethyl-octahydro-1H-pyrido[1,2-α]pyrazin-8-yl)phenol;
3-(7,8-dimethyl-2-(thiophen-3-ylmethyl)-octahydro-1H-pyrido[1,2-α]pyrazin-8-yl)phenol;
3-(2-(furan-3-ylmethyl)-7,8-dimethyl-octahydro-1H-pyrido[1,2-α]pyrazin-8-yl)phenol;
3-(7,8-dimethyl-2-(pyridin-3-ylmethyl)-octahydro-1H-pyrido[1,2-α]pyrazin-8-yl)phenol;
3-(2-(4-tert-butylbenzyl)-7,8-dimethyl-octahydro-1H-pyrido[1,2-α]pyrazin-8-yl)phenol;
3-(7,8-dimethyl-2-(2-methylbenzyl)-octahydro-1H-pyrido[1,2-α]pyrazin-8-yl)phenol;
3-(7,8-dimethyl-2-(4-phenoxybenzyl)-octahydro-1H-pyrido[1,2-α]pyrazin-8-yl)phenol;
3-(7,8-dimethyl-2-(pyridin-4-ylmethyl)-octahydro-1H-pyrido[1,2-α]pyrazin-8-yl)phenol;
3-(2-(3-chlorobenzyl)-7,8-dimethyl-octahydro-1H-pyrido[1,2-α]pyrazin-8-yl)phenol;
3-(7,8-dimethyl-2-(3-methylbenzyl)-octahydro-1H-pyrido[1,2-α]pyrazin-8-yl)phenol;
3-(7,8-dimethyl-2-(3-phenoxybenzyl)-octahydro-1H-pyrido[1,2-α]pyrazin-8-yl)phenol;
3-(7,8-dimethyl-2-(thiophen-2-ylmethyl)-octahydro-1H-pyrido[1,2-α]pyrazin-8-yl)phenol;
3-(2-(4-methoxybenzyl)-7,8-dimethyl-octahydro-1H-pyrido[1,2-α]pyrazin-8-yl)phenol;
3-(2-(4-ethylbenzyl)-7,8-dimethyl-octahydro-1H-pyrido[1,2-α]pyrazin-8-yl)phenol;
3-(7,8-dimethyl-2-(naphthalen-1-ylmethyl)-octahydro-1H-pyrido[1,2-α]pyrazin-8-yl)phenol;
2-(8-(3-hydroxyphenyl)-7,8-dimethyl-hexahydro-1H-pyrido[1,2-α]pyrazin-2(6H)-yl)methyl)phenol;
3-(2-(4-isopropylbenzyl)-7,8-dimethyl-octahydro-1H-pyrido[1,2-α]pyrazin-8-yl)phenol;
3-(2-(furan-2-ylmethyl)-7,8-dimethyl-octahydro-1H-pyrido[1,2-α]pyrazin-8-yl)phenol;
3-(2-(2-chlorobenzyl)-7,8-dimethyl-octahydro-1H-pyrido[1,2-α]pyrazin-8-yl)phenol;
3-(2-(3-hydroxybenzyl)-7,8-dimethyl-octahydro-1H-pyrido[1,2-α]pyrazin-8-yl)phenol;
3-(2-(4-chlorobenzyl)-7,8-dimethyl-octahydro-1H-pyrido[1,2-α]pyrazin-8-yl)phenol;
3-(7,8-dimethyl-2-(naphthalen-2-ylmethyl)-octahydro-1H-pyrido[1,2-α]pyrazin-8-yl)phenol;
3-(2-(3-(benzyloxy)benzyl)-7,8-dimethyl-octahydro-1H-pyrido[1,2-α]pyrazin-8-yl)phenol;
3-(7,8-dimethyl-2-(4-(pyridin-4-yl)benzyl)-octahydro-1H-pyrido[1,2-α]pyrazin-8-yl)phenol;
3-(2-(2,3-dichlorobenzyl)-7,8-dimethyl-octahydro-1H-pyrido[1,2-α]pyrazin-8-yl)phenol;
3-(7,8-dimethyl-2-(quinolin-2-ylmethyl)-octahydro-1H-pyrido[1,2-α]pyrazin-8-yl)phenol;
3-(7,8-dimethyl-2-(2-(pyridin-4-yl)benzyl)-octahydro-1H-pyrido[1,2-α]pyrazin-8-yl)phenol;
3-(2-(4-(benzyloxy)benzyl)-7,8-dimethyl-octahydro-1H-pyrido[1,2-α]pyrazin-8-yl)phenol;
3-(7,8-dimethyl-2-(3-(pyridin-4-yl)benzyl)-octahydro-1H-pyrido[1,2-α]pyrazin-8-yl)phenol;
methyl 4-(8-(3-hydroxyphenyl)-7,8-dimethyl-hexahydro-1H-pyrido[1,2-α]pyrazin-2(6H)-yl)methyl)benzoate;
3-(2-(4-(dimethylamino)benzyl)-7,8-dimethyl-octahydro-1H-pyrido[1,2-α]pyrazin-8-yl)phenol;
3-(7,8-dimethyl-2-(4-(pyridin-3-yl)benzyl)-octahydro-1H-pyrido[1,2-α]pyrazin-8-yl)phenol;
3-(7,8-dimethyl-2-(quinolin-3-ylmethyl)-octahydro-1H-pyrido[1,2-α]pyrazin-8-yl)phenol;

methyl 3-(8-(3-hydroxyphenyl)-7,8-dimethyl-hexahydro-1H-pyrido[1,2-α]pyrazin-2(6H)-yl)methyl)benzoate;

3-(2-(4-(1H-imidazol-1-yl)benzyl)-7,8-dimethyl-octahydro-1H-pyrido[1,2-α]pyrazin-8-yl)phenol;

3-(2-(biphenyl-4-ylmethyl)-7,8-dimethyl-octahydro-1H-pyrido[1,2-α]pyrazin-8-yl)phenol;

3-(7,8-dimethyl-2-(quinolin-4-ylmethyl)-octahydro-1H-pyrido[1,2-α]pyrazin-8-yl)phenol;

3-(7,8-dimethyl-2-(2,4,5-trimethylbenzyl)-octahydro-1H-pyrido[1,2-α]pyrazin-8-yl)phenol; or 3-(2-(4-hydroxybenzyl)-7,8-dimethyl-octahydro-1H-pyrido[1,2-α]pyrazin-8-yl)phenol;

or a pharmaceutically acceptable salt thereof.

More preferably, the compound of formula I is:

3-((2R,3R,7S,9αS)-2,3-dimethyl-7-phenyl-octahydro-1H-quinolizin-2-yl)phenol;

1-((7R,8R,9αR)-8-(3-hydroxyphenyl)-7,8-dimethyl-hexahydro-1H-pyrido[1,2-α]pyrazin-2(6H)-yl)-2-phenylethanone;

3-((7R,8R,9αR)-7,8-dimethyl-2-phenethyl-octahydro-1H-pyrido[1,2-α]pyrazin-8-yl)phenol;

((7R,8R,9αR)-8-(3-hydroxyphenyl)-7,8-dimethyl-hexahydro-1H-pyrido[1,2-α]pyrazin-2(6H)-yl)(phenyl)methanone;

3-((7R,8R,9αR)-2-benzyl-7,8-dimethyl-octahydro-1H-pyrido[1,2-α]pyrazin-8-yl)phenol;

3-((7R,8R,9αR)-7,8-dimethyl-2-(phenylsulfonyl)-octahydro-1H-pyrido[1,2-α]pyrazin-8-yl)phenol;

3-((7R,8R,9αR)-7,8-dimethyl-2-phenyl-octahydro-1H-pyrido[1,2-α]pyrazin-8-yl)phenol;

3-((3S,7R,8R,9αR)-7,8-dimethyl-3-phenyl-octahydro-1H-pyrido[1,2-α]pyrazin-8-yl)phenol;

3-((3S,7R,8R,9αR)-2,7,8-trimethyl-3-phenyl-octahydro-1H-pyrido[1,2-α]pyrazin-8-yl)phenol;

2-((3S,7R,8R,9αR)-8-(3-hydroxyphenyl)-7,8-dimethyl-3-phenyl-hexahydro-1H-pyrido[1,2-α]pyrazin-2(6H)-yl) acetic acid;

3-((3S,7R,8R,9αR)-8-(3-hydroxyphenyl)-7,8-dimethyl-3-phenyl-hexahydro-1H-pyrido[1,2-α]pyrazin-2(6H)-yl) propanoic acid;

3-((3S,7R,8R,9αR)-2-benzyl-7,8-dimethyl-3-phenyl-octahydro-1H-pyrido[1,2-α]pyrazin-8-yl)phenol;

3-((3S,7R,8R,9αR)-2-benzyl-7,8-dimethyl-3-phenyl-octahydro-1H-pyrido[1,2-α]pyrazin-8-yl)benzamide;

3-((3S,7R,8R,9αR)-7,8-dimethyl-3-phenyl-octahydro-1H-pyrido[1,2-α]pyrazin-8-yl)benzamide;

3-((3S,7R,8R,9αR)-3-benzyl-7,8-dimethyl-octahydro-1H-pyrido[1,2-α]pyrazin-8-yl)phenol;

3-((3R,7R,8R,9αR)-3-benzyl-7,8-dimethyl-octahydro-1H-pyrido[1,2-α]pyrazin-8-yl)phenol;

3-((3S,7R,8R,9αR)-3-cyclohexyl-7,8-dimethyl-octahydro-1H-pyrido[1,2-α]pyrazin-8-yl)phenol;

3-((8R,9R,10αR)-2-benzyl-8,9-dimethyl-decahydropyrido[1,2-α][1,4]diazepin-9-yl)phenol;

3-((7R,8R,9αR)-2-(3-methoxybenzyl)-7,8-dimethyl-octahydro-1H-pyrido[1,2-α]pyrazin-8-yl)phenol;

3-((7R,8R,9αR)-7,8-dimethyl-2-(pyridin-2-ylmethyl)-octahydro-1H-pyrido[1,2-α]pyrazin-8-yl)phenol;

3-((7R,8R,9αR)-2-(cyclohexylmethyl)-7,8-dimethyl-octahydro-1H-pyrido[1,2-α]pyrazin-8-yl)phenol;

3-((7R,8R,9αR)-7,8-dimethyl-2-(4-methylbenzyl)-octahydro-1H-pyrido[1,2-α]pyrazin-8-yl)phenol;

3-((7R,8R,9αR)-2-(2,5-dimethylbenzyl)-7,8-dimethyl-octahydro-1H-pyrido[1,2-α]pyrazin-8-yl)phenol;

3-((7R,8R,9αR)-7,8-dimethyl-2-(thiophen-3-ylmethyl)-octahydro-1H-pyrido[1,2-α]pyrazin-8-yl)phenol;

3-((7R,8R,9αR)-2-(furan-3-ylmethyl)-7,8-dimethyl-octahydro-1H-pyrido[1,2-α]pyrazin-8-yl)phenol;

3-((7R,8R,9αR)-7,8-dimethyl-2-(pyridin-3-ylmethyl)-octahydro-1H-pyrido[1,2-α]pyrazin-8-yl)phenol;

3-((7R,8R,9αR)-2-(4-tert-butylbenzyl)-7,8-dimethyl-octahydro-1H-pyrido[1,2-α]pyrazin-8-yl)phenol;

3-((7R,8R,9αR)-7,8-dimethyl-2-(2-methylbenzyl)-octahydro-1H-pyrido[1,2-α]pyrazin-8-yl)phenol;

3-((7R,8R,9αR)-7,8-dimethyl-2-(4-phenoxybenzyl)-octahydro-1H-pyrido[1,2-α]pyrazin-8-yl)phenol;

3-((7R,8R,9αR)-7,8-dimethyl-2-(pyridin-4-ylmethyl)-octahydro-1H-pyrido[1,2-α]pyrazin-8-yl)phenol;

3-((7R,8R,9αR)-2-(3-chlorobenzyl)-7,8-dimethyl-octahydro-1H-pyrido[1,2-α]pyrazin-8-yl)phenol;

3-((7R,8R,9αR)-7,8-dimethyl-2-(3-methylbenzyl)-octahydro-1H-pyrido[1,2-α]pyrazin-8-yl)phenol;

3-((7R,8R,9αR)-7,8-dimethyl-2-(3-phenoxybenzyl)-octahydro-1H-pyrido[1,2-α]pyrazin-8-yl)phenol;

3-((7R,8R,9αR)-7,8-dimethyl-2-(thiophen-2-ylmethyl)-octahydro-1H-pyrido[1,2-α]pyrazin-8-yl)phenol;

3-((7R,8R,9αR)-2-(4-methoxybenzyl)-7,8-dimethyl-octahydro-1H-pyrido[1,2-α]pyrazin-8-yl)phenol;

3-((7R,8R,9αR)-2-(4-ethylbenzyl)-7,8-dimethyl-octahydro-1H-pyrido[1,2-α]pyrazin-8-yl)phenol;

3-((7R,8R,9αR)-7,8-dimethyl-2-(naphthalen-1-ylmethyl)-octahydro-1H-pyrido[1,2-α]pyrazin-8-yl)phenol;

2-(((7R,8R,9αR)-8-(3-hydroxyphenyl)-7,8-dimethyl-hexahydro-1H-pyrido[1,2-α]pyrazin-2(6H)-yl)methyl)phenol;

3-((7R,8R,9αR)-2-(4-isopropylbenzyl)-7,8-dimethyl-octahydro-1H-pyrido[1,2-α]pyrazin-8-yl)phenol;

3-((7R,8R,9αR)-2-(furan-2-ylmethyl)-7,8-dimethyl-octahydro-1H-pyrido[1,2-α]pyrazin-8-yl)phenol;

3-((7R,8R,9αR)-2-(2-chlorobenzyl)-7,8-dimethyl-octahydro-1H-pyrido[1,2-α]pyrazin-8-yl)phenol;

3-((7R,8R,9αR)-2-(3-hydroxybenzyl)-7,8-dimethyl-octahydro-1H-pyrido[1,2-α]pyrazin-8-yl)phenol;

3-((7R,8R,9αR)-2-(4-chlorobenzyl)-7,8-dimethyl-octahydro-1H-pyrido[1,2-α]pyrazin-8-yl)phenol;

3-((7R,8R,9αR)-7,8-dimethyl-2-(naphthalen-2-ylmethyl)-octahydro-1H-pyrido[1,2-α]pyrazin-8-yl)phenol;

3-((7R,8R,9αR)-2-(3-(benzyloxy)benzyl)-7,8-dimethyl-octahydro-1H-pyrido[1,2-α]pyrazin-8-yl)phenol;

3-((7R,8R,9αR)-7,8-dimethyl-2-(4-(pyridin-4-yl)benzyl)-octahydro-1H-pyrido[1,2-α]pyrazin-8-yl)phenol;

3-((7R,8R,9αR)-2-(2,3-dichlorobenzyl)-7,8-dimethyl-octahydro-1H-pyrido[1,2-α]pyrazin-8-yl)phenol;

3-((7R,8R,9αR)-7,8-dimethyl-2-(quinolin-2-ylmethyl)-octahydro-1H-pyrido[1,2-α]pyrazin-8-yl)phenol;

3-((7R,8R,9αR)-7,8-dimethyl-2-(2-(pyridin-4-yl)benzyl)-octahydro-1H-pyrido[1,2-α]pyrazin-8-yl)phenol;

3-((7R,8R,9αR)-2-(4-(benzyloxy)benzyl)-7,8-dimethyl-octahydro-1H-pyrido[1,2-α]pyrazin-8-yl)phenol;

3-((7R,8R,9αR)-7,8-dimethyl-2-(3-(pyridin-4-yl)benzyl)-octahydro-1H-pyrido[1,2-α]pyrazin-8-yl)phenol;

methyl 4-(((7R,8R,9αR)-8-(3-hydroxyphenyl)-7,8-dimethyl-hexahydro-1H-pyrido[1,2-α]pyrazin-2(6H)-yl)methyl)benzoate;

3-((7R,8R,9αR)-2-(4-(dimethylamino)benzyl)-7,8-dimethyl-octahydro-1H-pyrido[1,2-α]pyrazin-8-yl)phenol;

3-((7R,8R,9αR)-7,8-dimethyl-2-(4-(pyridin-3-yl)benzyl)-octahydro-1H-pyrido[1,2-α]pyrazin-8-yl)phenol;

3-((7R,8R,9αR)-7,8-dimethyl-2-(quinolin-3-ylmethyl)-octahydro-1H-pyrido[1,2-α]pyrazin-8-yl)phenol;

methyl 3-(((7R,8R,9αR)-8-(3-hydroxyphenyl)-7,8-dimethyl-hexahydro-1H-pyrido[1,2-α]pyrazin-2(6H)-yl)methyl)benzoate;

3-((7R,8R,9αR)-2-(4-(1H-imidazol-1-yl)benzyl)-7,8-dimethyl-octahydro-1H-pyrido[1,2-α]pyrazin-8-yl)phenol;

3-((7R,8R,9αR)-2-(biphenyl-4-ylmethyl)-7,8-dimethyl-octahydro-1H-pyrido[1,2-α]pyrazin-8-yl)phenol;

3-((7R,8R,9αR)-7,8-dimethyl-2-(quinolin-4-ylmethyl)-octahydro-1H-pyrido[1,2-α]pyrazin-8-yl)phenol;

3-((7R,8R,9αR)-7,8-dimethyl-2-(2,4,5-trimethylbenzyl)-octahydro-1H-pyrido[1,2-α]pyrazin-8-yl)phenol; or 3-((7R,8R,9αR)-2-(4-hydroxybenzyl)-7,8-dimethyl-octahydro-1H-pyrido[1,2-α]pyrazin-8-yl)phenol;

or a pharmaceutically acceptable salt thereof.

In still more preferred embodiments, the compound of formula I is:

3-(2,3-dimethyl-7-phenyl-octahydro-1H-quinolizin-2-yl)phenol;

(8-(3-hydroxyphenyl)-7,8-dimethyl-hexahydro-1H-pyrido[1,2-α]pyrazin-2(6H)-yl)(phenyl)methanone;

3-(2-benzyl-7,8-dimethyl-octahydro-1H-pyrido[1,2-α]pyrazin-8-yl)phenol;

3-(7,8-dimethyl-3-phenyl-octahydro-1H-pyrido[1,2-α]pyrazin-8-yl)phenol;

3-(7,8-dimethyl-3-phenyl-octahydro-1H-pyrido[1,2-α]pyrazin-8-yl)benzamide;

3-(3-cyclohexyl-7,8-dimethyl-octahydro-1H-pyrido[1,2-α]pyrazin-8-yl)phenol;

3-(2-(cyclohexylmethyl)-7,8-dimethyl-octahydro-1H-pyrido[1,2-α]pyrazin-8-yl)phenol;

3-(7,8-dimethyl-2-(thiophen-2-ylmethyl)-octahydro-1H-pyrido[1,2-α]pyrazin-8-yl)phenol;

3-(7,8-dimethyl-2-(2-(pyridin-4-yl)benzyl)-octahydro-1H-pyrido[1,2-α]pyrazin-8-yl)phenol;

3-(2-(2-chlorobenzyl)-7,8-dimethyl-octahydro-1H-pyrido[1,2-α]pyrazin-8-yl)phenol;

2-(8-(3-hydroxyphenyl)-7,8-dimethyl-3-phenyl-hexahydro-1H-pyrido[1,2-α]pyrazin-2(6H)-yl)acetic acid;

3-(7,8-dimethyl-2-(2-methylbenzyl)-octahydro-1H-pyrido[1,2-α]pyrazin-8-yl)phenol;

3-(2-(3-chlorobenzyl)-7,8-dimethyl-octahydro-1H-pyrido[1,2-α]pyrazin-8-yl)phenol;

3-(7,8-dimethyl-2-(3-methylbenzyl)-octahydro-1H-pyrido[1,2-α]pyrazin-8-yl)phenol; or 2-(8-(3-hydroxyphenyl)-7,8-dimethyl-hexahydro-1H-pyrido[1,2-α]pyrazin-2(6H)-yl)methyl)phenol;

or a pharmaceutically acceptable salt thereof.

More preferably the compound of formula I is:

3-((2R,3R,7S,9αS)-2,3-dimethyl-7-phenyl-octahydro-1H-quinolizin-2-yl)phenol;

((7R,8R,9αR)-8-(3-hydroxyphenyl)-7,8-dimethyl-hexahydro-1H-pyrido[1,2-α]pyrazin-2(6H)-yl)(phenyl)methanone;

3-((7R,8R,9αR)-2-benzyl-7,8-dimethyl-octahydro-1H-pyrido[1,2-α]pyrazin-8-yl)phenol;

3-((3S,7R,8R,9αR)-7,8-dimethyl-3-phenyl-octahydro-1H-pyrido[1,2-α]pyrazin-8-yl)phenol;

3-((3S,7R,8R,9αR)-7,8-dimethyl-3-phenyl-octahydro-1H-pyrido[1,2-α]pyrazin-8-yl)benzamide;

3-((3S,7R,8R,9αR)-3-cyclohexyl-7,8-dimethyl-octahydro-1H-pyrido[1,2-α]pyrazin-8-yl)phenol;

3-((7R,8R,9αR)-2-(cyclohexylmethyl)-7,8-dimethyl-octahydro-1H-pyrido[1,2-α]pyrazin-8-yl)phenol;

3-((7R,8R,9αR)-7,8-dimethyl-2-(thiophen-2-ylmethyl)-octahydro-1H-pyrido[1,2-α]pyrazin-8-yl)phenol;

3-((7R,8R,9αR)-7,8-dimethyl-2-(2-(pyridin-4-yl)benzyl)-octahydro-1H-pyrido[1,2-α]pyrazin-8-yl)phenol;

3-((7R,8R,9αR)-2-(2-chlorobenzyl)-7,8-dimethyl-octahydro-1H-pyrido[1,2-α]pyrazin-8-yl)phenol;

2-((3S,7R,8R,9αR)-8-(3-hydroxyphenyl)-7,8-dimethyl-3-phenyl-hexahydro-1H-pyrido[1,2-α]pyrazin-2(6H)-yl)acetic acid;

3-((7R,8R,9αR)-7,8-dimethyl-2-(2-methylbenzyl)-octahydro-1H-pyrido[1,2-α]pyrazin-8-yl)phenol;

3-((7R,8R,9αR)-2-(3-chlorobenzyl)-7,8-dimethyl-octahydro-1H-pyrido[1,2-α]pyrazin-8-yl)phenol;

3-((7R,8R,9αR)-7,8-dimethyl-2-(3-methylbenzyl)-octahydro-1H-pyrido[1,2-α]pyrazin-8-yl)phenol; or 2-(((7R,8R,9αR)-8-(3-hydroxyphenyl)-7,8-dimethyl-hexahydro-1H-pyrido[1,2-α]pyrazin-2(6H)-yl)methyl)phenol;

or a pharmaceutically acceptable salt thereof.

In yet more preferred embodiments, the compound of formula I is:

3-(2,3-dimethyl-7-phenyl-octahydro-1H-quinolizin-2-yl)phenol;

(8-(3-hydroxyphenyl)-7,8-dimethyl-hexahydro-1H-pyrido[1,2-α]pyrazin-2(6H)-yl)(phenyl)methanone;

3-(2-benzyl-7,8-dimethyl-octahydro-1H-pyrido[1,2-α]pyrazin-8-yl)phenol;

3-(7,8-dimethyl-3-phenyl-octahydro-1H-pyrido[1,2-α]pyrazin-8-yl)phenol;

3-(7,8-dimethyl-3-phenyl-octahydro-1H-pyrido[1,2-α]pyrazin-8-yl)benzamide;

3-(3-cyclohexyl-7,8-dimethyl-octahydro-1H-pyrido[1,2-α]pyrazin-8-yl)phenol;

3-(2-(cyclohexylmethyl)-7,8-dimethyl-octahydro-1H-pyrido[1,2-α]pyrazin-8-yl)phenol;

3-(7,8-dimethyl-2-(thiophen-2-ylmethyl)-octahydro-1H-pyrido[1,2-α]pyrazin-8-yl)phenol;

3-(7,8-dimethyl-2-(2-(pyridin-4-yl)benzyl)-octahydro-1H-pyrido[1,2-α]pyrazin-8-yl)phenol; or 3-(2-(2-chlorobenzyl)-7,8-dimethyl-octahydro-1H-pyrido[1,2-α]pyrazin-8-yl)phenol;

or a pharmaceutically acceptable salt thereof.

More preferably, the compound of formula I is:

3-((2R,3R,7S,9αS)-2,3-dimethyl-7-phenyl-octahydro-1H-quinolizin-2-yl)phenol;

((7R,8R,9αR)-8-(3-hydroxyphenyl)-7,8-dimethyl-hexahydro-1H-pyrido[1,2-α]pyrazin-2(6H)-yl)(phenyl)methanone;

3-((7R,8R,9αR)-2-benzyl-7,8-dimethyl-octahydro-1H-pyrido[1,2-α]pyrazin-8-yl)phenol;

3-((3S,7R,8R,9αR)-7,8-dimethyl-3-phenyl-octahydro-1H-pyrido[1,2-α]pyrazin-8-yl)phenol;

3-((3S,7R,8R,9αR)-7,8-dimethyl-3-phenyl-octahydro-1H-pyrido[1,2-α]pyrazin-8-yl)benzamide;

3-((3S,7R,8R,9αR)-3-cyclohexyl-7,8-dimethyl-octahydro-1H-pyrido[1,2-α]pyrazin-8-yl)phenol;

3-((7R,8R,9αR)-2-(cyclohexylmethyl)-7,8-dimethyl-octahydro-1H-pyrido[1,2-α]pyrazin-8-yl)phenol;

3-((7R,8R,9αR)-7,8-dimethyl-2-(thiophen-2-ylmethyl)-octahydro-1H-pyrido[1,2-α]pyrazin-8-yl)phenol;

3-((7R,8R,9αR)-7,8-dimethyl-2-(2-(pyridin-4-yl)benzyl)-octahydro-1H-pyrido[1,2-α]pyrazin-8-yl)phenol; or 3-((7R,8R,9αR)-2-(2-chlorobenzyl)-7,8-dimethyl-octahydro-1H-pyrido[1,2-α]pyrazin-8-yl)phenol;

or a pharmaceutically acceptable salt thereof.

In still more preferred embodiments, the compound of formula I is:

3-(2,3-dimethyl-7-phenyl-octahydro-1H-quinolizin-2-yl)phenol;

(8-(3-hydroxyphenyl)-7,8-dimethyl-hexahydro-1H-pyrido[1,2-α]pyrazin-2(6H)-yl) (phenyl)methanone;

3-(2-benzyl-7,8-dimethyl-octahydro-1H-pyrido[1,2-α]pyrazin-8-yl)phenol;

3-(7,8-dimethyl-3-phenyl-octahydro-1H-pyrido[1,2-α]pyrazin-8-yl)phenol; or 3-(7,8-dimethyl-3-phenyl-octahydro-1H-pyrido[1,2-α]pyrazin-8-yl)benzamide;

or a pharmaceutically acceptable salt thereof.

More preferably the compound of formula I is:

3-((2R,3R,7S,9αS)-2,3-dimethyl-7-phenyl-octahydro-1H-quinolizin-2-yl)phenol;

((7R,8R,9αR)-8-(3-hydroxyphenyl)-7,8-dimethyl-hexahydro-1H-pyrido[1,2-α]pyrazin-2(6H)-yl)(phenyl)methanone;

3-((7R,8R,9αR)-2-benzyl-7,8-dimethyl-octahydro-1H-pyrido[1,2-α]pyrazin-8-yl)phenol;

3-((3S,7R,8R,9αR)-7,8-dimethyl-3-phenyl-octahydro-1H-pyrido[1,2-α]pyrazin-8-yl)phenol; or 3-((3S,7R,8R,9αR)-7,8-dimethyl-3-phenyl-octahydro-1H-pyrido[1,2-α]pyrazin-8-yl)benzamide;

or a pharmaceutically acceptable salt thereof.

In an alternate embodiment, the present invention provides compounds of formula III:

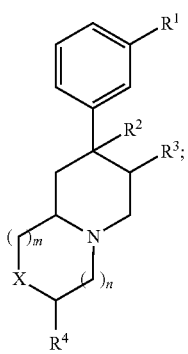

III wherein:
R$^1$ is —OH, —OR$^a$, —CH$_2$OH, —C(=O)OR$^6$, —C(=O)NR$^6$R$^7$, or —NR$^6$R$^7$;
R$^2$ and R$^3$ are each independently alkyl or alkenyl;
R$^4$ is H, alkyl, cycloalkyl, cycloalkylalkyl, aryl, heteroaryl, aralkyl, alkylaralkyl, or heteroarylalkyl;
X is CH$_2$ or NR$^5$;
R$^5$ is H, alkyl, cycloalkyl, cycloalkylalkyl, aryl, heteroaryl, aralkyl, alkylaralkyl, heteroarylalkyl, heterocycloalkylalkyl, —C(=O)OR$^{8a}$, —S(=O)$_2$R$^{8a}$, —C(=O)R$^{8b}$, or —C(=O)NR$^{8b}$R$^{8c}$;
R$^6$ is H, alkyl, cycloalkyl, alkylcycloalkyl, or aralkyl;
R$^7$ is H, alkyl, aralkyl, or aryl;
R$^{8a}$ is alkyl, cycloalkyl, cycloalkylalkyl, heteroaryl, heteroarylalkyl, aralkyl, or aryl;
R$^{8b}$ and R$^{8c}$ are each independently H, alkyl, cycloalkyl, cycloalkylalkyl, heteroaryl, heterocycloalkyl, heterocycloalkylalkyl, heteroarylalkyl, aralkyl, or aryl; or R$^{8b}$ and R$^{8c}$ taken together with the nitrogen atom to which they are connected form a 4- to 8-membered heterocycloalkyl ring;
R$^a$ is a hydroxyl protecting group;
m is 1 or 2; and
n is 0, 1, or 2;
with the provisos that:
at least one of m and n is other than 2; and
when X is NR$^5$, then n is 1 or 2;
or a pharmaceutically acceptable salt thereof.

In certain preferred embodiments, the compounds of formula III have the structure IIIa:

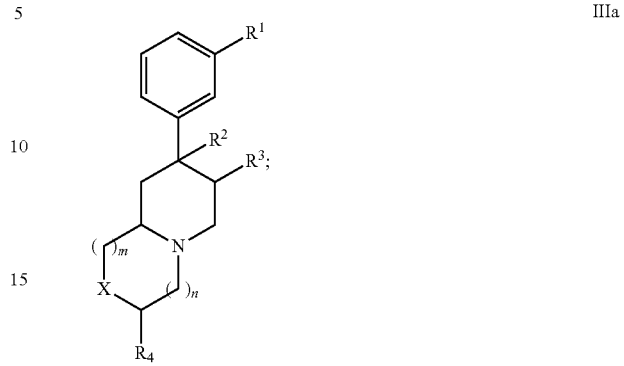

IIIa wherein:
R$^1$ is —OH, —CH$_2$OH, —C(=O)OR$^6$, —C(=O)NR$^6$R$^7$, or —NR$^6$R$^7$;
R$^2$ and R$^3$ are each independently alkyl or alkenyl;
R$^4$ is H, alkyl, cycloalkyl, cycloalkylalkyl, aryl, heteroaryl, aralkyl, alkylaralkyl, or heteroarylalkyl;
X is CH$_2$ or NR$^5$;
R$^5$ is H, alkyl, cycloalkyl, cycloalkylalkyl, aryl, heteroaryl, aralkyl, alkylaralkyl, heteroarylalkyl, heterocycloalkylalkyl, —C(=O)OR$^{8a}$, —S(=O)$_2$R$^{8a}$, —C(=O)R$^{8b}$, or —C(=O)NR$^{8b}$R$^{8c}$;
R$^6$ is H, alkyl, cycloalkyl, alkylcycloalkyl, or aralkyl;
R$^7$ is H, alkyl, aralkyl, or aryl;
R$^{8a}$ is alkyl, cycloalkyl, cycloalkylalkyl, heteroaryl, heteroarylalkyl, aralkyl, or aryl;
R$^{8b}$ and R$^{8c}$ are each independently H, alkyl, cycloalkyl, cycloalkylalkyl, heteroaryl, heterocycloalkyl, heterocycloalkylalkyl, heteroarylalkyl, aralkyl, or aryl; or R$^{8b}$ and R$^{8c}$ taken together with the nitrogen atom to which they are connected form a 4- to 8-membered heterocycloalkyl ring;
m is 1 or 2; and
n is 0, 1, or 2;
with the provisos that:
at least one of m and n is other than 2; and
when X is NR$^5$, then n is 1 or 2;
or a pharmaceutically acceptable salt thereof.

More preferably when compounds of formula III have the structure IIIa, R$^1$ is —OH, —C(=O)OR$^6$, —C(=O)NR$^6$R$^7$, or —NR$^6$R$^7$, yet more preferably —OH, —C(=O)NR$^6$R$^7$, or —NR$^6$R$^7$, still more preferably —OH or —C(=O)NR$^6$R$^7$.

In certain preferred embodiments of compounds of formula III, R$^2$ and R$^3$ are each independently C$_1$-C$_6$alkyl or C$_2$-C$_6$alkenyl, more preferably C$_1$-C$_3$alkyl or C$_2$-C$_3$alkenyl, more preferably still C$_1$-C$_3$alkyl, yet more preferably C$_1$alkyl, still more preferably methyl.

In certain preferred embodiments of compounds of formula III, R$^4$ is H, alkyl, cycloalkyl, cycloalkylalkyl, aryl, heteroaryl, aralkyl, alkylaralkyl, or heteroarylalkyl, with H, alkyl, cycloalkyl, aryl, or aralkyl being more preferred. When R$^4$ is alkyl, it is preferably C$_1$-C$_6$alkyl, more preferably C$_1$-C$_3$alkyl, yet more preferably C$_3$alk-2-yl, still more preferably isopropyl. When R$^4$ is cycloalkyl, it is preferably C$_3$-C$_{10}$cycloalkyl, more preferably C$_3$-C$_8$cycloalkyl, yet more preferably C$_3$-C$_6$cycloalkyl, still more preferably C$_5$-C$_6$cycloalkyl, still more preferably optionally substituted cyclopentyl or optionally substituted cyclohexyl. When $R^4$ is cycloalkylalkyl, it is preferably $C_3$-$C_{10}$cycloalkyl$C_1$-$C_6$alkyl, more preferably $C_3$-$C_8$cycloalkyl$C_1$-$C_3$alkyl, yet more preferably $C_3$-$C_6$cycloalkyl$C_1$-$C_3$alkyl, still more preferably $C_5$-$C_6$cycloalkyl$C_1$-$C_3$alkyl, still more preferably optionally substituted cyclopentylmethyl or optionally substituted cyclohexylmethyl. When $R^4$ is aryl, it is preferably $C_6$-$C_{10}$aryl, more preferably $C_6$aryl, yet more preferably phenyl. When $R^4$ is heteroaryl, it is preferably $C_5$-$C_{10}$heteroaryl, more preferably $C_5$-$C_6$heteroaryl, still more preferably pyridinyl or thienyl. When $R^4$ is aralkyl, it is preferably $C_6$-$C_{10}$aryl$C_1$-$C_6$alkyl, more preferably $C_6$-$C_{10}$aryl$C_1$-$C_3$alkyl, yet more preferably $C_6$aryl$C_1$-$C_3$alkyl, still more preferably $C_6$aryl$C_1$alkyl, yet more preferably optionally substituted benzyl. When $R^4$ is alkylaralkyl, it is preferably $C_1$-$C_6$alkyl$C_6$-$C_{10}$aryl$C_1$-$C_6$alkyl, more preferably $C_1$-$C_4$alkyl$C_6$-$C_{10}$aryl$C_1$-$C_3$alkyl, yet more preferably $C_1$-$C_4$alkyl$C_6$aryl$C_1$-$C_3$alkyl, still more preferably $C_1$alkyl$C_6$aryl$C_1$alkyl, yet more preferably optionally substituted methylbenzyl. When $R^4$ is heteroarylalkyl, it is preferably $C_5$-$C_{10}$heteroaryl$C_1$-$C_6$alkyl, more preferably $C_5$-$C_{10}$heteroaryl$C_1$-$C_3$alkyl, yet more preferably $C_5$-$C_6$heteroaryl$C_1$-$C_3$alkyl, still more preferably $C_5$-$C_6$heteroaryl$C_1$alkyl. In certain preferred embodiments, $R^4$ is H.

In certain preferred embodiments of compounds of formula III, X is $NR^5$.

In certain preferred embodiments of compounds of formula III, $R^5$ is H, alkyl, aryl, cycloalkylalkyl, aralkyl, alkylaralkyl, heteroarylalkyl, heterocycloalkylalkyl, $—S(=O)_2R^{8a}$, $—C(=O)R^{8b}$, or $—C(=O)NR^{8b}R^{8c}$, more preferably $—C(=O)R^{8b}$ or $—S(=O)_2R^{8a}$, still more preferably $—C(=O)R^{8b}$. In other preferred embodiments, $R^5$ is H, alkyl, aryl, cycloalkylalkyl, aralkyl, alkylaralkyl, heteroarylalkyl, or heterocycloalkylalkyl, more preferably heterocycloalkylalkyl or aralkyl, with heterocycloalkylalkyl being even more preferred. When $R^5$ is alkyl, it is preferably $C_1$-$C_6$alkyl, more preferably $C_1$-$C_3$alkyl, yet more preferably $C_1$alkyl, still more preferably methyl optionally substituted with carboxy. When $R^5$ is cycloalkyl, it is preferably $C_3$-$C_{10}$cycloalkyl, more preferably $C_3$-$C_8$cycloalkyl, yet more preferably $C_3$-$C_6$cycloalkyl, still more preferably $C_5$-$C_6$cycloalkyl, still more preferably optionally substituted cyclopentyl or optionally substituted cyclohexyl. When $R^5$ is cycloalkylalkyl, it is preferably $C_3$-$C_{10}$cycloalkyl$C_1$-$C_6$alkyl, more preferably $C_3$-$C_8$cycloalkyl$C_1$-$C_3$alkyl, yet more preferably $C_3$-$C_6$cycloalkyl$C_1$-$C_3$alkyl, still more preferably $C_5$-$C_6$cycloalkyl$C_1$-$C_3$alkyl, still more preferably optionally substituted cyclopentylmethyl or optionally substituted cyclohexylmethyl. When $R^5$ is aryl, it is preferably $C_6$-$C_{10}$aryl, more preferably $C_6$aryl, yet more preferably phenyl. When $R^5$ is heteroaryl, it is preferably $C_5$-$C_{10}$heteroaryl, more preferably $C_5$-$C_6$heteroaryl, even more preferably pyridinyl or pyrimidinyl. When $R^5$ is aralkyl, it is preferably $C_6$-$C_{10}$aryl$C_1$-$C_6$alkyl, more preferably $C_6$-$C_{10}$aryl$C_1$-$C_3$alkyl, yet more preferably $C_6$aryl$C_1$-$C_3$alkyl, still more preferably $C_6$aryl$C_1$alkyl, yet more preferably benzyl optionally substituted with $C_1$-$C_6$alkyl, halo, hydroxy, or heteroaryl, yet more preferably 2-chlorobenzyl, 3-chlorobenzyl, 2-hydroxylbenzyl, 2-methylbenzyl, 3-methylbenzyl, 2,4,5-trimethylbenzyl, or 2-(pyrid-4-yl)benzyl. When $R^5$ is alkylaralkyl, it is preferably $C_1$-$C_6$alkyl$C_6$-$C_{10}$aryl$C_1$-$C_6$alkyl, more preferably $C_1$-$C_4$alkyl$C_6$-$C_{10}$aryl$C_1$-$C_3$alkyl, yet more preferably $C_1$-$C_4$alkyl$C_6$aryl$C_1$-$C_3$alkyl, still more preferably $C_1$alkyl$C_6$aryl$C_1$alkyl, yet more preferably optionally substituted methylbenzyl. When $R^5$ is heteroarylalkyl, it is preferably $C_5$-$C_{10}$heteroaryl$C_1$-$C_6$alkyl, more preferably $C_5$-$C_{10}$heteroaryl$C_1$-$C_3$alkyl, yet more preferably $C_5$-$C_6$heteroaryl$C_1$-$C_3$alkyl, still more preferably $C_5$-$C_6$heteroaryl$C_1$alkyl, yet more preferably optionally substituted thienylmethyl. When $R^5$ is heterocycloalkylalkyl, it is preferably $C_5$-$C_{20}$heterocycloalkylalkyl, more preferably $C_9$-$C_{14}$heterocycloalkylalkyl, yet more preferably optionally substituted tetrahydroquinolinylmethyl or optionally substituted tetrahydroisoquinolinylmethyl, still more preferably optionally substituted 1,2,3,4-tetrahydroquinolin-3-ylmethyl or optionally substituted 1,2,3,4-tetrahydroisoquinolin-3-ylmethyl, even more preferably optionally substituted 1,2,3,4-tetrahydroisoquinolin-3-ylmethyl, with 6-hydroxy-1,2,3,4-tetrahydroisoquinolin-3-ylmethyl being even more preferred. In certain preferred embodiments, $R^5$ is H. In certain other embodiments, when $R^5$ is optionally substituted, it is preferably substituted with at least one hydroxy, alkyl, or $—C(=O)N(alkyl)(alkyl)$, more preferably with at least one hydroxy.

When $R^5$ is optionally substituted 1,2,3,4-tetrahydroquinolin-3-ylmethyl, a stereoisomeric center exists at the 3-position of the tetrahydroquinoline ring. As such, the 1,2,3,4-tetrahydroquinolin-3-ylmethyl moiety may exist as a racemate, a single stereoisomeric moiety, or any non-racemic combination of the (R-) and (S)-stereoisomeric moieties. In certain preferred embodiments, the 1,2,3,4-tetrahydroquinolin-3-ylmethyl moiety is present in an optically enriched form, more preferably optically enriched in its (R)-form; still more preferably substantially optically enriched in its (R)-form; and most preferably as substantially optically pure 1,2,3,4-tetrahydroquinolin-3(R)-ylmethyl. In particularly preferred embodiments, $R^5$ is substantially optically pure:

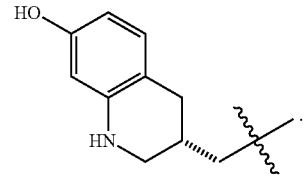 [SMILES: *C[C@@H]1CNc2cc(O)ccc2C1]

When $R^5$ is optionally substituted tetrahydroisoquinolinylmethyl, a stereoisomeric center exists at the 3-position of the tetrahydroisoquinoline ring. As such, the 1,2,3,4-tetrahydroisoquinolin-3-ylmethyl moiety may exist as a racemate, a single stereoisomeric moiety, or any non-racemic combination of the (R)- and (S)-stereoisomeric moieties. In certain preferred embodiments, the 1,2,3,4-tetrahydroisoquinolin-3-ylmethyl moiety is present in an optically enriched form, more preferably optically enriched in its (R)-form; still more preferably substantially optically enriched in its (R)-form; and most preferably as substantially optically pure 1,2,3,4-tetrahydroisoquinolin-3(R)-ylmethyl. In other preferred embodiments, $R^5$ is substantially optically pure:

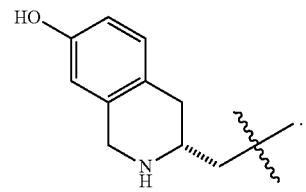

In certain preferred embodiments of compounds of formula III, $R^6$ is H, alkyl, cycloalkyl, alkylcycloalkyl, or aralkyl, with H, alkyl, alkylcycloalkyl, or aralkyl being more preferred. When $R^6$ is alkyl, it is preferably $C_1$-$C_6$alkyl, more preferably $C_1$-$C_3$alkyl, yet more preferably $C_1$alkyl, still more preferably methyl. When $R^6$ is cycloalkyl, it is preferably $C_3$-$C_{10}$cycloalkyl, more preferably $C_3$-$C_8$cycloalkyl, yet more preferably $C_3$-$C_6$cycloalkyl, still more preferably $C_5$-$C_6$cycloalkyl, still more preferably optionally substituted cyclopentyl or optionally substituted cyclohexyl. When $R^6$ is alkylcycloalkyl, it is preferably $C_1$-$C_6$alkyl$C_3$-$C_{10}$cycloalkyl$C_1$-$C_6$alkyl, more preferably $C_1$-$C_4$alkyl$C_3$-$C_8$cycloalkyl$C_1$-$C_3$alkyl, yet more preferably $C_1$-$C_4$alkyl$C_3$-$C_6$cycloalkyl$C_1$-$C_3$alkyl, still more preferably $C_1$alkyl$C_5$-$C_6$cycloalkyl$C_1$alkyl, yet more preferably optionally substituted methylcyclopentylmethyl or optionally substituted methylcyclohexylmethyl. When $R^6$ is aralkyl, it is preferably $C_6$-$C_{10}$aryl$C_1$-$C_6$alkyl, more preferably $C_6$-$C_{10}$aryl$C_1$-$C_3$alkyl, yet more preferably $C_6$aryl$C_1$-$C_3$alkyl, still more preferably $C_6$aryl$C_1$alkyl, yet more preferably benzyl. In certain preferred embodiments, $R^6$ is H.

In preferred embodiments of compounds of formula III, m is 1. Also in preferred embodiments of compounds of formula I, n is 0 or 1. In certain preferred embodiments, m and n are each 1.

In some preferred embodiments of compounds of formula III, at least one of $R^4$ and $R^5$ is H.

In certain preferred embodiments of compounds of formula III, $R^7$ is H, alkyl, aralkyl, or aryl, with H being more preferred. When $R^7$ is alkyl, it is preferably $C_1$-$C_6$alkyl, more preferably $C_1$-$C_3$alkyl, yet more preferably $C_1$alkyl, still more preferably methyl. When $R^7$ is aralkyl, it is preferably $C_6$-$C_{10}$aryl$C_1$-$C_6$alkyl, more preferably $C_6$-$C_{10}$aryl$C_1$-$C_3$alkyl, yet more preferably $C_6$aryl$C_1$-$C_3$alkyl, still more preferably $C_6$aryl$C_1$alkyl, yet more preferably benzyl. When $R^7$ is aryl, it is preferably $C_6$-$C_{10}$aryl, more preferably $C_6$aryl, yet more preferably phenyl.

In certain preferred embodiments of compounds of formula III, $R^{8a}$ is alkyl, cycloalkyl, cycloalkylalkyl, heteroaryl, heteroarylalkyl, aralkyl, or aryl. When $R^{8a}$ is alkyl, it is preferably $C_1$-$C_6$alkyl, more preferably $C_1$-$C_3$alkyl, yet more preferably $C_1$alkyl, still more preferably methyl. When $R^{8a}$ is cycloalkyl, it is preferably $C_3$-$C_{10}$cycloalkyl, more preferably $C_3$-$C_8$cycloalkyl, yet more preferably $C_3$-$C_6$cycloalkyl, still more preferably $C_5$-$C_6$cycloalkyl, still more preferably optionally substituted cyclopentyl or optionally substituted cyclohexyl. When $R^{8a}$ is cycloalkylalkyl, it is preferably $C_3$-$C_{10}$cycloalkyl$C_1$-$C_6$alkyl, more preferably $C_3$-$C_8$cycloalkyl$C_1$-$C_3$alkyl, yet more preferably $C_3$-$C_6$cycloalkyl$C_1$-$C_3$alkyl, still more preferably $C_5$-$C_6$cycloalkyl$C_1$-$C_3$alkyl, still more preferably cyclopentyl$C_1$-$C_3$alkyl or cyclohexyl$C_1$-$C_3$alkyl, yet more preferably optionally substituted cyclopentylmethyl or optionally substituted cyclohexylmethyl. When $R^{8a}$ is aryl, it is preferably $C_6$-$C_{10}$aryl, more preferably $C_6$aryl, yet more preferably phenyl. When $R^{8a}$ is heteroaryl, it is preferably $C_5$-$C_{10}$heteroaryl, more preferably $C_5$-$C_6$heteroaryl, even more preferably pyridinyl or pyrimidinyl. When $R^{8a}$ is aralkyl, it is preferably $C_6$-$C_{10}$aryl$C_1$-$C_6$alkyl, more preferably $C_6$-$C_{10}$aryl$C_1$-$C_3$alkyl, yet more preferably $C_6$aryl$C_1$-$C_3$alkyl, still more preferably $C_6$aryl$C_1$alkyl, yet more preferably benzyl. When $R^{8a}$ is heteroarylalkyl, it is preferably $C_5$-$C_{10}$heteroaryl$C_1$-$C_6$alkyl, more preferably $C_5$-$C_{10}$heteroaryl$C_1$-$C_3$alkyl, yet more preferably $C_5$-$C_6$heteroaryl$C_1$-$C_3$alkyl, still more preferably $C_5$-$C_6$heteroaryl$C_1$alkyl.

In certain preferred embodiments of compounds of formula III, $R^{8b}$ and $R^{8c}$ are each independently H, alkyl, cycloalkyl, cycloalkylalkyl, heteroaryl, heteroarylalkyl, heterocycloalkyl, heterocycloalkylalkyl, aralkyl, or aryl, more preferably aryl, heterocycloalkyl, heterocycloalkylalkyl, or aralkyl, with heterocycloalkyl, heterocycloalkylalkyl, or aralkyl being more preferred. In some other preferred embodiments of compounds of formula III, $R^{8b}$ and $R^{8c}$ are each independently aryl or aralkyl. In still other preferred embodiments, $R^{8b}$ and $R^{8c}$ are each independently heterocycloalkyl, aryl, or aralkyl, more preferably heterocycloalkyl. When $R^{8b}$ or $R^{8c}$ is alkyl, it is preferably $C_1$-$C_6$alkyl, more preferably $C_1$-$C_3$alkyl, yet more preferably $C_1$alkyl, still more preferably methyl. When $R^{8b}$ or $R^{8c}$ is cycloalkyl, it is preferably $C_3$-$C_{10}$cycloalkyl, more preferably $C_3$-$C_8$cycloalkyl, yet more preferably $C_3$-$C_6$cycloalkyl, still more preferably $C_5$-$C_6$cycloalkyl, still more preferably optionally substituted cyclopentyl or optionally substituted cyclohexyl. When $R^{8b}$ or $R^{8c}$ is cycloalkylalkyl, it is preferably $C_3$-$C_{10}$cycloalkyl$C_1$-$C_6$alkyl, more preferably $C_3$-$C_8$cycloalkyl$C_1$-$C_3$alkyl, yet more preferably $C_3$-$C_6$cycloalkyl$C_1$-$C_3$alkyl, still more preferably $C_5$-$C_6$cycloalkyl$C_1$-$C_3$alkyl, still more preferably optionally substituted cyclopentylmethyl or optionally substituted cyclohexylmethyl. When $R^{8b}$ or $R^{8c}$ is aryl, it is preferably $C_6$-$C_{10}$aryl, more preferably $C_6$aryl, yet more preferably phenyl. When $R^{8b}$ or $R^{8c}$ is heteroaryl, it is preferably $C_5$-$C_{10}$heteroaryl, more preferably $C_5$-$C_6$heteroaryl, even more preferably pyridinyl. When $R^{8b}$ or $R^{8c}$ is aralkyl, it is preferably $C_6$-$C_{10}$aryl$C_1$-$C_6$alkyl, more preferably $C_6$-$C_{10}$aryl$C_1$-$C_3$alkyl, yet more preferably $C_6$aryl$C_1$-$C_3$alkyl, still more preferably $C_6$aryl$C_2$alkyl, yet more preferably optionally substituted phenethyl, with 1-(4-hydroxyphenyl)ethyl being even more preferred. When $R^{8b}$ or $R^{8c}$ is heteroarylalkyl, it is preferably $C_5$-$C_{10}$heteroaryl$C_1$-$C_6$alkyl, more preferably $C_5$-$C_{10}$heteroaryl$C_1$-$C_3$alkyl, yet more preferably $C_5$-$C_6$heteroaryl$C_1$-$C_3$alkyl, still more preferably $C_5$-$C_6$heteroaryl$C_1$alkyl. When $R^{8b}$ or $R^{8c}$ is heterocycloalkylalkyl, it is preferably $C_5$-$C_{10}$heterocycloalkyl$C_1$-$C_6$alkyl, more preferably $C_5$-$C_{10}$heterocycloalkyl$C_1$-$C_3$alkyl, still more preferably $C_5$-$C_{10}$heterocycloalkyl$C_1$alkyl, yet more preferably $C_5$-$C_{10}$heterocycloalkylmethyl, even more preferably optionally substituted tetrahydroquinolinylmethyl or optionally substituted tetrahydroisoquinolinylmethyl, still more preferably optionally substituted 1,2,3,4-tetrahydroquinolin-3-ylmethyl or optionally substituted 1,2,3,4-tetrahydroisoquinolin-3-ylmethyl, even more preferably optionally substituted 1,2,3,4-tetrahydroisoquinolin-3-ylmethyl, with 6-hydroxy-1,2,3,4-tetrahydroisoquinolin-3-ylmethyl being even more preferred. When $R^{8b}$ or $R^{8c}$ is heterocycloalkyl, it is preferably $C_5$-$C_{15}$heterocycloalkyl, more preferably $C_9$-$C_{14}$heterocycloalkyl, yet more preferably optionally substituted tetrahydroquinolinylmethyl or optionally substituted tetrahydroisoquinolinylmethyl, still more preferably optionally substituted 1,2,3,4-tetrahydroquinolin-3-ylmethyl or optionally substituted 1,2,3,4-tetrahydroisoquinolin-3-ylmethyl, even more preferably optionally substituted 1,2,3,4-tetrahydroisoquinolin-3-ylmethyl, with 6-hydroxy-1,2,3,4-tetrahydroisoquinolin-3-ylmethyl being even more preferred. In certain other embodiments, when $R^{8b}$ or $R^{8c}$ is optionally substituted, it is preferably substituted with at least one hydroxy, alkyl, or —C(=O)N(alkyl)(alkyl), more preferably with at least one hydroxy.

When $R^{8b}$ or $R^{8c}$ is optionally substituted 1,2,3,4-tetrahydroquinolin-3-ylmethyl, a stereoisomeric center exists at the 3-position of the tetrahydroquinoline ring. As such, the 1,2,3,4-tetrahydroquinolin-3-ylmethyl moiety may exist as a racemate, a single stereoisomeric moiety, or any non-racemic combination of the (R)- and (S)-stereoisomeric moieties. In certain preferred embodiments, the 1,2,3,4-tetrahydroquinolin-3-ylmethyl moiety is present in an optically enriched configuration, more preferably optically enriched in its (R)-configuration; still more preferably substantially optically enriched in its (R)-configuration; and most preferably as substantially optically pure 1,2,3,4-tetrahydroquinolin-3(R)-ylmethyl. In other preferred embodiments, $R^{8b}$ or $R^{8c}$ is substantially optically pure:

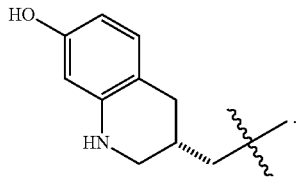 [SMILES: *C[C@@H]1CNc2cc(O)ccc2C1]

When $R^{8b}$ or $R^{8c}$ is optionally substituted tetrahydroisoquinolinylmethyl, a stereocenter exists at the 3-position of the tetrahydroisoquinoline ring. As such, the 1,2,3,4-tetrahydroisoquinolin-3-ylmethyl moiety may exist as a racemate, a single stereoisomeric moiety, or any non-racemic combination of the (R)- and (S)-stereoisomeric moieties. In certain preferred embodiments, the 1,2,3,4-tetrahydroisoquinolin-3-ylmethyl moiety is present in an optically enriched configuration, more preferably optically enriched in its (R)-configuration; still more preferably substantially optically enriched in its (R)-configuration; and most preferably as substantially optically pure 1,2,3,4-tetrahydroisoquinolin-3(R)-ylmethyl. In other preferred embodiments, $R^{8b}$ or $R^{8c}$ is substantially optically pure:

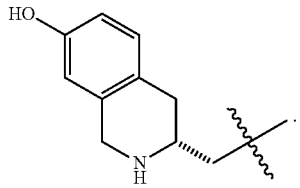 [SMILES: *C[C@H]1Cc2ccc(O)cc2CN1]

When $R^{8b}$ or $R^{8c}$ is optionally substituted 1,2,3,4-tetrahydroquinolin-3-yl, a stereoisomeric center exists at the 3-position of the tetrahydroquinoline ring. As such, the 1,2,3,4-tetrahydroquinolin-3-yl moiety may exist as a racemate, a single stereoisomeric moiety, or any non-racemic combination of the (R)- and (S)-stereoisomeric moieties. In certain preferred embodiments, the 1,2,3,4-tetrahydroquinolin-3-yl moiety is present in an optically enriched configuration, more preferably optically enriched in its (R)-configuration; still more preferably substantially optically enriched in its (R)-configuration; and most preferably as substantially optically pure 1,2,3,4-tetrahydroquinolin-3(R)-yl. In other preferred embodiments, $R^{8b}$ or $R^{8c}$ is substantially optically pure:

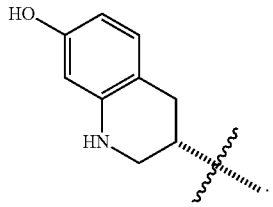

When $R^{8b}$ or $R^{8c}$ is optionally substituted tetrahydroisoquinolinyl, a stereocenter exists at the 3-position of the tetrahydroisoquinoline ring. As such, the 1,2,3,4-tetrahydroisoquinolin-3-yl moiety may exist as a racemate, a single stereoisomeric moiety, or any non-racemic combination of the (R)- and (S)-stereoisomeric moieties. In certain preferred embodiments, the 1,2,3,4-tetrahydroisoquinolin-3-yl moiety is present in an optically enriched configuration, more preferably optically enriched in its (R)-configuration; still more preferably substantially optically enriched in its (R)-configuration; and most preferably as substantially optically pure 1,2,3,4-tetrahydroisoquinolin-3(R)-yl. In other preferred embodiments, $R^{8b}$ or $R^{8c}$ is substantially optically pure:

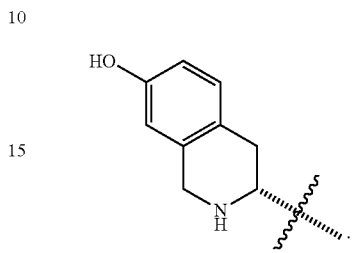

In certain other preferred embodiments of compounds of formula III, $R^{8b}$ and $R^{8c}$, taken together with the nitrogen atom to which they are connected, form a 4- to 8-membered heterocycloalkyl ring, more preferably a 5- to 7-membered heterocycloalkyl ring, more preferably still, a 5- to 6-membered heterocycloalkyl ring, yet more preferably an optionally substituted morpholine ring.

In some preferred embodiments, the compounds of formula III have the structure corresponding to formula IVa:

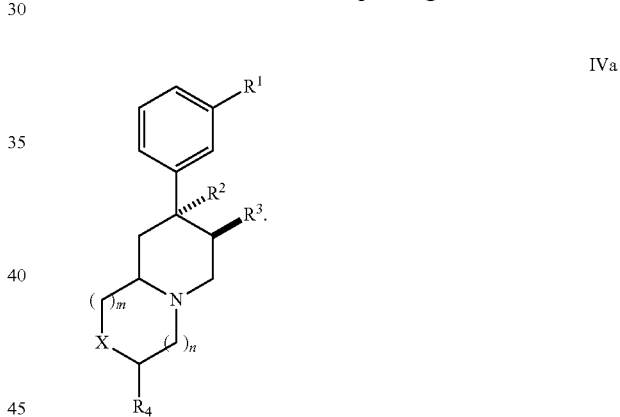

In some preferred embodiments, the compounds of formula I have the structure corresponding to formula IVb:

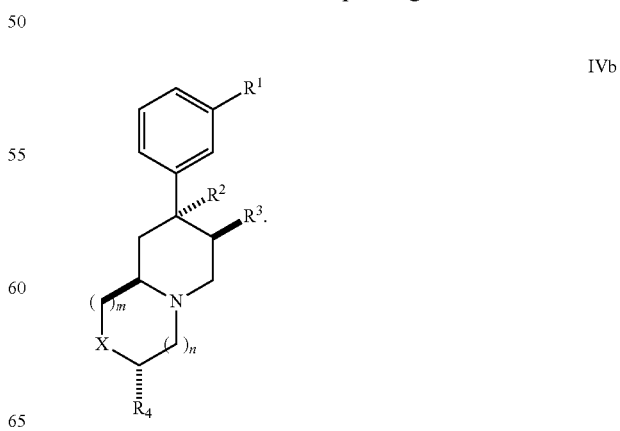

In particularly preferred embodiments, the compound of formula III is:
3-(4-hydroxyphenyl)-1-(8-(3-hydroxyphenyl)-3-isopropyl-7,8-dimethyl-hexahydro-1H-pyrido[1,2-α]pyrazin-2(6H)-yl)propan-1-one;
(7-hydroxy-1,2,3,4-tetrahydroisoquinolin-3-yl)-(8-(3-hydroxyphenyl)-3-isopropyl-7,8-dimethyl-hexahydro-1H-pyrido[1,2-α]pyrazin-2(6H)-yl)methanone;
3-(2,3-dimethyl-octahydro-1H-quinolizin-2-yl)phenol;
1-(8-(3-hydroxyphenyl)-7,8-dimethyl-3-phenyl-hexahydro-1H-pyrido[1,2-α]pyrazin-2(6H)-yl)ethanone;
methyl-3-(2-benzyl-7,8-dimethyl-3-phenyl-octahydro-1H-pyrido[1,2-α]pyrazin-8-yl)benzoate;
3-(2-benzyl-7,8-dimethyl-3-phenyl-octahydro-1H-pyrido[1,2-α]pyrazin-8-yl)benzoic acid;
3-(7,8-dimethyl-octahydro-1H-pyrido[1,2-α]pyrazin-8-yl)phenol;
3-(3-isopropyl-7,8-dimethyl-octahydro-1H-pyrido[1,2-α]pyrazin-8-yl)phenol;
3-(2,7,8-trimethyl-octahydro-1H-pyrido[1,2-α]pyrazin-8-yl)phenol;
1-(8-(3-hydroxyphenyl)-7,8-dimethyl-hexahydro-1H-pyrido[1,2-α]pyrazin-2(6H)-yl)ethanone;
1-(8-(3-hydroxyphenyl)-7,8-dimethyl-hexahydro-1H-pyrido[1,2-α]pyrazin-2(6H)-yl)-3-phenylpropan-1-one;
3-(7,8-dimethyl-2-(3-phenylpropyl)-octahydro-1H-pyrido[1,2-α]pyrazin-8-yl)phenol;
3-(7,8-dimethyl-2-(methylsulfonyl)-octahydro-1H-pyrido[1,2-α]pyrazin-8-yl)phenol; or
8-(3-hydroxyphenyl)-7,8-dimethyl-N-phenyl-hexahydro-1H-pyrido[1,2-α]pyrazine-2(6H)-carboxamide;
or a pharmaceutically acceptable salt thereof.
More preferably the compound of formula III is:
3-(4-hydroxyphenyl)-1-((3S,7R,8R,9αR)-8-(3-hydroxyphenyl)-3-isopropyl-7,8-dimethyl-hexahydro-1H-pyrido[1,2-α]pyrazin-2(6H)-yl)propan-1-one;
((R)-7-hydroxy-1,2,3,4-tetrahydroisoquinolin-3-yl)((3S,7R,8R,9αR)-8-(3-hydroxyphenyl)-3-isopropyl-7,8-dimethyl-hexahydro-1H-pyrido[1,2-α]pyrazin-2(6H)-yl)methanone;
3-((2R,3R,9αR)-2,3-dimethyl-octahydro-1H-quinolizin-2-yl)phenol;
3-((2R,3R,9αS)-2,3-dimethyl-octahydro-1H-quinolizin-2-yl)phenol;
1-((3S,7R,8R,9αR)-8-(3-hydroxyphenyl)-7,8-dimethyl-3-phenyl-hexahydro-1H-pyrido[1,2-α]pyrazin-2(6H)-yl)ethanone;
methyl-3-((3S,7R,8R,9αR)-2-benzyl-7,8-dimethyl-3-phenyl-octahydro-1H-pyrido[1,2-α]pyrazin-8-yl)benzoate;
3-((3S,7R,8R,9αR)-2-benzyl-7,8-dimethyl-3-phenyl-octahydro-1H-pyrido[1,2-α]pyrazin-8-yl)benzoic acid;
3-((3R,7R,8R,9αR)-7,8-dimethyl-3-phenyl-octahydro-1H-pyrido[1,2-α]pyrazin-8-yl)phenol;
3-((7R,8R,9αR)-7,8-dimethyl-octahydro-1H-pyrido[1,2-α]pyrazin-8-yl)phenol;
3-((3S,7R,8R,9αR)-3-Isopropyl-7,8-dimethyl-octahydro-1H-pyrido[1,2-α]pyrazin-8-yl)phenol;
3-((7R,8R,9αR)-2,7,8-trimethyl-octahydro-1H-pyrido[1,2-α]pyrazin-8-yl)phenol;
1-((7R,8R,9αR)-8-(3-hydroxyphenyl)-7,8-dimethyl-hexahydro-1H-pyrido[1,2-α]pyrazin-2(6H)-yl)ethanone;
1-((7R,8R,9αR)-8-(3-hydroxyphenyl)-7,8-dimethyl-hexahydro-1H-pyrido[1,2-α]pyrazin-2(6H)-yl)-3-phenylpropan-1-one;
3-((7R,8R,9αR)-7,8-dimethyl-2-(3-phenylpropyl)-octahydro-1H-pyrido[1,2-α]pyrazin-8-yl)phenol;
3-((7R,8R,9αR)-7,8-dimethyl-2-(methylsulfonyl)-octahydro-1H-pyrido[1,2-α]pyrazin-8-yl)phenol; or
(7R,8R,9αR)-8-(3-hydroxyphenyl)-7,8-dimethyl-N-phenyl-hexahydro-1H-pyrido[1,2-α]pyrazine-2(6H)-carboxamide;
or a pharmaceutically acceptable salt thereof.

In other particularly preferred embodiments, the compound of formula III is:
3-(4-hydroxyphenyl)-1-(8-(3-hydroxyphenyl)-3-isopropyl-7,8-dimethyl-hexahydro-1H-pyrido[1,2-α]pyrazin-2(6H)-yl)propan-1-one; or
(7-hydroxy-1,2,3,4-tetrahydroisoquinolin-3-yl)-(8-(3-hydroxyphenyl)-3-isopropyl-7,8-dimethyl-hexahydro-1H-pyrido[1,2-α]pyrazin-2(6H)-yl)methanone,
or a pharmaceutically acceptable salt thereof.

In certain other more preferred embodiments, the compound of formula III is:
3-(4-hydroxyphenyl)-1-((3S,7R,8R,9αR)-8-(3-hydroxyphenyl)-3-isopropyl-7,8-dimethyl-hexahydro-1H-pyrido[1,2-α]pyrazin-2(6H)-yl)propan-1-one; or
((R)-7-hydroxy-1,2,3,4-tetrahydroisoquinolin-3-yl)((3S,7R,8R,9αR)-8-(3-hydroxyphenyl)-3-isopropyl-7,8-dimethyl-hexahydro-1H-pyrido[1,2-α]pyrazin-2(6H)-yl)methanone;
or a pharmaceutically acceptable salt thereof.

In yet other embodiments, the invention is directed to methods for binding opioid receptors in a patient in need thereof, comprising the step of:
administering to the patient a composition comprising an effective amount of a compound of the invention, preferably a compound of formula Ia or formula IIIa; or a pharmaceutically acceptable salt thereof.

In some preferred embodiments, the present methods are directed to binding μ, κ, or δ opioid receptors. In certain more preferred embodiments wherein μ opioid receptors are bound, the receptors are located in the central nervous system; in other more preferred embodiments the receptors are located peripherally to the central nervous system. In certain other more preferred embodiments wherein κ opioid receptors are bound, the receptors are located in the central nervous system; in other more preferred embodiments the receptors are located peripherally to the central nervous system. In still other more preferred embodiments wherein δ opioid receptors are bound, the receptors are located in the central nervous system; in other more preferred embodiments the receptors are located peripherally to the central nervous system. In still other preferred embodiments of methods that bind opioid receptors in a patient in need thereof, the binding antagonizes the activity of the opioid receptors. In some preferred embodiments of methods that bind opioid receptors in a patient in need thereof, the compound administered exhibits activity toward the opioid receptors. In some more preferred embodiments, the compound administered does not substantially cross the blood-brain barrier.

In certain embodiments of methods for binding opioid receptors in a patient in need thereof, the methods comprise the step of:
administering to the patient a composition comprising an effective amount of a compound of the invention, preferably a compound of formula Ia or formula IIIa. In certain embodiments, the patient is in need of prevention or treatment of a condition or disease caused by an opioid wherein the opioid may be endogenous or exogenous. In certain preferred embodiments, the compound of the invention, preferably a compound of formula Ia or formula IIIa, may be administered in combination with an effective amount of at least one opioid.

In other embodiments, the invention is directed to methods of preventing or treating gastrointestinal dysfunction, comprising the step of:

administering to a patient in need thereof, a composition comprising an effective amount of a compound of the invention, preferably a compound of formula Ia or formula IIIa, or a pharmaceutically acceptable salt thereof.

In yet other embodiments, the invention is directed to methods of preventing or treating ileus, comprising the step of:

administering to a patient in need thereof, a composition comprising an effective amount of a compound of the invention, preferably a compound of formula Ia or formula IIIa, or a pharmaceutically acceptable salt thereof. Preferably, the ileus is post-operative ileus.

In yet other embodiments, the invention is directed to methods of preventing or treating obesity, comprising the step of:

administering to a patient in need thereof, a composition comprising an effective amount of a compound of the invention, preferably a compound of formula Ia or formula IIIa, or a pharmaceutically acceptable salt thereof.

In other embodiments, the invention is directed to methods of preventing or treating a side effect associated with an opioid, comprising the step of:

administering to a patient in need thereof, a composition comprising an effective amount of a compound of the invention, preferably a compound of formula Ia or formula IIIa, or a pharmaceutically acceptable salt thereof.

In certain preferred embodiments, the side effect is selected from the group consisting of constipation, nausea, vomiting, and combinations thereof. In other preferred embodiments, the administering step occurs before, during or after a step of administering at least one opioid.

In yet other embodiments, the invention is directed to methods of preventing or treating pain, comprising the step of:

administering to a patient in need thereof, a composition, comprising:

an effective amount of an opioid; and an effective amount of a compound of the invention, preferably a compound of formula Ia or formula IIIa, or a pharmaceutically acceptable salt thereof.

The compounds employed in the methods of the present invention may exist in prodrug form. As used herein, "prodrug" is intended to include any covalently bonded carriers which release the active parent drug, for example, as according to compounds of the invention, preferably compounds of formula Ia or formula IIIa, employed in the methods of the present invention in vivo when such prodrug is administered to a mammalian subject. Since prodrugs are known to enhance numerous desirable qualities of pharmaceuticals (e.g., solubility, bioavailability, manufacturing, etc.) the compounds employed in the present methods may, if desired, be delivered in prodrug form. Thus, the present invention contemplates methods of delivering prodrugs. Prodrugs of the compounds employed in the present invention, for example compounds of the invention, preferably compounds of formula Ia or formula IIIa, or a pharmaceutically acceptable salt thereof, may be prepared by modifying functional groups present in the compound in such a way that the modifications are cleaved, either in routine manipulation or in vivo, to the parent compound.

Accordingly, prodrugs include, for example, compounds described herein in which a hydroxy, amino, or carboxy group is bonded to any group that, when the prodrug is administered to a mammalian subject, cleaves to form a free hydroxyl, free amino, or carboxylic acid, respectively. Examples include, but are not limited to, acetate, formate and benzoate derivatives of alcohol and amine functional groups; and alkyl, carbocyclic, aryl, and alkylaryl esters such as methyl, ethyl, propyl, iso-propyl, butyl, isobutyl, sec-butyl, tert-butyl, cyclopropyl, phenyl, benzyl, and phenethyl esters, and the like.

The compounds employed in the methods of the present invention may be prepared in a number of ways well known to those skilled in the art. The compounds can be synthesized, for example, by the methods described below, or variations thereon as appreciated by the skilled artisan. All processes disclosed in association with the present invention are contemplated to be practiced on any scale, including milligram, gram, multigram, kilogram, multikilogram or commercial industrial scale.

As discussed in detail above, compounds employed in the present methods may contain one or more asymmetrically substituted carbon atoms, and may be isolated in optically active or racemic forms. Thus, all non-racemic (e.g., any molecule having one or more stereoisomeric centers whose configuration or configurations is/are optically enriched, substantially optically enriched, or substantially optically pure), diastereomeric, or racemic forms and all geometric isomeric forms of a structure are intended, unless the specific stereochemistry or isomeric form is specifically indicated. It is well known in the art how to prepare and isolate such optically active forms. For example, mixtures of stereoisomers may be separated by standard techniques including, but not limited to, resolution of racemic forms, normal, reverse-phase, and chiral chromatography, preferential salt formation, recrystallization, and the like, or by chiral synthesis either from chiral starting materials or by deliberate synthesis of target chiral centers.

As will be readily understood, functional groups present may contain protecting groups during the course of synthesis. Protecting groups are known per se as chemical functional groups that can be selectively appended to and removed from functionalities, such as hydroxyl groups and carboxy groups. These groups are present in a chemical compound to render such functionality inert to chemical reaction conditions to which the compound is exposed. Any of a variety of protecting groups may be employed with the present invention. Preferred protecting groups include the benzyloxycarbonyl group and the tert-butyloxycarbonyl groups. Preferred hydroxyl protecting groups include the benzyl and the tertiary-butyldimethylsilyl groups. Other preferred protecting groups that may be employed in accordance with the present invention may be described in Greene, T. W. and Wuts, P. G. M., *Protective Groups in Organic Synthesis* 3d. Ed., Wiley & Sons, 1991.

While not intending to be bound by any theory or theories of operation, it is contemplated that opioid side effects, such as constipation, vomiting, and nausea, may result from undesirable interaction of the opioid with peripheral opioid receptors, such as peripheral µ receptors. According to one aspect of the present invention, administration of the compounds of the invention, preferably the compounds of formula Ia or formula IIIa, as described herein, or a pharmaceutically acceptable salt thereof, may block interaction of the opioid compounds with the peripheral receptors, thereby preventing and/or inhibiting the side effects, while preferably not interfering with the therapeutic effect of the opioid in the CNS.

As noted above, certain embodiments of the present invention involve, inter alia, an opioid compound. A wide variety of opioids is available that may be suitable for use in the present methods and compositions. Generally speaking, it is only necessary that the opioid provide the desired effect (for example, pain alleviation), and be capable of being incorporated into the present combination products and methods (discussed in detail below). In preferred embodiments, the present methods and compositions may involve an opioid that is selected from alfentanil, buprenorphine, butorphanol, codeine, dezocine, dihydrocodeine, fentanyl, hydrocodone, hydromorphone, levorphanol, meperidine (pethidine), methadone, morphine, nalbuphine, oxycodone, oxymorphone, pentazocine, propiram, propoxyphene, sufentanil and/or tramadol, and/or mixtures thereof. More preferably, the opioid is selected from morphine, codeine, oxycodone, hydrocodone, dihydrocodeine, propoxyphene, fentanyl, tramadol, and/or mixtures thereof.

The opioid component of the present methods and compositions may further include one or more other active ingredients that may be conventionally employed in analgesic and/or cough-cold-antitussive combination products. Such conventional ingredients include, for example, aspirin, acetaminophen, phenylpropanolamine, phenylephrine, chlorpheniramine, caffeine, and/or guaifenesin. Typical or conventional ingredients that may be included in the opioid component are described, for example, in the *Physicians' Desk Reference,* 1999, the disclosure of which is hereby incorporated herein by reference, in its entirety.

In addition, the opioid component may further include one or more compounds that may be designed to enhance the analgesic potency of the opioid and/or to reduce analgesic tolerance development. Such compounds include, for example, dextromethorphan or other NMDA antagonists (Mao, M. J., et al., *Pain,* 1996, 67, 361), L-364, 718 and other CCK antagonists (Dourish, C. T., et al., *Eur. J. Pharmacol.,* 1988, 147, 469), NOS inhibitors (Bhargava, H. N., et al., *Neuropeptides,* 1996, 30, 219), PKC inhibitors (Bilsky, E. J., et al., *J. Pharmacol. Exp. Ther.,* 1996, 277, 484), and dynorphin antagonists or antisera (Nichols, M. L., et al., *Pain,* 1997, 69, 317). The disclosures of each of the foregoing documents are hereby incorporated herein by reference, in their entireties.

Other opioids, optional conventional opioid components, and optional compounds for enhancing the analgesic potency of the opioid and/or for reducing analgesic tolerance development, that may be employed in the methods and compositions of the present invention, in addition to those exemplified above, would be readily apparent to one of ordinary skill in the art, once armed with the teachings of the present disclosure.

Although the compounds of the present invention may be administered as the pure chemicals, it is preferable to present the active ingredient as a pharmaceutical composition. The invention thus further provides a pharmaceutical composition comprising an effective amount of one or more of the compounds of the invention, preferably one or more compounds of formula Ia or formula IIIa, as described herein, together with one or more pharmaceutically acceptable carriers therefore and, optionally, other therapeutic and/or prophylactic ingredients. The carrier(s) must be acceptable in the sense of being compatible with the other ingredients of the composition and not deleterious to the recipient thereof.

The compounds of the invention may be administered in an effective amount by any of the conventional techniques well-established in the medical field. The compounds employed in the methods of the present invention including, for example, opioids and the compounds of the invention, preferably compounds of formula Ia or formula IIIa, as described herein, or a pharmaceutically acceptable salt thereof, may be administered by any means that results in the contact of the active agent(s) with the relevant site or site(s) of action in the body of a patient. The compounds may be administered by any conventional means available for use in conjunction with pharmaceuticals, either as individual therapeutic agents or in a combination of therapeutic agents. For example, they may be administered as the sole active agents in a pharmaceutical composition, or they can be used in combination with other therapeutically active ingredients.

The compounds are preferably combined with a pharmaceutical carrier selected on the basis of the chosen route of administration and standard pharmaceutical practice as described, for example, in *Remington's Pharmaceutical Sciences* (Mack Pub. Co., Easton, Pa., 1980), the disclosures of which are hereby incorporated herein by reference, in their entirety.

Compounds of the present invention, preferably compounds of formula Ia or formula IIIa, may be administered to a mammalian host in a variety of forms adapted to the chosen route of administration, e.g., orally or parenterally. Parenteral administration in this respect includes administration by the following routes: intravenous, intramuscular, subcutaneous, intraocular, intrasynovial, transepithelial including transdermal, ophthalmic, sublingual and buccal; topically including ophthalmic, dermal, ocular, rectal and nasal inhalation via insufflation, aerosol, and rectal systemic.

The active compound may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the active compound may be incorporated with excipient and used in the form of ingestible tablets, buccal tablets, troches, capsules, elixirs, suspensions, syrups, wafers, and the like. The amount of active compound(s) in such therapeutically useful compositions is preferably such that a suitable dosage will be obtained. Preferred compositions or preparations according to the present invention may be prepared so that an oral dosage unit form contains from about 0.1 to about 1000 mg of active compound, and all combinations and subcombinations of dosage ranges and specific dosage amounts therein.

The tablets, troches, pills, capsules and the like may also contain one or more of the following: a binder, such as gum tragacanth, acacia, corn starch, or gelatin; an excipient, such as dicalcium phosphate; a disintegrating agent, such as corn starch, potato starch, alginic acid, and the like; a lubricant, such as magnesium stearate; a sweetening agent such as sucrose, lactose or saccharin; or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, and/or a dye and flavoring, such as cherry or orange flavor. Of course, any material used in preparing any dosage unit form is preferably pharmaceutically pure and substantially non-toxic in the amounts employed. In addition, the active compound may be incorporated into sustained-release preparations and formulations.

The active compound may also be administered parenterally or intraperitoneally. Solutions of the active compounds as free bases or pharmacologically acceptable salts can be prepared in water suitably mixed with a surfactant, such as hydroxypropylcellulose. A dispersion can also be prepared in glycerol, liquid polyethylene glycols, and mixtures thereof and in oils. Under ordinary conditions of storage and use, these preparations may contain a preservative to prevent the growth of microorganisms.

The pharmaceutical forms suitable for injectable use include, for example, sterile aqueous solutions or dispersions and sterile powders for the extemporaneous preparation of sterile injectable solutions or dispersions. In all cases, the form is preferably sterile and fluid to provide easy syringability. It is preferably stable under the conditions of manufacture and storage and is preferably preserved against the contaminating action of microorganisms such as bacteria and fungi. The carrier may be a solvent or dispersion medium containing, for example, water, ethanol, polyol (for example, glycerol, propylene glycol, liquid polyethylene glycol, and the like), suitable mixtures thereof, and vegetable oils. The proper fluidity can be maintained, for example, by the use of a coating, such as lecithin, by the maintenance of the required particle size in the case of a dispersion, and by the use of surfactants. The prevention of the action of microorganisms may be achieved by various antibacterial and antifungal agents, for example, parabens, chlorobutanol, phenol, sorbic acid, thimerosal, and the like. In many cases, it will be preferable to include isotonic agents, for example, sugars, or sodium chloride. Prolonged absorption of the injectable compositions may be achieved by the use of agents delaying absorption, for example, aluminum monostearate and gelatin.

Sterile injectable solutions may be prepared by incorporating the active compounds in the required amounts, in the appropriate solvent, with various of the other ingredients enumerated above, as required, followed by filtered sterilization. Generally, dispersions may be prepared by incorporating the sterilized active ingredient into a sterile vehicle which contains the basic dispersion medium and the required other ingredients from those enumerated above. In the case of sterile powders for the preparation of sterile injectable solutions, the preferred methods of preparation may include vacuum drying and the freeze drying technique that yields a powder of the active ingredient, plus any additional desired ingredient from the previously sterile-filtered solution thereof.

The therapeutic compounds of this invention may be administered to a patient alone or in combination with a pharmaceutically acceptable carrier. The relative proportions of active ingredient and carrier may be determined, for example, by the solubility and chemical nature of the compounds, chosen route of administration, and standard pharmaceutical practice.

The dosage of the compounds of the present invention that will be most suitable for prophylaxis or treatment will vary with the form of administration, the particular compound chosen and the physiological characteristics of the particular patient under treatment. Generally, small dosages may be used initially and, if necessary, increased by small increments until the desired effect under the circumstances is reached. Generally speaking, oral administration may require higher dosages. Although the proper dosage of the products of this invention will be readily ascertainable by one skilled in the art, once armed with the present disclosure, by way of general guidance, for example, typically a daily dosage of the compound of the invention, preferably a compound of formula Ia or formula IIIa, as described herein, may range from about 0.001 to about 100 milligrams (and all combinations and subcombinations of ranges and specific dosage amounts therein), per kilogram of patient body weight. Preferably, the daily dosage may be about 0.01 to about 10 milligrams of the compound of the invention, preferably a compound of formula Ia or formula IIIa per kilogram of patient body weight. Even more preferably, the daily dosage may be about 0.1 milligrams of the compound of the invention, preferably a compound of formula Ia or formula IIIa per kilogram of patient body weight. With regard to a typical dosage form of this type, such as a tablet, the compounds of the invention, preferably a compound of formula Ia or formula IIIa, generally may be present in an amount of about 0.1 to about 4 milligrams.

The combination products of this invention, such as pharmaceutical compositions comprising one or more opioids in combination with one or more compounds of the invention, preferably one or more compounds of formula Ia or formula IIIa, as described herein, or one or more pharmaceutically acceptable salts thereof, may be in any dosage form, such as those described herein, and can also be administered in various ways, as described herein. In a preferred embodiment, the combination products of the invention are formulated together, in a single dosage form (that is, combined together in one capsule, tablet, powder, or liquid, etc.). When the combination products are not formulated together in a single dosage form, the opioid compound and the compound of the invention, preferably a compound of formula Ia or formula IIIa, may be administered at the same time (that is, together), or in any order. When not administered at the same time, preferably the administration of an opioid and the compound of the invention, preferably a compound of formula Ia or formula IIIa, occur less than about one hour apart, more preferably less than about 30 minutes apart, even more preferably less than about 15 minutes apart, and still more preferably less than about 5 minutes apart. Preferably, administration of the combination products of the invention is oral, although other routes of administration, as described above, are contemplated to be within the scope of the present invention. Although it is preferable that the opioid and the compound of the invention, preferably a compound of formula Ia or formula IIIa, are both administered in the same fashion (that is, for example, both orally), if desired, they may each be administered in different fashions (that is, for example, one component of the combination product may be administered orally, and another component may be administered intravenously). The dosage of the combination products of the invention may vary depending upon various factors such as the pharmacodynamic characteristics of the particular agent and its mode and route of administration, the age, health and weight of the recipient, the nature and extent of the symptoms, the kind of concurrent treatment, the frequency of treatment, and the effect desired.

Although the proper dosage of the combination products of this invention will be readily ascertainable by one skilled in the art, once armed with the present disclosure, by way of general guidance, where an opioid compound is combined with a compound of the invention, preferably a compound of formula Ia or formula IIIa, as described herein, for example, typically a daily dosage may range from about 0.01 to about 100 milligrams of the opioid (and all combinations and subcombinations of ranges and specific dosage amounts therein) and about 0.001 to about 100 milligrams of the compound of the invention, preferably a compound of formula Ia or formula IIIa, (and all combinations and subcombinations of ranges and specific dosage amounts therein), per kilogram of patient body weight. Preferably, a daily dosage may be about 0.1 to about 10 milligrams of the opioid and about 0.01 to about 10 milligrams of the compound of the invention, preferably a compound of formula Ia or formula IIIa, per kilogram of patient body weight. Even more preferably, the daily dosage may be about 1.0 milligrams of the opioid and about 0.1 milligrams of the compound of the invention, preferably a compound of formula Ia or formula IIIa, per kilogram of patient body weight. With regard to a typical dosage form of this type of combination product, such as a tablet, the opioid compound (e.g., morphine) generally may be present in an amount of about 15 to about 200 milligrams, and the compound of the invention, preferably a compound of formula Ia or formula IIIa, in an amount of about 0.1 to about 4 milligrams.

Particularly when provided as a single dosage form, the potential exists for a chemical interaction between the combined active ingredients (for example, an opioid and a compound of the invention, preferably a compound of formula Ia or formula IIIa). For this reason, the preferred dosage forms of the combination products of this invention are formulated such that although the active ingredients are combined in a single dosage form, the physical contact between the active ingredients is minimized (that is, reduced).

In order to minimize contact, one embodiment of this invention where the product is orally administered provides for a combination product wherein one active ingredient is enteric coated. By enteric coating one or more of the active ingredients, it is possible not only to minimize the contact between the combined active ingredients, but also, it is possible to control the release of one of these components in the gastrointestinal tract such that one of these components is not released in the stomach but rather is released in the intestines. Another embodiment of this invention where oral administration is desired provides for a combination product wherein one of the active ingredients is coated with a sustained-release material that effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low-viscosity grade of hydroxypropyl methylcellulose (HPMC) or other appropriate materials as known in the art, in order to further separate the active components. The polymer coating serves to form an additional barrier to interaction with the other component.

Dosage forms of the combination products of the present invention wherein one active ingredient is enteric coated can be in the form of tablets such that the enteric coated component and the other active ingredient are blended together and then compressed into a tablet or such that the enteric coated component is compressed into one tablet layer and the other active ingredient is compressed into an additional layer. Optionally, in order to further separate the two layers, one or more placebo layers may be present such that the placebo layer is between the layers of active ingredients. In addition, dosage forms of the present invention can be in the form of capsules wherein one active ingredient is compressed into a tablet or in the form of a plurality of microtablets, particles, granules or non-perils, which are then enteric coated. These enteric coated microtablets, particles, granules or non-perils are then placed into a capsule or compressed into a capsule along with a granulation of the other active ingredient.

These as well as other ways of minimizing contact between the components of combination products of the present invention, whether administered in a single dosage form or administered in separate forms but at the same time by the same manner, will be readily apparent to those skilled in the art, once armed with the present disclosure.

Pharmaceutical kits useful in, for example, the treatment of pain, which comprise a therapeutically effective amount of an opioid along with a therapeutically effective amount of one or more quinolizidine and octahydropyridopyrazine compounds of the invention, in one or more sterile containers, are also within the ambit of the present invention. Sterilization of the container may be carried out using conventional sterilization methodology well known to those skilled in the art. The sterile containers of materials may comprise separate containers, or one or more multi-part containers, as exemplified by the UNIVIAL™ two-part container (available from Abbott Labs, Chicago, Ill.), as desired. The opioid compound and the compound of the invention, preferably a compound of formula Ia or formula IIIa, may be separate, or combined into a single dosage form as described above. Such kits may further include, if desired, one or more of various conventional pharmaceutical kit components, such as for example, one or more pharmaceutically acceptable carriers, additional vials for mixing the components, etc., as will be readily apparent to those skilled in the art. Instructions, either as inserts or as labels, indicating quantities of the components to be administered, guidelines for administration, and/or guidelines for mixing the components, may also be included in the kit.

It will be further appreciated that the amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The dose may also be provided by controlled release of the compound, by techniques well known to those in the art.

The compounds of the present invention may be used in methods to bind opioid receptors, including $\mu$, $\kappa$, and/or $\delta$ opioid receptors. Such binding may be accomplished by contacting the receptor with an effective amount of the compound of the invention. Preferably, the contacting step conducted in an aqueous medium, preferably at physiologically relevant ionic strength, pH, and the like.

In certain preferred embodiments, the compounds of the present invention bind $\mu$ and/or $\kappa$ opioid receptors, or combinations thereof. The opioid receptors may be located in the central nervous system or located peripherally to the central nervous system or in both locations.

In certain other preferred embodiments, the compounds of the present invention bind $\kappa$ opioid receptors.

In preferred embodiments of the methods of the invention, the compounds antagonize the activity of the opioid receptors. In other preferred embodiments, the compounds prevent or treat a condition or disease caused by an opioid (either endogenous or exogenous). In certain embodiments of the method, particularly where the opioid are exogenous, the compounds of the invention preferably do not substantially cross the blood-brain barrier.

The compounds of the present invention may be used in methods to antagonize $\mu$, $\kappa$, and/or $\delta$ opioid receptors or any combinations or subcombinations of those opioid receptors, particularly where undesirable symptoms or conditions are side effects of administering exogenous opioids. Furthermore, the compounds of the invention may be used as to treat patients having disease states that are ameliorated by binding opioid receptors or in any treatment wherein temporary suppression of the μ, κ, or both types of opioid receptor system is desired.

Such symptoms, conditions or diseases include the complete or partial antagonism of opioid-induced sedation, confusion, respiratory depression, euphoria, dysphoria, hallucinations, pruritus (itching), increased biliary tone, increased biliary colic, and urinary retention, ileus, emesis, and addiction liability; prevention or treatment of opioid and cocaine dependence; rapid opioid detoxification; treatment of alcoholism; treatment of alcoholic coma; detection of opioid use or abuse (pupil test); treatment of eating disorders; treatment of obesity; treatment of post-concussional syndrome; adjunctive therapy in septic, hypovolemic or endotoxin-induced shock; potentiation of opioid analgesia (especially at ultra-low doses); reversal or prevention of opioid tolerance and physical dependence (especially at ultra-low doses); treatment of psychosis (especially wherein the symptoms are associated with schizophrenia, schizophreniform disorder, schizoaffective disorder, unipolar disorder, bipolar disorder, psychotic depression, Alzheimer's disease, Parkinson's disease, compulsive disorders, and other psychiatric or neurologic disorders with psychosis as symptoms); treatment of dyskinesia, treatment of autism; treatment of the endocrine system (including increased release of leutinizing hormone, treatment of infertility, increasing number of multiple births in animal husbandry, and male and female sexual behavior); treatment of the immune system and cancers associated with binding of the opioid receptors; treatment of anxiolysis; treatment of diuresis; treatment and regulation of blood pressure; treatment of tinnitus or impaired hearing; treatment of epilepsy; treatment of cachexia; treatment of general cognitive dysfunctions; and treatment of kleptomania.

The compounds of the present invention may also be used as cytostatic agents, as antimigraine agents, as immunomodulators, as immunosuppressives, as antiarthritic agents, as antiallergic agents, as virucides, to treat diarrhea, antipsychotics, as antischizophrenics, as antidepressants, as uropathic agents, as antitussives, as antiaddictive agents, as anti-smoking agents, to treat alcoholism, as hypotensive agents, to treat and/or prevent paralysis resulting from traumatic ischemia, general neuroprotection against ischemic trauma, as adjuncts to nerve growth factor treatment of hyperalgesia and nerve grafts, as anti-diuretics, as stimulants, as anti-convulsants, or to treat obesity. Additionally, the present compounds may be used in the treatment of Parkinson's disease as an adjunct to L-dopa for treatment dyskinesia associated with the L-dopa treatment.

In certain preferred embodiments, the compounds of the invention may be used in methods for preventing or treating gastrointestinal dysfunction, including, but not limited to, irritable bowel syndrome, opioid-bowel dysfunction, colitis, post-operative and opioid-induced emesis (nausea and vomiting), decreased gastric motility and emptying, inhibition of small and/or large intestinal propulsion, increased amplitude of non-propulsive segmental contractions, constriction of sphincter of Oddi, increased anal sphincter tone, impaired reflex relaxation with rectal distention, diminished gastric, biliary, pancreatic or intestinal secretions, increased absorption of water from bowel contents, gastro-esophageal reflux, gastroparesis, cramping, bloating, abdominal or epigastric pain and discomfort, constipation, and delayed absorption of orally administered medications or nutritive substances.

Methods of Preparation

The examples listed in Table 1 were prepared according to Schemes 1-9. The synthesis of compound 1 is outlined in Scheme 1. Condensation of 1.1 with di-tert butyldicarbonate 1.2 afforded N-boc-(3R,4R)-4-(3-hydroxyphenyl)-3,4-dimethyl-piperidine 1.3. Alkylation of 1.3 with benzyl bromide 1.4 in the presence of potassium carbonate gave the benzyl ether derivative 1.5. Treatment of 1.5 with anhydrous hydrogen chloride in dioxane at room temperature followed by treatment with aqueous sodium bicarbonate solution yielded the free base 1.6. Oxidation of 1.6 using sodium tungstate and hydrogen peroxide solution afforded the regioisomers 1.7a/b. Alkylation of 1.7a/b with allylmagnesium chloride 1.8 gave a mixture of regio- and stereoisomers (1.9, 1.10, 1.11 and 1.12) that were separated by column chromatography. Sonication of 1.9 in acetic acid/water in the presence of zinc dust provided the piperidine derivative 1.13. Peptidic type coupling of 1.13 with benzoylformic acid 1.14 in the presence of O-benzotriazol-1-yl-N,N,N',N'-tetramethyluronium tetrafluoroborate (TBTU) gave 1.15. Condensation of 1.15 with 1.16 under standard Wittig conditions provided 1.17. Compound 1.19 was synthesized by refluxing a solution of 1.17 in dichloromethane in the presence of a catalytic amount of (1,3-Bis-(2,4,6-trimethylphenyl)-2-imidazolidinylidene)dichloro (phenylmethylene)-(tricyclohexylphosphine)ruthenium, 1.18, (Grubbs catalyst, $2^{nd}$ generation) in a ring closure metathesis (RCM) reaction. Hydrogenation of 1.19 using palladium 10 wt. %. (dry basis) on activated carbon gave a mixture of 1.20 and 1.21, separated by column chromatography. Reduction of 1.20 with borane-dimethylsulfide complex provided the target compound 1.

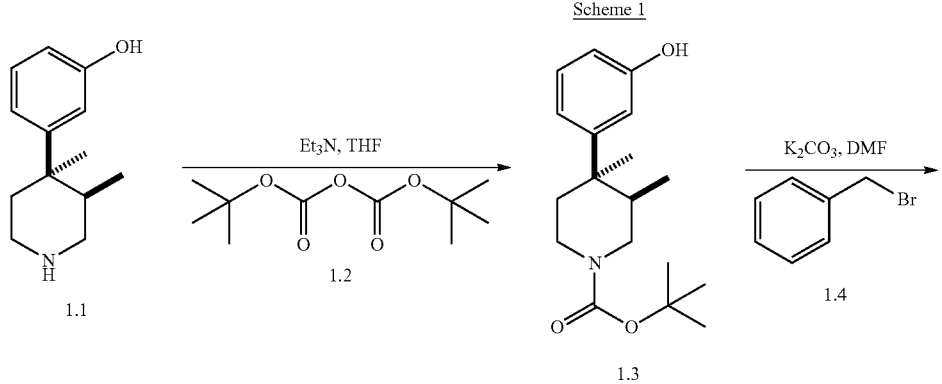

Scheme 1

-continued
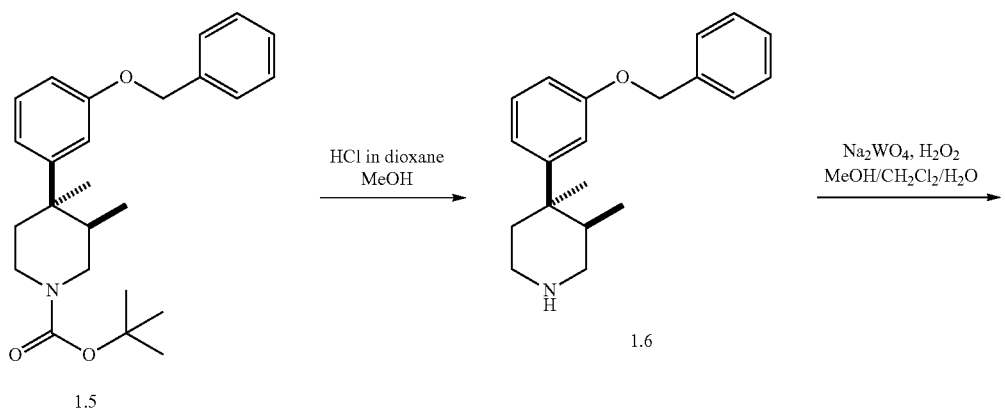
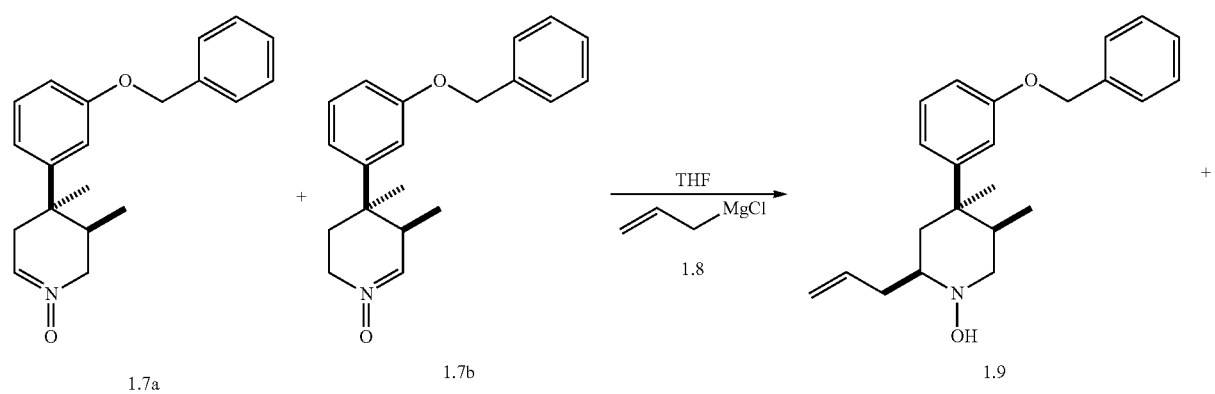
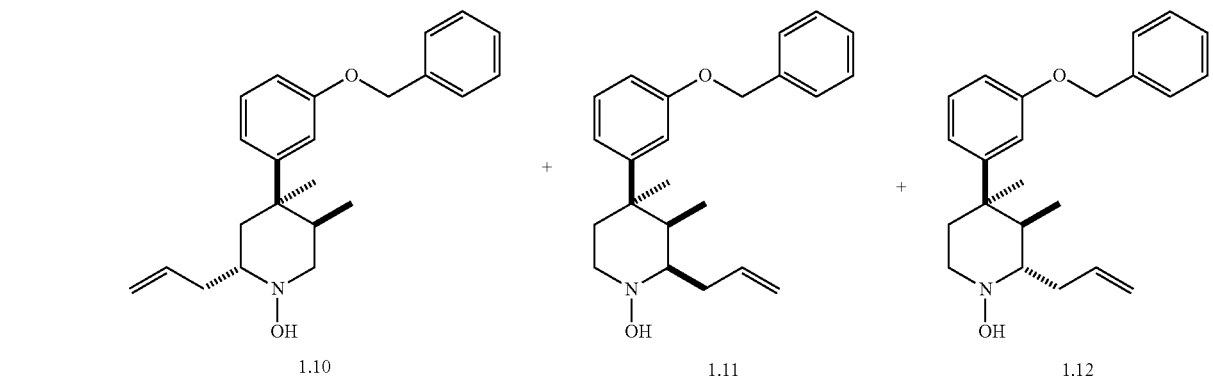
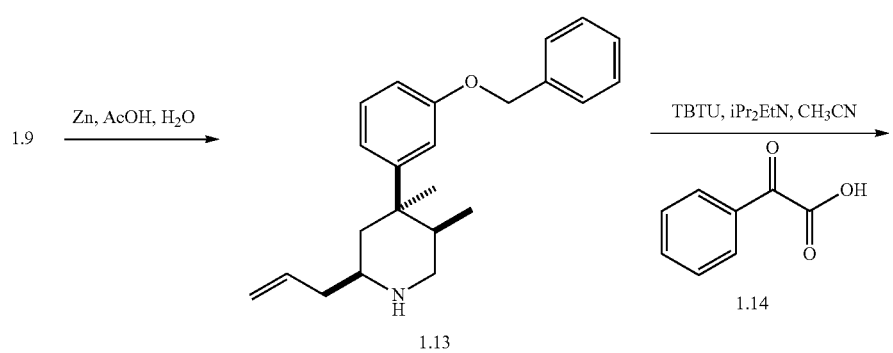

-continued
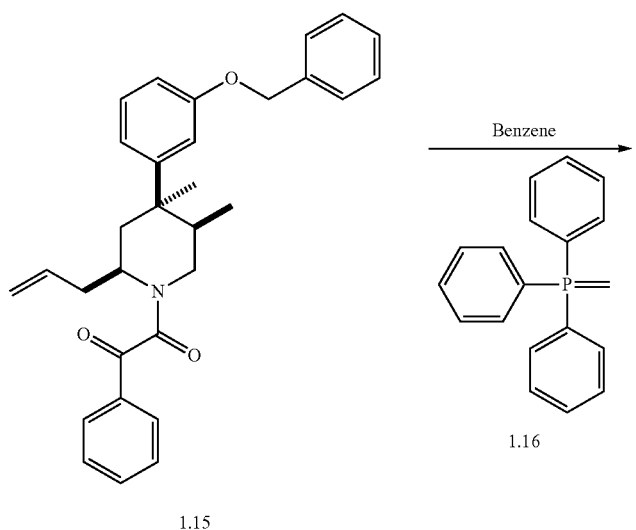
1.15 → Benzene, 1.16
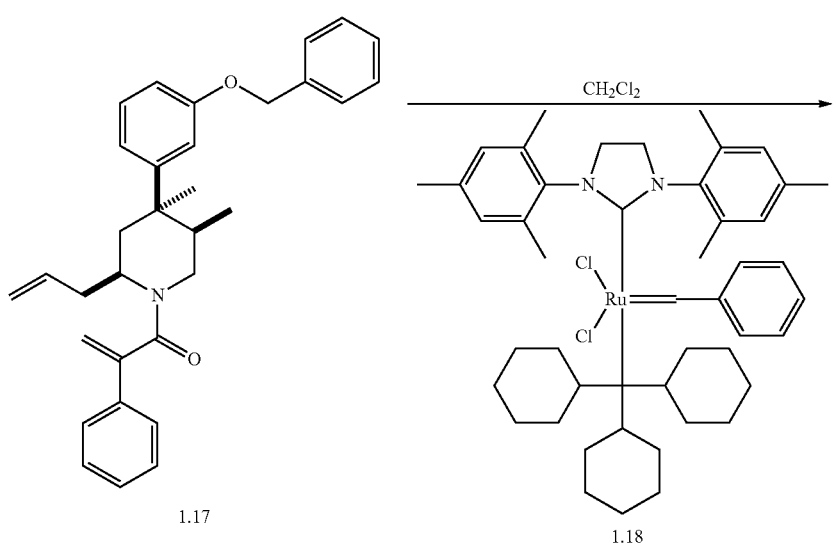
1.17 → CH₂Cl₂, 1.18
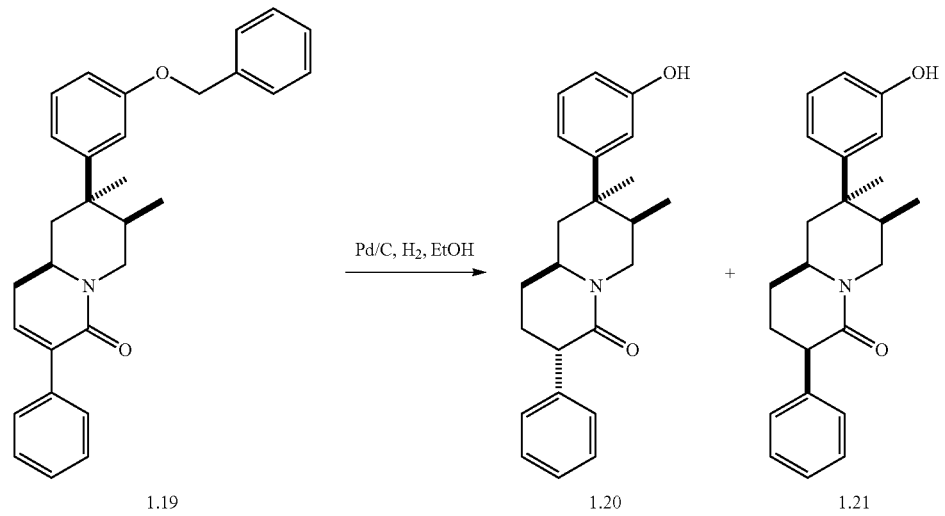
1.19 → Pd/C, H₂, EtOH → 1.20 + 1.21

-continued

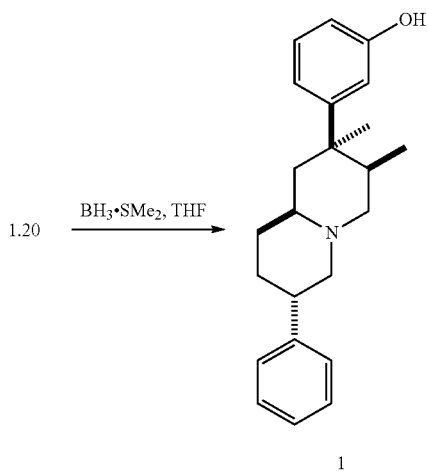

The syntheses of compounds 2A-2F are outlined in Scheme 2. Compound 1.2 was reacted with tert-butyldimethylchlorosilane 2.1 to give compound 2.2. Treatment of a solution of 2.2 in diethyl ether at −78° C. with sec-butyl lithium, followed by addition of carbon dioxide gas yielded carboxylic acid derivative 2.3. The reaction was found to be highly regio- and stereospecific. Peptidic type coupling of 2.3 with glycine methyl ester hydrochloride 2.4 provided 2.5. Conversion of 2.5 to 2.6 was achieved in two steps, i.e.: (a) cleavage of the Boc and TBDMS protecting groups of 2.5 under acidic conditions; (b) cyclization in methanol in the presence of triethylamine. Reduction of the lactam 2.6 with borane-dimethylsulfide complex provided compound 2.7. Condensation of 2.7 with phenylacetyl chloride 2.8 in the presence of triethylamine provided compound 2A. Reduction of compound 2A using borane-methyl sulfide complex afforded compound 2B. Condensation of 2.7 with benzoyl chloride 2.9 provided compound 2C. Reduction of compound 2C using borane-dimethylsulfide complex afforded compound 2D. Condensation of compound 2.7 with di-tert-butyl-dicarbonate 1.2 gave compound 2.10 which reacted with benzyl bromide 1.4 in the presence of potassium carbonate to afford compound 2.11. Boc deprotection of 2.11 using an anhydrous solution of hydrogen chloride in dioxane, followed by treatment with a saturated solution of sodium bicarbonate gave the free base 2.12. Condensation of compound 2.12 with benzene sulfonyl chloride 2.13 afforded the sulfonamide 2.14. Removal of the benzyl protecting group of 2.14 under hydrogenation conditions provided compound 2E. Condensation of compound 2.12 with potassium phenyltrifluoroborate 2.15 in the presence of copper (II) acetate and triethylamine gave compound 2.16. Hydrogenation of 2.16 yielded compound 2F.

Scheme 2

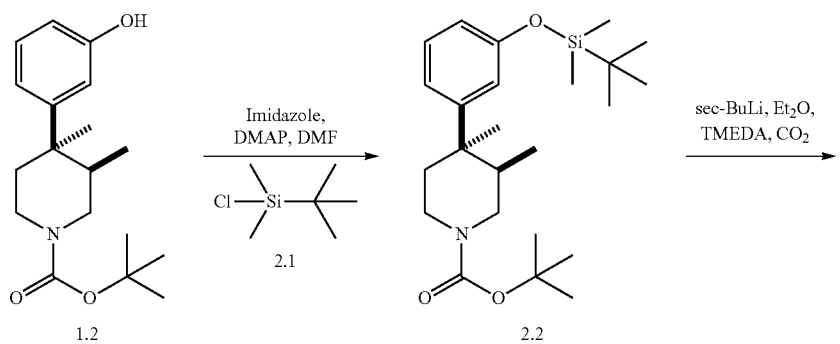

-continued
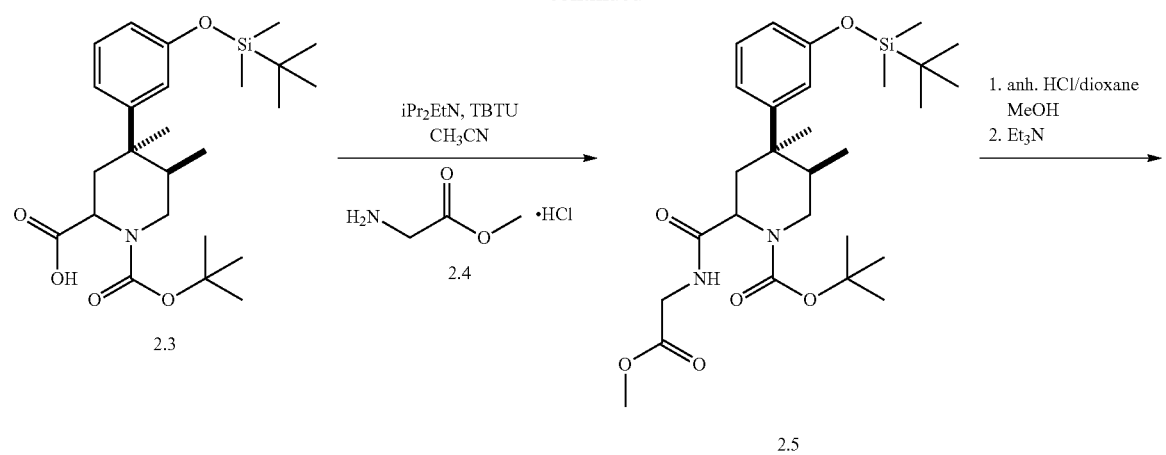
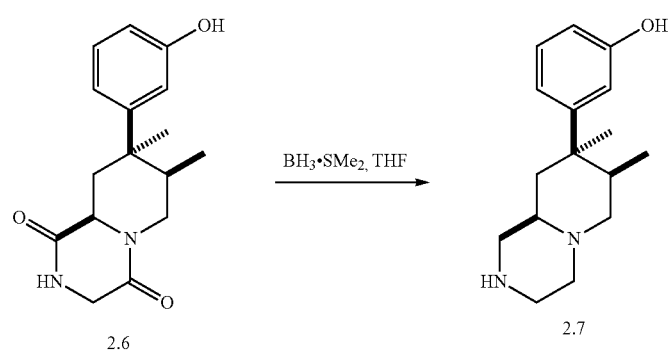
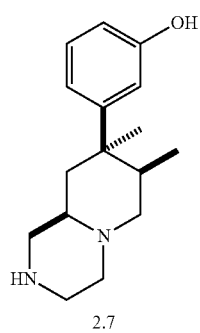
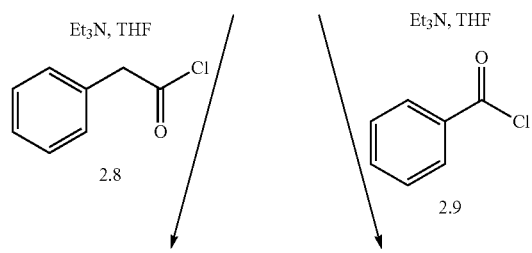

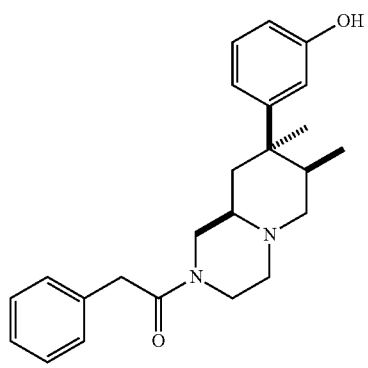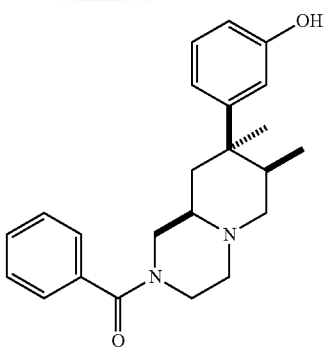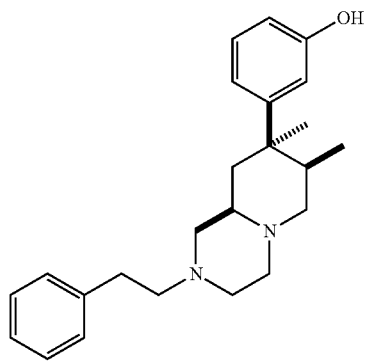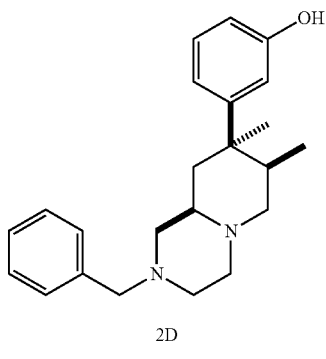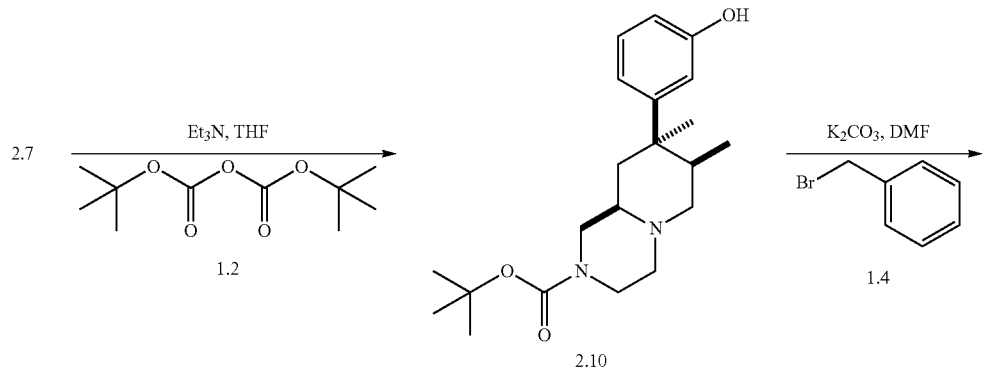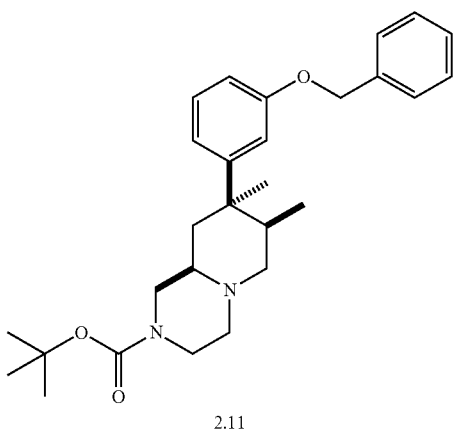

-continued
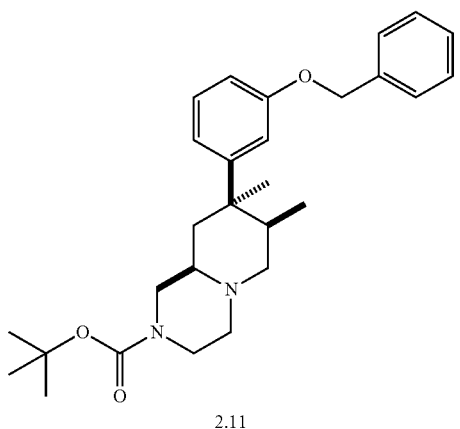
2.11
↓ anh. HCl/dioxane, MeOH
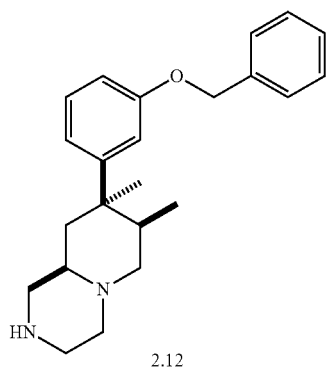
2.12
Et₃N, THF 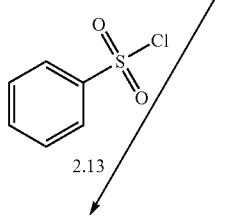 2.13
Et₃N, Cu(OAc)₂ CH₂Cl₂ 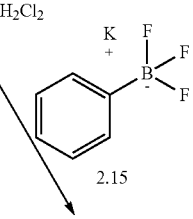 2.15

-continued

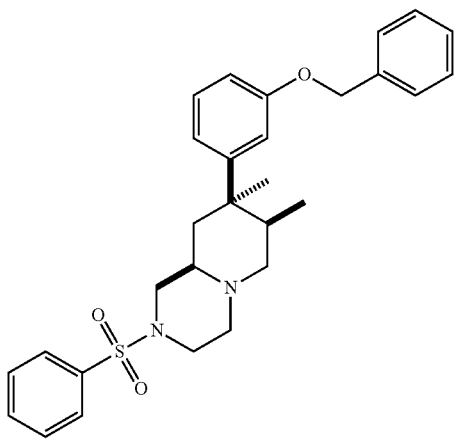

2.14

Pd/C, H₂
EtOH ↓

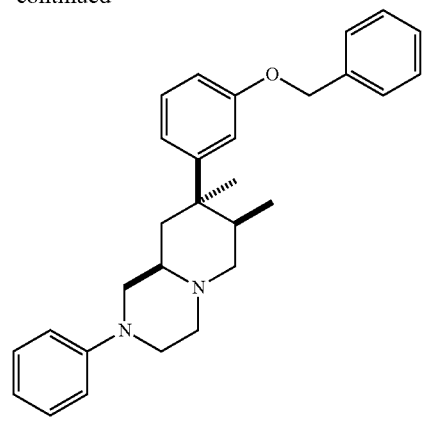

2.16

Pd/C, H₂
EtOH ↓

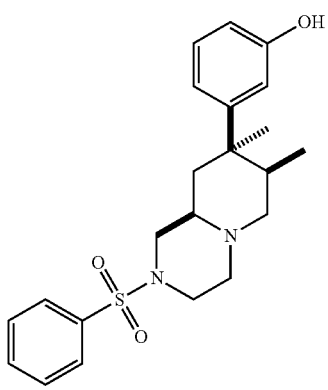

2E

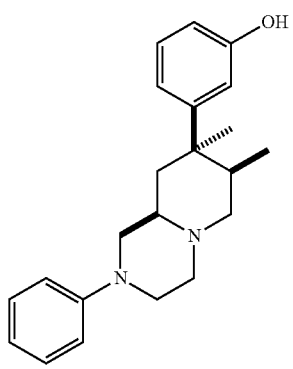

2F

The syntheses of compounds 3A-3G are outlined in Scheme 3. Peptidic type coupling of 2.3 with L-phenylglycine methyl ester hydrochloride 3.1 provided 3.2. Treatment of 3.2 with anhydrous hydrogen chloride in dioxane in refluxing methanol, followed by treatment with a saturated solution of sodium bicarbonate gave 3.3 as the free base. Intramolecular cyclization of 3.3 provided the lactam 3.4. Reduction of 3.4 with borane-dimethylsulfide complex gave compound 3A. Condensation of compound 3A with formaldehyde 3.5 under reductive amination conditions using sodium cyanoborohydride as the reducing agent provided compound 3B. Alkylation of compound 3A with tert-butyl bromoacetate 3.6 in the presence of potassium carbonate afforded compound 3.7, which was hydrolyzed under acidic conditions to give compound 3C. The 1,4-addition of compound 3A with tert-butyl acrylate 3.8 afforded compound 3.9, which was hydrolyzed under acidic conditions to give compound 3D. Condensation of compound 3A with benzaldehyde 3.10 under reductive amination conditions using borane-pyridine complex as the reducing agent provided compound 3E. Condensation of 3E with N-phenyltrifluoromethanesulfonimide 3.11 gave the triflate 3.12. Palladium catalyzed carbonylation of the triflate 3.12 using palladium (II) acetate and 1,1'-bis (diphenylphosphino)ferrocene (dppf) in a methanol, dimethylsulfoxide mixture provided the methyl ester 3.13 which was hydrolyzed under basic conditions to provide the carboxylic acid 3.14. Peptidic type coupling of 3.14 with ammonium chloride afforded 3F. Hydrogenation of 3F yielded 3G.

Scheme 3
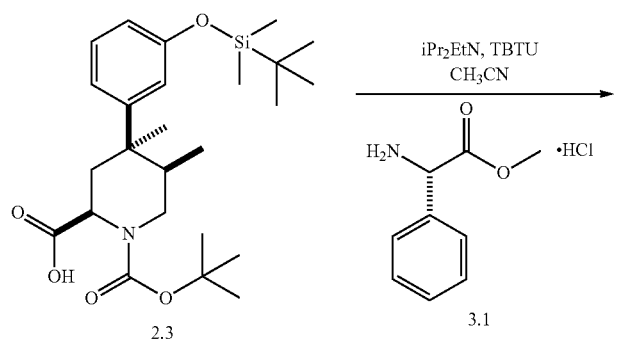
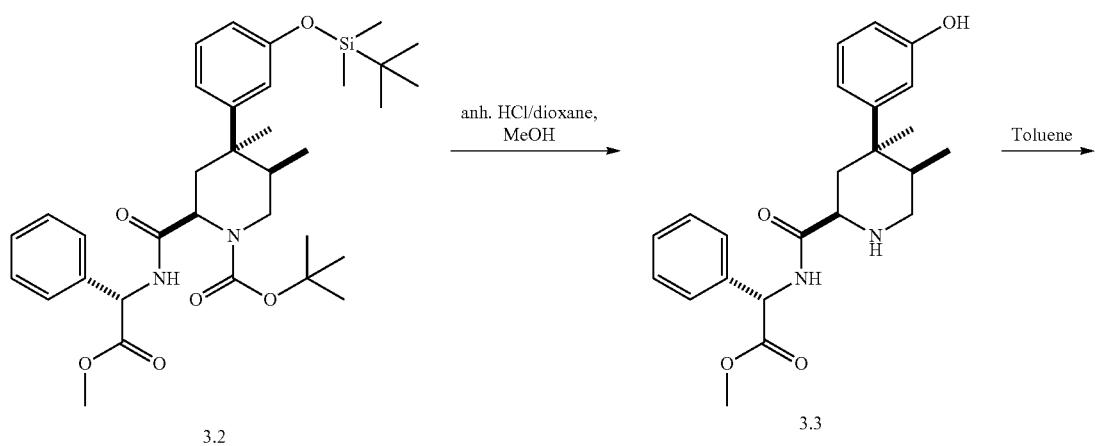
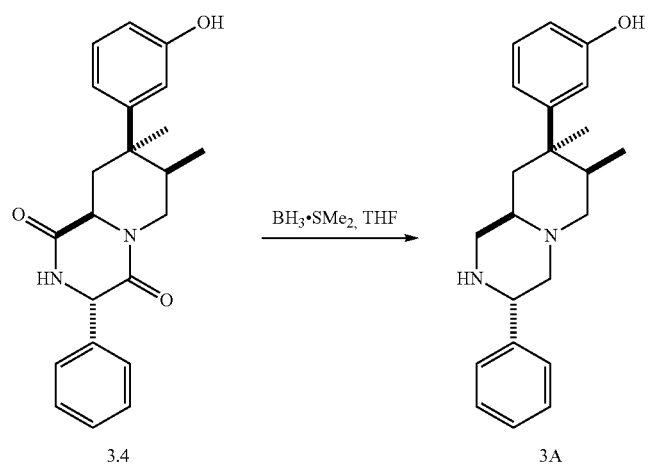

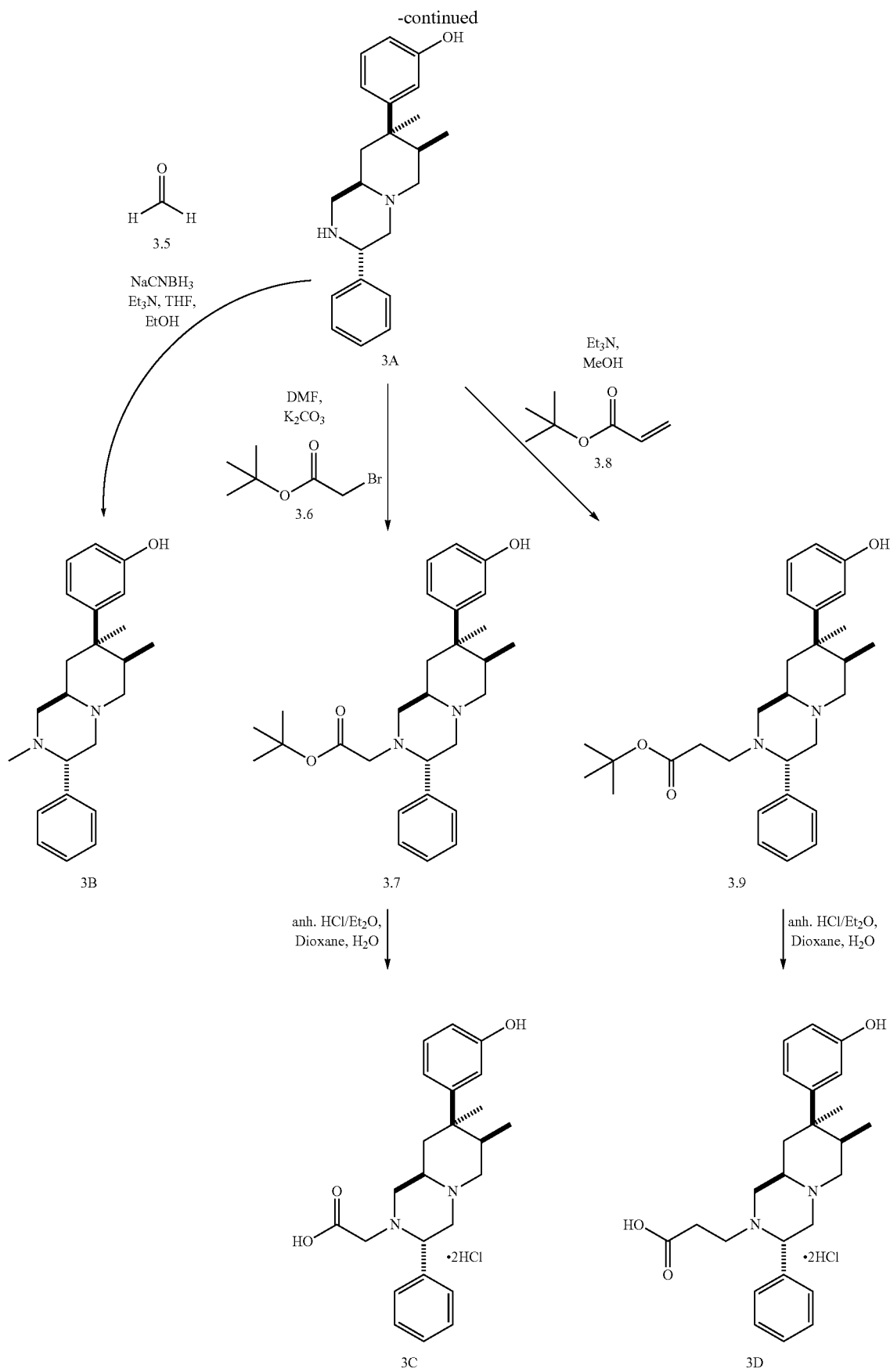

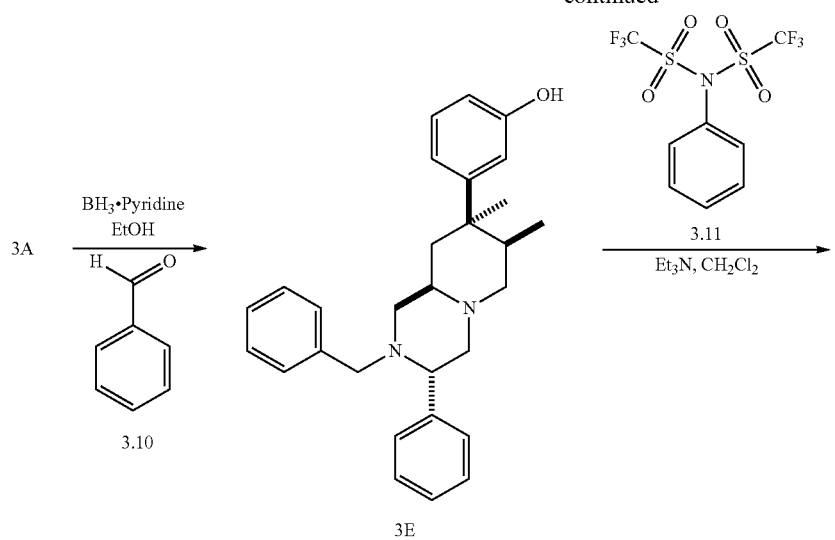
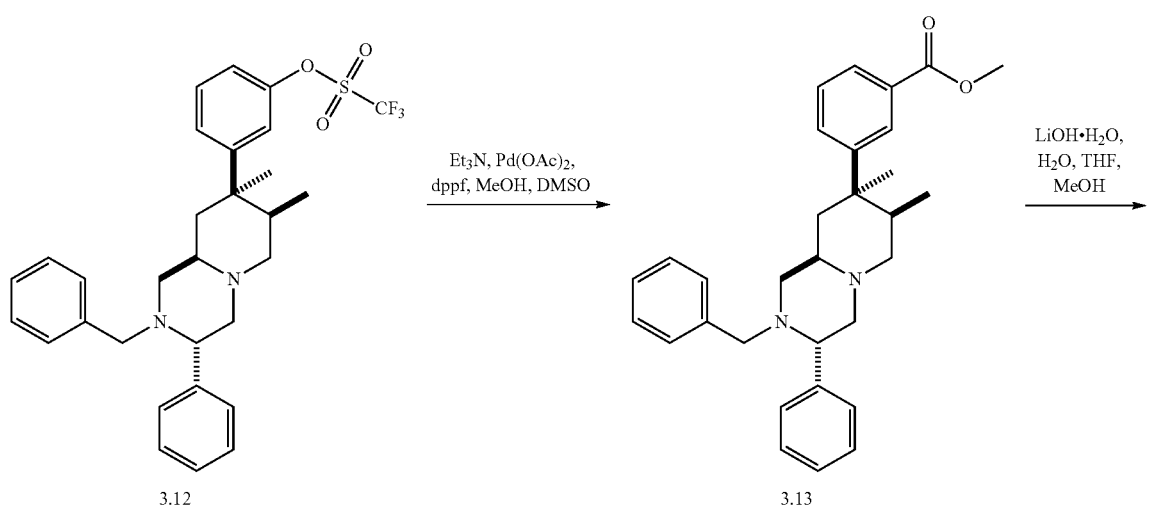
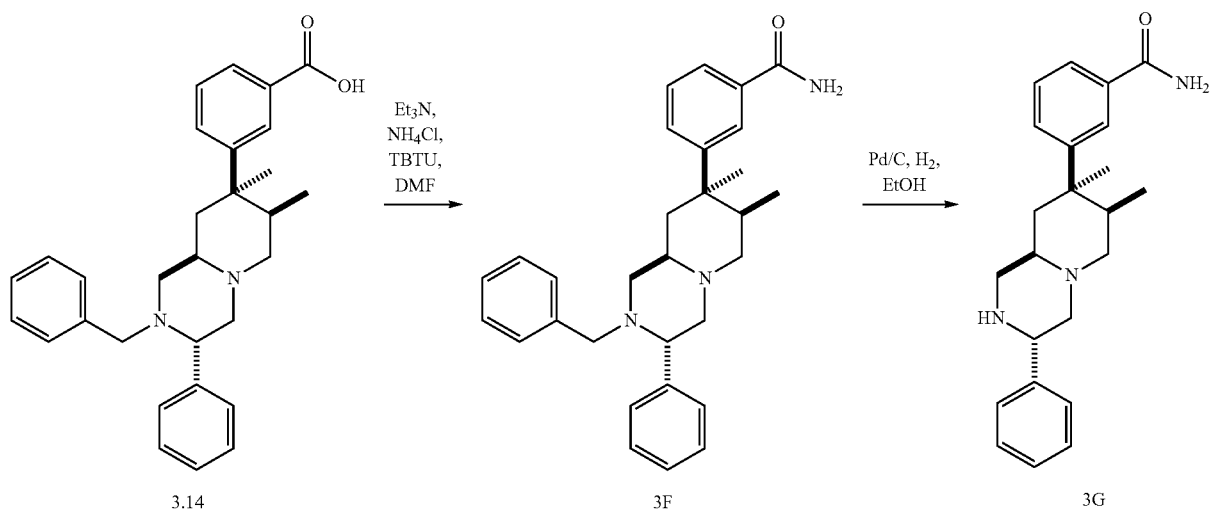

The synthesis of compound 4 is outlined in Scheme 4. Peptidic type coupling of 2.3 with L-phenylalanine methyl ester hydrochloride 4.1 provided 4.2. Treatment of 4.2 with anhydrous hydrogen chloride in dioxane in refluxing methanol, followed by treatment with a saturated solution of sodium bicarbonate gave 4.3 as the free base. Cyclization of 4.3 to 4.4 was achieved by refluxing a solution of 4.3 in toluene. Reduction of 4.4 with borane-dimethylsulfide complex gave compound 4.

Scheme 4

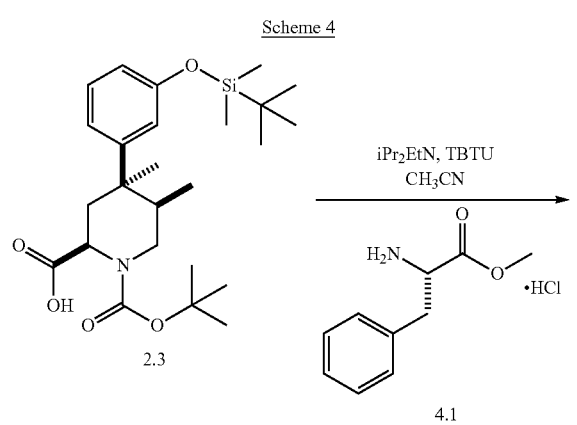

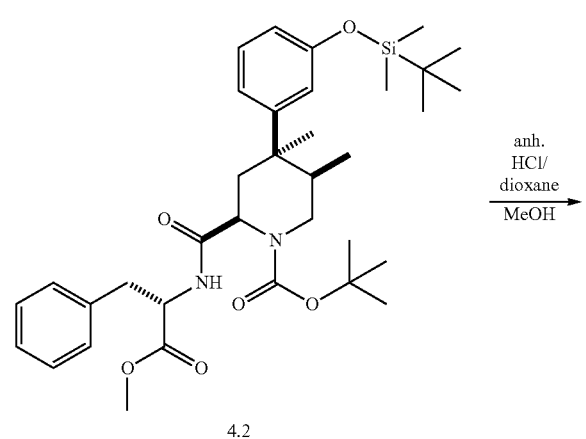

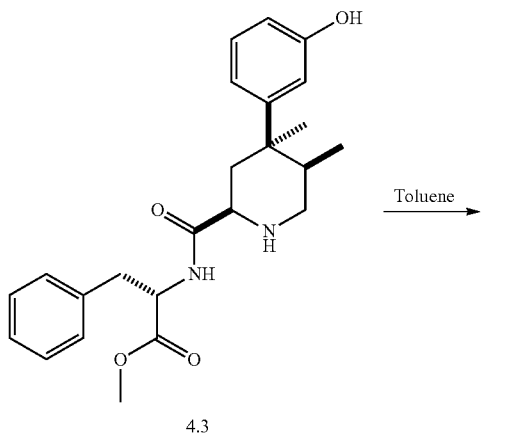

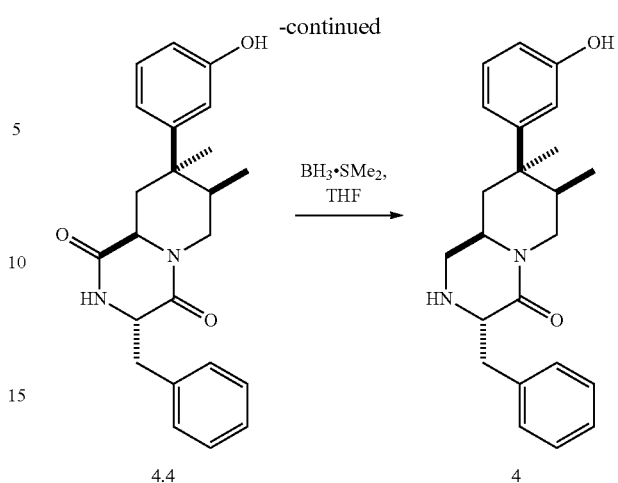

The synthesis of compound 5 is described in Scheme 5. Peptidic type coupling of 2.3 with D-phenylalanine methyl ester hydrochloride 5.1 provided 5.2. Treatment of 5.2 with anhydrous hydrogen chloride in dioxane in refluxing methanol, followed by treatment with a saturated solution of sodium bicarbonate gave 5.3 as the free base. Cyclization of 5.3 to 5.4 was achieved by refluxing a solution of 5.3 in toluene. Reduction of 5.4 with borane-dimethylsulfide complex gave compound 5.

Scheme 5

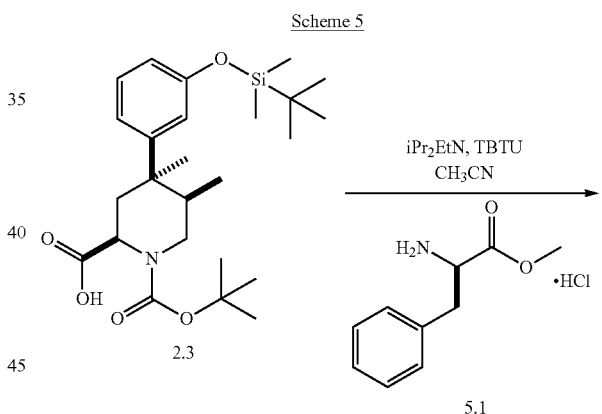

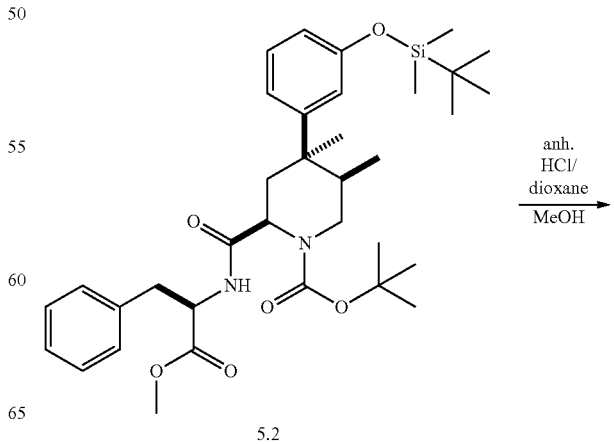

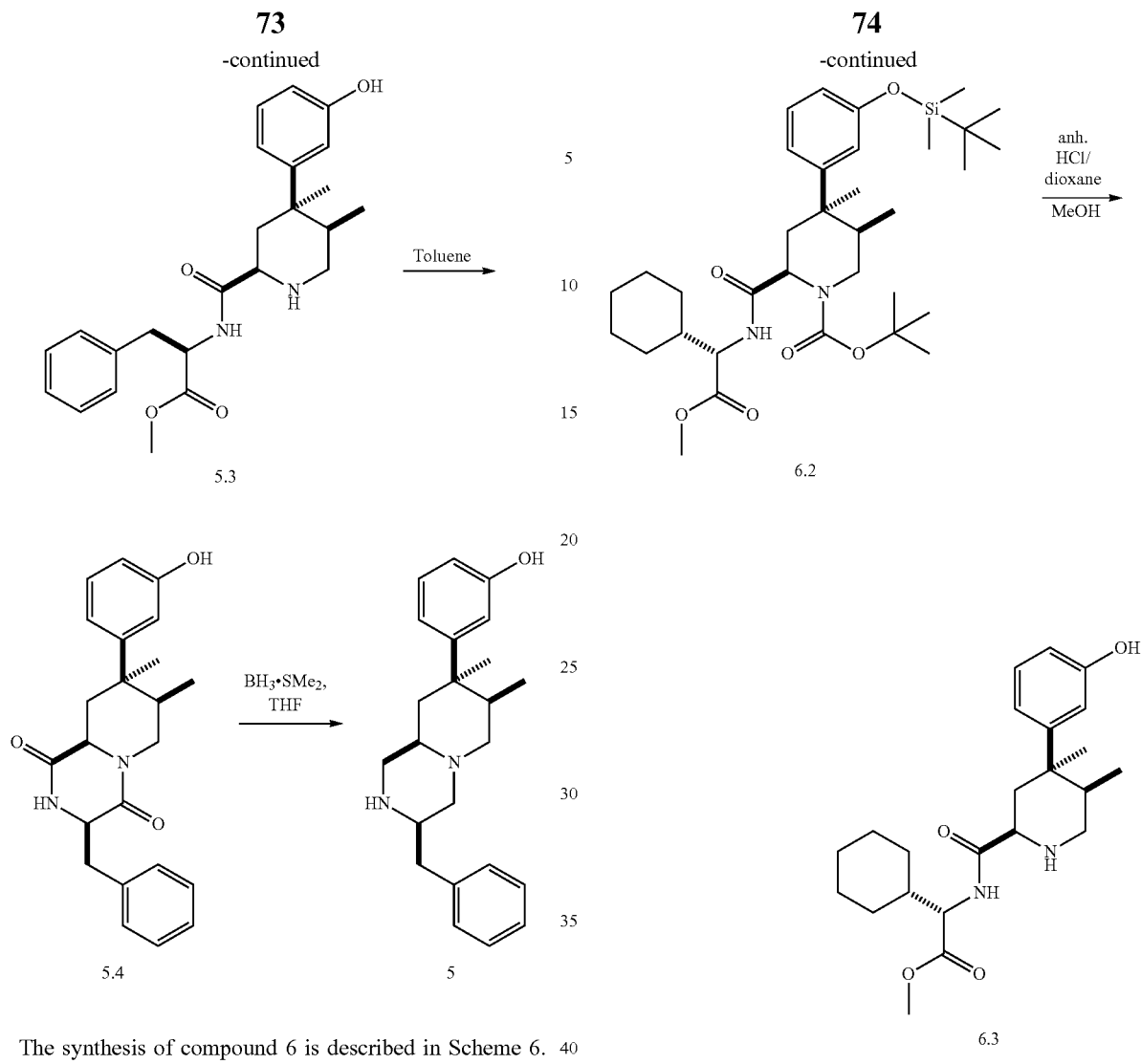

The synthesis of compound 6 is described in Scheme 6. Peptidic type coupling of 2.3 with L-cyclohexylglycine methyl ester hydrochloride 6.1 provided 6.2. Treatment of 6.2 with anhydrous hydrogen chloride in dioxane in refluxing methanol, followed by treatment with a saturated solution of sodium bicarbonate gave 6.3 as the free base. Cyclization of 6.3 to 6.4 was achieved by refluxing a solution of 6.3 in o-xylene. Reduction of 6.4 with borane-dimethylsulfide complex gave compound 6.

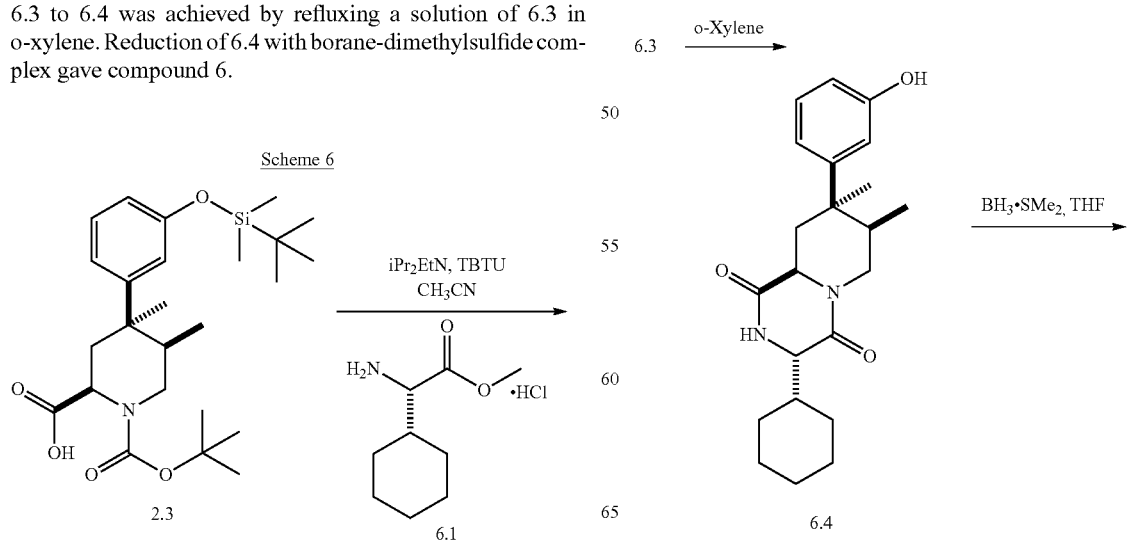

Scheme 6

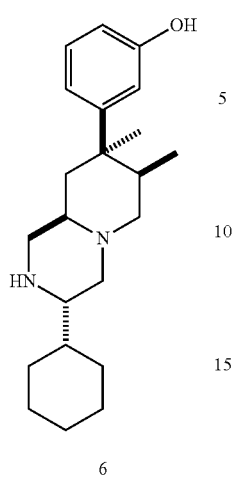

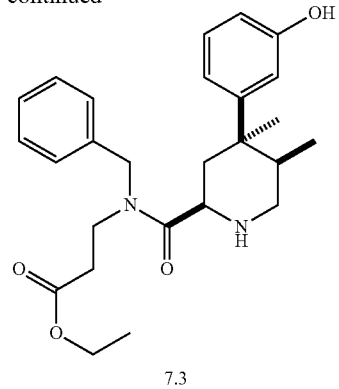

The synthesis of compound 7 is described in Scheme 7. Peptidic type coupling of 2.3 with N-benzyl-beta-alanine ethyl ester 7.1 provided 7.2. Treatment of 7.2 with anhydrous hydrogen chloride in dioxane and ethanol, followed by treatment with a saturated solution of sodium bicarbonate gave 7.3 as the free base. Cyclization of 7.3 to 7.4 was achieved by refluxing a solution of 7.3 in o-xylene. Reduction of 7.4 with borane-dimethylsulfide complex gave compound 7.

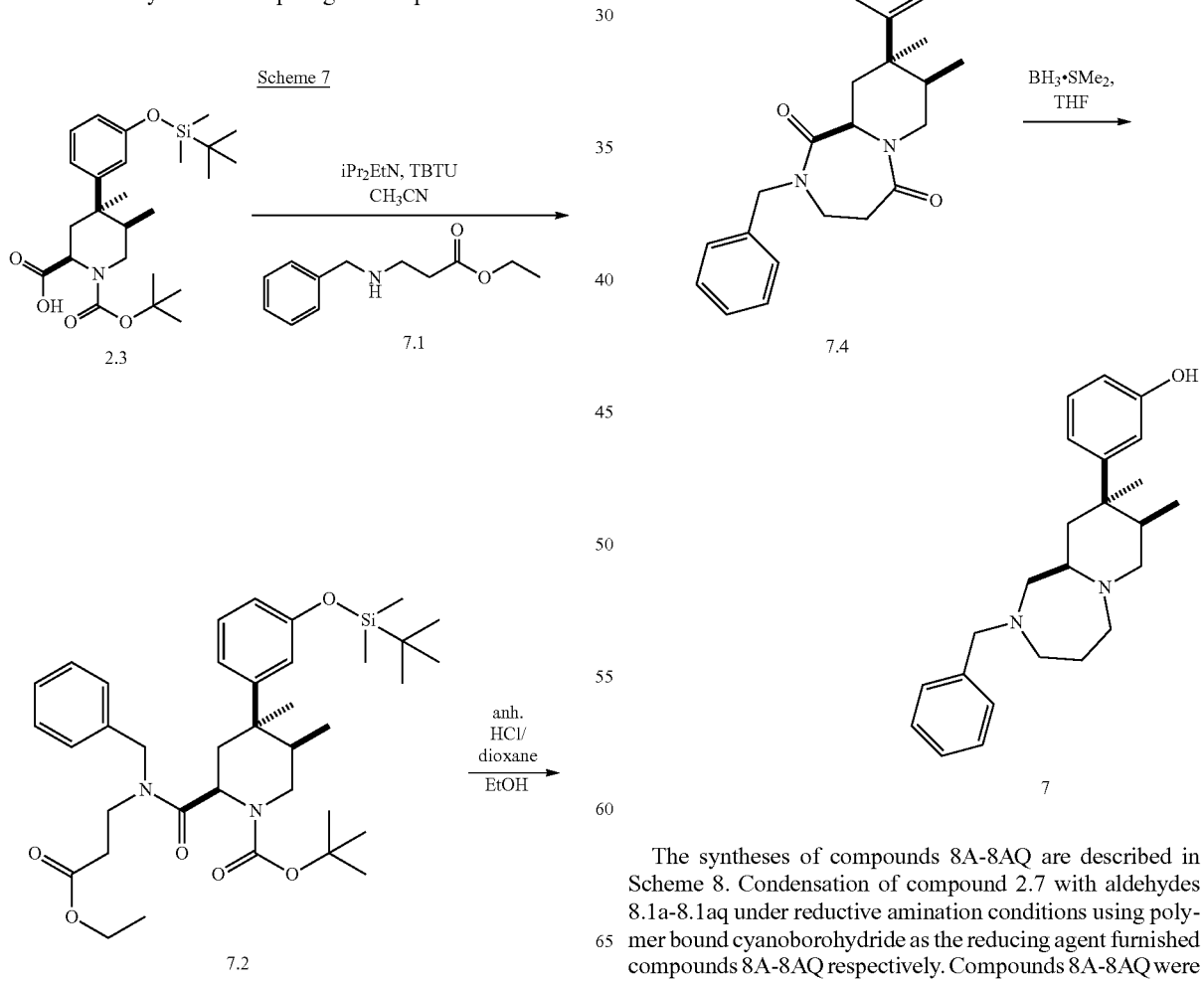

The syntheses of compounds 8A-8AQ are described in Scheme 8. Condensation of compound 2.7 with aldehydes 8.1a-8.1aq under reductive amination conditions using polymer bound cyanoborohydride as the reducing agent furnished compounds 8A-8AQ respectively. Compounds 8A-8AQ were purified by liquid chromatography.

Scheme 8
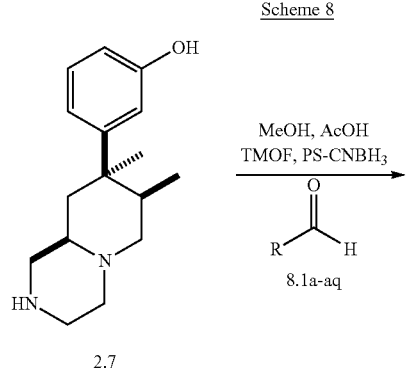
Commercially available aldehydes used in the synthesis of 8A-8AQ:
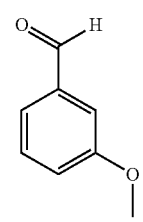
8.1a
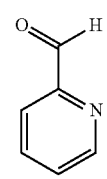
8.1b
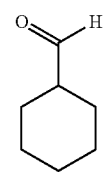
8.1c
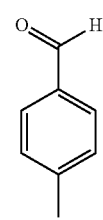
8.1d
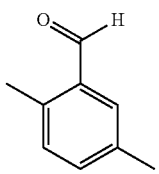
8.1e
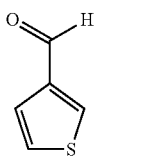
8.1f
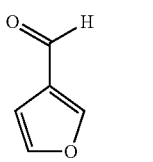
8.1g
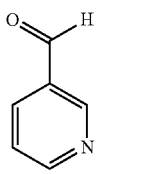
8.1h
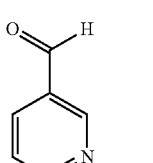
8.1i
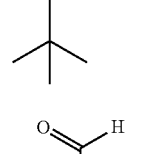
8.1j
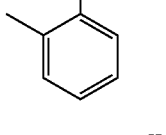
8.1k
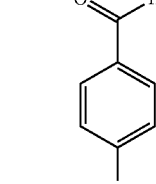
8.1l

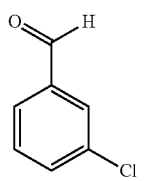 8.1m
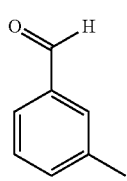 8.1n
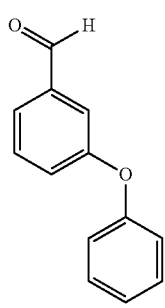 8.1o
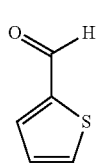 8.1p
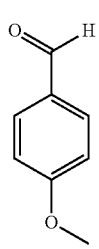 8.1q
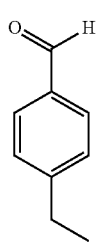 8.1r
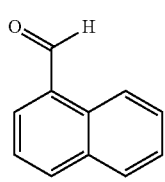 8.1s
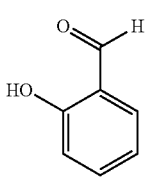 8.1t
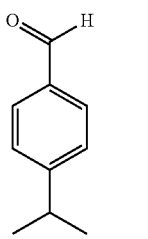 8.1u
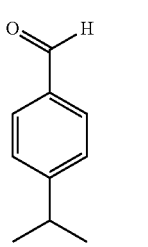 8.1v
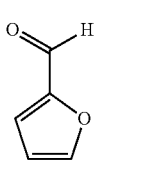 8.1w
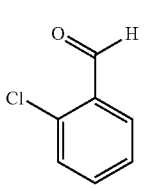 8.1x
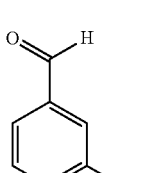 8.1y
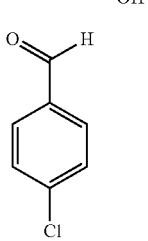 8.1z
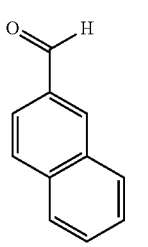 8.1aa
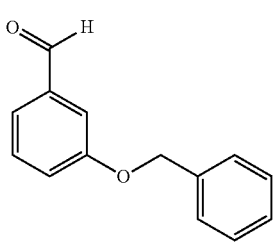

| | |
|---|---|
| 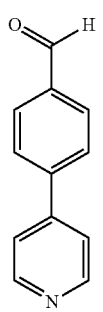 | 8.1ab 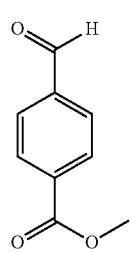 8.1ah |
| 8.1ac 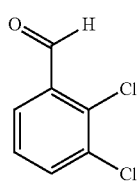 | 8.1ac 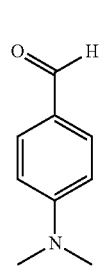 8.1ai |
| 8.1ad 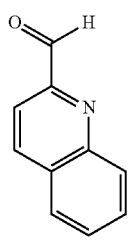 | 8.1ad 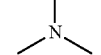 |
| 8.1ae 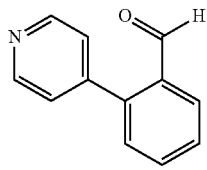 | 8.1aj 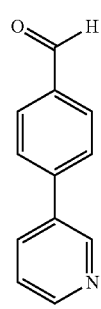 |
| 8.1af 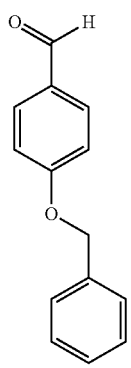 | 8.1ak 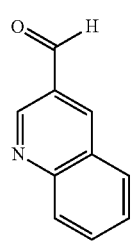 |
| 8.1ag 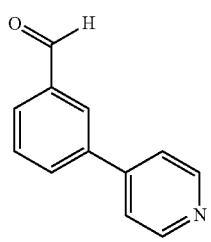 | 8.1al 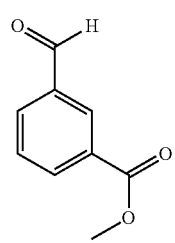 |

8.1am

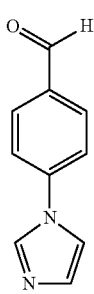

8.1ap

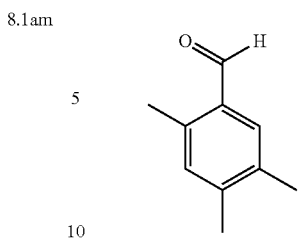

8.1an 8.1aq 8.1ao

The syntheses of compounds 9A-9B are outlined in Scheme 9. Peptidic type coupling of 2.3 with 9.1 provided 9.2. Treatment of 9.2 with anhydrous hydrogen chloride in dioxane, followed by treatment with a saturated solution of sodium bicarbonate gave 9.3 as the free base. Intramolecular cyclization of 9.3 provided the lactam 9.4. Reduction of 9.4 with borane-dimethylsulfide complex gave compound 9.5. Peptidic type coupling of 9.5 with 3-(4-hydroxyphenyl)propionic acid 9.6 in the presence of O-benzotriazol-1-yl-N,N,N',N'-tetramethyluronium tetrafluoroborate (TBTU) gave 9A. Peptidic type coupling of 9.5 with N-t-butyloxycarbonyl-7-hydroxy-D-1,2,3,4-tetrahydroisoquinoline-3-carboxylic acid 9.7 in the presence of O-benzotriazol-1-yl-N,N,N',N'-tetramethyluronium tetrafluoroborate (TBTU) gave compound 9.8, which was converted to 9B under acidic conditions.

Scheme 9

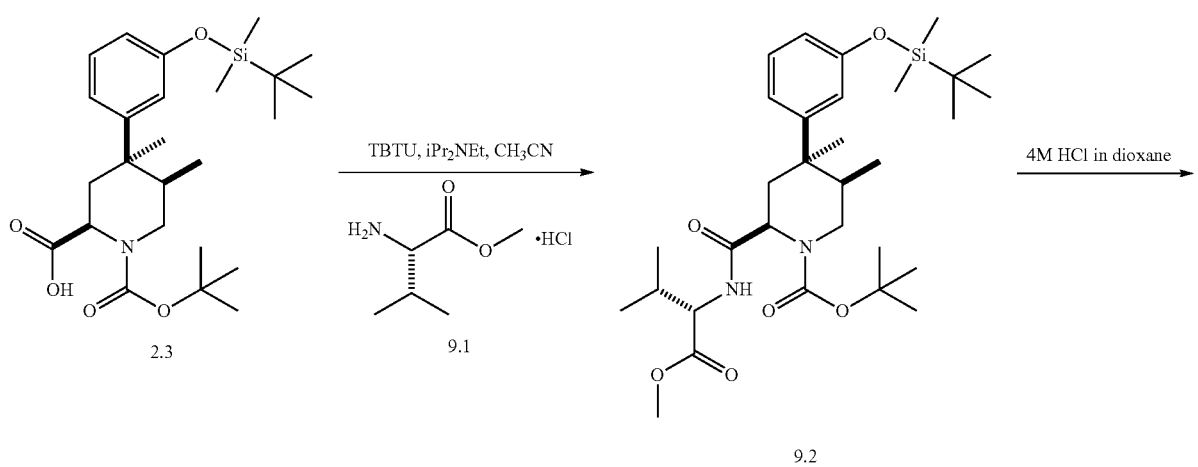

-continued
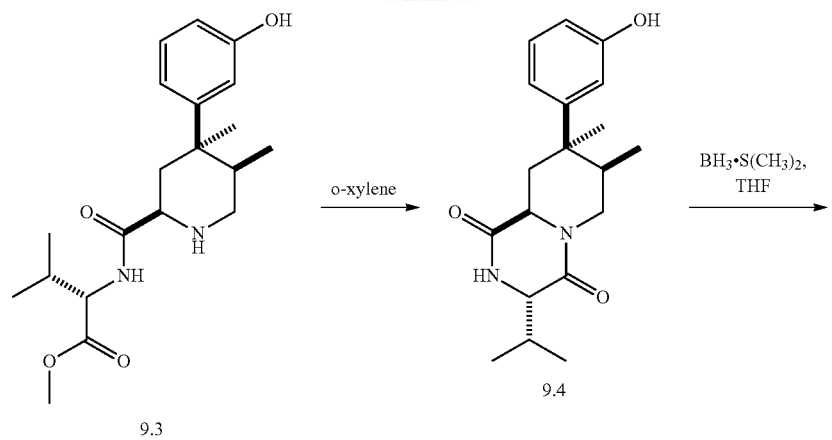
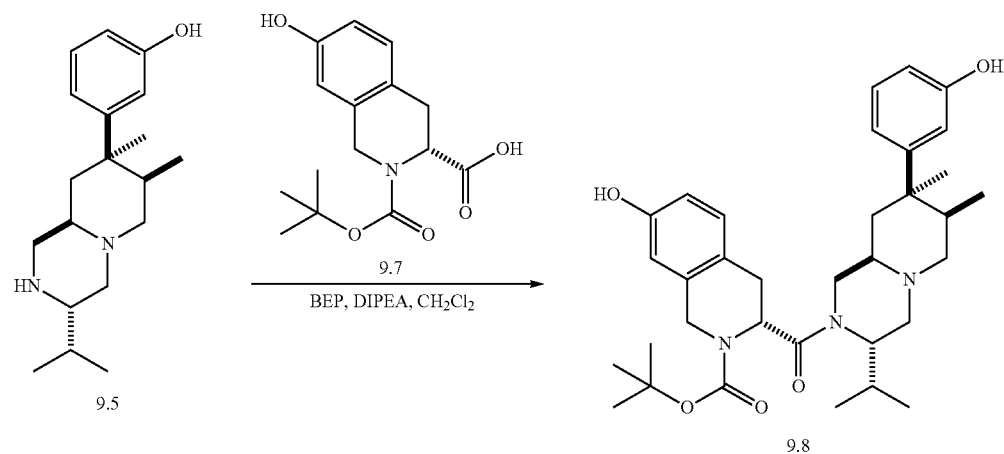
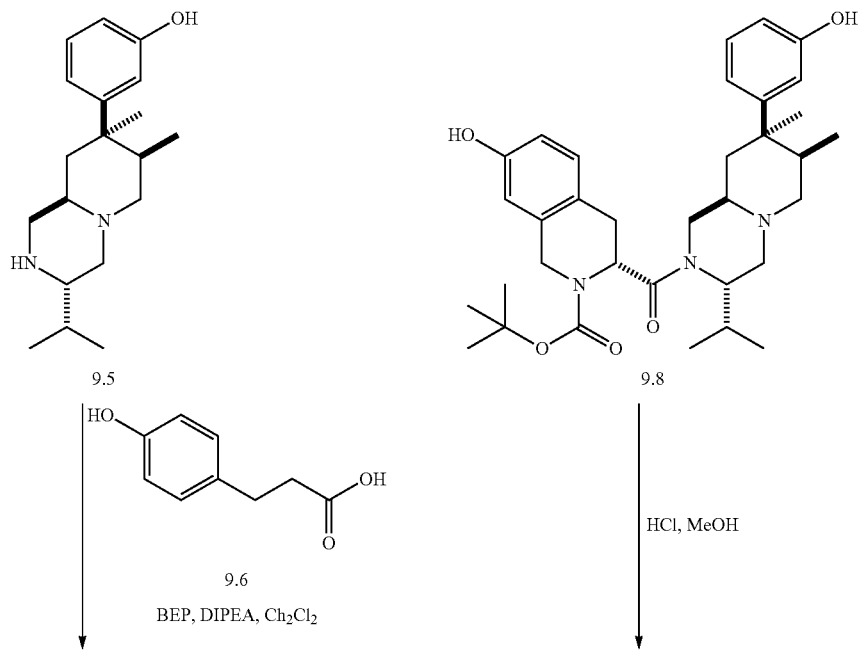

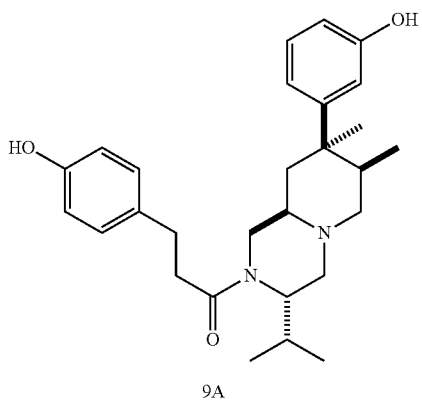

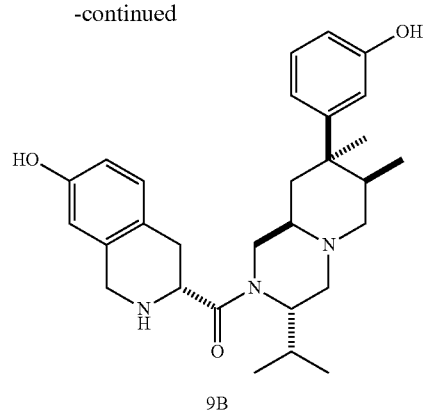

9A

9B

The present invention will now be illustrated by reference to the following specific, non-limiting examples. Those skilled in the art of organic synthesis may be aware of still other synthetic routes to the invention compounds. The reagents and intermediates used herein are either commercially available or prepared according to standard literature procedures.

EXAMPLES

Materials: All chemicals were reagent grade, purchased from Aldrich Chemical Company, Milwaukee, Wis. or Lancaster Synthesis, Windham, N.H., and used without further purification. General: Thin-layer chromatography (TLC) was performed on silica gel 6F glass backed plates (250 microns) from Analtech and visualized by UV 254 irradiation and iodine. Flash chromatography was conducted using the ISCO CombiFlash with RediSep silica gel cartridges (4 g, 12 g, 40 g, 120 g). Chromatographic elution solvent systems are reported as volume:volume ratios. All $^1$H NMR spectra were recorded at ambient temperature on a Bruker-400 MHz spectrometer. They are reported in ppm on the δ scale, from TMS. LC-MS data were obtained using a Thermo-Finnigan Surveyor HPLC and a Thermo-Finnigan AQA MS using either positive or negative electrospray ionization. Program (positive) Solvent A: 10 mM ammonium acetate, pH 4.5, 1% acetonitrile; solvent B: acetonitrile; column: Michrom Bioresources Magic C18 Macro Bullet, detector: PDA λ=220-300 nm. Gradient: 96% A-100% B in 3.2 minutes, hold 100% B for 0.4 minutes. Program (negative) Solvent A: 1 mM ammonium acetate, pH 4.5, 1% acetonitrile; solvent B: acetonitrile; column: Michrom Bioresources Magic C18 Macro Bullet, detector: PDA λ=220-300 nm. Gradient: 96% A-100% B in 3.2 minutes, hold 100% B for 0.4 minutes.

Example 1

Preparation of 1.3

To a stirred solution of 1.1 (30 g, 146 mmol) in tetrahydrofuran (150 mL) under nitrogen at 0° C., was added a solution of 1.2 (35 g, 160 mmol) and triethylamine (24.45 mL, 175 mmol) in tetrahydrofuran (150 mL) over 1 hour. The solution was stirred at room temperature for 18 hours. The reaction mixture was concentrated under reduced pressure and the residue dissolved in ethyl acetate (300 mL). The solution was then washed with 0.5M aqueous solution of hydrochloric acid (2×60 mL) and dried over sodium sulfate. The reaction mixture was concentrated under reduced pressure and used in the next step without further purification.

Yield: 100% $^1$H NMR (400 MHz, CDCl$_3$) δ: 0.64 (d, J=7 Hz, 3H), 1.35 (s, 3H), 1.47 (s, 9H), 1.53 (m, 1H), 1.97 (br s, 1H), 2.19 (dt, J=13 Hz and 5 Hz, 1H), 3.05 (br s, 1H), 3.30 (br s, 1H), 3.82 (br s, 1H), 4.10 (br s, 0.5H), 4.24 (br s, 0.5H), 6.23 (br s, 1H), 6.68 (m, 1H), 6.78 (m, 2H), 7.17 (t, J=8 Hz 1H)

Mass Spectral Analysis, m/z ESI 306 (M+H$^+$)

Preparation of 1.5

To a stirred solution of 1.3 (44.63 g, 146 mmol) in N,N-dimethylformamide (450 mL) was added 1.4 (20.8 mL, 175 mmol) and potassium carbonate (60.50 g, 438 mmol) and the reaction stirred at room temperature for 18 hours. The reaction mixture was then poured into water (300 mL) and extracted with hexanes. The combined organics were washed with water, brine and dried over sodium sulfate. The mixture was filtered and the filtrate concentrated under reduced pressure. The desired product was used for the next step without further purification.

Yield: 100% $^1$H NMR (400 MHz, CDCl$_3$) δ: 0.62 (d, J=7 Hz, 3H), 1.35 (s, 3H), 1.46 (s, 9H), 1.56 (m, 1H), 1.96 (br s, 1H), 2.18 (dt, J=13 Hz and 5 Hz, 1H), 3.02 (br s, 1H), 3.27 (br s, 1H), 3.82 (br s, 1H), 4.18 (br s, 1H), 5.05 (s, 2H), 6.80 (m, 1H), 6.86 (m, 2H), 7.24 (t, J=8 Hz 1H), 7.32 (m, 1H), 7.38 (m, 2H), 7.44 (m, 2H)

Mass Spectral Analysis, m/z ESI 396 (M+H$^+$)

Preparation of 1.6

To a stirred solution of 1.5 (57.80 g, 146 mmol) in methanol (300 mL) was added a 4M anhydrous solution of hydrogen chloride in dioxane (200 mL) and the reaction mixture was stirred at room temperature for 18 hours. The solvents were then removed under reduced pressure and the residue stirred with saturated sodium bicarbonate solution (400 mL), ethyl acetate (200 mL) and dichloromethane (200 mL) for 4 hours. The layers were separated and the organic layer washed with brine and dried over sodium sulfate. The reaction mixture was filtered and the filtrate concentrated under reduced pressure. The desired product used for the next step without further purification.

Yield: 96% $^1$H NMR (400 MHz, CDCl$_3$) δ: 0.73 (d, J=7 Hz, 3H), 1.37 (s, 3H), 1.56 (d, J=14 Hz, 1H), 1.93 (m, 1H), 2.15 (dt, J=13 Hz and 5 Hz, 1H), 2.76 (d, J=12 Hz, 1H), 3.01 (dt, J=12 Hz and 3 Hz, 1H), 3.09 (d, J=13 Hz, 1H), 3.26 (dd, J=13

Hz and 3 Hz, 1H), 5.06 (s, 2H), 6.80 (m, 1H), 6.88 (m, 2H), 7.24 (t, J=8 Hz 1H), 7.33 (m, 1H), 7.39 (m, 2H), 7.45 (m, 2H)

Mass Spectral Analysis, m/z ESI 296 (M+H$^+$)

Preparation of 1.7a-b

To a stirred solution of 1.6 (29.35 g, 99.49 mmol) in methanol (200 mL) and dichloromethane (200 mL) was added a solution of sodium tungstate (1.50 g, 3.98 mmol) in water (50 mL). To this was then added hydrogen peroxide (35 mL, 298.47 mmol) and the reaction was stirred at room temperature for 18 hours. The mixture was then poured into saturated ammonium chloride solution (500 mL) and extracted with dichloromethane. The combined organic fractions were dried over sodium sulfate and concentrated under reduced pressure. The crude product was purified by column chromatography (eluent: dichloromethane/methanol mixtures of increasing polarity). Note: 1.7a and 1.7b could not be separated by column chromatography. Yield: 68% $^1$H NMR (400 MHz, CDCl$_3$) (1.7a/1.7b) δ: 0.75 and 0.83 (d, J=7 Hz, 3H), 1.39 and 1.43 (s, 3H), 2.33 (m, 1H), 2.58 (dd, J=20 Hz and 2 Hz, 1H), 2.92 (d, J=20 Hz, 1H), 3.41 (dd, J=15 Hz and 3 Hz, 1H), 3.94 (d, J=15 Hz, 2H), 5.06 (s, 2H), 6.82-6.89, (m, 3H), 7.26-7.43 (m, 6H)

Mass Spectral Analysis, m/z ESI 310 (M+H$^+$)

Preparation of 1.9

An oven dried flask was charged with a solution of 1.7a-b (25 g, 80.91 mmol) in anhydrous tetrahydrofuran (500 mL) and the solution, under a nitrogen atmosphere, was cooled in an ice bath. To the mixture was then added, dropwise, a 2M solution of 1.8 in tetrahydrofuran (122 mL, 244 mmol). Once the addition was complete the ice bath was removed and the reaction was stirred at room temperature for 1.5 hours. The reaction mixture was poured into a mixture of saturated ammonium chloride solution (250 mL) and saturated sodium bicarbonate solution (250 mL). The mixture was extracted with ethyl acetate and the combined organic extracts were washed with brine and dried over sodium sulfate. The mixture was filtered and the filtrate was concentrated under reduced pressure. The crude material was purified by column chromatography (eluent: hexane/ethyl acetate mixtures of increasing polarity). Yield: 8%

$^1$H NMR (400 MHz, CDCl$_3$) δ: 0.73 (d, J=7 Hz, 3H), 1.36 (s, 3H), 1.41 (m, 0.5H), 1.58 (m, 0.5H), 1.78 (d, J=14 Hz, 1H), 1.97 (t, J=13 Hz, 0.5H), 2.06-2.13 (br m, 1.5H), 2.24 (m, 0.5H), 2.78-2.82, (br m, 2H), 3.08 (d, J=10 Hz 0.5H), 3.18 (d, J=11 Hz, 0.5H), 3.65 (t, J=6 Hz, 0.5H), 5.05 (s, 2H), 5.08-5.17 (m, 2H), 5.88 (m, 1H), 6.13 (br s, 1H), 6.79 (d, J=8 Hz, 1H), 6.84 (br d, J=7 Hz, 2H), 7.23 (t, J=8 Hz, 1H), 7.33-7.45 (m, 5H)

Mass Spectral Analysis, m/z ESI 352 (M+H$^+$)

Preparation of 1.13

To a solution of 1.9 (1.62 g, 4.62 mmol) in acetic acid/water (1:1, 30 mL) was added zinc dust (1.50 g, 23.08 mmol) and the reaction mixture was sonicated for 2 hours. The reaction mixture was then filtered through celite and the filtrate was basified with saturated sodium bicarbonate solution. The aqueous was extracted with ethyl acetate and the organic extracts were washed with brine, dried over sodium sulfate and concentrated under reduced pressure. The desired product was used for the next step without further purification. Yield: 92%

$^1$H NMR (400 MHz, CDCl$_3$) δ: 0.67 (d, J=7 Hz, 3H), 1.36 (s, 3H), 1.58 (d, J=13 Hz, 1H), 1.74 (t, J=12 Hz, 2H), 1.89 (m, 1H), 2.22 (m, 2H), 2.76 (d, J=13 Hz, 1H), 2.94 (m, 1H), 3.29 (dd, J=13 Hz and 3 Hz, 1H), 5.04 (s, 2H), 5.12 (m, 2H), 5.86 (m, 1H), 6.79 (d, J=7 Hz, 1H), 6.89 (m, 2H), 7.23 (t, J=8 Hz, 1H), 7.31 (t, J=8 Hz, 1H), 7.35 (t, J=7 Hz, 2H), 7.44 (t, J=13 Hz, 2H)

Mass Spectral Analysis, m/z ESI 336 (M+H$^+$)

Preparation of 1.15

To a stirred solution of 1.13 (1.5 g, 4.48 mmol) in acetonitrile (20 mL) under a nitrogen atmosphere was added, sequentially, diisopropylethylamine (2.3 mL, 13.44 mmol), 1.14 (0.81 g, 5.37 mmol) and O-benzotriazol-1-yl-N,N,N',N'-tetramethyluronium tetrafluoroborate (TBTU) (2.16 g, 6.72 mmol). The reaction mixture was stirred at room temperature for 3 hours, poured into saturated ammonium chloride solution and extracted with ethyl acetate. The organic extracts were washed with brine, dried over sodium sulfate and concentrated under reduced pressure. The crude material was purified by column chromatography (eluent: hexane/ethyl acetate mixtures of increasing polarity). Yield: 26%

$^1$H NMR (400 MHz, CDCl$_3$) δ: 0.40 (d, J=7 Hz, 3H), 1.39 (s, 1H), 1.44 (s, 3H), 1.93 (m, 1H), 2.08 (m, 1H), 2.46 (m, 2H), 2.92 (dd, J=11 Hz and 3 Hz, 1H), 3.40 (dd, J=15 Hz and 7 Hz, 1H), 4.58 (m, 1H), 5.06 (s, 2H), 5.17 (m, 2H), 5.92 (m, 1H), 6.81 (dd, J=8 Hz and 3 Hz, 1H), 6.87 (m, 2H), 7.22 (t, J=8 Hz, 1H), 7.33 (t, J=7 Hz, 1H), 7.38 (t, J=7 Hz, 2H), 7.44 (d, J=7 Hz, 2H), 7.52 (t, J=8 Hz, 2H), 7.65 (t, J=8 Hz, 1H), 7.99 (d, J=7 Hz, 2H)

Mass Spectral Analysis, m/z ESI 468 (M+H$^+$)

Preparation of 1.17

To a suspension of methyl phosphonium bromide (0.83 g, 2.31 mmol) in anhydrous tetrahydrofuran (10 mL) under a nitrogen atmosphere, was added potassium tert-butoxide (0.29 g, 2.55 mmol) in one portion. The bright yellow mixture was stirred at room temperature for 30 minutes to give 1.16. The solution of 1.16 was transferred to a solution of 1.15 (0.54 g, 1.16 mmol) in anhydrous benzene (10 mL). The reaction mixture was then heated to reflux for 2 hours and concentrated under reduced pressure. The crude product was purified by column chromatography (eluent: hexane/ethyl acetate mixtures of increasing polarity). Yield: 71%

$^1$H NMR (400 MHz, CDCl$_3$) δ: 0.34 (br s, 3H), 1.34 (s, 3H), 1.73-1.84 (m, 2H), 1.99 (d, J=14 Hz, 1H), 2.38-2.43 (m, 2H), 2.78 (t, J=13 Hz, 1H), 3.65 (br s, 1H), 4.55 (br s, 1H), 5.04 (s, 2H), 5.07 (m, 2H), 5.37 (s, 1H), 5.71 (s, 1H), 5.84 (br s, 1H), 6.79 (dd, J=8 Hz and 2 Hz, 1H), 6.86 (s, 2H), 7.20 (t, J=8 Hz, 1H), 7.31-7.38 (m, 6H), 7.42 (d, J=13 Hz, 2H), 7.48 (d, J=8 Hz, 2H)

Mass Spectral Analysis, m/z ESI 466 (M+H$^+$)

Preparation of 1.19

A solution of 1.17 (0.38 g, 0.82 mmol) in anhydrous dichloromethane (20 mL) was purged with nitrogen for 20 minutes. The second generation Grubbs catalyst 1.18 (0.035 g, 0.04 mmol) was added to the reaction mixture, which was then heated to reflux for 2 hours. The mixture was then concentrated under reduced pressure. The crude product was purified by column chromatography (eluent: hexane/ethyl acetate mixtures of increasing polarity).

Yield: 95% $^1$H NMR (400 MHz, CDCl$_3$) δ: 0.72 (d, J=7 Hz, 3H), 1.41 (s, 3H), 1.56 (s, 1H), 1.83 (dd, J=13 Hz and 3 Hz, 1H), 2.18 (m, 2H), 2.49 (m, 1H), 2.61 (t, J=6 Hz, 0.6H), 2.65 (t, J=6 Hz, 0.4H), 3.32 (dd, J=14 Hz and 3 Hz, 1H), 3.89 (m, 1H), 4.30 (dd, J=14 Hz and 2 Hz, 1H), 5.07 (s, 2H), 6.62 (dd, J=6 Hz and 2 Hz, 1H), 6.83 (dd, J=8 Hz and 2 Hz, 1H), 6.91 (m, 2H), 7.26-7.35 (m, 5H), 7.38-7.47 (m, 5H)

Mass Spectral Analysis, m/z ESI 438 (M+H$^+$).

Preparation of 1.20

To a solution of 1.19 (0.34 g, 0.77 mmol) in ethanol (20 mL) was added 10% palladium on charcoal (0.02 g) and the mixture was stirred at room temperature under a hydrogen atmosphere for 16 hours. The mixture was then filtered through celite. The celite was washed with ethanol and the filtrate was evaporated under reduced pressure. The crude product was purified by column chromatography (eluent: hexane/ethyl acetate mixtures of increasing polarity). Yield: 15% $^1$H NMR (400 MHz, CD$_3$OD) δ: 0.64 (d, J=7 Hz, 3H), 1.47 (s, 3H), 1.80 (d, J=13 Hz, 2H), 2.18 (m, 3H), 3.28 (dd, J=13 Hz and 3 Hz, 1H), 3.33 (s, 2H), 3.67 (dd, J=10 Hz and 5 Hz, 1H), 3.92 (m, 1H), 4.54 (dd, J=13 Hz and 3 Hz, 1H), 6.63 (dd, J=7 Hz and 2 Hz, 1H), 6.77 (s, 1H), 6.81 (d, J=8 Hz, 1H), 7.16 (t, J=8 Hz, 1H), 7.23 (m, 3H), 7.32 (t, J=8 Hz, 2H) Mass Spectral Analysis, m/z ESI 350 (M+H$^+$).

Preparation of 1

To a solution of 1.20 (0.04 g, 0.11 mmol) in anhydrous tetrahydrofuran (10 mL) was added borane-dimethyl sulfide complex (2M solution in tetrahydrofuran, 0.11 mL, 0.22 mmol) and the reaction mixture was heated to reflux under a nitrogen atmosphere for 16 hours. The mixture was then cooled to 0° C. and methanol (10 mL) was added. The reaction mixture was stirred at 0° C. for 1 hour. A 2M solution of hydrogen chloride in diethyl ether (10 mL) was then added to the mixture, which was heated to reflux for 1 hour. The mixture was concentrated under reduced pressure. The residue was taken up in methanol (10 mL) and the solution was concentrated under reduced pressure. This process was repeated 5 times. The residue was then basified with 1N aqueous solution of sodium hydroxide (5 mL) and the mixture was extracted with CH$_2$Cl$_2$/MeOH (9:1) (100 mL). The organic extracts were collected, washed with brine and dried over sodium sulfate. The mixture was filtered and the filtrate concentrated under reduced pressure. The crude product was purified by column chromatography (eluent: hexane/ethyl acetate mixture of increasing polarity) Yield: 78% $^1$H NMR (400 MHz, CD$_3$OD) δ: 0.79 (d, J=7 Hz, 3H), 1.38 (s, 3H), 1.57 (m, 1H), 1.67 (m, 2H), 1.83 (m, 1H), 1.98 (m, 2H), 2.09 (m, 1H), 2.33 (m, 1H), 2.42 (m, 1H), 2.68 (d, J=7 Hz, 1H), 2.92 (m, 3H), 6.59 (dd, J=8 Hz and 2 Hz, 1H), 6.73 (m, 1H), 6.77 (d, J=7 Hz, 1H), 7.11 (t, J=8 Hz, 1H), 7.19 (m, 1H), 7.27 (m, 4H)

Mass Spectral Analysis, m/z ESI 336 (M+H$^+$).

Example 2A

Preparation of 2.2

To a solution of 1.2 (72.69 g, 238 mmol) in N,N-dimethylformamide (500 mL) was added imidazole (43.13 g, 309 mmol), N,N-dimethylaminopyridine (DMAP) (2.9 g, 23.8 mmol) and 2.1 (43.13 g, 286 mmol). The reaction mixture was stirred at room temperature for 16 hours. The reaction mixture was then poured into water and extracted with hexanes. The combined organic extracts were washed successively with water and brine solution, dried over sodium sulfate and concentrated under reduced pressure. The crude product was purified by column chromatography (eluent: hexane/ethyl acetate mixtures of increasing polarity). Yield: 86%

$^1$H NMR (400 MHz, CDCl$_3$) δ: 0.18 (s, 6H), 0.62 (d, J=6 Hz, 3H), 0.98 (s, 9H), 1.26 (s, 1H), 1.34 (s, 3H), 1.46 (s, 9H), 1.96 (m, 1H), 2.17 (m, 1H), 3.03 (m, 1H), 3.30 (m, 1H), 3.79 (m, 0.6H), 3.88 (m, 0.4H), 4.06 (m, 0.5H), 4.23 (m, 0.5H), 6.67 (dd, J=8 Hz and 2 Hz, 1H), 6.73 (s, 1H), 6.84 (d, J=7 Hz, 1H), 7.16 (t, J=8 Hz, 1H)

Mass Spectral Analysis, m/z ESI 420 (M+H$^+$)

Preparation of 2.3

An oven dried flask under nitrogen atmosphere was charged with a solution of 2.2 (5.73 g, 13.64 mmol) and N,N,N',N'-tetramethylethylenediamine (TMEDA) in diethyl ether (30 mL). The solution was cooled to −78° C. and sec-butyl lithium (1.4M in cyclohexane, 14.6 mL, 20.46 mmol) was added drop wise over 30 minutes. After stirring at −78° C. for 4.5 hours, carbon dioxide was bubbled through the solution and the reaction mixture was allowed to warm to room temperature overnight. The mixture was poured into saturated ammonium chloride solution and the aqueous layer extracted once with diethyl ether. The ether extract was washed with water, brine, dried over sodium sulfate, filtered and concentrated under reduced pressure. The crude product purified by column chromatography (eluent: dichloromethane/methanol/acetic acid mixtures of increasing polarity). Yield: 73% $^1$H NMR (400 MHz, CDCl$_3$) δ: 0.19 (s, 6H), 0.69 (d, J=7 Hz, 3H), 0.98 (s, 9H), 1.37 (s, 3H), 1.46 (s, 9H), 2.01 (dd, J=14 Hz and 6 Hz, 2H), 2.40 (t, J=12 Hz, 1H), 3.37 (dd, J=14 Hz and 8 Hz, 1H), 3.74 (m, 1H), 4.30 (dd, J=11 Hz and 6 Hz, 1H), 6.67 (dd, J=8 Hz and 2 Hz, 1H), 6.77 (s, 1H), 6.88 (d, J=7 Hz, 1H), 7.14 (t, J=8 Hz, 1H)

Mass Spectral Analysis, m/z ESI 464 (M+H$^+$)

Preparation of 2.5

To a stirred solution of 2.3 (1 g, 2.16 mmol) in acetonitrile (10 mL) under a nitrogen atmosphere was added, sequentially, diisopropylethylamine (1.11 mL, 8.64 mmol), 2.4 (0.325 g, 2.59 mmol) and O-benzotriazol-1-yl-N,N,N',N'-tetramethyluronium tetrafluoroborate (TBTU) (1.04 g, 3.24 mmol). The reaction was stirred at room temperature overnight, poured into saturated ammonium chloride solution and extracted with ethyl acetate. The organic extracts were washed with brine, dried over sodium sulfate, filtered and concentrated under reduced pressure. The crude product was purified by column chromatography (eluent: hexane/ethyl acetate mixtures of increasing polarity). Yield: 95% $^1$H NMR (400 MHz, CDCl$_3$) δ: 0.18 (s, 6H), 0.53 (d, J=6 Hz 3H), 0.98 (s, 9H), 1.35 (s, 3H), 1.48 (s, 9H), 2.39 (t, J=13 Hz, 1H), 3.04 (dd, J=14 Hz and 9 Hz, 1H), 3.76 (s, 3H), 3.89 (dd, J=14 Hz and 6 Hz, 1H), 4.05 (dd, J=10 Hz and 5 Hz, 2H), 4.35 (dd, J=11 Hz and 6 Hz, 1H), 6.60 (br s, 1H), 6.67 (dd, J=8 Hz and 2 Hz, 1H), 6.76 (t, J=2 Hz, 1H), 6.87 (dd, J=8 Hz and 1 Hz, 1H), 7.14 (t, J=8 Hz, 3H)

Mass Spectral Analysis, m/z ESI 535 (M+H$^+$)

Preparation of 2.6

To a solution of 2.5 (1.55 g, 2.90 mmol) in methanol (20 mL) was added a 4M anhydrous solution of hydrogen chloride in dioxane (2.2 mL, 8.8 mmol) and the mixture was heated to reflux for 2 hours. Triethylamine (3.51 g, 34.8 mmol) was then added and the mixture was heated to reflux for 60 hours. The reaction mixture was concentrated under reduced pressure. The crude product was purified by column chromatography (eluent: dichloromethane/methanol mixtures of increasing polarity). Yield: 100% $^1$H NMR (400 MHz, CDCl$_3$) δ: 0.64 (d, J=6 Hz, 3H), 1.43 (s, 3H), 1.59 (s, 1H), 2.16 (m, 1H), 2.22 (t, J=13 Hz, 1H), 2.37 (m, 1H), 3.16 (dd, J=14 Hz and 3 Hz, 1H), 3.49 (s, 1H), 4.23 (dd, J=14 Hz and 3 Hz, 1H), 4.50 (dd, J=14 Hz and 3 Hz, 1H), 6.26 (br s, 1H), 6.70 (m, 2H), 6.81 (d, J=8 Hz, 1H), 7.20 (t, J=8 Hz, 1H) Mass Spectral Analysis, m/z ESI 287 (M–H$^+$).

Preparation of 2.7

To a solution of 2.6 (0.98 g, 3.4 mmol) in anhydrous tetrahydrofuran (100 mL) was added borane-dimethyl sulfide complex (2M solution in tetrahydrofuran, 5.8 mL, 13.6 mmol) and the reaction heated to reflux under a nitrogen atmosphere for 16 hours. The mixture was then cooled to 0° C. Methanol (20 mL) was added to the reaction mixture which was stirred at 0° C. for 1 hour. A 2M anhydrous solution of hydrogen chloride in diethyl ether (20 mL) was then added to the reaction mixture, which was heated to reflux for 1 hour. After cooling, aqueous ammonium hydroxide solution (5 mL) was added to the mixture, which was stirred for 10 minutes at room temperature. The mixture was concentrated under reduced pressure. The residue was dissolved in methanol (20 mL) and concentrated under reduced pressure. This process was repeated 3 times. The crude product was purified by column chromatography (eluent: dichloromethane/methanol/ammonium hydroxide mixtures of increasing polarity).

Yield: 73% $^1$H NMR (400 MHz, CDCl$_3$) δ: 0.79 (d, J=8 Hz, 3H), 1.36 (s, 3H), 1.46 (d, J=12 Hz, 1H), 1.95 (t, J=12 Hz, 1H), 2.03 (br s, 1H), 2.17 (dt, J=11 Hz and 7 Hz, 1H), 2.25 (t, J=11 Hz, 1H), 2.52 (dd, J=11 Hz and 2 Hz, 1H), 2.74 (m, 3H), 3.02 (m, 3H), 6.60 (s, 1H), 6.63 (dd, J=9 Hz and 1 Hz, 1H), 6.78 (d, J=9 Hz, 1H), 7.19 (t, J=8 Hz, 1H)

Mass Spectral Analysis, m/z ESI 261(M+H$^+$).

Preparation of 2A

A solution of 2.7 (0.1 g, 0.38 mmol) in tetrahydrofuran (5 mL) was treated sequentially with triethylamine (0.115 g, 1.14 mmol) and 2.8 (0.13 g, 0.84 mmol) and the mixture was stirred at room temperature for 2 hours. A 1N aqueous solution of sodium hydroxide (5 mL) was added to the mixture, which was stirred at room temperature for a further 12 hours. The mixture was poured into saturated ammonium chloride solution and extracted with ethyl acetate. The organic extracts were washed with water, brine, dried over sodium sulfate, filtered and concentrated under reduced pressure. The crude product was purified by column chromatography (eluent: dichloromethane/methanol mixtures of increasing polarity). Yield: 96% $^1$H NMR (400 MHz, CD$_3$OD), δ: 0.72 (d, J=7 Hz, 1H), 0.75 (d, J=7 Hz, 2H), 1.13 (s, 1.5H), 1.30 (s, 1.5H), 1.55 (d, J=14 Hz, 0.5H), 1.79 (m, 1H), 1.89 (d, J=11 Hz, 0.5H), 1.98 (m, 1.4H), 2.04 (m, 1H), 2.19 (m, 0.6H), 2.53 (m, 2H), 2.65 (m, 1.7H), 2.86 (m, 1.3H), 3.78 (d, J=15 Hz, 1.5H), 3.86 (d, J=15 Hz, 1H), 3.96 (dd, J=13 Hz and 2 Hz, 0.5H), 4.43 (dt, J=13 Hz and 2 Hz, 0.5H), 4.49 (dd, J=13 Hz and 2 Hz, 0.5H), 6.57 (d, J=8 Hz, 1H), 6.65 (s, 1H), 6.70 (s, 1H), 6.74 (d, J=8 Hz, 1H), 7.09 (m, 1H), 7.25 (m, 1H), 7.32 (m, 3H) Mass Spectral Analysis, m/z ESI 379 (M+H$^+$)

Example 2B

Preparation of 2B

To a solution of 2A (0.1 g, 0.26 mmol) in anhydrous tetrahydrofuran (10 mL) was added borane-dimethyl sulfide complex (2M solution in tetrahydrofuran, 0.4 mL, 0.8 mmol) and the reaction heated to reflux under a nitrogen atmosphere for 16 hours. The mixture was then cooled to 0° C. Methanol (5 mL) was added to the reaction mixture which was stirred at 0° C. for 1 hour. A 2M anhydrous solution of hydrogen chloride in diethyl ether (2.5 mL) was then added to the reaction mixture, which was then heated to reflux for 1 hour. The mixture was cooled to room temperature. Aqueous ammonium hydroxide solution (2.5 mL) was added to the mixture, which was stirred for 10 minutes at room temperature. The mixture was concentrated under reduced pressure. The residue was dissolved in methanol and the solution was concentrated under reduced pressure. This process was repeated 3 times. The crude product was purified by column chromatography (eluent: dichloromethane/methanol/ammonium hydroxide mixtures of increasing polarity). Yield: 42% $^1$H NMR (400 MHz, CD$_3$OD) δ: 0.76 (d, J=7 Hz, 3H), 1.36 (s, 3H), 1.53 (d, J=13 Hz, 1H), 1.65 (m, 0.5H), 1.93 (t, J=13 Hz, 1H), 1.98 (m, 0.5H), 2.07 (m, 1H), 2.16 (t, J=11 Hz, 1H), 2.44 (m, 2H), 2.61 (d, J=12 Hz, 1H), 2.71 (m, 2H), 2.79 (d, J=10 Hz, 1H), 2.87 (m, 2H), 3.00 (d, J=9 Hz, 1H), 3.05 (d, J=9 Hz, 1H), 3.58 (m, 1H), 6.58 (dd, J=7 Hz and 2 Hz, 1H), 6.70 (s, 1H), 6.74 (d, J=8 Hz, 1H), 7.10 (t, J=8 Hz, 1H), 7.19 (m, 1H), 7.24 (m, 2H), 7.28 (m, 2H) Mass Spectral Analysis, m/z ESI 365 (M+H$^+$)

Example 2C

Preparation of 2C

A solution of 2.7 (0.1 g, 0.38 mmol) in tetrahydrofuran (5 mL) was treated with triethylamine (0.115 g, 1.14 mmol) and 2.9 (0.12 g, 0.84 mmol) and the mixture stirred at room temperature for 3 hours. A 1N aqueous solution of sodium hydroxide (5 mL) was added to the mixture, which was stirred at room temperature for a further 12 hours. The mixture was poured into saturated ammonium chloride solution and extracted with ethyl acetate. The organic extracts were washed with water and brine, dried over sodium sulfate, filtered and concentrated under reduced pressure. The crude product was purified by column chromatography (eluent: dichloromethane/methanol/ammonium hydroxide mixtures of increasing polarity). Yield: 57%

$^1$H NMR (400 MHz, CD$_3$OD), δ: 0.78 (br s, 3H), 1.29 (br s, 1.5H), 1.37 (br s, 1.5H), 1.63 (m, 0.5H), 1.82 (m, 0.5H), 1.99 (m, 0.5H), 2.06 (br s, 1H), 2.25-2.35 (m, 1.4H), 2.38 (m, 0.6H), 2.61 (m, 1H), 2.70 (m, 1H), 2.79 (dd, J=12 Hz and 2 Hz, 1H), 2.86 (m, 0.5H), 3.06 (m, 1H), 3.37 (m, 1H), 3.59 (m, 1H), 4.60 (m, 1H), 6.58 (m, 1H), 6.67 (m, 1H), 6.77 (m, 1H), 7.11 (m, 1H), 7.44 (m, 2H), 7.48 (m, 3H) Mass Spectral Analysis, m/z ESI 365 (M+H$^+$)

Example 2D

Preparation of 2D

To a solution of 2C (0.07 g, 0.19 mmol) in anhydrous tetrahydrofuran (10 mL) was added borane-dimethyl sulfide complex (2M solution in tetrahydrofuran, 0.3 mL, 0.6 mmol) and the reaction heated to reflux under a nitrogen atmosphere for 16 hours. The mixture was then cooled to 0° C. Methanol (5 mL) was added to the reaction mixture which was stirred at 0° C. for 1 hour. A 2M anhydrous solution of hydrogen chloride in diethyl ether (2.5 mL) was then added to the reaction mixture, which was then heated to reflux for 1 hour. The mixture was cooled to room temperature. Aqueous ammonium hydroxide solution (2.5 mL) was added to the mixture, which was stirred for 10 minutes at room temperature. The mixture was concentrated under reduced pressure. The residue was dissolved in methanol and the solution was concentrated under reduced pressure. This process was repeated 3 times. The crude product was purified by column chromatography (eluent: dichloromethane/methanol/ammonium hydroxide mixtures of increasing polarity). Yield: 100% $^1$H NMR (400 MHz, CD$_3$OD) δ: 0.73 (d, J=7 Hz, 3H), 1.32 (s, 3H), 1.41 (d, J=13 Hz, 1H), 1.65 (m, 1H), 1.84 (m, 2H), 2.00 (m, 1H), 2.33 (m, 1H), 2.43 (t, J=11 Hz, 1H), 2.56 (dd, J=11 Hz and 2 Hz, 1H), 2.70 (m, 1H), 2.74 (m, 1H), 2.82 (dd, J=8 Hz and 2 Hz, 1H), 3.56 (m, 2H), 3.58 (m, 1H), 6.56 (dd, J=8 Hz and 2 Hz, 1H), 6.68 (m, 1H), 6.72 (d, J=8 Hz, 1H), 7.08 (t, J=8 Hz, 1H), 7.27 (m, 1H), 7.34 (m, 4H)

Mass Spectral Analysis, m/z ESI 351 (M+H$^+$)

Example 2E

Preparation of 2.10

To a stirred solution of 2.7 (1 g, 3.85 mmol) in tetrahydrofuran (20 mL) under nitrogen at 0° C., was added triethylamine (2.14 mL, 15.40 mmol) and 1.2 (1.84 g, 8.46 mmol). The solution was stirred at room temperature for 18 hours. The mixture was concentrated under reduced pressure and the residue was dissolved in ethyl acetate (20 mL). The solution was then washed with 0.5M aqueous solution of hydrochloric acid (2×25 mL) and dried over sodium sulfate. The mixture was filtered and the residue concentrated under reduced pressure. The crude product was purified by column chromatography (eluent: hexane/ethyl acetate mixtures of increasing polarity). Yield: 74% $^1$H NMR (400 MHz, CDCl$_3$) δ: 0.73 (d, J=7 Hz, 3H), 1.35 (s, 3H), 1.48 (s, 9H), 1.52 (s, 1H), 1.66 (s, 1H), 1.97 (m, 2H), 2.19 (dt, J=12 Hz and 4 Hz, 1H), 2.26 (m, 1H), 2.56 (dd, J=12 Hz and 2 Hz, 1H), 2.68 (m, 3H), 3.02 (br s, 1H), 4.00 (br s, 1H), 6.64 (dd, J=8 Hz and 2 Hz, 1H), 6.74 (t, J=2 Hz, 1H), 6.80 (d, J=8 Hz 1H), 7.17 (t, J=8 Hz 1H) Mass Spectral Analysis, m/z ESI 361 (M+H$^+$)

Preparation of 2.11

To a stirred solution of 2.10 (1.03 g, 2.86 mmol) in N,N-dimethylformamide (10 mL) was added 1.4 (0.41 mL, 3.43 mmol) and potassium carbonate (1.18 g, 8.58 mmol) and the reaction mixture was stirred at room temperature for 18 hours. The reaction mixture was then poured into water (20 mL) and extracted with hexanes. The combined organics were washed with water, brine and dried over sodium sulfate. The mixture was filtered and the filtrate was concentrated under reduced pressure. The desired product used for next step without further purification.

Yield: 99% $^1$H NMR (400 MHz, CDCl$_3$) δ: 0.75 (d, J=7 Hz, 3H), 1.33 (s, 3H), 1.48 (s, 10H), 1.51 (s, 1H), 1.60 (s, 1H), 1.87 (t, J=12 Hz, 1H), 2.01 (m, 1H), 2.18 (m, 1H), 2.52 (dd, J=11 Hz and 2 Hz, 2H), 2.67 (m, 2H), 2.96 (br s, 1H), 3.98 (br s, 1H), 5.05 (s, 2H), 6.81 (dd, J=8 Hz and 2 Hz, 1H), 6.89 (m, 2H), 7.23 (d, J=9 Hz 1H), 7.34 (m, 1H), 7.39 (t, J=8 Hz, 2H), 7.45 (d, J=9 Hz, 2H) Mass Spectral Analysis, m/z ESI 451 (M+H$^+$)

Preparation of 2.12

To a stirred solution of 2.11 (1.27 g, 2.82 mmol) in methanol (10 mL) was added a 2M anhydrous solution of hydrogen chloride in diethyl ether (6 mL) and the reaction mixture was stirred at room temperature for 18 hours. The mixture was concentrated under reduced pressure. A saturated sodium bicarbonate solution (20 mL) and ethyl acetate (20 mL) were added to the residue and the resultant mixture was stirred at room temperature for 1 hour. The layers were separated and the organic layer was washed with brine and dried over sodium sulfate. The mixture was filtered and the filtrate was concentrated under reduced pressure. The desired product was used for the next step without further purification. Yield: 100% $^1$H NMR (400 MHz, CDCl$_3$) δ: 0.75 (d, J=7 Hz, 3H), 1.34 (s, 3H), 1.45 (d, J=13 Hz, 1H), 1.88 (t, J=12 Hz, 1H), 2.00 (m, 1H), 2.27 (m, 2H), 2.48 (dd, J=12 Hz and 2 Hz, 1H), 2.60 (t, J=11 Hz, 1H), 2.70 (m, 2H), 2.94 (m, 2H), 2.99 (m, 2H), 5.05 (s, 2H), 6.79 (dd, J=9 Hz and 2 Hz, 1H), 6.87 (m, 2H), 7.23 (t, J=8 Hz 1H), 7.32 (m, 1H), 7.38 (t, J=8 Hz, 2H), 7.44 (m, 2H)

Mass Spectral Analysis, m/z ESI 351 (M+H$^+$)

Preparation of 2.14

To a solution of 2.12 (0.5 g, 1.43 mmol) in tetrahydrofuran (10 mL) was added with triethylamine (0.6 mL, 4.26 mmol) and 2.13 (0.22 mL, 1.72 mmol). The mixture was stirred at room temperature for 2 hours. The mixture was poured into saturated ammonium chloride solution and extracted with ethyl acetate. The organic extracts were washed with water and brine, dried over sodium sulfate, filtered and concentrated under reduced pressure. The crude product was purified by column chromatography (eluent: hexane/ethyl acetate mixtures of increasing polarity). Yield: 70% $^1$H NMR (400 MHz, CDCl$_3$), δ: 0.64 (d, J=7 Hz, 3H), 1.33 (s, 3H), 1.49 (dd, J=12 Hz and 2 Hz, 1H), 1.78 (t, J=12 Hz, 1H), 1.99 (m, 1H), 2.09 (t, J=11 Hz, 1H), 2.39 (m, 1H), 2.48 (m, 3H), 2.71 (m, 2H), 3.60 (dt, J=11 Hz and 2 Hz, 1H), 3.69 (dt, J=8 Hz and 2 Hz, 1H), 5.04 (s, 2H), 6.78 (m, 1H), 6.82 (m, 2H), 7.22 (t, J=8 Hz, 1H), 7.34 (m, 1H), 7.39 (t, J=8 Hz, 2H), 7.45 (d, J=8 Hz, 2H), 7.56 (m, 2H), 7.61 (m, 1H), 7.78 (d, J=8 Hz, 1H)

Mass Spectral Analysis, m/z ESI 491 (M+H$^+$)

Preparation of 2E

To a solution of 2.14 (0.52 g, 1.06 mmol) in ethanol (20 mL) was added 10% palladium on charcoal (0.05 g) and the mixture stirred at room temperature under a hydrogen atmosphere for 16 hours. The mixture was then filtered through celite. The celite was washed with ethanol and the filtrate was concentrated under reduced pressure. The crude product was purified by column chromatography (eluent: dichloromethane/methanol/ammonium hydroxide mixtures of increasing polarity). Yield: 85% $^1$H NMR (400 MHz, CD$_3$OD) δ: 0.65 (d, J=7 Hz, 3H), 1.31 (s, 3H), 1.52 (d, J=12 Hz, 1H), 1.77 (t, J=12 Hz, 1H), 2.00 (m, 1H), 2.10 (t, J=11 Hz, 1H), 2.30 (dt, J=11 Hz and 3 Hz, 1H), 2.37 (m, 1H), 2.43 (dd, J=12 Hz and 3 Hz, 1H), 2.52 (m, 2H), 3.60 (d, J=11 Hz, 1H), 3.65 (d, J=11 Hz, 1H), 6.57 (dd, J=8 Hz and 3 Hz, 1H), 6.67 (s, 1H), 6.70 (d, J=7 Hz, 1H), 7.08 (t, J=8 Hz, 1H), 7.63 (m, 2H), 7.68 (m, 1H), 7.79 (d, J=8 Hz, 2H)

Mass Spectral Analysis, m/z ESI 401 (M+H$^+$).

Example 2F

Preparation of 2.16

To a solution of 2.12 (0.5 g, 1.43 mmol) in dichloromethane (10 mL) was added 2.15 (0.5 g, 2.71 mmol), triethylamine (0.4 mL, 2.86 mmol) and cupric acetate (0.2 g, 1.43 mmol). The mixture was stirred at room temperature for 2 days. The mixture was poured into water and extracted with dichloromethane. The organic extracts were washed with water and brine, dried over sodium sulfate, filtered and concentrated under reduced pressure. The crude product was purified by column chromatography (eluent: dichloromethane/methanol/ammonium hydroxide mixtures of increasing polarity). Yield: 30% $^1$H NMR (400 MHz, CDCl$_3$), δ: 0.78 (d, J=7 Hz, 3H), 1.37 (s, 3H), 1.55 (t, J=12 Hz, 1H), 2.02 (m, 2H), 2.44 (m, 1H), 2.49 (m, 1H), 2.60 (t, J=12 Hz, 1H), 2.75 (dd, J=11 Hz and 3 Hz, 1H), 2.81 (dd, J=11 Hz and 3 Hz, 1H), 2.94 (dt, J=12 Hz and 3 Hz, 1H), 3.51 (dd, J=11 Hz and 2 Hz, 1H), 3.57 (d, J=11 Hz, 1H), 5.06 (s, 2H), 6.81 (dd, J=8 Hz and 2 Hz, 1H), 6.85 (d, J=8 Hz, 1H), 6.88 (d, J=5 Hz, 1H), 6.91 (s, 2H), 6.96 (d, J=7 Hz, 2H), 7.28 (m, 2H), 7.33 (d, J=7 Hz, 1H), 7.39 (t, J=8 Hz, 2H), 7.46 (d, J=7 Hz, 2H) Mass Spectral Analysis, m/z ESI 427 (M+H$^+$)

Preparation of 2F

To a solution of 2.16 (0.18 g, 0.42 mmol) in ethanol (20 mL) was added 10% palladium on charcoal (0.02 g) and the mixture stirred at room temperature under a hydrogen atmosphere for 16 hours. The mixture was then filtered through celite. The celite was washed with ethanol and the filtrate evaporated under reduced pressure. The crude product was purified by column chromatography (eluent: dichloromethane/methanol/ammonium hydroxide mixtures of increasing polarity). Yield: 50% $^1$H NMR (400 MHz, CD$_3$OD) δ: 0.79 (d, J=7 Hz, 3H), 1.37 (s, 3H), 1.61 (d, J=12 Hz, 1H), 1.99 (t, J=12 Hz, 1H), 2.08 (m, 1H), 2.44 (dt, J=11 Hz and 2 Hz, 1H), 2.54 (m, 2H), 2.63 (dd, J=11 Hz and 2 Hz, 1H), 2.77 (dd, J=12 Hz and 3 Hz, 1H), 2.84 (m, 1H), 2.90 (m, 1H), 3.55 (t, J=11 Hz, 2H), 6.58 (dd, J=8 Hz and 2 Hz, 1H), 6.74 (m, 1H), 6.77 (d, J=8 Hz, 1H), 6.83 (t, J=7 Hz, 1H), 6.99 (d, J=8 Hz, 2H), 7.11 (t, J=8 Hz, 1H), 7.23 (t, J=8 Hz, 2H) Mass Spectral Analysis, m/z ESI 337 (M+H$^+$).

Example 3A

Preparation of 3.2

To a stirred solution of 2.3 (2 g, 4.32 mmol) in acetonitrile (20 mL) under a nitrogen atmosphere was added, sequentially, diisopropylethylamine (3 mL, 17.28 mmol), 3.1 (1.04 g, 5.18 mmol) and O-benzotriazol-1-yl-N,N,N',N'-tetramethyluronium tetrafluoroborate (TBTU) (2.08 g, 6.48 mmol). The reaction was stirred at room temperature overnight, poured into saturated ammonium chloride solution and extracted with ethyl acetate. The organic extracts were washed with saturated brine, dried over sodium sulfate, filtered and concentrated under reduced pressure. The crude product was purified by column chromatography (eluent: hexane/ethyl acetate mixtures of increasing polarity). Yield: 82% $^1$H NMR (400 MHz, CDCl$_3$) δ: 0.18 (s, 6H), 0.54 (d, J=6 Hz, 3H), 0.98 (s, 9H), 1.34 (s, 3H), 1.38 (s, 9H), 2.03 (m, 2H), 2.40 (t, J=13 Hz, 1H), 3.03 (dd, J=13 Hz and 8 Hz, 1H), 3.74 (s, 3H), 3.92 (dd, J=11 Hz and 8 Hz, 1H), 4.33 (dd, J=12 Hz and 6 Hz, 1H), 5.59 (d, J=7 Hz, 1H), 6.68 (dd, J=8 Hz and 2 Hz, 1H), 6.75 (t, J=2 Hz, 1H), 6.87 (d, J=8 Hz, 1H), 7.14 (t, J=8 Hz, 2H), 7.33 (m, 1H), 7.35 (m, 4H)
Mass Spectral Analysis, m/z ESI 611 (M+H$^+$)

Preparation of 3.3

To a solution of 3.2 (2.16 g, 3.54 mmol) in methanol (75 mL) was added a 4M solution of anhydrous hydrogen chloride in dioxane (3.8 mL, 14.4 mmol). The mixture was heated to reflux for 2 hours. The mixture was concentrated under reduced pressure and the residue taken up in ethyl acetate (75 mL). A saturated solution of sodium bicarbonate was added to the mixture which was stirred for 2 hours at room temperature. The layers were separated and the organic layer was washed with water, brine, dried over sodium sulfate, filtered and concentrated under reduced pressure. The crude product was washed with hexanes and used for the next step without further purification. Yield: 95% $^1$H NMR (400 MHz, CDCl$_3$) δ: 0.73 (d, J=7 Hz, 3H), 1.28 (s, 4H), 1.92 (m, 1H), 2.03 (m, 1H), 2.81 (dd, J=12 Hz and 2 Hz, 1H), 3.29 (dd, J=12 Hz and 3 Hz, 1H), 3.61 (dd, J=11 Hz and 4 Hz, 1H), 3.74 (s, 3H), 5.63 (d, J=13 Hz, 1H), 6.64 (dd, J=8 Hz and 2 Hz, 1H), 6.72 (s, 1H), 6.79 (d, J=7 Hz, 1H), 7.15 (t, J=8 Hz, 1H), 7.38 (m, 5H), 7.92 (d, J=7 Hz, 1H) Mass Spectral Analysis, m/z ESI 397 (M+H$^+$)

Preparation of 3.4

A solution of 3.3 (1.33 g, 3.36 mmol) in toluene (200 mL) was heated to reflux for 60 hours. The mixture was concentrated under reduced pressure. The crude product was purified by column chromatography (eluent: dichloromethane/methanol mixtures of increasing polarity).
Yield: 47% $^1$H NMR (400 MHz, CDCl$_3$) δ: 0.64 (d, J=7 Hz, 3H), 1.39 (s, 3H), 2.11 (m, 1H), 2.26 (t, J=13 Hz, 1H), 2.43 (dd, J=14 Hz and 2 Hz, 1H), 3.12 (dd, J=14 Hz and 3 Hz, 1H), 4.35 (dd, J=12 Hz and 3 Hz, 1H), 4.41 (dd, J=14 Hz and 2 Hz, 1H), 5.16 (s, 1H), 6.51 (s, 1H), 6.67 (dd, J=8 Hz and 2 Hz, 1H), 6.73 (s, 1H), 6.79 (d, J=8 Hz, 2H), 7.19 (t, J=8 Hz, 1H), 7.39 (m, 5H) Mass Spectral Analysis, m/z ESI 363 (M−H$^+$)

Preparation of 3A

To a solution of 3.4 (0.57 g, 1.57 mmol) in anhydrous tetrahydrofuran (10 mL) was added borane-dimethyl sulfide complex (2M solution in tetrahydrofuran, 4.7 mL, 9.4 mmol) and the reaction was heated to reflux under a nitrogen atmosphere for 16 hours. The mixture was then cooled to 0° C. Methanol (20 mL) was added to the reaction mixture, which was stirred at 0° C. for 1 hour. A 2M anhydrous solution of hydrogen chloride in diethyl ether (5 mL) was then added to the reaction, which was heated to reflux for 1 hour. After cooling to room temperature, an aqueous ammonium hydroxide solution (5 mL) was added to the mixture, which was stirred for 10 minutes at room temperature. The mixture was concentrated under reduced pressure. The residue was dissolved in methanol and concentrated under reduced pressure. This process was repeated 3 times. The crude product was purified by column chromatography (eluent: dichloromethane/methanol/ammonium hydroxide mixtures of increasing polarity).
Yield: 69% $^1$H NMR (400 MHz, CD$_3$OD) δ: 0.79 (d, J=7 Hz, 3H), 1.38 (s, 3H), 1.57 (d, J=13 Hz, 1H), 1.95 (t, J=12 Hz, 1H), 2.06 (m, 1H), 2.30 (t, J=13 Hz, 1H), 2.49 (t, J=11 Hz, 1H), 2.57 (dd, J=12 Hz and 2 Hz, 1H), 2.81 (m, 3H), 3.06 (dd, J=13 Hz and 2 Hz, 1H), 4.04 (dd, J=11 Hz and 3 Hz, 1H), 6.59 (dd, J=8 Hz and 2 Hz, 1H), 6.72 (t, J=2 Hz, 1H), 6.76 (d, J=7 Hz, 1H), 7.11 (t, J=8 Hz, 1H), 7.30 (m, 1H), 7.36 (t, J=7 Hz, 2H), 7.41 (d, J=7 Hz, 2H)
Mass Spectral Analysis, m/z ESI 337 (M+H$^+$)

Example 3B

Preparation of 3B

To a solution of 3A (0.1 g, 0.30 mmol) in tetrahydrofuran (5 mL) and ethanol (5 mL) was added triethylamine (0.067 g, 0.66 mmol) and 3.5 (0.05 mL, 0.60 mmol). After 10 minutes sodium cyanoborohydride (0.03 g, 0.36 mmol) was added to the mixture, which was stirred at room temperature for 60 hours. The mixture was concentrated under reduced pressure. The crude product was purified by column chromatography (eluent: dichloromethane/methanol/ammonium hydroxide mixtures of increasing polarity).

Yield: 76% $^1$H NMR (400 MHz, CD$_3$OD) δ: 0.77 (d, J=7 Hz, 3H), 1.37 (s, 3H), 1.57 (d, J=13 Hz, 1H), 1.96 (t, J=13 Hz, 1H), 2.07 (s, 4H), 2.24 (t, J=11 Hz, 1H), 2.32 (t, J=11 Hz, 1H), 2.55 (m, 1H), 2.66 (m, 2H), 2.74 (m, 1H), 2.92 (d, J=10 Hz, 1H), 3.24 (d, J=9 Hz, 1H), 6.58 (dd, J=8 Hz and 2 Hz, 1H), 6.72 (t, J=2 Hz, 1H), 6.76 (d, J=8 Hz, 1H), 7.11 (t, J=8 Hz, 1H), 7.29 (m, 1H), 7.36 (m, 4H) Mass Spectral Analysis, m/z ESI 351 (M+H$^+$)

Example 3C

Preparation of 3.7

To a solution of 3A (0.2 g, 0.60 mmol) in N,N-dimethylformamide (10 mL) was added 3.6 (0.13 mL, 0.89 mmol) and potassium carbonate (0.25 g, 1.80 mmol). The reaction was stirred at room temperature for 3 hours, poured into a saturated solution of ammonium chloride and extracted with ethyl acetate. The organic extracts were washed with saturated brine, dried over sodium sulfate, filtered and concentrated under reduced pressure. The crude product was purified by column chromatography (eluent: hexane/ethyl acetate mixtures of increasing polarity). Yield: 49% $^1$H NMR (400 MHz, CDCl$_3$), δ: 0.77 (d, J=7 Hz, 3H), 1.26 (br s, 2H), 1.37 (s, 3H), 1.42 (s, 9H), 2.00 (t, J=12 Hz, 1H), 2.31 (t, J=11 Hz, 1H), 2.47 (m, 1H), 2.62 (m, 1H), 2.70 (m, 2H), 2.79 (d, J=16 Hz, 1H), 3.06 (dd, J=11 Hz and 3 Hz, 1H), 3.18 (d, J=16 Hz, 1H), 3.71 (dd, J=11 Hz and 3 Hz, 1H), 4.98 (m, 1H), 6.64 (dd, J=8 Hz and 2 Hz, 1H), 6.76 (s, 1H), 6.84 (d, J=8 Hz, 1H), 7.18 (t, J=8 Hz, 1H), 7.26 (m, 1H), 7.33 (m, 2H), 7.41 (d, J=7 Hz, 1H) Mass Spectral Analysis, m/z ESI 451 (M+H$^+$)

Preparation of 3C

A solution of 3.7 (0.13 g, 0.29 mmol) in dioxane (5 mL) and water (5 mL) was treated with a 1M anhydrous solution of hydrogen chloride in diethyl ether (1 mL, 1 mmol). The reaction mixture was stirred at room temperature for 2 days and concentrated under reduced pressure. The residue was triturated with acetonitrile. The precipitate was collected by filtration and further washed with acetonitrile (3 mL). Yield: 67% $^1$H NMR (400 MHz, CD$_3$OD), δ: 0.90 (d, J=7 Hz, 3H), 1.56 (s, 3H), 2.06 (d, J=14 Hz, 1H), 2.35 (t, J=14 Hz, 1H), 2.45 (dd, J=14 Hz and 2 Hz, 1H), 3.41 (dd, J=13 Hz and 2 Hz, 1H), 3.59 (d, J=13 Hz, 1H), 3.71 (dd, J=13 Hz and 4 Hz, 1H), 3.80 (m, 4H), 3.94 (t, J=12 Hz, 1H), 4.25 (m, 1H), 5.14 (dd, J=12 Hz and 3 Hz, 1H), 6.67 (dd, J=8 Hz and 2 Hz, 1H), 6.74 (s, 1H), 6.79 (d, J=8 Hz, 1H), 7.17 (t, J=8 Hz, 1H), 7.51 (m, 3H), 7.63 (m, 2H) Mass Spectral Analysis, m/z ESI 395 (M+H$^+$)

Example 3D

Preparation of 3.9

To a solution of 3A (0.2 g, 0.60 mmol) in methanol (10 mL) was added 3.8 (0.13 mL, 0.89 mmol) and triethylamine (0.25 mL, 1.80 mmol). The reaction was heated to reflux for 18 hours and then concentrated under reduced pressure. The crude product was purified by column chromatography (eluent: hexane/ethyl acetate mixtures of increasing polarity). Yield: 62%

$^1$H NMR (400 MHz, CDCl$_3$), δ: 0.71 (d, J=7 Hz, 3H), 1.37 (s, 3H), 1.42 (s, 9H), 1.53 (d, J=13 Hz, 1H), 1.97 (m, 1H), 2.11 (t, J=12 Hz, 1H), 2.30 (m, 5H), 2.54 (t, J=13 Hz, 2H), 2.66 (dd, J=11 Hz and 3 Hz, 1H), 2.74 (dd, J=12 Hz and 3 Hz, 1H), 2.85 (m, 1H), 3.07 (dd, J=11 Hz and 2 Hz, 1H), 3.48 (dd, J=11 Hz and 3 Hz, 1H), 6.66 (dd, J=8 Hz and 2 Hz, 1H), 6.80 (d, J=2 Hz, 2H), 7.17 (t, J=8 Hz, 1H), 7.31 (m, 5H) Mass Spectral Analysis, m/z ESI 465 (M+H$^+$)

Preparation of 3D

A solution of 3.9 (0.17 g, 0.37 mmol) in dioxane (5 mL) and water (5 mL) was treated with a 1M anhydrous solution of hydrogen chloride in diethyl ether (1 mL, 1 mmol). The reaction mixture was stirred at room temperature for 2 days and concentrated under reduced pressure. The residue was triturated with dichloromethane. The precipitate was collected by filtration and further washed with dichloromethane (3 mL). Yield: 88% $^1$H NMR (400 MHz, CD$_3$OD), δ: 0.94 (d, J=7 Hz, 3H), 1.56 (s, 3H), 2.11 (d, J=13 Hz, 1H), 2.43 (m, 2H), 2.78 (m, 2H), 3.22 (m, 1H), 3.35 (m, 1H), 3.45 (m, 1H), 3.81 (m, 3H), 4.06 (m, 2H), 4.42 (t, J=12 Hz, 1H), 5.18 (d, J=11 Hz, 1H), 6.67 (dd, J=8 Hz and 2 Hz, 1H), 6.74 (s, 1H), 6.79 (d, J=8 Hz, 1H), 7.18 (t, J=8 Hz, 1H), 7.56 (m, 3H), 7.63 (br s, 2H)

Mass Spectral Analysis, m/z ESI 409 (M+H$^+$)

Example 3E

Preparation of 3E

To a solution of 3A (1 g, 2.98 mmol) in ethanol (20 mL) was added 3.10 (0.95 g, 8.93 mmol) and the reaction mixture was stirred at room temperature for 10 minutes. To this was then added borane-pyridine complex (BAP) (0.82 g, 8.93 mmol) and the reaction stirred at room temperature for 18 hours. The mixture was concentrated under reduced pressure. The residue was taken up in ethyl acetate. The mixture was washed with a saturated aqueous sodium bicarbonate solution, water, brine, dried over magnesium sulfate, filtered and concentrated under reduced pressure. The crude product was purified by column chromatography (eluent: dichloromethane/methanol/ammonium hydroxide mixtures of increasing polarity).

Yield: 71% $^1$H NMR (400 MHz, CD$_3$OD) δ: 0.76 (d, J=7 Hz, 3H), 1.31 (s, 3H), 1.38 (d, J=13 Hz, 1H), 1.89 (t, J=13 Hz, 1H), 2.04 (m, 2H), 2.32 (t, J=11 Hz, 1H), 2.48 (m, 1H), 2.54 (dd, J=11 Hz and 2 Hz, 1H), 2.69 (t, J=3 Hz, 1H), 2.72 (t, J=3 Hz, 1H), 2.79 (dd, J=11 Hz and 2 Hz, 1H), 2.90 (d, J=13 Hz, 1H), 3.51 (dd, J=10 Hz and 3 Hz, 1H), 3.74 (d, J=13 Hz, 1H), 6.55 (dd, J=7 Hz and 1 Hz, 1H), 6.67 (t, J=2 Hz, 1H), 6.71 (d, J=7 Hz, 1H), 7.08 (t, J=8 Hz, 1H), 7.21 (m, 1H), 7.28 (m, 5H), 7.37 (t, J=8 Hz, 2H), 7.53 (d, J=6 Hz, 2H), Mass Spectral Analysis, m/z ESI 427 (M+H$^+$)

Example 3F

Preparation of 3.12

To a solution of 3E (0.9 g, 2.11 mmol) in dichloromethane (10 mL) at 0° C. under a nitrogen atmosphere was added 3.11 (0.83 g, 2.32 mmol) and triethylamine (0.71 mL, 5.06 mmol). The reaction mixture was allowed to warm to room temperature overnight and the concentrated under reduced pressure. The residue was taken up in ethyl acetate. The organic mixture was washed successively with brine, a 1N aqueous solution of sodium hydroxide, brine, dried over sodium sulfate, filtered and concentrated under reduced pressure. The crude product was purified by column chromatography (eluent: hexane/ethyl acetate mixtures of increasing polarity). Yield: 72% $^1$H NMR (400 MHz, CDCl$_3$) δ: 0.75 (d, J=7 Hz, 3H), 1.33 (s, 3H), 1.44 (d, J=12 Hz, 1H), 1.57 (s, 1H), 1.88 (t, J=12 Hz, 1H), 2.05 (m, 1H), 2.32 (t, J=11 Hz, 1H), 2.44 (m, 1H), 2.51 (dd, J=12 Hz and 2 Hz, 1H), 2.67 (dd, J=12 Hz and 3 Hz, 1H), 2.76 (dd, J=11 Hz and 3 Hz, 1H), 2.83 (dd, J=11 Hz and 2 Hz, 1H), 2.88 (d, J=14 Hz, 1H), 3.51 (dd, J=11 Hz and 3 Hz, 1H), 3.82 (d, J=13 Hz, 1H), 7.09 (m, 2H), 7.24 (m, 4H), 7.30 (m, 4H), 7.37 (m, 3H), 7.53 (m, 1H) Mass Spectral Analysis, m/z ESI 559 (M+H$^+$)

Preparation of 3.13

To a solution of 3.12 (0.5 g, 0.90 mmol) in methanol (6 mL) and dimethylsulfoxide (8 mL) was added triethylamine (0.28 mL, 1.97 mmol). Carbon monoxide was then bubbled through the solution for 5 minutes. Palladium (II) acetate (0.02 g, 0.09 mmol) and 1,1'-bis(diphenylphosphino)ferrocene (dppf) (0.1 g, 0.18 mmol) were added to the mixture. Carbon monoxide was bubbled through the reaction mixture for 15 minutes while the reaction was heated to 65° C. The reaction mixture was heated at 65° C. under an atmosphere of carbon monoxide for 18 hours. The reaction mixture was poured into water and extracted with ethyl acetate. The organic extracts were washed with water, saturated brine solution, dried over sodium sulfate, filtered and concentrated under reduced pressure. The crude product was purified by column chromatography (eluent: hexane/ethyl acetate mixtures of increasing polarity). Yield: 76% $^1$H NMR (400 MHz, CD$_3$OD) δ: 0.72 (d, J=7 Hz, 3H), 1.36 (s, 3H), 1.50 (d, J=13 Hz, 1H), 1.98 (t, J=13 Hz, 1H), 2.11 (m, 2H), 2.35 (t, J=11 Hz, 1H), 2.54 (m, 2H), 2.74 (m, 2H), 2.84 (dd, J=11 Hz and 2 Hz, 1H), 2.92 (d, J=13 Hz, 1H), 3.52 (dd, J=10 Hz and 3 Hz, 1H), 3.74 (d, J=13 Hz, 1H), 3.89 (s, 3H), 7.22 (m, 1H), 7.28 (m, 5H), 7.39 (m, 3H), 7.53 (d, J=8 Hz, 3H), 7.82 (dd, J=8 Hz and 2 Hz, 1H), 7.90 (s, 1H)

Mass Spectral Analysis, m/z ESI 469 (M+H$^+$)

Preparation of 3.14

A solution of 3.13 (0.29 g, 0.62 mmol) in tetrahydrofuran (4 mL) and water (2 mL) was treated with lithium hydroxide monohydrate (0.08 g, 1.86 mmol) and methanol (10 mL) and the mixture was stirred at room temperature for 2 days. The reaction mixture was neutralized to pH ~6-7 by addition of 1N aqueous solution of hydrochloric acid. The mixture was then concentrated under reduced pressure. The residue was taken up in dichloromethane. The organic solution was dried over sodium sulfate, filtered and concentrated under reduced pressure. The product was isolated without further purification. Yield: 100% $^1$H NMR (400 MHz, CD$_3$OD) δ: 0.76 (d, J=7 Hz, 3H), 1.42 (s, 3H), 1.69 (d, J=13 Hz, 1H), 2.14 (t, J=13 Hz, 1H), 2.27 (m, 1H), 2.34 (m, 1H), 2.80 (t, J=11 Hz, 1H), 2.88 (dd, J=13 Hz and 2 Hz, 1H), 2.95 (dd, J=12 Hz and 2 Hz, 1H), 3.02 (m, 3H), 3.11 (dd, J=12 Hz and 3 Hz, 1H), 3.75 (m, 2H), 7.22 (m, 1H), 7.28 (m, 4H), 7.36 (m, 2H), 7.42 (m, 3H), 7.56 (d, J=7 Hz, 2H), 7.81 (d, J=8 Hz, 1H), 7.90 (s, 1H) Mass Spectral Analysis, m/z ESI 455 (M+H$^+$)

Preparation of 3F

To a stirred solution of 3.14 (0.22 g, 0.48 mmol) in N,N-dimethylformamide (10 mL) were added, sequentially, triethylamine (0.15 mL, 1.06 mmol), ammonium chloride (0.1 g, 2.40 mmol) and O-benzotriazol-1-yl-N,N,N',N'-tetramethyluronium tetrafluoroborate (TBTU) (0.23 g, 0.72 mmol). The reaction was stirred at room temperature for 4 hours, poured into saturated ammonium chloride solution and extracted with ethyl acetate. The organic extracts were washed with saturated brine, dried over sodium sulfate and concentrated under reduced pressure. The crude product was purified by column chromatography (eluent: dichloromethane/methanol/ammonium hydroxide mixtures of increasing polarity).

Yield: 91% $^1$H NMR (400 MHz, CD$_3$OD) δ: 0.74 (d, J=7 Hz, 3H), 1.39 (s, 3H), 1.64 (d, J=13 Hz, 1H), 2.06 (t, J=13 Hz, 1H), 2.22 (m, 2H), 2.59 (t, J=12 Hz, 1H), 2.76 (m, 2H), 2.89 (m, 1H), 2.95 (m, 3H), 3.61 (dd, J=11 Hz and 3 Hz, 1H), 3.75 (d, J=13 Hz, 1H), 7.22 (m, 1H), 7.28 (m, 6H), 7.40 (t, J=8 Hz, 3H), 7.47 (d, J=8 Hz, 1H), 7.54 (m, 2H), 7.68 (m, 2H), 7.778 (s, 1H) Mass Spectral Analysis, m/z ESI 454 (M+H$^+$)

Example 3G

Preparation of 3G

To a solution of 3F (0.1 g, 0.22 mmol) in ethanol (20 mL) was added 10% palladium on charcoal (0.01 g) and the mixture stirred at room temperature under a hydrogen atmosphere for 16 hours. The mixture was then filtered through celite. The celite was washed with ethanol and the filtrate was evaporated under reduced pressure. The crude product was purified by column chromatography (eluent: dichloromethane/methanol/ammonium hydroxide mixtures of increasing polarity). Yield: 12%

$^1$H NMR (400 MHz, CD$_3$OD) δ: 0.77 (d, J=7 Hz, 3H), 1.43 (s, 3H), 1.67 (d, J=12 Hz, 1H), 2.02 (t, J=12 Hz, 1H), 2.18 (m, 1H), 2.24 (t, J=11 Hz, 1H), 2.46 (m, 1H), 2.58 (dd, J=11 Hz and 2 Hz, 1H), 2.79 (m, 3H), 3.04 (dd, J=12 Hz and 3 Hz, 1H), 3.97 (dd, J=11 Hz and 3 Hz, 1H), 7.27 (m, 1H), 7.33 (t, J=8 Hz, 2H), 7.42 (m, 3H), 7.52 (d, J=8 Hz, 1H), 7.70 (dd, J=8 Hz and 2 Hz, 1H), 7.83 (s, 1H) Mass Spectral Analysis, m/z ESI 364 (M+H$^+$).

Example 4

Preparation of 4.2

To a stirred solution of 2.3 (2 g, 4.32 mmol) in acetonitrile (20 mL) under a nitrogen atmosphere were added, sequentially, diisopropylethylamine (3 mL, 17.28 mmol), 4.1 (1.12 g, 5.18 mmol) and O-benzotriazol-1-yl-N,N,N',N'-tetramethyluronium tetrafluoroborate (TBTU) (2.08 g, 6.48 mmol). The reaction mixture was stirred at room temperature overnight, poured into a saturated aqueous solution of ammonium chloride and extracted with ethyl acetate. The organic extracts were washed with saturated brine, dried over sodium sulfate and concentrated under reduced pressure. The crude product was purified by column chromatography (eluent: hexane/ethyl acetate mixtures of increasing polarity). Yield: 81% $^1$H NMR (400 MHz, CDCl$_3$) δ: 0.18 (s, 6H), 0.45 (d, J=7 Hz, 3H), 0.98 (s, 9H), 1.32 (s, 3H), 1.45 (s, 9H), 1.98 (m, 2H), 2.33 (t, J=13 Hz, 1H), 2.89 (dd, J=14 Hz and 9 Hz, 1H), 3.12 (t, J=6 Hz, 2H), 3.70 (s, 3H), 3.88 (dd, J=8 Hz and 3 Hz, 1H), 4.33 (dd, J=12 Hz and 6 Hz, 1H), 4.84 (q, J=6 Hz, 1H), 6.66 (dd, J=8 Hz and 2 Hz, 1H), 6.73 (t, J=2 Hz, 1H), 6.84 (d, J=8 Hz, 1H), 7.13 (m, 3H), 7.24 (m, 1H), 7.29 (m, 2H) Mass Spectral Analysis, m/z ESI 625 (M+H$^+$)

Preparation of 4.3

To a solution of 4.2 (2.18 g, 3.49 mmol) in methanol (75 mL) was added a 1M solution of hydrogen chloride in diethyl ether (14 mL, 14 mmol) and the mixture was heated to reflux for 2 hours. The solvents were removed under vacuum and the residue taken up in ethyl acetate (75 mL). A saturated aqueous solution of sodium bicarbonate (100 mL) was then added to the mixture which was stirred for 2 hours at room temperature. The layers were separated and the organic layer was washed with water, brine, dried over sodium sulfate, filtered and concentrated under reduced pressure. The product was washed with hexanes and used in the next step without further purification. Yield: 99% $^1$H NMR (400 MHz, CDCl$_3$) δ: 0.67 (d, J=7 Hz, 3H), 1.28 (s, 3H), 1.92 (m, 3H), 2.75 (dd, J=13 Hz and 2 Hz, 1H), 3.08 (d, J=13 Hz, 0.5H), 3.11 (d, J=6 Hz, 0.5H), 3.21 (d, J=6 Hz, 1H), 3.27 (m, 2H), 3.55 (dd, J=11 Hz and 6 Hz, 1H), 3.74 (s, 3H), 4.88 (q, J=6 Hz, 1H), 6.64 (dd, J=8 Hz and 2 Hz, 1H), 6.70 (s, 1H), 6.77 (d, J=7 Hz, 1H), 7.15 (m, 3H), 7.21 (m, 2H), 7.31 (m, 3H) Mass Spectral Analysis, m/z ESI 411 (M+H$^+$)

Preparation of 4.4

A solution of 4.3 (1.42 g, 3.46 mmol) in toluene (200 mL) was heated to reflux for 60 hours. The mixture was concentrated under reduced pressure. The crude product was purified by column chromatography (eluent: dichloromethane/methanol mixtures of increasing polarity).
Yield 38% $^1$H NMR (400 MHz, CDCl$_3$) δ: 0.59 (d, J=7 Hz, 3H), 1.21 (s, 3H), 2.00 (m, 1H), 2.16 (m, 1H), 2.87 (dd, J=14 Hz and 3 Hz, 1H), 3.05 (d, J=11 Hz, 1H), 3.20 (t, J=4 Hz, 2H), 4.38 (m, 2H), 6.31 (br s, 1H), 6.64 (m, 1H), 6.69 (m, 1H), 6.76 (d, J=8 Hz, 1H), 7.17 (t, J=8 Hz, 2H), 7.21 (dd, J=8 Hz and 2 Hz, 2H), 7.31 (t, J=7 Hz, 1H), 7.36 (m, 2H)
Mass Spectral Analysis, m/z ESI 377 (M–H$^+$)

Preparation of 4

To a solution of 4.4 (0.50 g, 1.32 mmol) in anhydrous tetrahydrofuran (10 mL) was added borane-dimethyl sulfide complex (2M solution in tetrahydrofuran, 4 mL, 8 mmol) and the reaction heated to reflux under a nitrogen atmosphere for 16 hours. The mixture was then cooled to 0° C. Methanol (20 mL) was added to the reaction mixture, which was stirred at 0° C. for 1 hour. A 2M anhydrous solution of hydrogen chloride in diethyl ether (5 mL) was then added to the reaction mixture, which was then heated to reflux for 1 hour. After cooling to room temperature, an aqueous ammonium hydroxide solution (5 mL) was added to the mixture, which was stirred for 10 minutes at room temperature. The mixture was concentrated under reduced pressure. The residue was dissolved in methanol and concentrated under reduced pressure. This process was repeated 3 times. The crude product was purified by column chromatography (eluent: dichloromethane/methanol/ammonium hydroxide mixtures of increasing polarity).
Yield: 43% $^1$H NMR (400 MHz, CD$_3$OD) δ: 0.67 (d, J=7 Hz, 3H), 1.29 (s, 3H), 1.43 (d, J=8 Hz, 1H), 1.79 (t, J=12 Hz, 1H), 1.87 (t, J=11 Hz, 1H), 1.96 (m, 3H), 2.25 (dt, J=13 Hz and 3 Hz, 1H), 2.40 (dd, J=12 Hz and 2 Hz, 1H), 2.52 (d, J=12 Hz, 1H), 2.56 (m, 1H), 2.67 (m, 2H), 2.82 (dd, J=12 Hz and 2 Hz, 1H), 3.03 (m, 1H), 6.52 (dd, J=8 Hz and 2 Hz, 1H), 6.64 (t, J=2 Hz, 1H), 6.68 (d, J=8 Hz, 1H), 7.04 (t, J=8 Hz, 1H), 7.17 (d, J=7 Hz, 3H), 7.25 (t, J=7 Hz, 2H) Mass Spectral Analysis, m/z ESI 351 (M+H$^+$)

Example 5

Preparation of 5.2

To a stirred solution of 2.3 (3.87 g, 8.36 mmol) in acetonitrile (40 mL) under a nitrogen atmosphere were added, sequentially, diisopropylethylamine (5.8 mL, 33.44 mmol), 5.1 (2.17 g, 10.03 mmol) and O-benzotriazol-1-yl-N,N,N',N'-tetramethyluronium tetrafluoroborate (TBTU) (4.03 g, 12.54 mmol). The reaction mixture was stirred at room temperature overnight, poured into a saturated aqueous solution of ammonium chloride and extracted with ethyl acetate. The organic extracts were washed with brine, dried over sodium sulfate, filtered and concentrated under reduced pressure. The crude product was purified by column chromatography (eluent: hexane/ethyl acetate mixtures of increasing polarity). Yield: 71% $^1$H NMR (400 MHz, CDCl$_3$) δ: 0.19 (s, 6H), 0.43 (d, J=7 Hz, 3H), 0.99 (s, 9H), 1.30 (s, 3H), 1.44 (s, 9H), 1.98 (dd, J=14 Hz and 6 Hz, 2H), 2.14 (m, 1H), 2.79 (m, 1H), 3.05 (dd, J=14 Hz and 6 Hz, 1H), 3.22 (dd, J=14 Hz and 6 Hz, 1H), 3.74 (s, 3H), 3.82 (dd, J=12 Hz and 4 Hz, 1H), 4.25 (q, J=6 Hz, 1H), 4.92 (m, 1H), 6.55 (m, 1H), 6.68 (m, 1H), 6.72 (t, J=2 Hz, 1H), 6.81 (d, J=8 Hz, 1H), 7.12 (m, 1H), 7.16 (t, J=8 Hz, 2H), 7.24 (m, 3H) Mass Spectral Analysis, m/z ESI 625 (M+H$^+$)

Preparation of 5.3

To a solution of 5.2 (3.68 g, 5.90 mmol) in methanol (40 mL) was added a 4M solution of hydrogen chloride in dioxane (5.9 mL, 23.6 mmol) and the mixture was heated to reflux for 2 hours. The mixture was concentrated under reduced pressure and the residue taken up in ethyl acetate (75 mL). A saturated aqueous solution of sodium bicarbonate (100 mL) was then added to the mixture which was stirred for 2 hours at room temperature. The layers were separated and the organic layer was washed with water, brine, dried over sodium sulfate, filtered and concentrated under reduced pressure. The product was washed with hexanes and used for the next step without further purification. Yield: 77% $^1$H NMR (400 MHz, CDCl$_3$) δ: 0.68 (d, J=7 Hz, 3H), 1.28 (s, 3H), 1.73 (m, 1H), 1.86 (m, 1H), 1.94 (m, 1H), 2.79 (dd, J=12 Hz and 2 Hz, 1H), 3.07 (dd, J=14 Hz and 8 Hz, 1H), 3.23 (dd, J=14 Hz and 6 Hz, 1H), 3.30 (dd, J=13 Hz and 3 Hz, 1H), 3.59 (dd, J=12 Hz and 3 Hz, 1H), 3.75 (s, 3H), 4.96 (m, 1H), 6.66 (m, 2H), 6.74 (d, J=9 Hz, 1H), 7.17 (m, 2H), 7.27 (m, 4H), 7.38 (d, J=9 Hz, 1H)
Mass Spectral Analysis, m/z ESI 411 (M+H$^+$)

Preparation of 5.4

A solution of 5.3 (2.01 g, 4.90 mmol) in toluene (70 mL) was heated to reflux for 60 hours. The mixture was concentrated under reduced pressure. The crude product was purified by column chromatography (eluent: dichloromethane/methanol mixtures of increasing polarity).
Yield 70% $^1$H NMR (400 MHz, CD$_3$OD) δ: 0.17 (d, J=7 Hz, 3H), 0.98 (t, J=13 Hz, 1H), 1.30 (s, 3H), 1.80 (d, J=12 Hz, 1H), 1.93 (m, 1H), 3.01 (dd, J=14 Hz and 5 Hz, 1H), 3.07 (dd, J=13 Hz and 3 Hz, 1H), 3.30 (m, 1H), 4.07 (m, 1H), 4.24 (dd, J=13 Hz and 2 Hz, 1H), 4.43 (t, J=4 Hz, 1H), 6.45 (m, 2H), 6.58 (dd, J=8 Hz and 2 Hz, 1H), 7.07 (t, J=8 Hz, 1H), 7.22 (m, 5H)
Mass Spectral Analysis, m/z ESI 377 (M–H$^+$)

Preparation of 5

To a solution of 5.4 (1.29 g, 3.4 mmol) in anhydrous tetrahydrofuran (20 mL) was added borane-dimethyl sulfide complex (2M solution in tetrahydrofuran, 10.3 mL, 20.6 mmol) and the reaction heated to reflux under a nitrogen atmosphere for 16 hours. The mixture was then cooled to 0° C. Methanol (10 mL) was added to the reaction mixture which was stirred at 0° C. for 1 hour. A 2M anhydrous solution of hydrogen chloride in diethyl ether (10 mL) was then added to the reaction mixture, which was heated to reflux for 1 hour. After cooling, aqueous ammonium hydroxide solution (5 mL) was added to the mixture, which was stirred for 10 minutes at room temperature. The mixture was concentrated under reduced pressure. The residue was dissolved in methanol (10 mL) and concentrated under reduced pressure. This process was repeated 3 times. The crude product was purified by column chromatography (eluent: dichloromethane/methanol/ammonium hydroxide mixtures of increasing polarity).

Yield: 80% $^1$H NMR (400 MHz, CD$_3$OD) δ: 0.89 (d, J=7 Hz, 3H), 1.33 (s, 3H), 1.56 (d, J=14 Hz, 1H), 2.06 (m, 2H), 2.29 (dd, J=12 Hz and 3 Hz, 1H), 2.38 (dd, J=12 Hz and 2 Hz, 1H), 2.50 (m, 2H), 2.70 (dd, J=12 Hz and 3 Hz, 1H), 2.92 (m, 2H), 3.10 (t, J=11 Hz, 1H), 3.38 (d, J=10 Hz, 2H), 6.60 (dd, J=8 Hz and 2 Hz, 1H), 6.73 (t, J=2 Hz, 1H), 6.77 (d, J=8 Hz, 1H), 7.12 (t, J=8 Hz, 1H), 7.23 (d, J=7 Hz, 3H), 7.30 (t, J=8 Hz, 2H)

Mass Spectral Analysis, m/z ESI 351 (M+H$^+$)

Example 6

Preparation of 6.2

To a stirred solution of 2.3 (2 g, 4.32 mmol) in acetonitrile (20 mL) under a nitrogen atmosphere were added, sequentially, diisopropylethylamine (3 mL, 17.28 mmol), 6.1 (1.08 g, 5.18 mmol) and O-benzotriazol-1-yl-N,N,N',N'-tetramethyluronium tetrafluoroborate (TBTU) (2.08 g, 6.48 mmol). The reaction was stirred at room temperature overnight, poured into a saturated aqueous solution of ammonium chloride and extracted with ethyl acetate. The organic extracts were washed with brine, dried over sodium sulfate, filtered and concentrated under reduced pressure. The crude product was purified by column chromatography (eluent: hexane/ethyl acetate mixtures of increasing polarity). Yield: 82% $^1$H NMR (400 MHz, CDCl$_3$) δ: 0.18 (s, 6H), 0.50 (d, J=7 Hz, 3H), 0.98 (s, 9H), 1.04-1.16 (m, 2H), 1.19-1.28 (m, 2H), 1.34 (s, 3H), 1.50 (s, 9H), 1.59 (s, 2H), 1.60-1.69 (m, 2H), 1.70-1.84 (m, 3H), 2.00 (m, 2H), 2.34 (t, J=13 Hz, 1H), 2.92 (dt, J=14 Hz and 4 Hz, 1H), 3.73 (s, 3H), 3.96 (br s, 1H), 4.38 (dd, J=11 Hz and 6 Hz, 1H), 4.54 (dd, J=9 Hz and 5 Hz, 1H), 6.67 (dd, J=8 Hz and 2 Hz, 1H), 6.74 (t, J=2 Hz, 1H), 6.86 (dd, J=9 Hz and 1 Hz, 1H), 7.13 (t, J=8 Hz, 1H)

Mass Spectral Analysis, m/z ESI 617 (M+H$^+$)

Preparation of 6.3

To a solution of 6.2 (2.17 g, 3.52 mmol) in methanol (80 mL) was added a 4M anhydrous solution of hydrogen chloride in dioxane (5 mL, 20 mmol) and the mixture was heated to reflux for 2 hours. The mixture was concentrated under reduced pressure and the residue taken up in ethyl acetate (75 mL). To this was added a saturated aqueous solution of sodium bicarbonate (100 mL), which was stirred for 2 hours at room temperature. The layers were separated and the organic layer was washed with water, saturated brine, dried over sodium sulfate and concentrated under reduced pressure. The product was washed with hexanes and used for the next step without further purification. Yield: 97% $^1$H NMR (400 MHz, CDCl$_3$) δ: 0.72 (d, J=7 Hz, 3H), 1.02-1.16 (m, 3H), 1.18-1.23 (m, 1H), 1.30 (s, 3H), 1.64 (m, 4H), 1.76 (m, 3H), 1.81-1.89 (m, 1H), 1.93 (m, 1H), 1.99 (m, 1H), 2.84 (dd, J=13 Hz and 2 Hz, 1H), 3.32 (dd, J=12 Hz and 3 Hz, 1H), 3.63 (dd, J=10 Hz and 6 Hz, 1H), 3.76 (s, 3H), 4.56 (dd, J=9 Hz and 5 Hz, 1H), 6.65 (dd, J=7 Hz and 2 Hz, 1H), 6.72 (t, J=2 Hz, 1H), 6.79 (d, J=8 Hz, 1H), 7.16 (t, J=8 Hz, 1H), 7.44 (d, J=9 Hz, 1H) Mass Spectral Analysis, m/z ESI 403 (M+H$^+$)

Preparation of 6.4

A solution of 6.3 (1.37 g, 3.41 mmol) in o-xylene (100 mL) was heated to reflux for 60 hours. The mixture was concentrated under reduced pressure. The crude product was purified by column chromatography (eluent: dichloromethane/methanol mixtures of increasing polarity).

Yield 37% $^1$H NMR (400 MHz, DMSO-D$_6$) δ: 0.49 (d, J=7 Hz, 3H), 1.00-1.29 (m, 6H), 1.34 (s, 3H), 1.45 (m, 1H), 1.53 (d, J=8 Hz, 1H), 1.62 (d, J=8 Hz, 1H), 1.72 (t, J=8 Hz, 1H), 1.84 (m, 1H), 1.96 (t, J=13 Hz, 1H), 2.10 (m, 1H), 2.50 (m, 1H), 3.12 (dd, J=14 Hz and 3 Hz, 1H), 3.74 (t, J=2 Hz, 1H), 4.15 (dd, J=12 Hz and 2 Hz, 1H), 4.24 (dd, J=13 Hz and 2 Hz, 1H), 6.57 (dd, J=8 Hz and 1 Hz, 1H), 6.65 (d, J=2 Hz, 1H), 6.69 (d, J=8 Hz, 1H), 7.11 (t, J=8 Hz, 1H), 8.24 (d, J=3 Hz, 1H), 9.24 (s, 1H) Mass Spectral Analysis, m/z ESI 369 (M−H$^+$)

Preparation of 6

To a solution of 6.4 (0.47 g, 1.27 mmol) in anhydrous tetrahydrofuran (10 mL) was added borane-dimethyl sulfide complex (2M solution in tetrahydrofuran, 3.8 mL, 7.6 mmol) and the reaction heated to reflux under a nitrogen atmosphere for 16 hours. The mixture was then cooled to 0° C. Methanol (10 mL) was added to the reaction mixture which was stirred at 0° C. for 1 hour. A 2M anhydrous solution of hydrogen chloride in diethyl ether (5 mL) was then added to the reaction mixture, which was heated to reflux for 1 hour. After cooling, aqueous ammonium hydroxide solution (5 mL) was added to the mixture, which was stirred for 10 minutes at room temperature. The mixture was concentrated under reduced pressure. The residue was dissolved in methanol (10 mL) and concentrated under reduced pressure. This process was repeated 3 times. The crude product was purified by column chromatography (eluent: dichloromethane/methanol/ammonium hydroxide mixtures of increasing polarity).

Yield: 68% $^1$H NMR (400 MHz, CD$_3$OD) δ: 0.76 (d, J=7 Hz, 3H), 1.12 (m, 2H), 1.25 (m, 2H), 1.34 (m, 4H), 1.47 (m, 1H), 1.56 (d, J=13 Hz, 1H), 1.70 (d, J=10 Hz, 1H), 1.84 (m, 5H), 2.09 (m, 2H), 2.46 (m, 1H), 2.59 (dd, J=11 Hz and 2 Hz, 1H), 2.77 (m, 2H), 2.93 (m, 2H), 3.13 (dd, J=12 Hz and 3 Hz, 1H), 6.59 (dd, J=8 Hz and 2 Hz, 1H), 6.73 (m, 2H), 7.10 (t, J=8 Hz, 1H)

Mass Spectral Analysis, m/z ESI 343 (M+H$^+$)

Example 7

Preparation of 7.2

To a stirred solution of 2.3 (5 g, 10.8 mmol) in acetonitrile (50 mL) under a nitrogen atmosphere was added, sequentially, triethylamine (4 mL, 32.4 mmol), 7.1 (2.7 g, 12.96 mmol) and O-benzotriazol-1-yl-N,N,N',N'-tetramethyluronium tetrafluoroborate (TBTU) (5.2 g, 16.2 mmol). The reaction mixture was stirred at room temperature overnight, poured into a saturated aqueous solution of ammonium chloride and extracted with ethyl acetate. The organic extracts were washed with brine, dried over sodium sulfate, filtered and concentrated under reduced pressure. The crude product was purified by column chromatography (eluent: hexane/ethyl acetate mixtures of increasing polarity). Yield: 60% $^1$H NMR (400 MHz, CDCl$_3$) δ: 0.18 (s, 6H), 0.47 (m, 3H), 0.88 (m, 1H), 0.98 (s, 9H), 1.14 (s, 2H), 1.24 (m, 4H), 1.47 (s, 9H), 1.64 (s, 1H), 1.89 (m, 1H), 2.01 (m, 0.5H), 2.35 (m, 0.5H), 2.47 (m, 0.5H), 2.56 (m, 0.5H), 2.70 (t, J=7 Hz, 1H), 3.36 (m, 1H), 3.54 (m, 1H), 3.89 (m, 1H), 4.11 (m, 2H), 4.46 (m, 0.5H), 4.61 (m, 2H), 4.96 (m, 0.5H), 6.65 (m, 2H), 6.77 (m, 1H), 6.90 (m, 1H), 7.13 (m, 1H), 7.30 (m, 4H)

Mass Spectral Analysis, m/z ESI 654 (M+H$^+$)

Preparation of 7.3

To a solution of 7.2 (4.15 g, 6.36 mmol) in ethanol (100 mL) was added a 4M anhydrous solution of hydrogen chloride in dioxane (60 mL, 240 mmol) and the mixture was stirred at room temperature for 18 hours. The mixture was concentrated under reduced pressure and the residue taken up in ethyl acetate (75 mL). A saturated aqueous solution of sodium bicarbonate (100 mL) was added, which was stirred for 2 hours at room temperature. The layers were separated and the organic layer was washed with water, brine, dried over sodium sulfate, filtered and concentrated under reduced pressure. The product was washed with hexanes and used for the next step without further purification. Yield: 92% $^1$H NMR (400 MHz, CDCl$_3$) δ: 0.65 (d, J=7 Hz, 2H), 0.69 (d, J=7 Hz, 1H), 1.23 (m, 5.5H), 1.38 (m, 0.5H), 1.46 (m, 1H), 1.50 (m, 0.5H), 1.66 (d, J=13 Hz, 0.5H), 1.82 (m, 0.5H), 1.90 (m, 0.5H), 2.08 (m, 1H), 2.20 (t, J=13 Hz, 0.5H), 2.47 (m, 0.5H), 2.59 (m, 1H), 2.67 (m, 1H), 2.81 (m, 0.5H), 2.86 (m, 1H), 3.27 (dd, J=14 Hz and 3 Hz, 0.5H), 3.37 (dd, J=14 Hz and 3 Hz, 0.5H), 3.62 (m, 1H), 3.71 (m, 1H), 3.93 (dd, J=12 Hz and 3 Hz, 0.5H), 4.11 (m, 2H), 4.63 (m, 2H), 6.66 (m, 2H), 6.75 (m, 1H), 7.14 (m, 1H), 7.20 (m, 2H), 7.28 (m, 3H) Mass Spectral Analysis, m/z ESI 439 (M+H$^+$)

Preparation of 7.4

A solution of 7.3 (2.58 g, 5.89 mmol) in o-xylene (200 mL) was heated to reflux for 60 hours. The mixture was concentrated under reduced pressure. The crude product was purified by column chromatography (eluent: dichloromethane/methanol mixtures of increasing polarity).

Yield 25% $^1$H NMR (400 MHz, DMSO-D$_6$) δ: 0.52 (d, J=7 Hz, 2H), 0.63 (d, J=7 Hz, 1H), 1.36 (s, 1H), 1.41 (s, 2H), 2.02 (m, 2H), 2.68 (m, 2H), 3.12 (m, 0.5H), 3.46 (m, 1H), 3.55 (m, 1H), 3.63 (dd, J=14 Hz and 4 Hz, 1H), 3.86 (dd, J=14 Hz and 6 Hz, 1H), 4.22 (m, 0.5H), 4.54 (m, 1H), 4.63 (dd, J=12 Hz and 3 Hz, 1H), 4.75 (d, J=14 Hz, 1H), 6.70 (m, 1H), 6.78 (m, 1H), 7.11 (m, 3H), 7.29 (m, 2H), 7.34 (m, 2H) Mass Spectral Analysis, m/z ESI 391 (M−H$^+$)

Preparation of 7

To a solution of 7.4 (0.57 g, 1.45 mmol) in anhydrous tetrahydrofuran (20 mL) was added borane-dimethyl sulfide complex (2M solution in tetrahydrofuran, 5 mL, 10 mmol) and the reaction heated to reflux under a nitrogen atmosphere for 16 hours. The mixture was then cooled to 0° C. Methanol (20 mL) was added to the reaction mixture which was stirred at 0° C. for 1 hour. A 2M anhydrous solution of hydrogen chloride in diethyl ether (10 mL) was then added to the reaction mixture, which was heated to reflux for 1 hour. After cooling, aqueous ammonium hydroxide solution (10 mL) was added to the mixture, which was stirred for 10 minutes at room temperature. The mixture was concentrated under reduced pressure. The residue was dissolved in methanol (10 mL) and concentrated under reduced pressure. This process was repeated 3 times. The crude product was purified by column chromatography (eluent: dichloromethane/methanol/ammonium hydroxide mixtures of increasing polarity).

Yield: 10% $^1$H NMR (400 MHz, CD$_3$OD) δ: 0.71 (d, J=7 Hz, 3H), 1.27 (m, 2H), 1.58 (m, 0.5H), 1.84 (m, 2H), 1.95 (m, 2H), 2.60 (m, 4H), 2.73 (m, 2H), 2.81 (m, 2H), 2.88 (m, 1H), 3.56 (m, 0.5H) 3.69 (q, J=13 Hz, 2H), 6.65 (dd, J=8 Hz and 2 Hz, 1H), 6.69 (s, 1H), 7.07 (t, J=8 Hz, 1H), 7.24 (m, 1H), 7.31 (t, J=8 Hz, 2H), 7.37 (m, 1H)

Mass Spectral Analysis, m/z ESI 365 (M+H$^+$)

Examples 8A-8AQ

Preparation of 8A

To a 10 μM solution of compound 2.7 (1000 in methanol/acetic acid (8:1) was added tetramethyl orthoformate (TMOF) (100 μl) and a 12 μM solution of aldehyde 8.1a (100 μl) in methanol/acetic acid (8:1). The reaction mixture was shaken for 16 hours. To this was added resin bound cyanoborohydride and shaking continued for 60 hours. The reaction mixture was filtered through SCX-2 cartridge and washed with methanol. The product was eluted from the cartridge by washing with a 2M solution of ammonia in methanol solution. The product was purified by liquid chromatographic methods.

Mass Spectral Analysis, m/z ESI 381 (M+H$^+$)

Preparation of 8B 8B was obtained according to a procedure similar to the one described for 8A, with the following exception: Aldehyde 8.1a was replaced with aldehyde 8.1b.

Mass Spectral Analysis, m/z ESI 352 (M+H$^+$)

Preparation of 8C 8C was obtained according to a procedure similar to the one described for 8A, with the following exception: Aldehyde 8.1a was replaced with aldehyde 8.1c.

Mass Spectral Analysis, m/z ESI 357 (M+H$^+$)

Preparation of 8D 8D was obtained according to a procedure similar to the one described for 8A, with the following exception: Aldehyde 8.1a was replaced with aldehyde 8.1d.

Mass Spectral Analysis, m/z ESI 365 (M+H$^+$)

Preparation of 8E 8E was obtained according to a procedure similar to the one described for 8A, with the following exception: Aldehyde 8.1a was replaced with aldehyde 8.1e.

Mass Spectral Analysis, m/z ESI 379 (M+H$^+$)

Preparation of 8F 8F was obtained according to a procedure similar to the one described for 8A, with the following exception: Aldehyde 8.1a was replaced with aldehyde 8.1f.

Mass Spectral Analysis, m/z ESI 357 (M+H$^+$)

Preparation of 8G 8G was obtained according to a procedure similar to the one described for 8A, with the following exception: Aldehyde 8.1a was replaced with aldehyde 8.1g.

Mass Spectral Analysis, m/z ESI 341 (M+H$^+$)

Preparation of 8H 8H was obtained according to a procedure similar to the one described for 8A, with the following exception: Aldehyde 8.1a was replaced with aldehyde 8.1h.
Mass Spectral Analysis, m/z ESI 352 (M+H$^+$)

Preparation of 8I 8I was obtained according to a procedure similar to the one described for 8A, with the following exception: Aldehyde 8.1a was replaced with aldehyde 8.1i.
Mass Spectral Analysis, m/z ESI 407 (M+H$^+$)

Preparation of 8J 8J was obtained according to a procedure similar to the one described for 8A, with the following exception: Aldehyde 8.1a was replaced with aldehyde 8.1j.
Mass Spectral Analysis, m/z ESI 365 (M+H$^+$)

Preparation of 8K 8K was obtained according to a procedure similar to the one described for 8A, with the following exception: Aldehyde 8.1a was replaced with aldehyde 8.1k.
Mass Spectral Analysis, m/z ESI 443 (M+H$^+$)

Preparation of 8L 8L was obtained according to a procedure similar to the one described for 8A, with the following exception: Aldehyde 8.1a was replaced with aldehyde 8.1l.
Mass Spectral Analysis, m/z ESI 352 (M+H$^+$)

Preparation of 8M 8M was obtained according to a procedure similar to the one described for 8A, with the following exception: Aldehyde 8.1a was replaced with aldehyde 8.1m.
Mass Spectral Analysis, m/z ESI 385 (M+H$^+$)

Preparation of 8N 8N was obtained according to a procedure similar to the one described for 8A, with the following exception: Aldehyde 8.1a was replaced with aldehyde 8.1n.
Mass Spectral Analysis, m/z ESI 365 (M+H$^+$)

Preparation of 8O 8O was obtained according to a procedure similar to the one described for 8A, with the following exception: Aldehyde 8.1a was replaced with aldehyde 8.1o.
Mass Spectral Analysis, m/z ESI 443 (M+H$^+$)

Preparation of 8P 8P was obtained according to a procedure similar to the one described for 8A, with the following exception: Aldehyde 8.1a was replaced with aldehyde 8.1p. Mass Spectral Analysis, m/z ESI 357 (M+H$^+$)

Preparation of 8Q 8Q was obtained according to a procedure similar to the one described for 8A, with the following exception: Aldehyde 8.1a was replaced with aldehyde 8.1q. Mass Spectral Analysis, m/z ESI 381 (M+H$^+$)

Preparation of 8R 8R was obtained according to a procedure similar to the one described for 8A, with the following exception: Aldehyde 8.1a was replaced with aldehyde 8.1r.
Mass Spectral Analysis, m/z ESI 379 (M+H$^+$)

Preparation of 8S 8S was obtained according to a procedure similar to the one described for 8A, with the following exception: Aldehyde 8.1a was replaced with aldehyde 8.1s.
Mass Spectral Analysis, m/z ESI 401 (M+H$^+$)

Preparation of 8T 8T was obtained according to a procedure similar to the one described for 8A, with the following exception: Aldehyde 8.1a was replaced with aldehyde 8.1t.
Mass Spectral Analysis, m/z ESI 367 (M+H$^+$)

Preparation of 8U 8U was obtained according to a procedure similar to the one described for 8A, with the following exception: Aldehyde 8.1a was replaced with aldehyde 8.1u.
Mass Spectral Analysis, m/z ESI 393 (M+H$^+$)

Preparation of 8V 8V was obtained according to a procedure similar to the one described for 8A, with the following exception: Aldehyde 8.1a was replaced with aldehyde 8.1v.
Mass Spectral Analysis, m/z ESI 341 (M+H$^+$)

Preparation of 8W 8W was obtained according to a procedure similar to the one described for 8A, with the following exception: Aldehyde 8.1a was replaced with aldehyde 8.1w. Mass Spectral Analysis, m/z ESI 385 (M+H$^+$)

Preparation of 8X 8X was obtained according to a procedure similar to the one described for 8A, with the following exception: Aldehyde 8.1a was replaced with aldehyde 8.1x.
Mass Spectral Analysis, m/z ESI 367 (M+H$^+$)

Preparation of 8Y 8Y was obtained according to a procedure similar to the one described for 8A, with the following exception: Aldehyde 8.1a was replaced with aldehyde 8.1y.
Mass Spectral Analysis, m/z ESI 385 (M+H$^+$)

Preparation of 8Z 8Z was obtained according to a procedure similar to the one described for 8A, with the following exception: Aldehyde 8.1a was replaced with aldehyde 8.1z.
Mass Spectral Analysis, m/z ESI 401 (M+H$^+$)

Preparation of 8AA

8AA was obtained according to a procedure similar to the one described for 8A, with the following exception: Aldehyde 8.1a was replaced with aldehyde 8.1aa.
Mass Spectral Analysis, m/z ESI 457 (M+H$^+$)

Preparation of 8AB

8AB was obtained according to a procedure similar to the one described for 8A, with the following exception: Aldehyde 8.1a was replaced with aldehyde 8.1ab.
Mass Spectral Analysis, m/z ESI 428 (M+H$^+$)

Preparation of 8AC

8AC was obtained according to a procedure similar to the one described for 8A, with the following exception: Aldehyde 8.1a was replaced with aldehyde 8.1ac. Mass Spectral Analysis, m/z ESI 419 (M+H$^+$)

Preparation of 8AD

8AD was obtained according to a procedure similar to the one described for 8A, with the following exception: Aldehyde 8.1a was replaced with aldehyde 8.1ad.
Mass Spectral Analysis, m/z ESI 402 (M+H$^+$)

Preparation of 8AE

8AE was obtained according to a procedure similar to the one described for 8A, with the following exception: Aldehyde 8.1a was replaced with aldehyde 8.1ae.
Mass Spectral Analysis, m/z ESI 428 (M+H$^+$)

Preparation of 8AF

8AF was obtained according to a procedure similar to the one described for 8A, with the following exception: Aldehyde 8.1a was replaced with aldehyde 8.1af.
Mass Spectral Analysis, m/z ESI 457 (M+H$^+$)

Preparation of 8AG

8AG was obtained according to a procedure similar to the one described for 8A, with the following exception: Aldehyde 8.1a was replaced with aldehyde 8.1ag.
Mass Spectral Analysis, m/z ESI 428 (M+H$^+$)

Preparation of 8AH

8AH was obtained according to a procedure similar to the one described for 8A, with the following exception: Aldehyde 8.1a was replaced with aldehyde 8.1ah.
Mass Spectral Analysis, m/z ESI 409 (M+H$^+$)

Preparation of 8AI

8AI was obtained according to a procedure similar to the one described for 8A, with the following exception: Aldehyde 8.1a was replaced with aldehyde 8.1ai.
Mass Spectral Analysis, m/z ESI 394 (M+H$^+$)

Preparation of 8AJ

8AJ was obtained according to a procedure similar to the one described for 8A, with the following exception: Aldehyde 8.1a was replaced with aldehyde 8.1aj.
Mass Spectral Analysis, m/z ESI 428 (M+H$^+$)

Preparation of 8AK

8AK was obtained according to a procedure similar to the one described for 8A, with the following exception: Aldehyde 8.1a was replaced with aldehyde 8.1ak.
Mass Spectral Analysis, m/z ESI 402 (M+H$^+$)

Preparation of 8AL

8AL was obtained according to a procedure similar to the one described for 8A, with the following exception: Aldehyde 8.1a was replaced with aldehyde 8.1al.
Mass Spectral Analysis, m/z ESI 409 (M+H$^+$)

Preparation of 8AM

8AM was obtained according to a procedure similar to the one described for 8A, with the following exception: Aldehyde 8.1a was replaced with aldehyde 8.1am.
Mass Spectral Analysis, m/z ESI 417 (M+H$^+$)

Preparation of Example 8AN

8AN was obtained according to a procedure similar to the one described for 8A, with the following exception: Aldehyde 8.1a was replaced with aldehyde 8.1an.
Mass Spectral Analysis, m/z ESI 427 (M+H$^+$)

Preparation of 8AO

8AO was obtained according to a procedure similar to the one described for 8A, with the following exception: Aldehyde 8.1a was replaced with aldehyde 8.1ao.
Mass Spectral Analysis, m/z ESI 402 (M+H$^+$)

Preparation of 8AP

8AP was obtained according to a procedure similar to the one described for 8A, with the following exception: Aldehyde 8.1a was replaced with aldehyde 8.1ap.
Mass Spectral Analysis, m/z ESI 393 (M+H$^+$)

Preparation of 8AQ

8AQ was obtained according to a procedure similar to the one described for 8A, with the following exception: Aldehyde 8.1a was replaced with aldehyde 8.1aq.
Mass Spectral Analysis, m/z ESI 367 (M+H$^+$)

Example 9A

Preparation of 9.2

To a stirred solution of 2.3 (2 g, 4.32 mmol) in acetonitrile (20 ml) under a nitrogen atmosphere was added, sequentially, diisopropylethylamine (3 ml, 17.28 mmol), 9.1 (0.87 g, 5.18 mmol) and O-benzotriazol-1-yl-N,N,N',N'-tetramethyluronium tetrafluoroborate (TBTU) (2.08 g, 6.48 mmol). The reaction was stirred at room temperature overnight, poured into saturated ammonium chloride solution and extracted with ethyl acetate. The organic extracts were washed with saturated brine, dried over sodium sulfate and concentrated under reduced pressure. The crude product was purified by column chromatography (eluent: hexane/ethyl acetate mixtures of increasing polarity). Yield: 75%

¹H NMR (400 MHz, CDCl₃) δ: 0.18 (s, 6H), 0.50 (d, J=7 Hz, 3H), 0.90 (d, J=7 Hz, 3H), 0.98 (s, 12H), 1.34 (s, 3H), 1.49 (s, 9H), 1.61 (br s, 1H), 2.05 (m, 2H), 2.19 (m, 1H), 2.36 (t, J=13 Hz, 1H), 2.93 (dd, J=14 Hz and 11 Hz, 1H), 3.74 (s, 3H), 4.40 (dd, J=12 Hz and 6 Hz, 1H), 4.56 (dd, J=9 Hz and 5 Hz, 1H), 6.67 (dd, J=8 Hz and 2 Hz, 1H), 6.75 (t, J=2 Hz, 1H), 6.87 (d, J=8 Hz, 1H), 7.13 (m, 1H). Mass Spectral Analysis, m/z ESI 577 (M+H⁺)

Preparation of 9.3

To a solution of 9.2 (1.85 g, 3.20 mmol) in methanol (50 ml) was added 4M hydrochloric acid in dioxane (5 ml, 20 mmol) and the mixture was heated to reflux for 2 hours. The solvents were removed under vacuum and the residue taken up in ethyl acetate (75 ml). This was then stirred over a solution of saturated sodium hydrogen carbonate (100 ml) for 2 hours. The layers were separated and the organic layer was washed with water, saturated brine, dried over sodium sulfate and concentrated under reduced pressure. The product was washed with hexanes and used in the next step without further purification. Yield: 100%

¹H NMR (400 MHz, CDCl₃) δ: 0.71 (d, J=7 Hz, 3H), 0.94 (d, J=7 Hz, 3H), 0.97 (d, J=7 Hz, 3H), 1.29 (s, 3H), 1.93 (m, 3H), 2.00 (d, J=8 Hz, 1H), 2.21 (m, 1H), 2.83 (dd, J=13 Hz and 2 Hz, 1H), 3.32 (dd, J=12 Hz and 3 Hz, 1H), 3.65 (t, J=8 Hz, 1H), 3.76 (s, 3H), 4.58 (dd, J=9 Hz and 5 Hz, 1H), 6.65 (dd, J=8 Hz and 2 Hz, 1H), 6.72 (t, J=2 Hz, 1H), 6.78 (d, J=8 Hz, 1H), 7.15 (t, J=8 Hz, 1H), 7.47 (d, J=9 Hz, 1H).

Mass Spectral Analysis, m/z ESI 363 (M+H⁺)

Preparation of 9.4

A solution of 9.3 (1.19 g, 3.30 mmol) in o-xylene (150 ml) was heated to reflux for 60 hours. Concentrated under reduced pressure. The crude product was purified by column chromatography (eluent: dichloromethane/methanol mixtures of increasing polarity). Yield 43%

¹H NMR (400 MHz, CDCl₃) δ: 0.72 (d, J=7 Hz, 3H), 0.94 (d, J=7 Hz, 3H), 0.97 (d, J=7 Hz, 3H), 1.32 (s, 3H), 1.99 (d, J=8 Hz, 2H), 2.32 (s, 0.5H), 2.37 (s, 0.5H), 2.45 (s, 1H), 2.83 (dd, J=14 Hz and 3 Hz, 1H), 3.34 (m, 1H), 3.64 (m, 1H), 4.58 (dd, J=9 Hz and 5 Hz, 1H), 6.66 (m, 1H), 6.72 (m, 1H), 6.80 (d, J=8 Hz, 1H), 7.11 (m, 1H)

Mass Spectral Analysis, m/z ESI 329 (M–H⁺)

Preparation of 9.5

To a solution of 9.4 (0.47 g, 1.42 mmol) in anhydrous tetrahydrofuran (20 ml) was added borane-dimethyl sulfide complex (2M in tetrahydrofuran, 4.3 ml, 8.6 mmol) and the reaction heated to reflux under a nitrogen atmosphere for 16 hours. The mixture was then cooled to 0° C. and methanol (20 ml) was added and the reaction stirred at 0° C. for 1 hour. A 2M hydrochloric acid in diethyl ether solution (10 ml) was then added and the reaction heated to reflux for 1 hour. After cooling, aqueous ammonium hydroxide solution (5 ml) was added and the mixture stirred for 10 minutes. Concentrated under reduced pressure. The residue was dissolved in methanol and concentrated under reduced pressure (×3). The crude product was purified by column chromatography (eluent: dichloromethane/methanol/ammonium hydroxide mixtures of increasing polarity). Yield: 22%

¹H NMR (400 MHz, CD₃OD) δ: 0.75 (d, J=7 Hz, 3H), 0.94 (d, J=7 Hz, 3H), 0.98 (d, J=7 Hz, 3H), 1.34 (s, 3H), 1.47 (d, J=13 Hz, 1H), 1.58 (sx, J=7 Hz, 1H), 1.83 (d, J=8 Hz, 1H), 1.88 (t, J=9 Hz, 1H), 2.03 (m, 1H), 2.26 (m, 1H), 2.55 (m, 3H), 2.72 (dd, J=12 Hz and 3 Hz, 1H), 2.79 (dd, J=11 Hz and 3 Hz, 1H), 2.88 (dd, J=12 Hz and 3 Hz, 1H), 6.57 (dd, J=8 Hz and 3 Hz, 1H), 6.70 (d, J=2 Hz, 1H), 6.73 (d, J=8 Hz, 1H), 7.09 (t, J=8 Hz, 1H)

Mass Spectral Analysis, m/z ESI 303 (M+H⁺)

Preparation of 9A

To a solution of 9.5 (0.13 g, 0.4 mmol) in dichloromethane (5 mL) was added 9.6 (0.077 g, 0.47 mmol), 2-bromo-1-ethylpyridinium tetrafluoroborate (0.13 g, 0.47 mmol) and diisopropylethylamine (0.32 mL, 1.4 mmol) and the reaction mixture stirred at room temperature overnight, poured into water and extracted with dichloromethane. The combined organic extracts were washed with water, saturated brine solution, dried over sodium sulfate and concentrated under vacuum. The crude product was purified by HPLC. Yield: 2%

¹H NMR (400 MHz, CD₃OD), δ 0.70 (d, J=7 Hz, 3H), 0.83 (d, J=7 Hz, 3H), 0.93 (d, J=7 Hz, 3H), 1.29 (m, 1H), 1.32 (s, 3H), 1.52 (d, J=12 Hz, 1H), 1.97 (m, 1H), 2.03 (m, 1H), 2.11 (q, J=12 Hz, 1H), 2.27 (dd, J=12 Hz and 8 Hz, 1H), 2.58 (dd, J=12 Hz and 2 Hz, 1H), 2.64 (m, 2H), 2.76 (t, J=8 Hz, 1H), 2.81 (m, 0.5H), 2.86 (m, 2H), 2.93 (m, 2H), 3.95 (br s, 1H), 6.58 (q, J=7 Hz and 2 Hz, 1H), 6.67 (d, J=8 Hz, 2H), 6.72 (m, 2H), 7.06 (d, J=8 Hz, 2H), 7.10 (t, J=8 Hz, 1H). Mass Spectral Analysis, m/z ESI 451 (M+H⁺)

Example 9B

Preparation of 9B

To a solution of 9.5 (0.13 g, 0.4 mmol) in dichloromethane (5 mL) was added 9.7 (0.077 g, 0.47 mmol), 2-bromo-1-ethylpyridinium tetrafluoroborate (0.13 g, 0.47 mmol) and diisopropylethylamine (0.32 mL, 1.4 mmol) and the reaction mixture stirred at room temperature overnight, poured into water and extracted with dichloromethane. The combined organic extracts were washed with water, saturated brine solution, dried over sodium sulfate and concentrated under vacuum. The crude product was partially purified by column chromatography (eluent: dichloromethane/methanol/ammonium hydroxide mixtures of increasing polarity).

Mass Spectral Analysis, m/z ESI 578 (M+H⁺)

The partially purified material was then dissolved in methanol (3 mL) and 4M hydrochloric acid in dioxane (5 ml, 20 mmol) was added. The mixture was stirred at room temperature overnight. The solvents were evaporated and the crude material was purified by HPLC. Yield: 7%

¹H NMR (CD₃OD), δ 0.81 (d, J=7 Hz, 3H), 0.94 (d, J=6 Hz, 3H), 1.08 (d, J=6 Hz, 3H), 1.50 (s, 3H), 2.05 (d, J=13 Hz, 1H), 2.35 (m, 2H), 2.50 (m, 1H), 3.02 (t, J=14 Hz, 1H), 3.36 (m, 2H), 3.74 (m, 2H), 3.89 (m, 1H), 3.99 (s, 2H), 4.36 (m, 1H), 4.46 (m, 2H), 4.53 (m, 1H), 6.66 (m, 2H), 6.78 (m, 3H), 7.14 (q, J=8 Hz, 2H). Mass Spectral Analysis, m/z ESI 478 (M+H⁺)

Biological Assays

TABLE 1

Table of Compounds

| Example | Structure | Name | [M + H]⁺ |
|---|---|---|---|
| 1 | 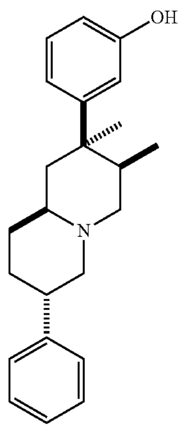 | 3-((2R,3R,7S,9αS)-2,3-dimethyl-7-phenyl-octahydro-1H-quinolizin-2-yl)phenol | 336.2 |
| 2A | 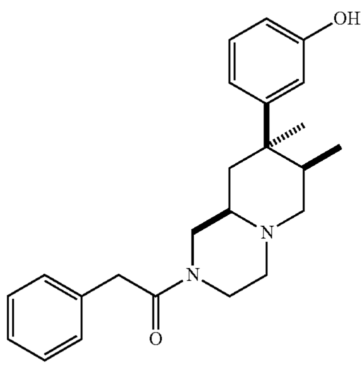 | 1-((7R,8R,9αR)-8-(3-hydroxyphenyl)-7,8-dimethyl-hexahydro-1H-pyrido[1,2-α]pyrazin-2(6H)-yl)-2-phenylethanone | 379.3 |
| 2B | 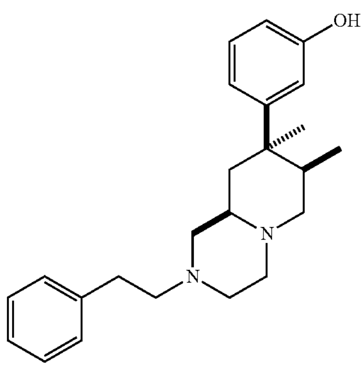 | 3-((7R,8R,9αR)-7,8-dimethyl-2-phenethyl-octahydro-1H-pyrido[1,2-a]pyrazin-8-yl)phenol | 365.3 |
| 2C | 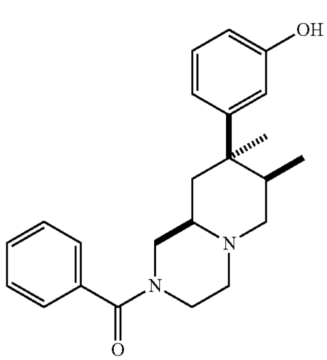 | ((7R,8R,9αR)-8-(3-hydroxyphenyl)-7,8-dimethyl-hexahydro-1H-pyrido[1,2-α]pyrazin-2(6H)-yl)(phenyl)methanone | 365.7 |

TABLE 1-continued

Table of Compounds

| Example | Structure | Name | [M + H]+ |
|---|---|---|---|
| 2D | 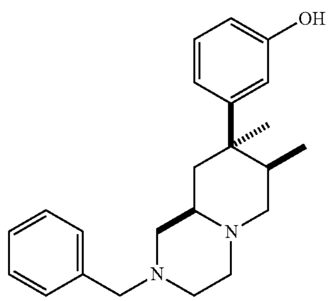 | 3-((7R,8R,9αR)-2-benzyl-7,8-dimethyl-octahydro-1H-pyrido[1,2-α]pyrazin-8-yl)phenol | 351.3 |
| 2E | 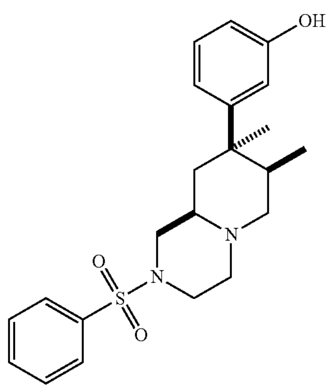 | 3-((7R,8R,9αR)-7,8-dimethyl-2-(phenylsulfonyl)-octahydro-1H-pyrido[1,2-α]pyrazin-8-yl)phenol | 401.8 |
| 2F | 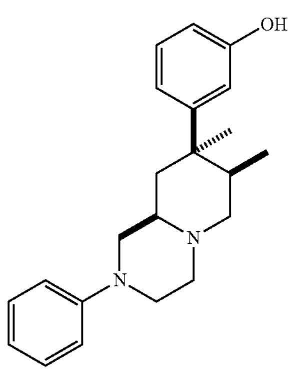 | 3-((7R,8R,9αR)-7,8-dimethyl-2-phenyl-octahydro-1H-pyrido[1,2-α]pyrazin-8-yl)phenol | 337.7 |
| 3A | 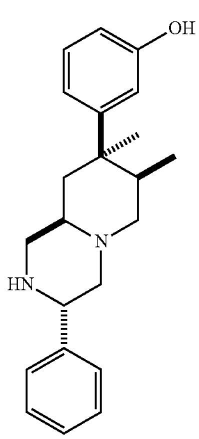 | 3-((3S,7R,8R,9αR)-7,8-dimethyl-3-phenyl-octahydro-1H-pyrido[1,2-α]pyrazin-8-yl)phenol | 337.2 |

TABLE 1-continued

Table of Compounds

| Example | Structure | Name | [M + H]+ |
|---|---|---|---|
| 3B | 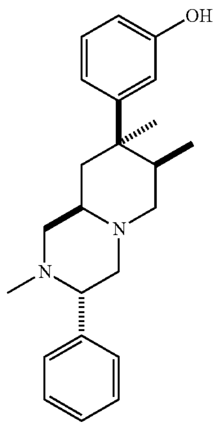 | 3-((3S,7R,8R,9αR)-2,7,8-trimethyl-3-phenyl-octahydro-1H-pyrido[1,2-α]pyrazin-8-yl)phenol | 351.3 |
| 3C | 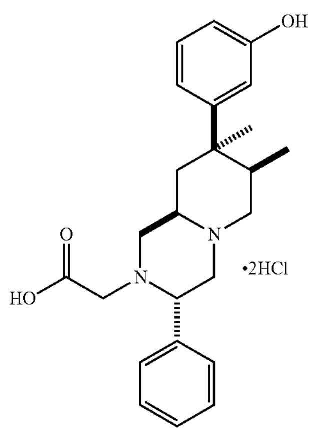 | 2-((3S,7R,8R,9αR)-8-(3-hydroxyphenyl)-7,8-dimethyl-3-phenyl-hexahydro-1H-pyrido[1,2-α]pyrazin-2(6H)-yl)acetic acid dihydrochloride | 395.8 |
| 3D | 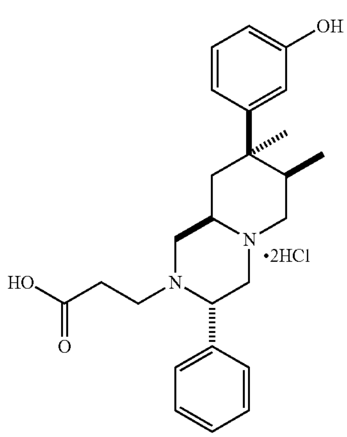 | 3-((3S,7R,8R,9αR)-8-(3-hydroxyphenyl)-7,8-dimethyl-3-phenyl-hexahydro-1H-pyrido[1,2-α]pyrazin-2(6H)-yl)propanoic acid dihydrochloride | 409.8 |

TABLE 1-continued

Table of Compounds

| Example | Structure | Name | [M + H]⁺ |
|---|---|---|---|
| 3E | 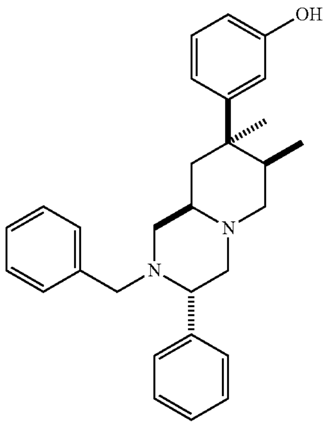 | 3-((3S,7R,8R,9αR)-2-benzyl-7,8-dimethyl-3-phenyl-octahydro-1H-pyrido[1,2-α]pyrazin-8-yl)phenol | 427.4 |
| 3F | 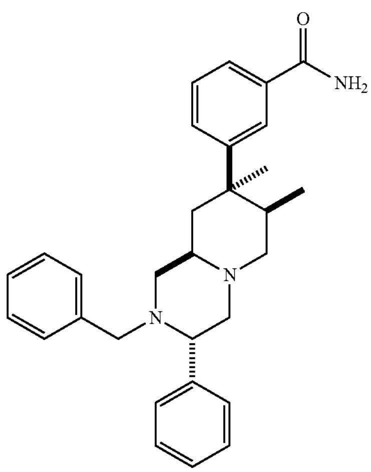 | 3-((3S,7R,8R,9αR)-2-benzyl-7,8-dimethyl-3-phenyl-octahydro-1H-pyrido[1,2-α]pyrazin-8-yl)benzamide | 454.9 |
| 3G | 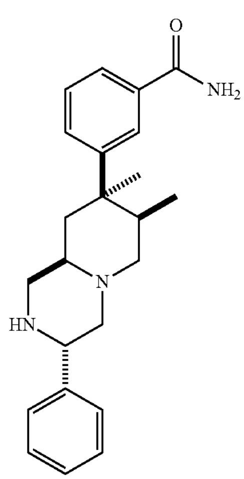 | 3-((3S,7R,8R,9αR)-7,8-dimethyl-3-phenyl-octahydro-1H-pyrido[1,2-α]pyrazin-8-yl)benzamide | 364.8 |

TABLE 1-continued

Table of Compounds

| Example | Structure | Name | [M + H]+ |
|---|---|---|---|
| 4 | 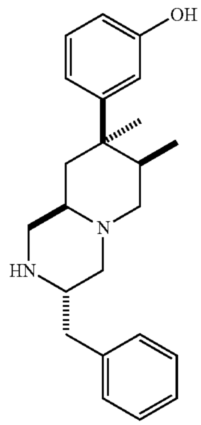 | 3-((3S,7R,8R,9αR)-3-benzyl-7,8-dimethyl-octahydro-1H-pyrido[1,2-α]pyrazin-8-yl)phenol | 351.2 |
| 5 | 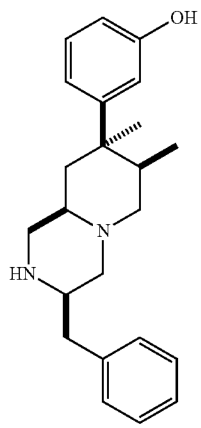 | 3-((3R,7R,8R,9αR)-3-benzyl-7,8-dimethyl-octahydro-1H-pyrido[1,2-α]pyrazin-8-yl)phenol | 351.2 |
| 6 | 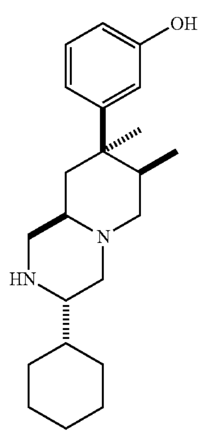 | 3-((3S,7R,8R,9αR)-3-cyclohexyl-7,8-dimethyl-octahydro-1H-pyrido[1,2-α]pyrazin-8-yl)phenol | 343.7 |

TABLE 1-continued

Table of Compounds

| Example | Structure | Name | [M + H]+ |
|---|---|---|---|
| 7 | 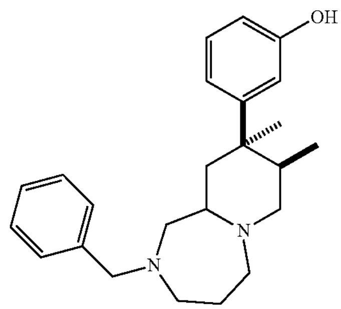 | 3-((8R,9R,10αR)-2-benzyl-8,9-dimethyl-decahydropyrido[1,2-α][1,4]diazepin-9-yl)phenol | 365.8 |
| 8A | 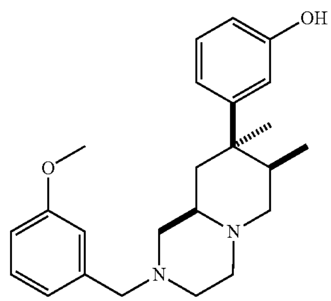 | 3-((7R,8R,9αR)-2-(3-methoxybenzyl)-7,8-dimethyl-octahydro-1H-pyrido[1,2-α]pyrazin-8-yl)phenol | 381.5 |
| 8B | 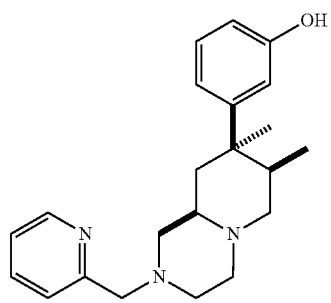 | 3-((7R,8R,9αR)-7,8-dimethy-2-(pydin-2-ylmethyl)-octahydro-1H-pyrido[1,2-α]pyrazin-8-yl)phenol | 352.4 |
| 8C | 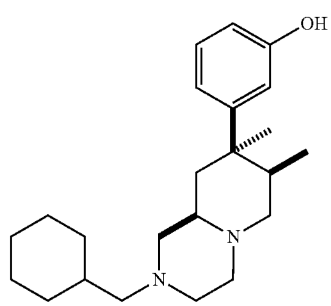 | 3-((7R,8R,9αR)-2-(cyclohexylmethyl)-7,8-dimethyl-octahydro-1H-pyrido[1,2-α]pyrazin-8-yl)phenol | 357.6 |
| 8D | 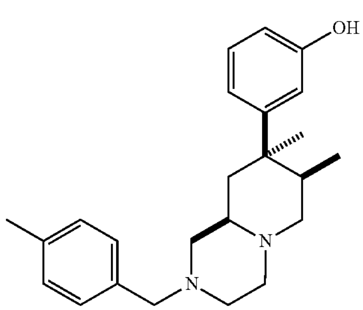 | 3-((7R,8R,9αR)-7,8-dimethyl-2-(4-methylbenzyl)-octahydro-1H-pyrido[1,2-α]pyrazin-8-yl)phenol | 365.5 |

TABLE 1-continued

Table of Compounds

| Example | Structure | Name | [M + H]⁺ |
|---|---|---|---|
| 8E | 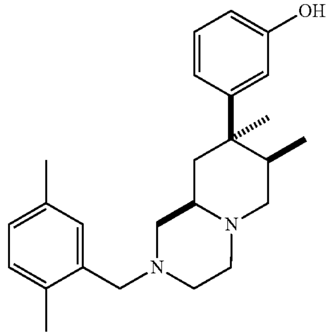 | 3-((7R,8R,9αR)-2-(2,5-dimethylbenzyl)-7,8-dimethyl-octahydro-1H-pyrido[1,2-α]pyrazin-8-yl)phenol | 379.4 |
| 8F | 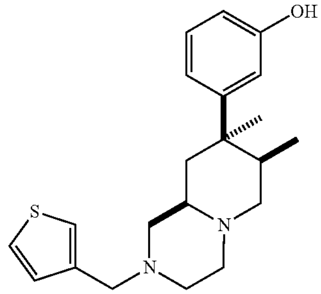 | 3-((7R,8R,9αR)-7,8-dimethyl-2-(thiophen-3-ylmethyl)-octahydro-1H-yl)phenol | 357.4 |
| 8G | 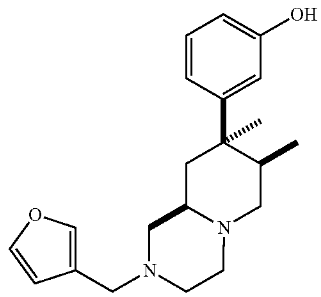 | 3-((7R,8R,9αR)-2-(furan-3-ylmethyl)-7,8-dimethyl-octahydro-1H-pyrido[1,2-α]pyrazin-8-yl)phenol | 341.1 |
| 8H | 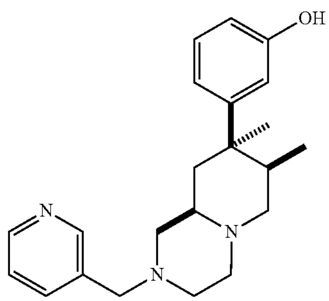 | 3-((7R,8R,9αR)-7,8-dimethyl-2-(pydin-3-ylmethyl)-octahydro-1H-pyrido[1,2-α]pyrazin-8-yl)phenol | 352.4 |
| 8I | 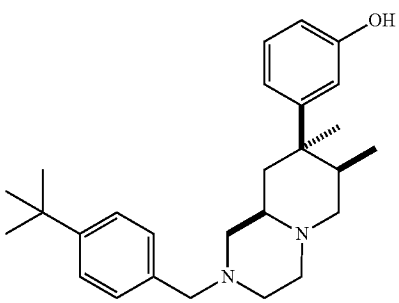 | 3-((7R,8R,9αR)-2-(4-tert-butylbenzyl)-7,8-dimethyl-octahydro-1H-pyrido[1,2-α]pyrazin-8-yl)phenol | 407.6 |

TABLE 1-continued

Table of Compounds

| Example | Structure | Name | [M + H]+ |
|---|---|---|---|
| 8J | 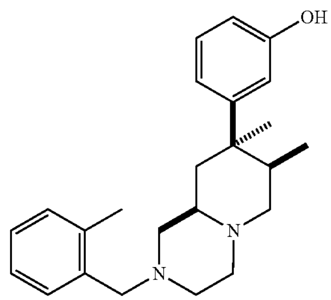 | 3-((7R,8R,9αR)-7,8-dimethyl-2-(2-methylbenzyl)-octahydro-1H-pyrido[1,2-α]pyrazin-8-yl)phenol | 365.5 |
| 8K | 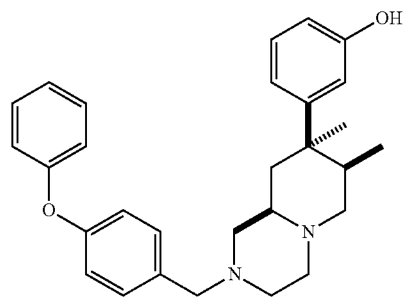 | 3-((7R,8R,9αR)-7,8-dimethyl-2-(4-phenoxybenzyl)-octahydro-1H-pyrido[1,2-α]pyrazin-8-yl)phenol | 443.4 |
| 8L | 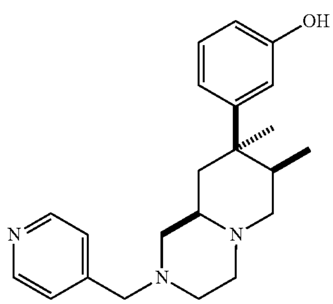 | 3-((7R,8R,9αR)-7,8-ylmethyl)-octahydro-1H-pyrido[1,2-α]pyrazin-8-yl)phenol | 352.4 |
| 8M | 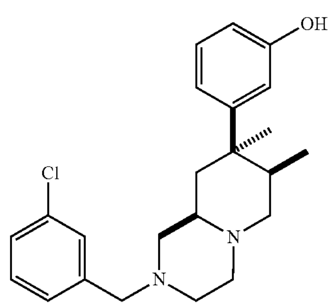 | 3-((7R,8R,9αR)-2-(3-chlorobenzyl)-7,8-dimethyl-octahydro-1H-pyrido[1,2-α]pyrazin-8-yl)phenol | 385.4 |
| 8N | 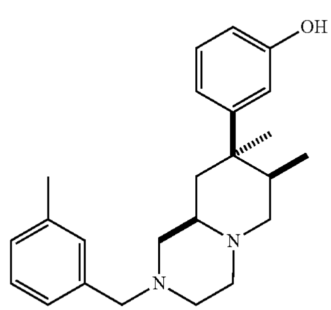 | 3-((7R,8R,9αR)-7,8-dimethyl-2-(3-methylbenzyl)-octahydro-1H-pyrido[1,2-α]pyrazin-8-yl)phenol | 365.5 |

TABLE 1-continued

Table of Compounds

| Example | Structure | Name | [M + H]+ |
|---|---|---|---|
| 8O | 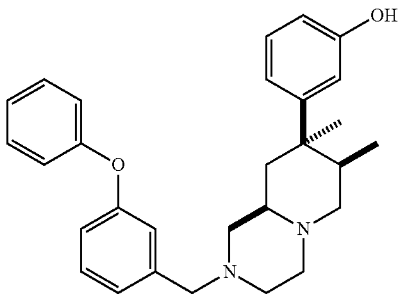 | 3-((7R,8R,9αR)-7,8-dimethyl-2-(3-phenoxybenzyl)-octahydro-1H-pyrido[1,2-α]pyrazin-8-yl)phenol | 443.5 |
| 8P | 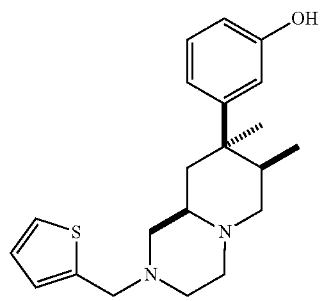 | 3-((7R,8R,9αR)-7,8-dimethyl-2-(thiophen-2-ylmethyl)-octahydro-1H-pyrido[1,2-α]pyrazin-8-yl)phenol | 357.4 |
| 8Q | 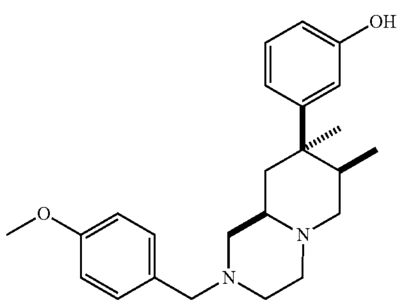 | 3-((7R,8R,9αR)-2-(4-methoxybenzyl)-7,8-dimethyl-octahydro-1H-pyrido[1,2-α]pyrazin-8-yl)phenol | 381.4 |
| 8R | 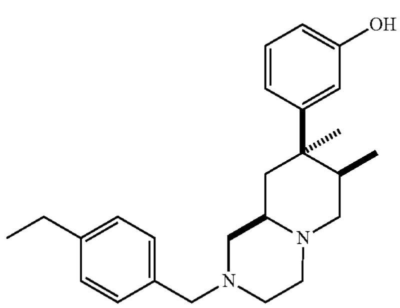 | 3-((7R,8R,9αR)-2-(4-ethylbenzyl)-7,8-dimethyl-octahydro-1H-pyrido[1,2-α]pyrazin-8-yl)phenol | 379.5 |
| 8S | 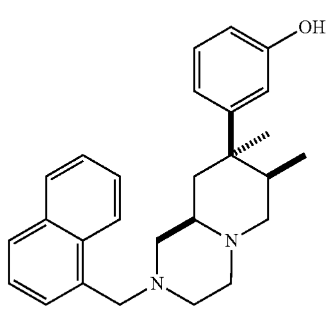 | 3-((7R,8R,9αR)-7,8-dimethyl-2-(naphthalen-1-ylmethyl)-octahydro-1H-pyrido[1,2-α]pyrazin-8-yl)phenol | 401.5 |

TABLE 1-continued

Table of Compounds

| Example | Structure | Name | [M + H]+ |
|---|---|---|---|
| 8T | 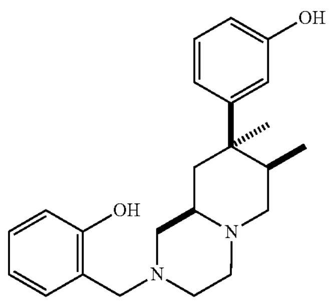 | 2-(((7R,8R,9αR)-8-(3-hydroxyphenyl)-7,8-dimethyl-hexahydro-1H-pyrido[1,2-α]pyrazin-2(6H)-yl)methyl)phenol | 367.4 |
| 8U | 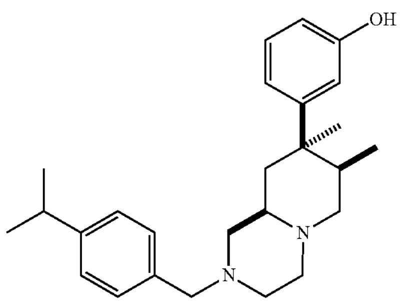 | 3-((7R,8R,9αR)-2-(4-isopropylbenzyl)-7,8-dimethyl-octahydro-1H-pyrido[1,2-α]pyrazin-8-yl)phenol | 393.6 |
| 8V | 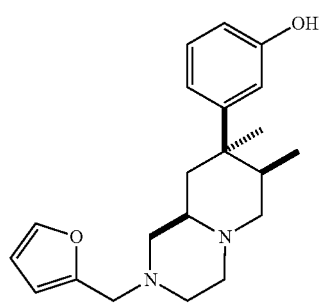 | 3-((7R,8R,9αR)-2-(furan-2-ylmethyl)-7,8-dimethyl-octahydro-1H-pyrido[1,2-α]pyrazin-8-yl)phenol | 341.4 |
| 8W | 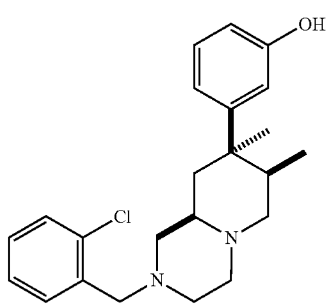 | 3-((7R,8R,9αR)-2-(2-chlorobenzyl)-7,8-dimethyl-octahydro-1H-pyrido[1,2-α]pyrazin-8-yl)phenol | 385.4 |
| 8X | 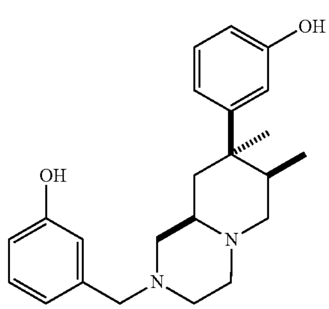 | 3-((7R,8R,9αR)-2-(3-hydroxybenzyl)-7,8-dimethyl-octahydro-1H-pyrido[1,2-α]pyrazin-8-yl)phenol | 367.4 |

TABLE 1-continued

Table of Compounds

| Example | Name | [M + H]+ |
|---|---|---|
| 8Y | 3-((7R,8R,9αR)-2-(4-chlorobenzyl)-7,8-dimethyl-octahydro-1H-pyrido[1,2-α]pyrazin-8-yl)phenol | 385.4 |
| 8Z | 3-((7R,8R,9αR)-7,8-ylmethyl)-octahydro-1H-pyrido[1,2-α]pyrazin-8-yl)phenol | 401.5 |
| 8AA | 3-((7R,8R,9αR)-2-(3-(benzyloxy)benzyl)-7,8-dimethyl-octahydro-1H-pyrido[1,2-α]pyrazin-8-yl)phenol | 457.5 |
| 8AB | 3-((7R,8R,9αR)-7,8-dimethyl-2-(4-(pyridin-4-yl)benzyl)-octahydro-1H-pyrido[1,2-α]pyrazin-8-yl)phenol | 428.4 |
| 8AC | 3-((7R,8R,9αR)-2-(2,3-dichlorobenzyl)-7,8-dimethyl-octahydro-1H-pyrido[1,2-α]pyrazin-8-yl)phenol | 419.3 |

TABLE 1-continued

Table of Compounds

| Example | Structure | Name | [M + H]+ |
|---|---|---|---|
| 8AD | 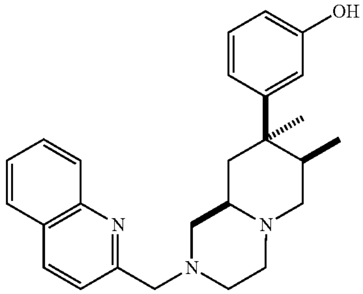 | 3-((7R,8R,9αR)-7,8-dimethyl-2-(quinolin-2-ylmethyl)-octahydro-1H-pyrido[1,2-α]pyrazin-8-yl)phenol | 402.4 |
| 8AE | 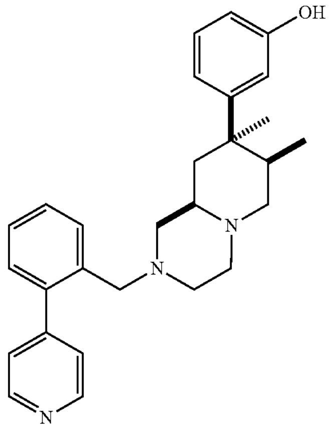 | 3-((7R,8R,9αR)-7,8-dimethyl-2-(2-(pyridin-4-yl)benzyl)-octahydro-1H-pyridol[2-α]pyrazin-8-yl)phenol | 428.5 |
| 8AF | 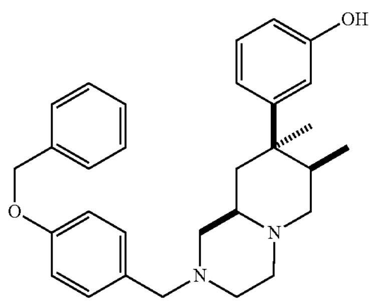 | 3-((7R,8R,9αR)-2-(4-(benzyloxy)benzyl)-7,8-dimethyl-octahydro-1H-pyrido[1,2-α]pyrazin-8-yl)phenol | 457.4 |
| 8AG | 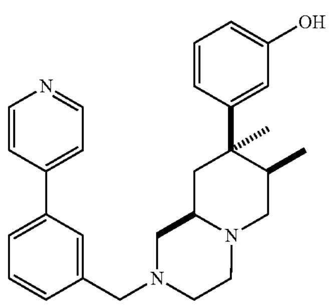 | 3-((7R,8R,9αR)-7,8-dimethyl-2-(3-(pyridin-4-yl)benzyl)-octahydro-1H-pyrido[1,2-α]pyrazin-8-yl)phenol | 428.4 |

TABLE 1-continued

Table of Compounds

| Example | Structure | Name | [M + H]+ |
|---|---|---|---|
| 8AH | 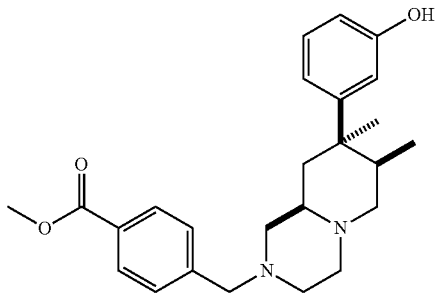 | methyl 4-(((7R,8R,9αR)-8-(3-hydroxyphenyl)-7,8-dimethyl-hexahydro-1H-pyrido[1,2-α]pyrazin-2(6H)-yl)methyl)benzoate | 409.4 |
| 8AI | 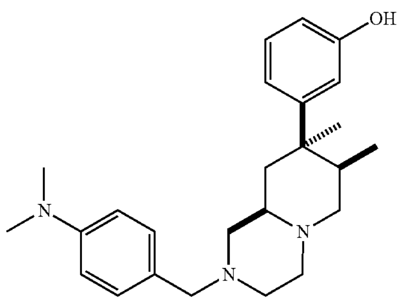 | 3-((7R,8R,9αR)-2-(4-(dimethylamino)benzyl)-7,8-dimethyl-octahydro-1H-pyrido[1,2-α]pyrazin-8-yl)phenol | 394.8 |
| 8AJ | 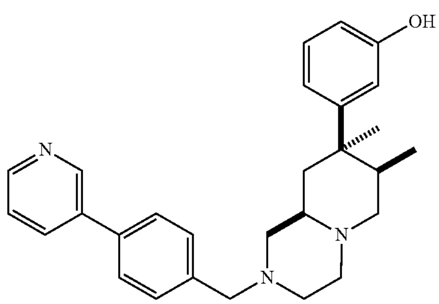 | 3-((7R,8R,9αR)-7,8-dimethyl-2-(4-(pyridin-3-yl)benzyl)-octahydro-1H-pyrido[1,2-α]pyrazin-8-yl)phenol | 428.4 |
| 8AK | 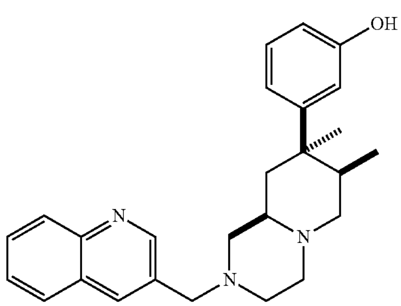 | 34(7R,8R,9αR)-7,8-dimethyl-2-(quinolin-3-ylmethyl)-octahydro-1H-pyrido[1,2-α]pyrazin-8-yl)phenol | 402.4 |
| 8AL | 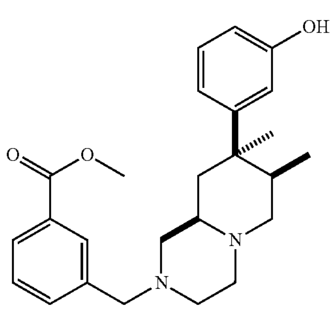 | methyl 3-(((7R,8R,9αR)-8-(3-hydroxyphenyl)-7,8-dimethyl-hexahydro-1H-pyrido[1,2-α]pyrazin-2(6H)-yl)methyl)benzoate | 409.4 |

TABLE 1-continued

Table of Compounds

| Example | Structure | Name | [M + H]⁺ |
|---------|-----------|------|----------|
| 8AM | 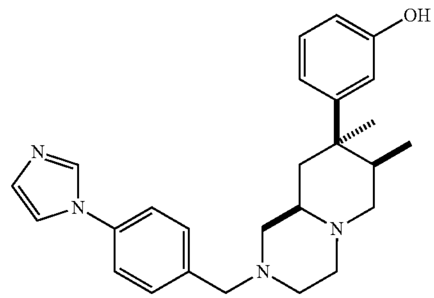 | 3-((7R,8R,9αR)-2-(4-(1H-imidazol-1-yl)benzyl)-7,8-dimethyl-octahydro-1H-pyrido[1,2-α]pyrazin-8-yl)phenol | 417.4 |
| 8AN | 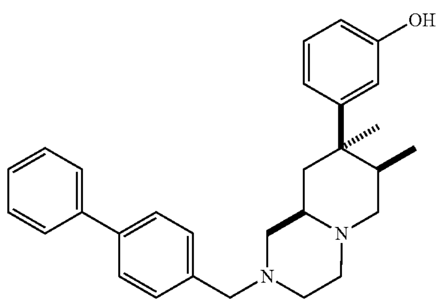 | 3-((7R,8R,9αR)-2-dimethyl-octahydro-1H-pyrido[1,2-α]pyrazin-8-yl)phenol | 427.4 |
| 8AO | 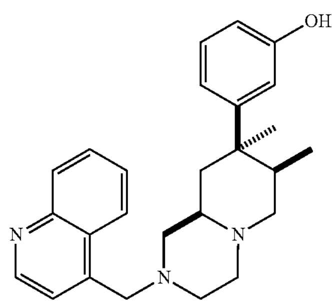 | 3-((7R,8R,9αR)-7,8-ylmethyl)-octahydro-1H-pyrido[1,2-α]pyrazin-8-yl)phenol | 402.4 |
| 8AP | 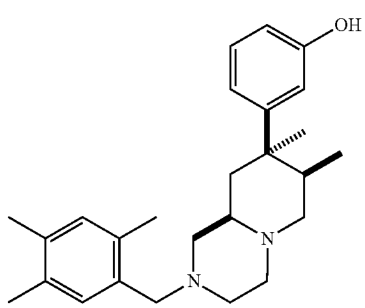 | 3-((7R,8R,9αR)-7,8-dimethyl-2-(2,4,5-trimethylbenzyl)-octahydro-1H-pyrido[1,2-α]pyrazin-8-yl)phenol | 393.5 |
| 8AQ | 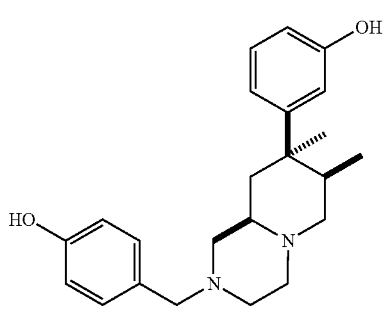 | 3-((7R,8R,9αR)-2-(4-hydroxybenzyl)-7,8-dimethyl-octahydro-1H-pyrido[1,2-α]pyrazin-8-yl)phenol | 367.3 |

TABLE 1-continued

Table of Compounds

| Example | Structure | Name | [M + H]+ |
|---|---|---|---|
| 9A | 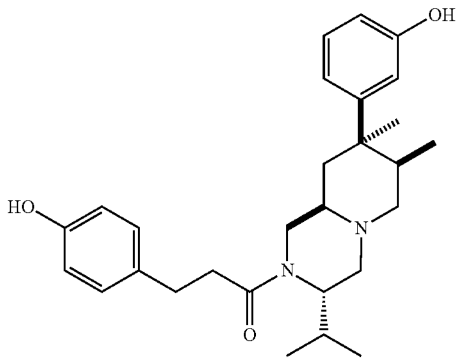 | 3-(4-hydroxyphenyl)-1-((3S,7R,8R,9αR)-8-(3-hydroxyphenyl)-3-isopropyl-7,8-dimethyl-hexahydro-1H-pyrido[1,2-α]pyrazin-2(6H)-yl)propan-1-one | 451.26 |
| 9B | 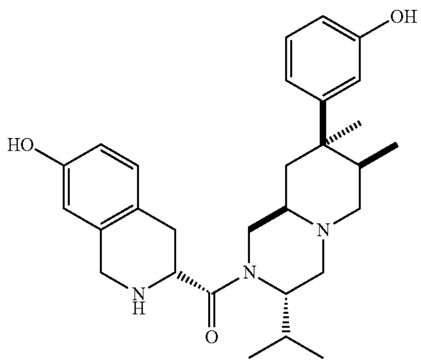 | ((R)-7-hydroxy-1,2,3,4-tetrahydroisoquinolin-3-yl)((3S,7R,8R,9αR)-8-(3-hydroxyphenyl)-3-isopropyl-7,8-dimethyl-hexahydro-1H-pyrido[1,2-α]pyrazin-2(6H)-yl)methanone | 478.20 |

Biological Methods

The potencies of the compounds were determined by testing the ability of a range of concentrations of each compound to inhibit the binding of the non-selective opioid antagonist, [$^3$H]diprenorphine, to the cloned human μ, κ, and δ opioid receptors, expressed in separate cell lines. $IC_{50}$ values were obtained by nonlinear analysis of the data using GraphPad Prism version 3.00 for Windows (GraphPad Software, San Diego). $K_i$ values were obtained by Cheng-Prusoff corrections of $IC_{50}$ values.

The receptor binding method (DeHaven and DeHaven-Hudkins, 1998) was a modification of the method of Raynor et al. (1994). After dilution in buffer A and homogenization as before, membrane proteins (10-80 μg) in 250 μL were added to mixtures containing test compound and [$^3$H]diprenorphine (0.5 to 1.0 nM, 40,000 to 50,000 dpm) in 250 μL of buffer A in 96-well deep-well polystyrene titer plates (Beckman). After incubation at room temperature for one hour, the samples were filtered through GF/B filters that had been presoaked in a solution of 0.5% (w/v) polyethylenimine and 0.1% (w/v) bovine serum albumin in water. The filters were rinsed 4 times with 1 mL of cold 50 mM Tris HCl, pH 7.8 and radioactivity remaining on the filters determined by scintillation spectroscopy. Nonspecific binding was determined by the minimum values of the titration curves and was confirmed by separate assay wells containing 10 μM naloxone. $K_i$ values were determined by Cheng-Prusoff corrections of $IC_{50}$ values derived from nonlinear regression fits of 12 point titration curves using GraphPad Prism® version 3.00 for Windows (GraphPad Software, San Diego, Calif.).

To determine the equilibrium dissociation constant for the inhibitors ($K_i$), radioligand bound (cpm) in the presence of various concentrations of test compounds was measured. The concentration to give half-maximal inhibition ($EC_{50}$) of radioligand binding was determined from a best nonlinear regression fit to the following equation, $$Y = \text{Bottom} + \frac{(\text{Top} - \text{Bottom})}{1 + 10^{X - LogEC50}}$$

where Y is the amount of radioligand bound at each concentration of test compound, Bottom is the calculated amount of radioligand bound in the presence of an infinite concentration of test compound, Top is the calculated amount of radioligand bound in the absence of test compound, X is the logarithm of the concentration of test compound, and LogEC50 is the log of the concentration of test compound where the amount of radioligand bound is half-way between Top and Bottom. The nonlinear regression fit was performed using the program Prism® (GraphPad Software, San Diego, Calif.). The $K_i$ values were then determined from the $EC_{50}$ values by the following equation, $$K_i = \frac{EC_{50}}{1 + \frac{[\text{ligand}]}{K_d}}$$

where [ligand] is the concentration of radioligand and $K_d$ is the equilibrium dissociation constant for the radioligand.

The potencies of the antagonists were assessed by their abilities to inhibit agonist-stimulated [$^{35}$S]GTPγS binding to membranes containing the cloned human µ, κ, or δ opioid receptors. The agonists used were loperamide for the µ opioid receptor.

To determine the $IC_{50}$ value, which was the concentration to give half-maximal inhibition of agonist-stimulated [$^{35}$S] GTPγS binding, the amount of [$^{35}$S]GTPγS bound in the presence of a fixed concentration of agonist and various concentrations of antagonist was measured. The fixed concentration of agonist was the $EC_{80}$ for the agonist, which was the concentration to give 80% of the relative maximum stimulation of [$^{35}$S]GTPγS binding. The $IC_{50}$ value was determined from a best nonlinear regression fit of the data to the following equation, $$Y = \text{Bottom} + \frac{(\text{Top} - \text{Bottom})}{1 + 10^{X - LogIC50}}$$

where Y is the amount of [$^{35}$S]GTPγS bound at each concentration of antagonist, Bottom is the calculated amount of [$^{35}$S]GTPγS bound in the presence of an infinite concentration of antagonist, Top is the calculated amount of [$^{35}$S]GTPγS bound in the absence of added antagonist, X is the logarithm of the concentration of antagonist, and $LogIC_{50}$ is the logarithm of the concentration of antagonist where the amount of [$^{35}$S]GTPγS bound is halfway between Bottom and Top. The nonlinear regression fit was performed using GraphPad Prism® version 3.00 for Windows (GraphPad Software, San Diego, Calif.).

The compounds described in Table 1 were tested for their affinity towards the µ, δ and κ opioid receptors. All of these compounds bind with affinity less than 100 µM to the µ, δ and κ opioid receptors. These compounds displayed various degrees of selectivity µvs. δ, µ vs. κ and κ vs. δ. The activity of selected ligands was also evaluated in vitro. Numerous compounds were found to be pure antagonist at the mu opioid receptor (no agonist activity detectable at concentration >10 µM). Binding data ($K_i$ values) and in vitro mu antagonist activities ($IC_{50}$) of selected compounds is indicated in Table 2.

TABLE 2

Opioid receptor (κ, µ, δ) binding data and in vitro antagonist activity (µ) and of Examples 1, 2B, 2C, 2D, 3A, 3B and 4.

| Example | $K_i(\mu)$ (nM) | $IC_{50}(\mu)$ (nM) | $K_i(\delta)$ (nM) | $K_i(\kappa)$ (nM) |
|---|---|---|---|---|
| 1 | 0.57 | 0.53 | 30 | 8.9 |
| 2B | 5.5 | 21 | 242 | 112 |
| 2C | 2 | 21 | 25 | 190 |
| 2D | 1.1 | 11 | 139 | 44 |
| 3A | 3.6 | 12 | 88 | 18 |
| 3B | 3.3 | 26 | 716 | 12 |
| 4 | 8.9 | 29 | 36 | 85 |

When ranges are used herein for physical properties, such as molecular weight, or chemical properties, such as chemical formulae, all combinations and subcombinations of ranges and specific embodiments therein are intended to be included.

The disclosures of each patent, patent application and publication cited or described in this document are hereby incorporated herein by reference, in their entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed:

1. A compound of formula I:

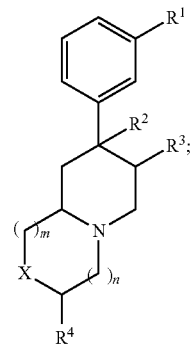

wherein:
$R^1$ is —C(═O)NR$^6$R$^7$;
$R^2$ and $R^3$ are each independently alkyl or alkenyl;
$R^4$ is H, alkyl, cycloalkyl, cycloalkylalkyl, aryl, heteroaryl, aralkyl, alkylaralkyl, or heteroarylalkyl;
X is NR$^5$;
$R^5$ is —C(═O)R$^{8b}$;
$R^6$ is H, alkyl, cycloalkyl, alkylcycloalkyl, or aralkyl;
$R^7$ is H, alkyl, aralkyl, or aryl;
$R^{8b}$ is H, alkyl, cycloalkyl, cycloalkylalkyl, heteroaryl, heteroarylalkyl, aralkyl, or aryl;
m is 1; and
n is 1,
or a pharmaceutically acceptable salt thereof.

2. The compound of claim 1, wherein $R^6$ is H or alkyl.

3. The compound of claim 2, wherein $R^7$ is H or alkyl.

4. The compound of claim 1, having the structure of formula IIa:

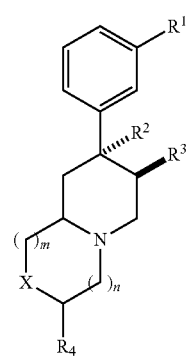

wherein
$R^6$ and $R^7$ are each independently alkyl;
$R^2$ and $R^3$ are each independently alkyl; and
$R^{8b}$ is heteroaryl, heteroarylalkyl, aralkyl, or aryl.

5. The compound according to claim 4, having the structure of formula IIb:

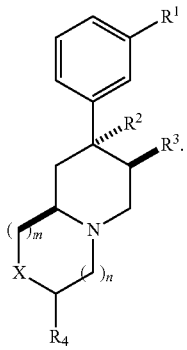

IIb

6. The compound of claim 4, wherein $R^6$ and $R^7$ are each independently methyl.

7. The compound of claim 4, wherein $R^{8b}$ is aralkyl or aryl.

8. The compound of claim 7, wherein $R^{8b}$ is aryl and $R^6$ and $R^7$ are each independently methyl.

9. The compound of claim 8, wherein $R^{8b}$ is aryl substituted with halo.

10. The compound of claim 9, wherein $R^{8b}$ is aryl substituted with fluoro.

11. A method for binding delta opioid receptors, comprising the step of: contacting one or more delta opioid receptors with a compound of formula (I) or a salt thereof in an amount effective to bind to the opioid receptor,

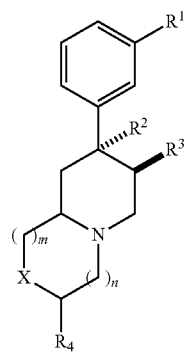

I wherein:
$R^1$ is —C(=O)NR$^6$R$^7$;
$R^2$ and $R^3$ are each independently alkyl or alkenyl;
$R^4$ is H, alkyl, cycloalkyl, cycloalkylalkyl, aryl, heteroaryl, aralkyl, alkylaralkyl, or heteroarylalkyl;
X is NR$^5$;
$R^5$ is —C(=O)R$^{8b}$;
$R^6$ is H, alkyl, cycloalkyl, alkylcycloalkyl, or aralkyl;
$R^7$ is H, alkyl, aralkyl, or aryl;
$R^{8b}$ is H, alkyl, cycloalkyl, cycloalkylalkyl, heteroaryl, heteroarylalkyl, aralkyl, or aryl;
m is 1; and
n is 1.

12. The method of claim 11, wherein the compound has the structure of formula IIa:

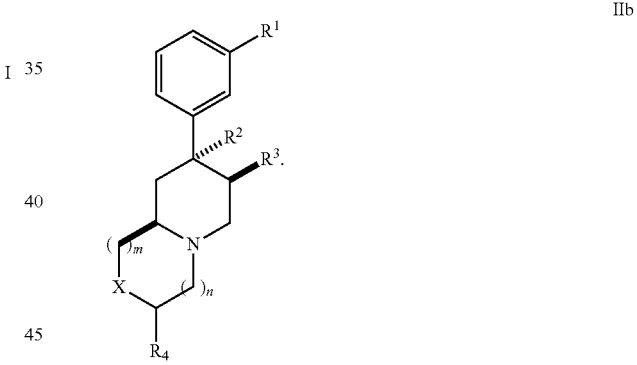

IIa wherein
$R^6$ and $R^7$ are each independently alkyl;
$R^2$ and $R^3$ are each independently alkyl; and
$R^{8b}$ is heteroaryl, heteroarylalkyl, aralkyl, or aryl.

13. The method of claim 12, wherein the compound has the structure of formula IIb:

IIb

14. The method of claim 12, wherein $R^6$ and $R^7$ are each independently methyl.

15. The method of claim 12, wherein $R^{8b}$ is aralkyl or aryl.

16. The method of claim 15, wherein $R^{8b}$ is aryl and $R^6$ and $R^7$ are each independently methyl.

17. The method of claim 16, wherein $R^{8b}$ is aryl substituted with halo.

18. The method of claim 17, wherein $R^{8b}$ is aryl substituted with fluoro.

* * * * *